US012252534B2

(12) United States Patent
Kim et al.

(10) Patent No.: US 12,252,534 B2
(45) Date of Patent: Mar. 18, 2025

(54) HUMANIZED ANTI-CD3 ANTIBODIES, CONJUGATES AND USES THEREOF

(71) Applicant: The Scripps Research Institute, La Jolla, CA (US)

(72) Inventors: Chanhyuk Kim, Daejeon (KR); Travis Young, La Jolla, CA (US); Minsoo Kim, San Diego, CA (US); Jennifer Ma, Los Angeles, CA (US); Leonard Presta, San Francisco, CA (US); Peter G. Schultz, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 1561 days.

(21) Appl. No.: 16/074,600

(22) PCT Filed: Feb. 3, 2017

(86) PCT No.: PCT/US2017/016407
§ 371 (c)(1),
(2) Date: Aug. 1, 2018

(87) PCT Pub. No.: WO2017/136659
PCT Pub. Date: Aug. 10, 2017

(65) Prior Publication Data
US 2023/0192844 A1 Jun. 22, 2023

Related U.S. Application Data

(60) Provisional application No. 62/291,143, filed on Feb. 4, 2016.

(51) Int. Cl.
*C07K 16/28* (2006.01)
*A61P 35/00* (2006.01)

(52) U.S. Cl.
CPC .......... *C07K 16/2803* (2013.01); *A61P 35/00* (2018.01); *C07K 2317/24* (2013.01); *C07K 2317/522* (2013.01); *C07K 2317/565* (2013.01); *C07K 2317/92* (2013.01)

(58) Field of Classification Search
CPC ............ C07K 16/2803; C07K 2317/24; C07K 2317/522; C07K 2317/565; C07K 2317/92; C07K 2317/33; C07K 2317/56; C07K 2317/73; C07K 2317/77; A61P 35/00; A61K 47/6803; A61K 47/6849; A61K 47/6869
See application file for complete search history.

(56) References Cited

U.S. PATENT DOCUMENTS

| 5,258,498 A | 11/1993 | Huston et al. |
| 5,766,886 A | 6/1998 | Studnicka et al. |
| 5,821,337 A | 10/1998 | Carter et al. |
| 6,982,321 B2 | 1/2006 | Winter |
| 7,087,409 B2 | 8/2006 | Barbas et al. |
| 7,416,541 B2 | 8/2008 | Yuzhakov et al. |
| 7,527,791 B2 | 5/2009 | Adams et al. |
| 8,236,308 B2 | 8/2012 | Kischel et al. |
| 9,493,563 B2 | 11/2016 | Blein et al. |
| 10,351,626 B2 | 7/2019 | Kim et al. |
| 2004/0044177 A1 | 3/2004 | Macke et al. |
| 2009/0140214 A1 | 6/2009 | Sonobe et al. |
| 2010/0285037 A1 | 11/2010 | Abo et al. |
| 2010/0324008 A1 | 12/2010 | Low et al. |
| 2012/0189621 A1 | 7/2012 | Dean et al. |
| 2013/0171095 A1 | 7/2013 | Bernett et al. |
| 2014/0099318 A1 | 4/2014 | Huang et al. |
| 2014/0120096 A1 | 5/2014 | Bakker et al. |
| 2014/0242080 A1 | 8/2014 | Jaeger et al. |
| 2014/0294823 A1 | 10/2014 | Moore et al. |
| 2014/0377270 A1 | 12/2014 | Moore et al. |
| 2015/0166661 A1 | 6/2015 | Chen et al. |
| 2016/0017058 A1 | 1/2016 | Kim et al. |
| 2016/0115232 A1 | 4/2016 | Kim et al. |
| 2017/0002076 A1 | 1/2017 | Kim |

FOREIGN PATENT DOCUMENTS

| JP | 2002534441 A | 10/2002 |
| JP | 2005505580 A | 2/2005 |
| JP | 2011523639 A | 8/2011 |
| WO | WO-03028527 A2 | 4/2003 |
| WO | WO-2004106380 A2 | 12/2004 |
| WO | WO-2007058725 A2 | 5/2007 |
| WO | WO-2007059312 A2 | 5/2007 |
| WO | WO-2007070659 A2 | 6/2007 |
| WO | WO-2007079130 A2 | 7/2007 |
| WO | WO-2007094916 A2 | 8/2007 |
| WO | WO-2007042261 A3 | 12/2007 |
| WO | WO-2008077079 A1 | 6/2008 |
| WO | WO-2008083346 A1 | 7/2008 |
| WO | WO-2009070642 A1 | 6/2009 |

(Continued)

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
Aggarwal et al. Comparative study of PSMA expression in the prostate of mouse, dog, monkey, and human. Prostate 66:903-10 (2006).
Agten et al. Oxime conjugation in protein chemistry: from carbonyl incorporation to nucleophilic catalysis. J Pept Sci 22:271-9 (2016).
Almagro and Fransson, Humanization of antibodies, Front. Biosci. vol. 13, pp. 1619-1633, 2008.
Austin et al. Endocytosis and sorting of ErbB2 and the site of action of cancer therapeutics trastuzumab and geldanamycin. Mol Biol Cell 15(12):5268-82 (2004).

(Continued)

*Primary Examiner* — Nelson B Moseley, II
(74) *Attorney, Agent, or Firm* — WILSON SONSINI GOODRICH & ROSATI

(57) ABSTRACT

The present invention provides for humanized anti-CD3 antibodies and conjugates thereof. These conjugates may be useful in the treatment of conditions such as prostate cancer.

20 Claims, 66 Drawing Sheets

Specification includes a Sequence Listing.

(56) References Cited

FOREIGN PATENT DOCUMENTS

| | | |
|---|---|---|
| WO | WO-2009139863 A2 | 11/2009 |
| WO | WO-2010037062 A1 | 4/2010 |
| WO | WO-2011028195 A2 | 3/2011 |
| WO | WO-2012142659 A1 | 10/2012 |
| WO | WO-2012166559 A1 | 12/2012 |
| WO | WO-2012166560 A1 | 12/2012 |
| WO | WO-2013093809 A1 | 6/2013 |
| WO | WO-2014056783 A1 | 4/2014 |
| WO | WO-2014059213 A1 | 4/2014 |
| WO | WO-2014153002 A1 | 9/2014 |
| WO | WO-2014153164 A1 | 9/2014 |
| WO | WO-2014185985 A1 | 11/2014 |
| WO | WO-2014195888 A1 | 12/2014 |
| WO | WO-2015057852 A1 | 4/2015 |
| WO | WO-2015184203 A1 | 12/2015 |
| WO | WO-2016014974 A2 | 1/2016 |
| WO | WO-2016014974 A3 | 3/2016 |
| WO | WO-2016168773 A2 | 10/2016 |
| WO | WO-2017136659 A2 | 8/2017 |

OTHER PUBLICATIONS

Axup et al. Synthesis of site-specific antibody-drug conjugates using unnatural amino acids. PNAS vol. 109, No. 40, pp. 16101-16106, Oct. 2, 2012.
Baeuerle et al. Bispecific T-cell engaging antibodies for cancer therapy. Cancer Res 69:4941-4944 (2009).
Barrett et al. First-in-man evaluation of 2 high-affinity PSMA-avid small molecules for imaging prostate cancer. J Nucl Med 54:380-7 (2013).
Bendig, M.M. Humanization of rodent monoclonal antibodies by CDR grafting. Methods: A Companion to Methods in Enzymology, 8; 83-93 (1995).
Borst et al. Target antigen of monoclonal reagent S5.7: comparison with T3 antigen. Hybridoma 2:265-74 (1983).
Brockman et al. Nomogram Predicting Prostate Cancer-specific Mortality for Men with Biochemical Recurrence After Radical Prostatectomy. Eur Urol 67:1160-67 (2015).
Casset et al. A peptide mimetic of an anti-CD4 monoclonal antibody by rational design. Biochemical and Biophysical Research Communication 307:198-205 (2003).
Chatterjee et al. A Versatile Platform for Single- and Multiple Unnatural Amino Acid Mutagenesis in *Escherichia coli*, Biochemistry, Mar. 12, 2013, vol. 52, No. 10.
Conrad et al. TCR and CD3 antibody cross-reactivity in 44 species. Cytometry A 71:925-33 (2007).
Coutrot, Federic et al. A New pH-Switchable Dimannosyl[c2]Daisy Chain Molecular Machine, Org. Lett. vol. 10, No. 17, pp. 3741-3744, Jul. 31, 2008.
Cui et al. Chemically Programmed Bispecific Antibodies That Recruit and Activate T Cells. The Journal of Biological Chemistry vol. 287, No. 34, pp. 28206-28214, Aug. 17, 2012.
Denmeade et al. Engineering a prostate-specific membrane antigen-activated tumor endothelial cell prodrug for cancer therapy. Sci Transl Med 4:140ra86 (2012).
Doods, HN et al. BIBP 3226, the first selective neuropeptide Y1 receptor antagonist: A review of its pharmacological properties. Regulatory Peptides, 65(1):71-77 (Aug. 27, 1996).
Dubrovska, Anna, et al. A Chemically Induced Vaccine Strategy for Prostate Cancer. ACS Chem. Biol., 6(11):1223-1231 (2011).
Facchini et al. Very Early PSA Response to Abiraterone in mCRPC Patients: A Novel Prognostic Factor Predicting Overall Survival. Front Pharmacol 7:123 (2016).
FDA. Immunogenicity Assessment for Therapeutic Protein Products, Guidance for Industry (39 pgs) (2014).
Friedrich, M. Regression of Human Prostate Cancer Xenografts in Mice by AMG 212/BAY2010112, a Novel PSMA/CD3-Bispecific BiTE Antibody Cross-Reactive with Non-Human Primate Antigens. Mol. Cancer Ther. 11(12):2664-2673 (Dec. 2012).

Genbank Accession No. AB064051: *Homo spaiens* IGK mRNA for immunoglobulin kappa light chain VLJ region.partial cds, clone:K10. Jul. 2, 2012.
Gharbi, R. et al. Condensation D'Alcenes Aromatiques Avec L'Acetaldehyde Catalysee Par Des Resines Echangeuses D'Ions—II, Tetrahedron, 39(18); 2953-2963 (1983).
Gicquiaux, H. et al. Rapid Internalization and Recycling of the Human Neuropeptide Y Y1 Receptor. The Journal of Biological Chemistry, 277(8):6645-6655 (Feb. 2002).
Hernandez-Hoyos et al. MOR209/ES414, a Novel Bispecific Antibody Targeting PSMA for the Treatment of Metastatic Castration-Resistant Prostate Cancer. Mol Cancer Ther 15:2155-65 (2016).
Humblet, Valerie et al. Multivalent Scaffolds for Affinity Maturation of Small Molecule Cell Surface Binders and Their Application to Prostate Tumor Targeting, J. Med. Chem, vol. 52, No. 2, pp. 544-550, 2009.
Hutchins et al. Site-specific coupling and sterically controlled formation of multimeric antibody fab fragments with unnatural amino acids. J. Mol. Biol., vol. 406, No. 4, pp. 595-603, Mar. 4, 2011.
International Application No. PCT/US2014/028612 International Preliminary Report on Patentability and Written Opinion Dated Sep. 24, 2015.
International Application No. PCT/US2014/028612 International Search Report and Written Opinion Dated Jul. 1, 2014.
International Application No. PCT/US2014/029379 International Preliminary Report on Patentability and Written Opinion Dated Sep. 24, 2015.
International Application No. PCT/US2014/029379 International Search Report and Written Opinion Dated Aug. 26, 2014.
International Application No. PCT/US2017/016407 International Search Report and Written Opinion Mailed Jul. 26, 2017.
Janthur, W.D. Drug Conjugates Such as Antibody Drug Conjugates (ADCs), Immunotoxins and Immunoliposomes Challenge Daily Clinical Practice. Int J Mol Sci. Nov. 28, 2012;13(12):16020-45.
Johnson, David et al. RF1 Knockout Allows Ribosomal Incorporation of Unnatural Amino Acids at Multiple Sites, Nat Chem Biol., vol. 7, No. 11, pp. 779-786, Sep. 18, 2011.
Kashmiri et al., SDR grafting—a new approach to antibody humanization, Methods vol. 36, No. 1, pp. 25-34, May 2005.
Kazane, Stephanie et al. Self-Assembled Antibody Multimers through Peptide Nucleic Acid Conjugation, J. Am. Chem. Soc. vol. 135, No. 1, pp. 340-346, Jan. 9, 2013.
Kiess et al. Prostate-specific membrane antigen as a target for cancer imaging and therapy. Q J Nucl Med Mol Imaging 59:241-68 (2015).
Kim et al. Bispecific small molecule-antibody conjugate targeting prostate cancer. PNAS USA 110:17796-801 (2013).
Kim et al. Protein conjugation with genetically encoded unnatural amino acids. Current Opinion in Chemical Biology, vol. 17, No. 3, pp. 412-419, May 9, 2013.
Kim et al. Synthesis of Bispecific Antibodies using Genetically Encoded Unnatural Amino Acids, J. Am. Chem. Soc., vol. 134, No. 24, pp. 9918-9921, 2012.
Kinoshita et al. Expression of prostate-specific membrane antigen in normal and malignant human tissues. World J Surg 30:628-36 (2006).
Klimka et al., Human anti-CD30 recombinant antibodies by guided phage antibody selection using cell panning, Br. J. Cancer, 83:252-260 (2000).
Kularatne et al. Prostate-specific membrane antigen targeted imaging and therapy of prostate cancer using a PSMA inhibitor as a homing ligand. Mol Pharm 6:780-9 (2009).
Kularatne et al. Recruiting Cytotoxic T Cells to Folate-Receptor-Positive Cancer Cells. Angew Chem Int Ed Engl. 52:12101-12104 (2013).
Kularatne, S. et al. Folate Receptor-Targeted T cells for Cancer Immunotherapy. Angew Chem. Int. Ed. Engl. 52(46):12101-12104 (Nov. 11, 2013).
Lang et al., Genetic encoding of bicyclononynes and trans-cyclooctenes for site-specific protein labeling in vitro and in live mammalian cells via rapid fluorogenic Diels-Alder Reactions. Journal of the American Chemical Society, vol. 134, No. 25, pp. 10317-10320(2012).

(56) References Cited

OTHER PUBLICATIONS

Lin et al. Transglutaminase-Catalyzed Site-Specific Conjugation of Small-Molecules to Proteins in Vitro and on the Surface of Living Cells. Journal of American Chemical Society 128(14):4542-4543 (2006).
Liu, et al. Adding new chemistries to the genetic code Annu. Rev. Biochem, vol. 79, pp. 413-444, Jul. 2010.
Liu, Ma et al. Hormone conjugated with antibody to CD3 mediates cytotoxic T cell lysis of human melanoma cells. Science. Jan. 22, 1988;239(4838):395-8.
Lutje et al. PSMA Ligands for Radionuclide Imaging and Therapy of Prostate Cancer: Clinical Status. Theranostics 5:1388-401 (2015).
MacCallum, R.M. et al. Antibody-antigen interactions: Contact analysis and binding site topography. Journal of Molecular Biology 262:732-745 (1998).
Maindron, Nicolas et al. Synthesis and luminescence properties of new red-shifted absorption lanthanide(III) chelates suitable for peptide and protein labelling, Organic & Biomolecular Chemistry, vol. 9, No. 7, Apr. 7, 2011.
Malik, Noeen et al. Radiosynthesis of a new PSMA targeting ligand ([18F]FPy-DUPA-Pep), Applied Radiation and Isotopes 69;1014-1018 (Apr. 8, 2011).
McNeel et al. The Society for Immunotherapy of Cancer consensus statement on immunotherapy for the treatment of prostate carcinoma. J Immunother Cancer 4:92 (2016).
Meller et al. Alterations in androgen deprivation enhanced prostate-specific membrane antigen (PSMA) expression in prostate cancer cells as a target for diagnostics and therapy. EJNMMI Res 5:66 (2015).
Molema et al. CD3 directed bispecific antibodies induce increased lymphocyte-endothelial cell interactions in vitro. Br J Cancer 82:472-9 (2000).
Paul, W.E., Fundamental Immunology, 3rd Edition, p. 292-295, 1993.
Queen C., et al., "A humanized antibody that binds to the interleukin 2 receptor," Dec. 1989, Proceedings of the National Academy of Sciences, National Academy of Sciences, vol. 86, No. 24, pp. 10029-10033, XP002614478.
Reubi, J.C. et al. Co-expressed peptide receptors in breast cancer as a molecular basis for in vivo multireceptor tumour targeting. European Journal of Nuclear Medicine, 29(7):855-862 (Jul. 2002).
Riechmann et al. Reshaping human antibodies for therapy, Nature vol. 332, pp. 323-329, 1988.
Ristau et al. The prostate-specific membrane antigen: lessons and current clinical implications from 20 years of research. Urol Oncol 32:272-9 (2014).
Roberts et al. Chemistry for peptide and protein PEGylation. Adv Drug Deliv Rev 54: 459-476 (2002).
Saber et al. An FDA oncology analysis of CD3 bispecific constructs and first-in-human dose selection. Regul Toxicol Pharmacol 90:144-52 (2017).
Schraa, Astrid J. et al. RGD-Modified Anti-CD3 Antibodies Redirect Cytolytic Capacity of Cytotoxic T Lumphocytes Toward αvβ3-Expressing Endothelial Cells, International Journal of Cancer, 112; 279-285 (2004).
Sigma-Aldrich Co. LLC, Monoclonal Anti-CD3, clone UCHT-1, Catalog No. C7048. (2012).
Silver et al. Prostate-specific membrane antigen expression in normal and malignant human tissues. Clin Cancer Res 3:81-5 (1997).
Sokoloff et al. A dual-monoclonal sandwich assay for prostate-specific membrane antigen: levels in tissues, seminal fluid and urine. Prostate 43:150-7 (2000).
Sweat et al. Prostate-specific membrane antigen expression is greatest in prostate adenocarcinoma and lymph node metastases. Urology 52:637-40 (1998).
Tai et al. Development of a peptide-drug conjugate for prostate cancer therapy. Molecular Pharmaceutics, vol. 8, No. 3, pp. 901-912, Jun. 6, 2011.
Takehisa et al. Natural infection of wild-born mandrills (*Mandrillus sphinx*) with two different types of simian immunodeficiency virus. AIDS Res Hum Retroviruses 17:1143-54 (2001).
Thomas, et al. Application of strain-promoted azide-alkyne cycloaddition and tetrazine ligation to targeted Fc-drug conjugates. Bioconjugate Chemistry, vol. 23, No. 10, pp. 2007-2013 (2012).
Thomson, S. et al. The construction and in vitro testing of photo-activatable cancer targeting folated anti-CD3 conjugates, Biochemical and Biophysical Research Communications 366;526-531 (2008).
Troyer et al. Detection and characterization of the prostate-specific membrane antigen (PSMA) in tissue extracts and body fluids. Int J Cancer 62:552-8 (1995).
U.S. Appl. No. 14/774,647 Final Office Action Mailed Sep. 11, 2018.
U.S. Appl. No. 14/774,647 Non-Final Office Action Mailed Feb. 8, 2018.
U.S. Appl. No. 14/774,649 Restriction Requirement Mailed Apr. 27, 2016.
U.S. Appl. No. 15/268,389 Non-Final Office Action Mailed Sep. 27, 2018.
Wang, Lei and Schultz, Peter. Expanding the Genetic Code. Angewandte Chemie Int. Ed, vol. 44, pp. 34-66, 2005.
Wright et al. Upregulation of prostate-specific membrane antigen after androgen-deprivation therapy. Urology 48:326-34 (1996).
Yang et al. Engineering a long-acting, potent GLP-1 analog for microstructure-based transdermal delivery. PNAS 113(15):4140-4145 (2016).
Young et al. Beyond the canonical 20 amino acids: expanding the genetic lexicon. J Biol Chem 285:11039-44 (2010).
Zhang et al. A remote arene-binding site on prostate specific membrane antigen revealed by antibody-recruiting small molecules. J Am Chem Soc. 132(36):12711-12716 (2010).
Strop et al. Location matters: site of conjugation modulates stability and pharmacokinetics of antibody drug conjugates. Chem Biol 20(2):161-167 (2013).
U.S. Appl. No. 16/420,062 Final Office Action dated Nov. 29, 2021.
U.S. Appl. No. 16/420,062 Non-Final Office Action dated Aug. 10, 2021.
U.S. Appl. No. 14/774,647 Notice of Allowance dated Feb. 26, 2019.
U.S. Appl. No. 14/774,647 Notice of Allowance dated Jan. 10, 2019.
U.S. Appl. No. 15/268,389 Restriction Requirement dated Jun. 12, 2018.
U.S. Appl. No. 14/774,647 Restriction Requirement dated Aug. 24, 2017.

* cited by examiner

VH sequences

```
Murine    EVQLVESGGGLVQPKRSLRLSCAAS HCDR1 WVRQAPGKGLEWVA HCDR2 RFTISRDDSQSILYLQMNNLKTEDTAMYYCVR HCDR3 WGQGTLVTVSS
              *                                                                ****                 *
IGHV3-73  EVQLVESGGGLVQPGGSLKLSCAAS       WVRQASGKGLEWVG       RFTISRDDSKNTAYLQMNSLKTEDTAVYYCTR       WGQGTLVTVSS
VH hu1    EVQLVESGGGLVQPGGSLRLSCAAS       WVRQAPGKGLEWVG       RFTISRDDSKNTLYLQMNSLKTEDTAVYYCVR       WGQGTLVTVSS
VH hu2    ------------------------- -----A ------------- ----- -------------------------------- ----- -----------
```

VL sequences

```
Murine     QAVVTQESALTTSPGETVTLTC LCDR1 WYQEKPDHLFTGLIG LCDR2 GVPARFSGSLLGGKAALTLSGAQPEDEAEYYC LCDR3 FGGGTKLTVL
              *   *                  ******                  *     *                           *
IGLV7-46   QAVVTQEPSLTVSPGGTVTLTC       WFQQKPGQAPRTLIY       WTPARFSGSLLGGKAALTLSGAQPEDEAEYYC       FGGGTKLTVL
VL hu1     QAVVTQEPSLTVSPGGTVTLTC       WFQQKPGQAPRTLIY       WTPARFSGSLLGGKAALTLSGAQPEDEAEYYC       FGGGTKLTVL
VL hu2     ---------------------- -Y---- ----------Y--- G---- W----------------Q-------------- E-Y- ----------
VL hu3     ---------------------- -Y---- ----------Y--- -F-G-- W----------------Q--I------------ E-Y- ----------
VL hu4     ---------------------- -Y---- ------DHLF-G-G W----------------Q--I-D--------- E-Y- ----------
VL hu5     ---------------------- -Y---- ------DHLF-T--Y G---- ----------------Q--I-D--------- E-Y- ----------
VL hu6     ---------------------- -F---- ------DHLF---Y G---- ----------------Q--I-D--------- E-Y- ----------
VL hu7     ---------------------- -Y---- ------GQAF-G--G G---- ----------------Q--I-D--------- E-Y- ----------
VL hu8     ---------------------- -Y---- ------DHLF-G--G G---- ----------------Q--I-D--------- E-Y- ----------
VL hu9     ---------------------- -Y---- ------GQAF-G--G GY-D- ----------------Q--I------------ E-Y- ----------
VL hu10    -----------T---------- -Y---- ------DHLF-G--G GV--- ----------------Q--I------------ E-Y- ----------
```

FIG. 2

C4-2 (PSMA$^{pos}$)

DU145 (PSMA$^{neg}$)

DUPA

CMCG tBuCMCG

CTCG

FIG. 20C
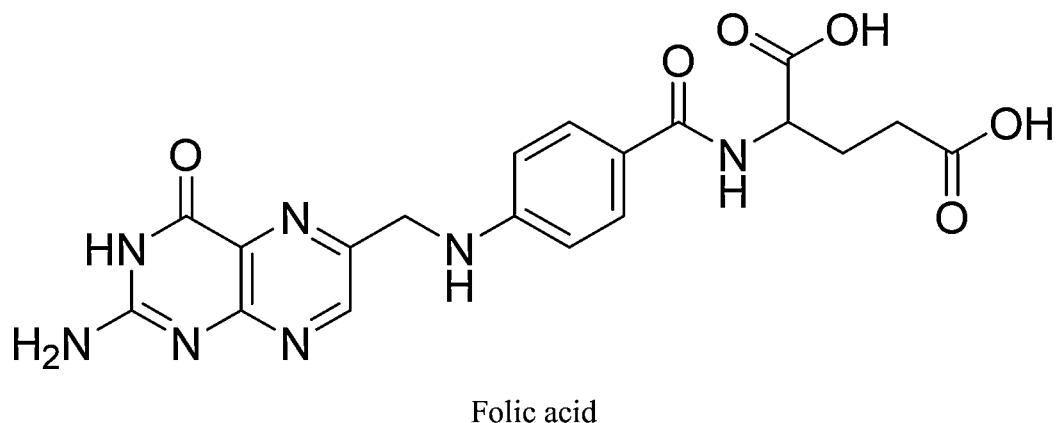
Folic acid
FIG. 20D
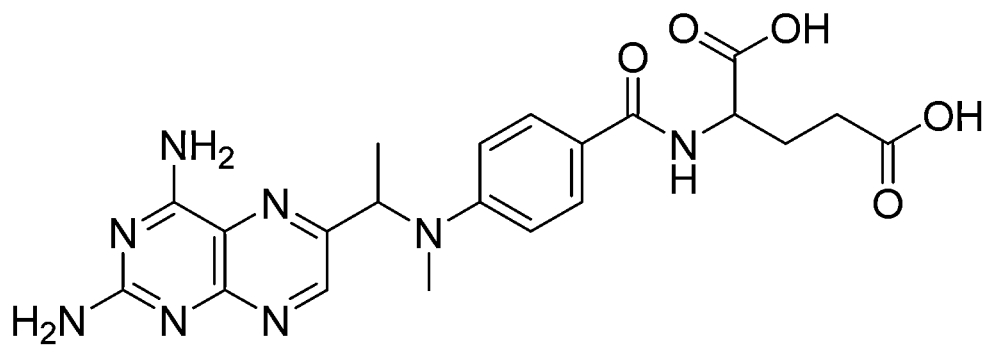
Denopterin
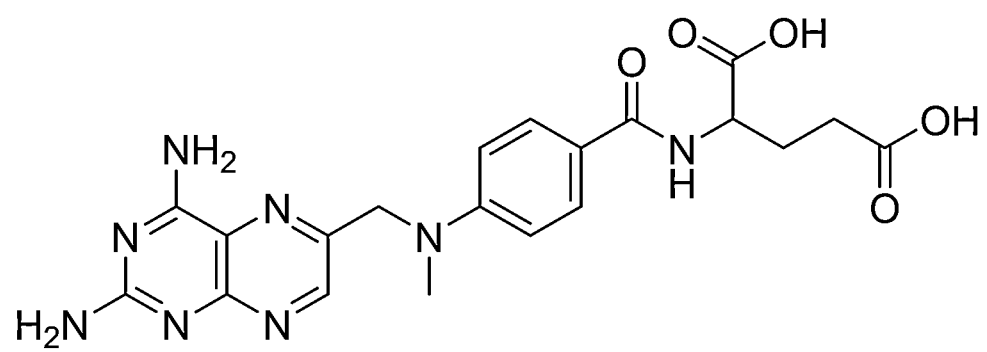
Methotrexate FIG. 26
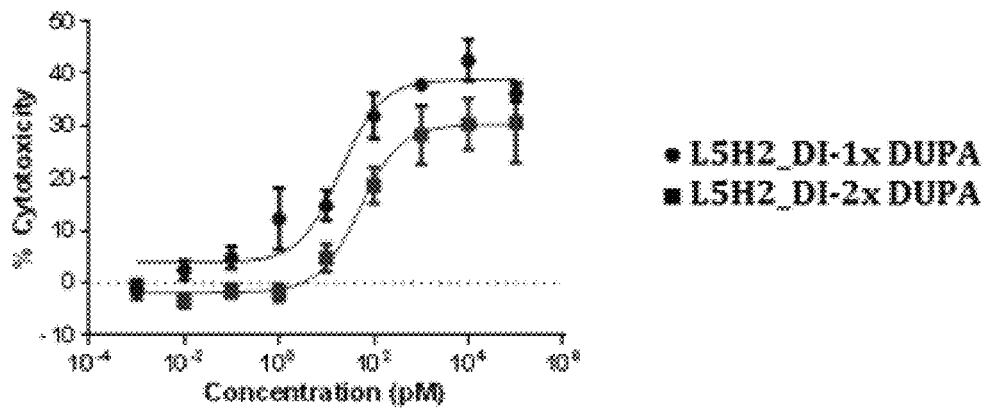
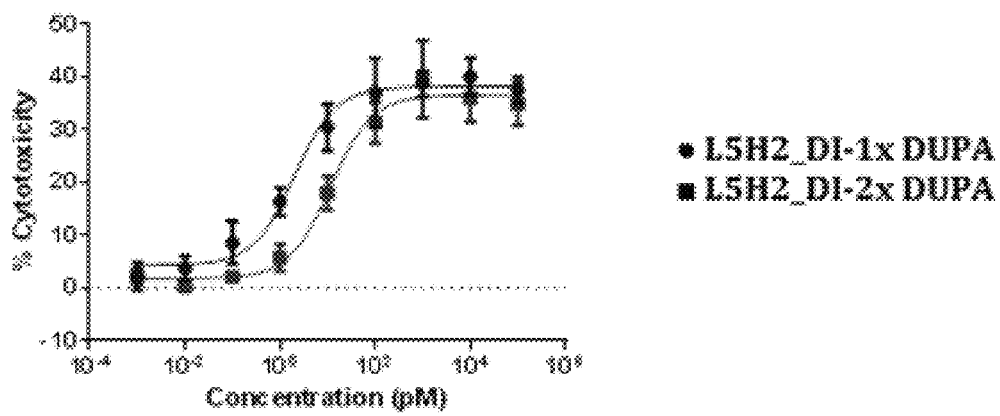
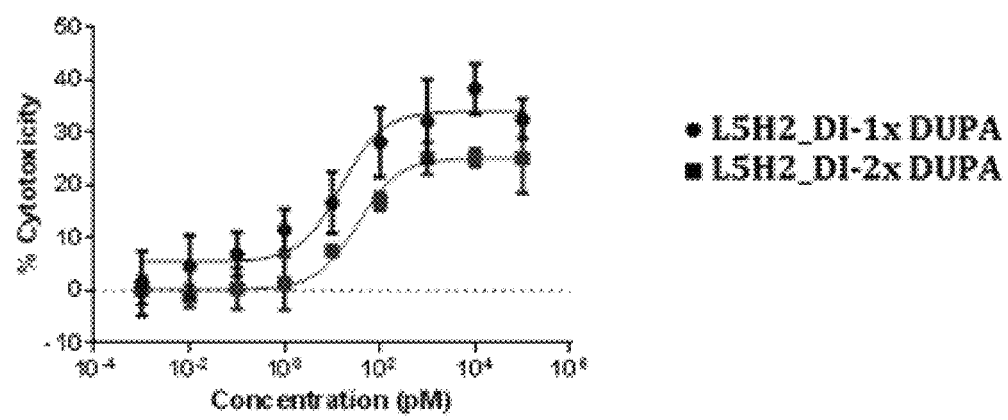

A  →  P00925 L5H2_DI 1xDUPA
B  →  P00774 L5H2_DI 2xDUPA
C  ⋯▲⋯  P00925 L5H2_DI 1xDUPA + huPSMA
D  ⋯▼⋯  P00774 L5H2_DI 2xDUPA + huPSMA

24hr LDH cytotoxicity assay
Effector cells: PBL (Fresh)
E:T: 10:1
Background killing: donor 5053, 1.3-3.4%

A  →  P00925 L5H2_DI 1xDUPA
B  →  P00774 L5H2_DI 2xDUPA
C  ⋯▲⋯  P00925 L5H2_DI 1xDUPA + huPSMA
D  ⋯▼⋯  P00774 L5H2_DI 2xDUPA + huPSMA

* = n.s., p>0.05 in two-sample t-test and Wilcoxon test.

| | |
|---|---|
| A | No Injections |
| B | PBS, QD |
| C | L5H2_DI-2xTAG (0.2mg/kg, QD) |
| D | L5H2_DI-2xDUPA (0.2mg/kg, QD) |
| E | L5H2_DI-1xTAG (0.2mg/kg, QD) |
| F | L5H2_DI-2xDUPA (0.2mg/kg, QD) |

FIG. 42
Controls
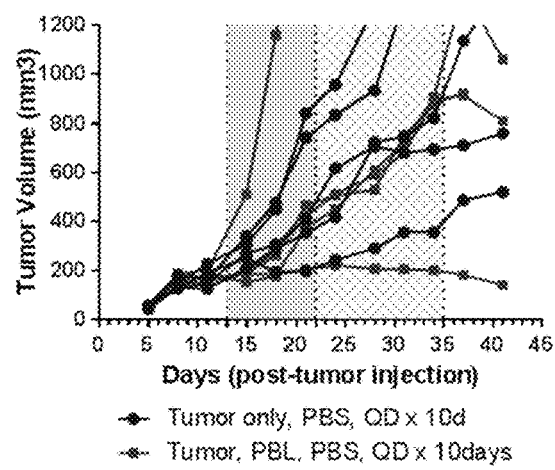
Treatment groups
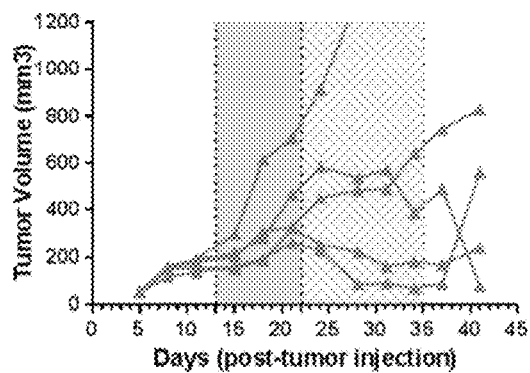
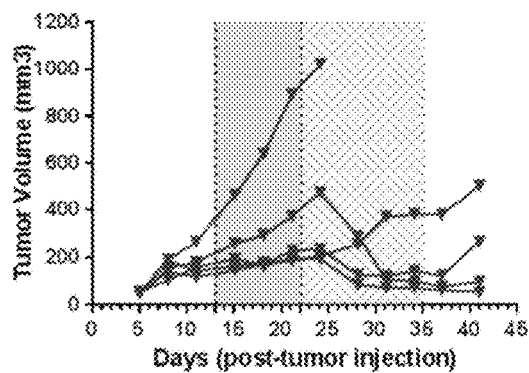
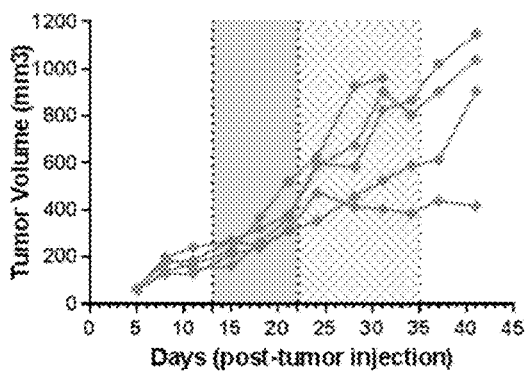
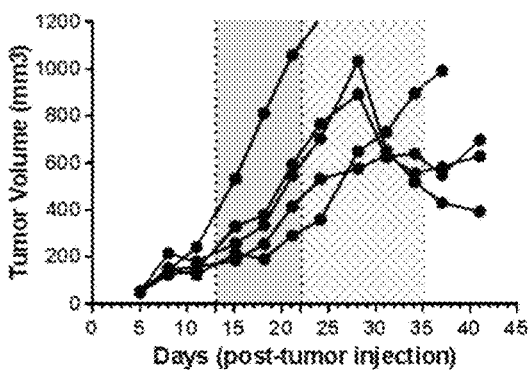

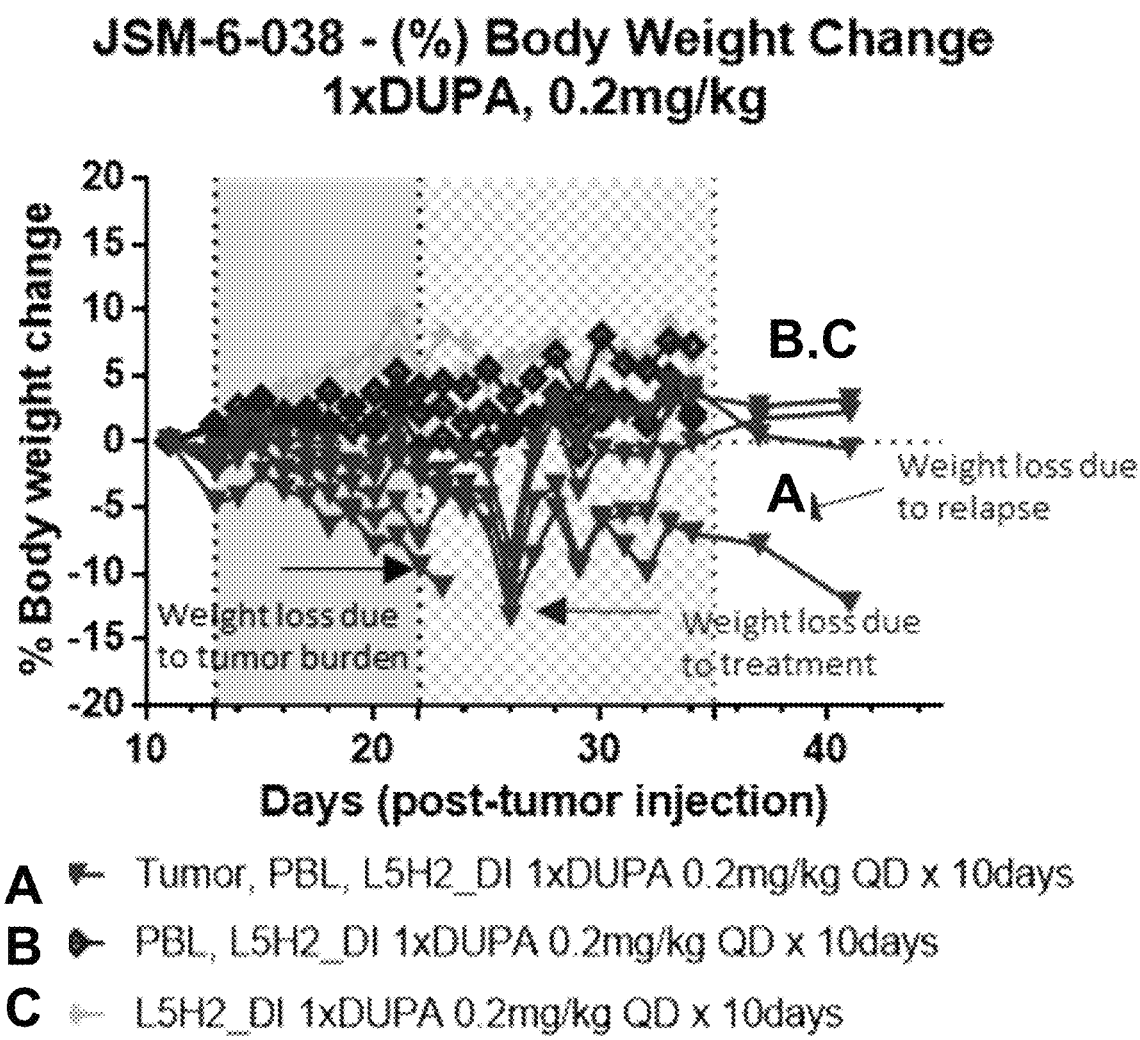

Dose line: *In vivo* dosing in efficacy models at 0.2 mg/kg (approx. 20 ug/mL or 400 nM)
EC50 line: cytotoxicity (activated T cells) approx. 10 pM (0.5 ng/mL) (40 pM for PBMC)
ULOQ and LLOQ = upper & lower limits of quantification for current assay

SEQUENCE LISTING

<160> NUMBER OF SEQ ID NOS: 126

<210> SEQ ID NO 1
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
caagcagttg tgacgcaaga atcggccctg accacgagtc cgggtgaaac cgttacgctg      60
acctgtcgct caagtaccgg cgctgttacc acgagtaact atgcgaattg ggtgcaggaa     120
aaaccggatc acctgtttac cggcctgatt ggcggtacga caaacgtgc gccgggtgtt     180 ccggcacgtt tctcgggcag cctgattggt gataaagcag cactgacgat caccggcgcc     240
caaaccgaag acgaagcaat ctattttgc gctctgtggt actctaacct gtgggtgttc     300
ggcggtggca cgaaactgac cgttctg                                          327
```

<210> SEQ ID NO 2
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
gaagtccagc tggttgaatc tggtggcggt ctggtgcaac cgaaaggctc tctgaaactg      60
agttgcgcag cttccggttt tacgttcaac acctatgcga tgaattgggt tcgccaggcg     120
ccgggtaaag gtctggaatg ggtcgcgcgt atccgcagca aatataacaa ttacgcaacc     180
tattacgctg attcagtgaa agaccgtttt acgatttcgc gcgatgactc ccagtcaatc     240
ctgtacctgc aaatgaacaa tctgaaaacg aagataccg ccatgtatta ctgcgtccgt     300
cacggcaact ttggtaattc ctatgtgtca tggttcgcat actggggcca gggtacgctg     360
gttaccgtca gctct                                                       375
```

<210> SEQ ID NO 3
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gaagtccagc tggttgaatc tggtggcggt ctggttcaac cgggcggttc gctgaaactg      60
agctgcgcag cttctggctt tacgttcaac acctatgcga tgaattgggt tcgccaggcc     120
tcaggcaaag gtctggaatg ggtcggtcgt attcgctcga aatataacaa ttacgcaacc     180
tattacgctg atagcgtgaa agaccgtttc accatcagtc gcgatgactc caaaaacacg     240
ctgtatctgc aaatgaatag cctgaaaacg aagataccg cggtctatta ctgcgtgcgt     300
catggcaact ttggtaattc ttatgtgagc tggttcgcct actggggcca gggtacgctg     360
gttaccgtca gctct                                                       375
```

<210> SEQ ID NO 4
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
gaagtccagc tggttgaatc tggtggcggt ctggttcaac cgggcggttc gctgaaactg      60
agctgcgcag cttctggctt tacgttcaac acctatgcga tgaattgggt tcgccaggcc     120
```

```
tcaggcaaag gtctggaatg ggtcgctcgt attcgctcga aatataacaa ttacgcaacc    180
tattacgctg atagcgtgaa agaccgtttc accatcagtc gcgatgactc caaaaacacg    240
ctgtatctgc aaatgaatag cctgaaaacg gaagataccg cggtctatta ctgcgtgcgt    300
catggcaact ttggtaattc ttatgtgagc tggttcgcct actggggcca gggtacgctg    360
gttaccgtca gctct                                                     375

<210> SEQ ID NO 5
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gaagtccagc tggttgaatc tggtggcggt ctggttcaac cgggcggttc gctgagactg     60
agctgcgcag cttctggctt tacgttcaac acctatgcga tgaattgggt tcgccaggcc    120
ccgggcaaag gtctggaatg ggtcgctcgt attcgctcga aatataacaa ttacgcaacc    180
tattacgctg atagcgtgaa agaccgtttc accatcagtc gcgatgactc caaaaacacg    240
ctgtatctgc aaatgaatag cctgagagcg gaagataccg cggtctatta ctgcgtgcgt    300
catggcaact ttggtaattc ttatgtgagc tggttcgcct actggggcca gggtacgctg    360
gttaccgtca gctct                                                     375

<210> SEQ ID NO 6
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
caagctgttg tgacccaaga accgagtctg accgtgtctc cgggcggcac cgttacgctg     60
acctgtggct cctctaccgg cgcagtcacc acgagcaact atgcaaattg gttccagcaa    120
aaaccgggtc aggctccgcg taccctgatt tacggtacga acaaacgtgc gccgtggacc    180
ccggcacgtt tttcgggcag cctgctgggc ggtaaagcag cactgaccat cagtggtgcg    240
cagccggaag atgaagcaga atattactgc gctctgtggt atagcaacct gtgggtcttt    300
ggcggtggca cgaaactgac cgtgctg                                        327

<210> SEQ ID NO 7
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
caagctgttg tgacccaaga accgagtctg accgtgtctc cgggcggcac cgttacgctg     60
acctgtggct cctctaccgg cgcagtcacc acgagcaact atgcaaattg ggtgcagcaa    120
aaaccgggtc aggcttttcg tggcctgatt tacggtacga acaaacgtgc gccgtggacc    180
ccggcacgtt tttcgggcag cctgctgggc ggtaaagcag cactgaccat cagtggtgcg    240
cagccggaag atgaagcaga atattactgc gctctgtggt atagcaacct gtgggtcttt    300
```

```
ggcggtggca cgaaactgac cgtgctg                                      327
```

<210> SEQ ID NO 8
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
caagctgttg tgacccaaga accgagtctg accgtgtctc cgggcggcac cgttacgctg    60
acctgtggct cctctaccgg cgcagtcacc acgagcaact atgcaaattg ggtgcagcaa   120
aaaccgggtc aggcttttcg tggcctgatt ggcggtacga acaaacgtgc gccgtggacc   180
ccggcacgtt tttcgggcag cctgctgggc ggtaaagcag cactgaccat cagtggtgcg   240
cagccggaag atgaagcaga atattactgc gctctgtggt atagcaacct gtgggtcttt   300
ggcggtggca cgaaactgac cgtgctg                                      327
```

<210> SEQ ID NO 9
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
caagctgttg tgacccaaga accgagtctg accgtgtctc cgggcggcac cgttacgctg    60
acctgtggct cctctaccgg cgcagtcacc acgagcaact atgcaaattg ggtgcagcaa   120
aaaccgggtc aggcttttcg tggcctgatt tacggtacga acaaacgtgc gccgtggacc   180
ccggcacgtt tttcgggcag cctgctgggc gataaagcag cactgaccat cagtggtgcg   240
cagccggaag atgaagcaga atattactgc gctctgtggt atagcaacct gtgggtcttt   300
ggcggtggca cgaaactgac cgtgctg                                      327
```

<210> SEQ ID NO 10
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
caagctgttg tgacccaaga accgagtctg accgtgtctc cgggcggcac cgttacgctg    60
acctgtcgct cctctaccgg cgcagtcacc acgagcaact atgcaaattg ggtgcagcaa   120
aaaccggatc atctgtttcg tggcctgatt ggcggtacga acaaacgtgc gccggggacc   180
ccggcacgtt tttcgggcag cctgctgggc gataaagcag cactgaccat cagtggtgcg   240
cagccggaag atgaagcaga atattactgc gctctgtggt atagcaacct gtgggtcttt   300
ggcggtggca cgaaactgac cgtgctg                                      327
```

<210> SEQ ID NO 11
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
caagctgttg tgacccaaga accgagtctg accgtgtctc cgggcggcac cgttacgctg    60
acctgtcgct cctctaccgg cgcagtcacc acgagcaact atgcaaattg gttccagcaa   120
aaaccggatc atctgccgcg taccctgatt tacggtacga acaaacgtgc gccggggacc   180
ccggcacgtt tttcgggcag cctgctgggc gataaagcag cactgaccat cagtggtgcg   240
cagccggaag atgaagcaga atattactgc gctctgtggt atagcaacct gtgggtcttt   300
ggcggtggca cgaaactgac cgtgctg                                       327

<210> SEQ ID NO 12
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
caagctgttg tgacccaaga accgagtctg accgtgtctc cgggcggcac cgttacgctg    60
acctgtcgct cctctaccgg cgcagtcacc acgagcaact atgcaaattg ggtgcagcaa   120
aaaccgggtc aggcgtttcg tggcctgatt ggcggtacga acaaacgtgc gccggggacc   180
ccggcacgtt tttcgggcag cctgctgggc gataaagcag cactgaccat cagtggtgcg   240
cagccggaag atgaagcaga atattactgc gctctgtggt atagcaacct gtgggtcttt   300
ggcggtggca cgaaactgac cgtgctg                                       327

<210> SEQ ID NO 13
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
caagctgttg tgacccaaga accgagtctg accgtgtctc cgggcggcac cgttacgctg    60
acctgtggct cctctaccgg cgcagtcacc acgagcaact atgcaaattg ggtgcagcaa   120
aaaccggatc atctgtttcg tggcctgatt ggcggtacga acaaacgtgc gccggggacc   180
ccggcacgtt tttcgggcag cctgctgggc ggtaaagcag cactgaccat cagtggtgcg   240
cagccggaag atgaagcaga atattactgc gctctgtggt atagcaacct gtgggtcttt   300
ggcggtggca cgaaactgac cgtgctg                                       327

<210> SEQ ID NO 14
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
caagctgttg tgacccaaga accgagtctg accgtgtctc cgggcggcac cgttacgctg    60
acctgtggct cctctaccgg cgcagtcacc acgagcaact atgcaaattg ggtgcagcaa   120
aaaccgggtc aggcgtttcg tggcctgatt ggcggtacga acaaacgtgc gccgggggtc   180

```
ccggatcgtt tttcgggcag cctgctgggc ggtaaagcag cactgaccat cagtggtgcg      240
cagccggaag atgaagcaga atattactgc gctctgtggt atagcaacct gtgggtcttt      300
ggcggtggca cgaaactgac cgtgctg                                          327
```

<210> SEQ ID NO 15
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
caagctgttg tgacccaaga accgagtctg accacgtctc cgggcggcac cgttacgctg       60
acctgtcgct cctctaccgg cgcagtcacc acgagcaact atgcaaattg ggtgcagcaa      120
aaaccggatc atctgtttac tggcctgatt ggcggtacga acaaacgtgc gccgggggtc      180
ccggcacgtt tttcgggcag cctgattggc gataaagcag cactgaccat cagtggtgcg      240
cagccggaag atgaagcaga atattactgc gctctgtggt atagcaacct gtgggtcttt      300
ggcggtggca cgaaactgac cgtgctg                                          327
```

<210> SEQ ID NO 16
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
caagctgttg tgacccaaga accgagtctg accgtgtctc cgggcggcac cgttacgctg       60
acctgtcgct cctctaccgg cgcagtcacc acgagcaact atgcaaattg ggtgcagcaa      120
aaaccggatc atctgtttcg tggcctgatt ggcggtacga acaaacgtgc gccggggacc      180
ccggcacgtt tttcgggcag cctgctgggc gataaagcag cactgaccat cagtggtgcg      240
cagccggaag atgaagcaga atattactgc gctctgtggt atagcaacct gtgggtcttt      300
ggcggtggca cgaaactgac cgtgctgggt cagccgaaag cagctccgag cgtcaccctg      360
tttccgccga gcagcgaaga actgcaagca aataaagcta ccctggtttg tctgattagc      420
gatttctatc cgggcgcagt cacggtggca tggaaagcag acagttcccc ggttaaagct      480
ggtgtcgaaa ccacgacccc gtctaaacag agtaacaata atatgcggc ctcatcgtac      540 ctgagtctga ccccggaaca gtggaaatcc catcgttctt acagttgcca agtgacccac      600
gaaggcagca cggtggaaaa aaccgttgcg ccgacggaat gtagc                      645
```

<210> SEQ ID NO 17
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
caagctgttg tgacccaaga accgagtctg accgtgtctc cgggcggcac cgttacgctg       60
acctgtcgct cctctaccgg cgcagtcacc acgagcaact atgcaaattg ggtgcagcaa      120
aaaccggatc atctgtttcg tggcctgatt ggcggtacga acaaacgtgc gccggggacc      180
```

```
ccggcacgtt tttcgggcag cctgctgggc gataaagcag cactgaccat cagtggtgcg    240
cagccggaag atgaagcaga atattactgc gctctgtggt atagcaacct gtgggtcttt    300
ggcggtggca cgaaactgac cgttctgaaa cgaactgtgg ctgcaccatc tgtcttcatc    360
ttcccgccat ctgatgagca gttgaaatct ggaactgcct ctgtcgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgtcttcgcc cgtcacaaag agcttcaaca ggggagagtg t             651
```

<210> SEQ ID NO 18
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
caagctgttg tgacccaaga accgagtctg accgtgtctc cgggcggcac cgttacgctg    60
acctgtcgct cctctaccgg cgcagtcacc acgagcaact atgcaaattg ggtgcagcaa    120
aaaccggatc atctgtttcg tggcctgatt ggcggtacga caaacgtgc gccggggacc     180 ccggcacgtt tttcgggcag cctgctgggc gataaagcag cactgaccat cagtggtgcg    240
cagccggaag atgaagcaga atattactgc gctctgtggt atagcaacct gtgggtcttt    300
ggcggtggca cgaaactgac cgttctgaaa cgaactgtgg ctgcaccatc tgtcttcatc    360
ttcccgccat ctgatgagca gttgaaatct ggaactgcct ctgtcgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgtagtcgcc cgtcacaaag agcttcaaca ggggagagtg t             651
```

<210> SEQ ID NO 19
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gaagtccagc tggttgaatc tggtggcggt ctggttcaac gggcggttc gctgaaactg     60 agctgcgcag cttctggctt tacgttcaac acctatgcga tgaattgggt tcgccaggcc    120
tcaggcaaag gtctgaatg gtcgctcgt attcgctcga aatataacaa ttacgcaacc      180
tattacgctg atagcgtgaa agaccgtttc accatcagtc gcgatgactc caaaaacacg    240
ctgtatctgc aaatgaatag cctgaaaacg gaagataccg cggtctatta ctgcgtgcgt    300
catggcaact ttggtaattc ttatgtgagc tggttcgcct actggggcca gggtacgctg    360
gttaccgtca gctctgcctc caccaagggc ccatcggtct tccccctggc accctcctcc    420
aagagcacct ctgggggcac agcggccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgactgtgcc ctctagcagc    600
```

```
ttgggcaccc agacctacat ctgcaacgtg aatcacaagc ccagcaacac caaggtggac      660
aagaaagttg agcccaaatc ttgtgacaaa actcacaca                            699

<210> SEQ ID NO 20
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gaagtccagc tggttgaatc tggtggcggt ctggttcaac cgggcggttc gctgaaactg       60
agctgcgcag cttctggctt tacgttcaac acctatgcga tgaattgggt tcgccaggcc      120
tcaggcaaag gtctggaatg ggtcgctcgt attcgctcga aatataacaa ttacgcaacc      180
tattacgctg atagcgtgaa agaccgtttc accatcagtc gcgatgactc caaaaacacg      240
ctgtatctgc aaatgaatag cctgaaaacg gaagataccg cggtctatta ctgcgtgcgt      300
catggcaact ttggtaattc ttatgtgagc tggttcgcct actggggcca gggtacgctg      360
gttaccgtca gctctgcctc caccaagggc ccatcggtct tccccctggc accctcctcc      420
tagagcacct ctgggggcac agcggccctg ggctgcctgg tcaaggacta cttccccgaa      480
ccggtgacgg tgtcgtggaa ctcaggcgcc ctgaccagcg gcgtgcacac cttcccggct      540
gtcctacagt cctcaggact ctactccctc agcagcgtgg tgactgtgcc ctcttagagc      600
ttgggcaccc agacctacat ctgcaacgtg aatcacaagc ccagcaacac caaggtggac      660
aagaaagttg agcccaaatc ttgtgacaaa actcacaca                            699

<210> SEQ ID NO 21
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gaagtccagc tggttgaatc tggtggcggt ctggttcaac cgggcggttc gctgagactg       60
agctgcgcag cttctggctt tacgttcaac acctatgcga tgaattgggt tcgccaggcc      120
ccgggcaaag gtctggaatg ggtcgctcgt attcgctcga aatataacaa ttacgcaacc      180
tattacgctg atagcgtgaa agaccgtttc accatcagtc gcgatgactc caaaaacacg      240
ctgtatctgc aaatgaatag cctgagagcg gaagataccg cggtctatta ctgcgtgcgt      300
catggcaact ttggtaattc ttatgtgagc tggttcgcct actggggcca gggtacgctg      360
gttaccgtca gctctgcctc caccaagggc ccatcggtct tccccctggc accctcctcc      420
aagagcacct ctgggggcac agcggccctg ggctgcctgg tcaaggacta cttccccgaa      480
ccggtgacgg tgtcgtggaa ctcaggcgcc ctgaccagcg gcgtgcacac cttcccggct      540
gtcctacagt cctcaggact ctactccctc agcagcgtgg tgactgtgcc ctccagcagc      600
ttgggcaccc agacctacat ctgcaacgtg aatcacaagc ccagcaacac caaggtggac      660
aagaaagttg agcccaaatc ttgtgacaaa actcacaca                            699

<210> SEQ ID NO 22
<211> LENGTH: 699
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 22

```
gaagtccagc tggttgaatc tggtggcggt ctggttcaac cgggcggttc gctgagactg    60
agctgcgcag cttctggctt tacgttcaac acctatgcga tgaattgggt tcgccaggcc   120
ccgggcaaag gtctggaatg ggtcgctcgt attcgctcga aatataacaa ttacgcaacc   180
tattacgctg atagcgtgaa agaccgtttc accatcagtc gcgatgactc aaaaacacg    240
ctgtatctgc aaatgaatag cctgagagcg aagataccg cggtctatta ctgcgtgcgt    300
catggcaact ttggtaattc ttatgtgagc tggttcgcct actggggcca gggtacgctg   360
gttaccgtca gctctgcctc caccaagggc ccatcggtct tccccctggc accctcctcc   420
tagagcacct ctgggggcac agcggccctg ggctgcctgg tcaaggacta cttccccgaa   480
ccggtgacgg tgtcgtggaa ctcaggcgcc ctgaccagcg gcgtgcacac cttcccggct   540
gtcctacagt cctcaggact ctactccctc agcagcgtgg tgactgtgcc ctctagcagc   600
ttgggcaccc agacctacat ctgcaacgtg aatcacaagc ccagcaacac caaggtggac   660
aagaaagttg agcccaaatc ttgtgacaaa actcacaca                          699
```

<210> SEQ ID NO 23
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Gln Ala Val Val Thr Gln Glu Ser Ala Leu Thr Thr Ser Pro Gly Glu
1               5                   10                  15
Thr Val Thr Leu Thr Cys Arg Ser Ser Thr Gly Ala Val Thr Thr Ser
            20                  25                  30
Asn Tyr Ala Asn Trp Val Gln Glu Lys Pro Asp His Leu Phe Thr Gly
        35                  40                  45
Leu Ile Gly Gly Thr Asn Lys Arg Ala Pro Gly Val Pro Ala Arg Phe
    50                  55                  60
Ser Gly Ser Leu Ile Gly Asp Lys Ala Ala Leu Thr Ile Thr Gly Ala
65                  70                  75                  80
Gln Thr Glu Asp Glu Ala Ile Tyr Phe Cys Ala Leu Trp Tyr Ser Asn
                85                  90                  95
Leu Trp Val Phe Gly Gly Gly Thr Lys Leu Thr Val Leu
            100                 105
```

<210> SEQ ID NO 24
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Glu Val Gln Leu Val Glu Ser Gly Gly Gly Leu Val Gln Pro Lys Gly
1               5                   10                  15
Ser Leu Lys Leu Ser Cys Ala Ala Ser Gly Phe Thr Phe Asn Thr Tyr
            20                  25                  30
```

```
Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Gln Ser Ile
 65                  70                  75                  80

Leu Tyr Leu Gln Met Asn Asn Leu Lys Thr Glu Asp Thr Ala Met Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125
```

<210> SEQ ID NO 25
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Thr Tyr
                 20                  25                  30

Ala Met Asn Trp Val Arg Gln Ala Ser Gly Lys Gly Leu Glu Trp Val
            35                  40                  45

Gly Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125
```

<210> SEQ ID NO 26
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Thr Tyr
                 20                  25                  30

Ala Met Asn Trp Val Arg Gln Ala Ser Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80
```

```
Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 27
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 28
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 29
```

```
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 30
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 31
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30
```

Asn Tyr Ala Asn Trp Val Gln Gln Lys Pro Gly Gln Ala Phe Arg Gly
            35                  40                  45

Leu Ile Tyr Gly Thr Asn Lys Arg Ala Pro Trp Thr Pro Ala Arg Phe
        50                  55                  60

Ser Gly Ser Leu Leu Gly Asp Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105

<210> SEQ ID NO 32
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Asp His Leu Phe Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Asp Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105

<210> SEQ ID NO 33
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Asp His Leu Pro Arg Thr
            35                  40                  45

Leu Ile Tyr Gly Thr Asn Lys Arg Ala Pro Gly Thr Pro Ala Arg Phe
        50                  55                  60

Ser Gly Ser Leu Leu Gly Asp Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105

```
<210> SEQ ID NO 34
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Asp Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 35
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Asp His Leu Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 36
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
```

```
                    20                  25                  30

Asn Tyr Ala Asn Trp Val Gln Gln Lys Pro Gly Gln Ala Phe Arg Gly
            35                  40                  45

Leu Ile Gly Gly Thr Asn Lys Arg Ala Pro Gly Val Pro Asp Arg Phe
        50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 37
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Ala Val Val Thr Gln Glu Pro Ser Leu Thr Thr Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Asp His Leu Phe Thr Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 38
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Asp His Leu Phe Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Asp Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
```

```
                100                 105                 110
Lys Ala Ala Pro Ser Val Thr Leu Phe Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 39
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Asp His Leu Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Asp Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 40
<211> LENGTH: 217
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (205)..(205)
<223> OTHER INFORMATION: P-acetylphenylalanine

<400> SEQUENCE: 40

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Asp His Leu Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Asp Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Phe Ser Pro Val
        195                 200                 205

Thr Lys Ser Phe Asn Arg Gly Glu Cys
    210                 215

<210> SEQ ID NO 41
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80
```

-continued

```
Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230
```

<210> SEQ ID NO 42
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (141)..(141)
<223> OTHER INFORMATION: P-acetylphenylalanine

<400> SEQUENCE: 42

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Phe Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

```
Thr Phe Pro Ala Val Leu Gln Ser Ser Gly Leu Tyr Ser Leu Ser Ser
                180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Asp Lys Thr His Thr
225                 230

<210> SEQ ID NO 43
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230

<210> SEQ ID NO 44
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (141)..(141)
```

<223> OTHER INFORMATION: P-acetylphenylalanine

<400> SEQUENCE: 44

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asn Thr Tyr
            20                  25                  30
Ala Met Asn Trp Val Arg Gln Ala Pro Gly Lys Gly Leu Glu Trp Val
        35                  40                  45
Ala Arg Ile Arg Ser Lys Tyr Asn Asn Tyr Ala Thr Tyr Tyr Ala Asp
    50                  55                  60
Ser Val Lys Asp Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Val Arg His Gly Asn Phe Gly Asn Ser Tyr Val Ser Trp Phe
            100                 105                 110
Ala Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Phe Ser Thr Ser
    130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Lys Val Glu
    210                 215                 220
Pro Lys Ser Cys Asp Lys Thr His Thr
225                 230
```

<210> SEQ ID NO 45
<211> LENGTH: 233
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asn Thr Tyr
            20                  25                  30
Ala Met Asn Trp Val Arg Gln Ala Ser Gly Lys Gly Leu Glu Trp Val
        35                  40                  45
Ala Arg Ile Arg Ser Lys Tyr Asn Asn Tyr Ala Thr Tyr Tyr Ala Asp
    50                  55                  60
Ser Val Lys Asp Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Val Arg His Gly Asn Phe Gly Asn Ser Tyr Val Ser Trp Phe
```

```
                100             105             110
Ala Tyr Trp Gly Gln Gly Thr Leu Val Thr Val Ser Ser Ala Ser Thr
            115             120             125

Lys Gly Pro Ser Val Phe Pro Leu Ala Pro Ser Ser Lys Ser Thr Ser
130             135             140

Gly Gly Thr Ala Ala Leu Gly Cys Leu Val Lys Asp Tyr Phe Pro Glu
145             150             155             160

Pro Val Thr Val Ser Trp Asn Ser Gly Ala Leu Thr Ser Gly Val His
            165             170             175

Thr Phe Pro Ala Val Leu Gln Ser Ser Gly Leu Tyr Ser Leu Ser Ser
            180             185             190

Val Val Thr Val Pro Ser Ser Leu Gly Thr Gln Thr Tyr Ile Cys
            195             200             205

Asn Val Asn His Lys Pro Ser Asn Thr Lys Val Asp Lys Lys Val Glu
            210             215             220

Pro Lys Ser Cys Asp Lys Thr His Thr
225             230

<210> SEQ ID NO 46
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Glu Ser Gly Gly Gly Leu Val Gln Pro Gly Gly
1               5               10              15

Ser Leu Lys Leu Ser Cys Ala Ala Ser Gly Phe Thr Phe Asn Thr Tyr
            20              25              30

Ala Met Asn Trp Val Arg Gln Ala Pro Gly Lys Gly Leu Glu Trp Val
            35              40              45

Ala Arg Ile Arg Ser Lys Tyr Asn Asn Tyr Ala Thr Tyr Tyr Ala Asp
        50              55              60

Ser Val Lys Asp Arg Phe Thr Ile Ser Arg Asp Asp Ser Lys Asn Thr
65              70              75              80

Leu Tyr Leu Gln Met Asn Ser Leu Lys Thr Glu Asp Thr Ala Val Tyr
            85              90              95

Tyr Cys Val Arg His Gly Asn Phe Gly Asn Ser Tyr Val Ser Trp Phe
            100             105             110

Ala Tyr Trp Gly Gln Gly Thr Leu Val Thr Val Ser Ser Ala Ser Thr
            115             120             125

Lys Gly Pro Ser Val Phe Pro Leu Ala Pro Ser Ser Lys Ser Thr Ser
130             135             140

Gly Gly Thr Ala Ala Leu Gly Cys Leu Val Lys Asp Tyr Phe Pro Glu
145             150             155             160

Pro Val Thr Val Ser Trp Asn Ser Gly Ala Leu Thr Ser Gly Val His
            165             170             175

Thr Phe Pro Ala Val Leu Gln Ser Ser Gly Leu Tyr Ser Leu Ser Ser
            180             185             190

Val Val Thr Val Pro Ser Ser Leu Gly Thr Gln Thr Tyr Ile Cys
            195             200             205

Asn Val Asn His Lys Pro Ser Asn Thr Lys Val Asp Lys Lys Val Glu
            210             215             220
```

```
Pro Lys Ser Cys Asp Lys Thr His Thr
225                 230
```

<210> SEQ ID NO 47
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230
```

<210> SEQ ID NO 48
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45
```

```
Ala Arg Ile Arg Ser Lys Tyr Asn Asn Tyr Ala Thr Tyr Tyr Ala Asp
    50                  55                  60
Ser Val Lys Asp Arg Phe Thr Ile Ser Arg Asp Asp Ser Lys Asn Thr
 65                  70                  75                  80
Leu Tyr Leu Gln Met Asn Ser Leu Arg Ala Glu Asp Thr Ala Val Tyr
                 85                  90                  95
Tyr Cys Val Arg His Gly Asn Phe Gly Asn Ser Tyr Val Ser Trp Phe
                100                 105                 110
Ala Tyr Trp Gly Gln Gly Thr Leu Val Thr Val Ser Ser Ala Ser Thr
            115                 120                 125
Lys Gly Pro Ser Val Phe Pro Leu Ala Pro Ser Ser Lys Ser Thr Ser
130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Leu Gly Thr Gln Thr Tyr Ile Cys
        195                 200                 205
Asn Val Asn His Lys Pro Ser Asn Thr Lys Val Asp Lys Lys Val Glu
210                 215                 220
Pro Lys Ser Cys Asp Lys Thr His Thr
225                 230

<210> SEQ ID NO 49
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Arg Leu Ser Cys Ala Ala Ser Gly Phe Thr Phe Asn Thr Tyr Ala Met
 1               5                  10                  15
Asn Trp Val Arg Gln Ala Pro Gly Lys Gly Leu Glu Trp Val Ala Arg
             20                  25                  30
Ile Arg Ser Lys Tyr Asn Asn Tyr Ala Thr Tyr Tyr Ala Asp Ser Val
         35                  40                  45
Lys Asp Arg Phe Thr Ile Ser Arg Asp Asp Ser Lys Asn Thr Leu Tyr
 50                  55                  60
Leu Gln Met Asn Ser Leu Arg Ala
 65                  70

<210> SEQ ID NO 50
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Pro Gly Lys Gly Leu Glu Trp Val Ala Arg Ile Arg Ser Lys Tyr Asn
 1               5                  10                  15
Asn Tyr Ala Thr Tyr Tyr Ala Asp Ser Val Lys Asp Arg Phe Thr Ile
             20                  25                  30
```

Ser Arg Asp Asp Ser Lys Asn Thr Leu Tyr Leu Gln Met Asn Ser Leu
        35                  40                  45

Arg Ala
    50

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ser Ser Thr Gly Ala Val Thr Thr Ser Asn Tyr Ala Asn
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Thr Asn Lys Arg Ala Pro
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Leu Trp Tyr Ser Asn Leu Trp Val
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Phe Thr Phe Asn Thr Tyr Ala Met Asn
1               5                   10

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ile Arg Ser Lys Tyr Asn Asn Tyr Ala Thr Tyr Tyr Ala Asp Ser
1               5                   10                  15

Val Lys Asp

```
<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Gly Asn Phe Gly Asn Ser Tyr Val Ser Trp Phe Ala Tyr
1               5                   10

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Val Gln Gln Lys Pro Gly Gln Ala Phe Arg Gly Leu Ile Tyr
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Val Gln Gln Lys Pro Gly Gln Ala Phe Arg Gly Leu Ile Gly
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Val Gln Gln Lys Pro Asp His Leu Phe Arg Gly Leu Ile Gly
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Phe Gln Gln Lys Pro Asp His Leu Phe Arg Thr Leu Ile Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61
```

```
Trp Val Gln Gln Lys Pro Gly Gln Ala Phe Arg Gly Leu Ile Gly
1               5                   10                  15

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp His Leu Phe Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Pro Asp His Leu Phe Arg
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Lys Pro Asp His Leu Phe Arg
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<223> OTHER INFORMATION: See specification as filed for detailed
      description of substitutions and preferred embodiments

<400> SEQUENCE: 65

Gln Xaa Xaa Asp His Leu Phe Arg
1               5

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
```

```
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<223> OTHER INFORMATION: See specification as filed for detailed
      description of substitutions and preferred embodiments

<400> SEQUENCE: 66

Xaa Val Xaa Xaa Xaa Xaa Asp His Leu Phe Arg Gly Xaa Xaa Gly
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<223> OTHER INFORMATION: See specification as filed for detailed
      description of substitutions and preferred embodiments

<400> SEQUENCE: 67

Xaa Val Xaa Gln Xaa Xaa Asp His Leu Phe Xaa Gly Xaa Xaa Gly
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
```

```
<223> OTHER INFORMATION: See specification as filed for detailed
      description of substitutions and preferred embodiments

<400> SEQUENCE: 68

Xaa Val Xaa Xaa Xaa Xaa Asp His Leu Phe Xaa Gly Xaa Xaa Gly
1               5                   10                  15

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Lys or Arg

<400> SEQUENCE: 69

Glu Val Gln Leu Val Glu Ser Gly Gly Gly Leu Val Gln Pro Gly Gly
1               5                   10                  15

Ser Leu Xaa Leu Ser Cys Ala Ala Ser
            20                  25

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Gly or Ala

<400> SEQUENCE: 70

Trp Val Arg Gln Ala Ser Gly Lys Gly Leu Glu Trp Val Xaa
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Gly or Ala

<400> SEQUENCE: 71

Trp Val Arg Gln Ala Pro Gly Lys Gly Leu Glu Trp Val Xaa
1               5                   10

<210> SEQ ID NO 72
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Trp Thr Pro Ala Arg Phe Ser Gly Ser Leu Leu Gly Gly Lys Ala Ala
1               5                   10                  15
```

Leu Thr Ile Ser Gly Ala Gln Pro Glu Asp Glu Ala Glu Tyr Tyr Cys
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Trp Thr Pro Ala Arg Phe Ser Gly Ser Leu Leu Gly Asp Lys Ala Ala
1               5                   10                  15

Leu Thr Ile Ser Gly Ala Gln Pro Glu Asp Glu Ala Glu Tyr Tyr Cys
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Thr Pro Ala Arg Phe Ser Gly Ser Leu Leu Gly Asp Lys Ala Ala
1               5                   10                  15

Leu Thr Ile Ser Gly Ala Gln Pro Glu Asp Glu Ala Glu Tyr Tyr Cys
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Thr Pro Ala Arg Phe Ser Gly Ser Leu Leu Gly Gly Lys Ala Ala
1               5                   10                  15

Leu Thr Ile Ser Gly Ala Gln Pro Glu Asp Glu Ala Glu Tyr Tyr Cys
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gly Val Pro Asp Arg Phe Ser Gly Ser Leu Leu Gly Gly Lys Ala Ala
1               5                   10                  15

Leu Thr Ile Ser Gly Ala Gln Pro Glu Asp Glu Ala Glu Tyr Tyr Cys
            20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gly Val Pro Ala Arg Phe Ser Gly Ser Leu Leu Gly Gly Lys Ala Ala
1               5                   10                  15

Leu Thr Ile Ser Gly Ala Gln Pro Glu Asp Glu Ala Glu Tyr Tyr Cys
            20                  25                  30

<210> SEQ ID NO 78
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Val Arg
            20                  25                  30

<210> SEQ ID NO 79
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Lys or Arg
<220> FEATURE:
<221> NAME/KEY: MOD_RES
<222> LOCATION: (22)..(22)
<223> OTHER INFORMATION: Thr or Ala

<400> SEQUENCE: 79

Arg Phe Thr Ile Ser Arg Asp Asp Ser Lys Asn Thr Leu Tyr Leu Gln
1               5                   10                  15

Met Asn Ser Leu Xaa Xaa Glu Asp Thr Ala Val Tyr Tyr Cys Val Arg
            20                  25                  30

<210> SEQ ID NO 80
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser
    130                 135                 140

<210> SEQ ID NO 81
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Ser Thr Ser Gly Gly Thr Ala Ala Leu Gly Cys Leu Val Lys Asp Tyr
1               5                   10                  15

Phe Pro Glu Pro Val Thr Val Ser Trp Asn Ser Gly Ala Leu Thr Ser
            20                  25                  30

Gly Val His Thr Phe Pro Ala Val Leu Gln Ser Ser Gly Leu Tyr Ser
        35                  40                  45

Leu Ser Ser Val Val Thr Val Pro Ser Ser Ser Leu Gly Thr Gln Thr
 50                 55                  60

Tyr Ile Cys Asn Val Asn His Lys Pro Ser Asn Thr Lys Val Asp Lys
65                  70                  75                  80

Lys Val Glu Pro Lys Ser Cys Asp Lys Thr His Thr
            85                  90

<210> SEQ ID NO 82
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Asp His Leu Phe Arg Gly
        35                  40                  45

Leu Ile Gly Gly Thr Asn Lys Arg Ala Pro Gly Thr Pro Ala Arg Phe
 50                 55                  60

Ser Gly Ser Leu Leu Gly Asp Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
            85                  90                  95

Leu Trp Val Phe Gly Gly Gly Thr Lys Leu Thr Val Leu Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu
        195                 200

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Pro Val Thr Lys Ser Phe Asn Arg Gly Glu Cys
1               5                   10

<210> SEQ ID NO 84
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 85

```
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr
225                 230

<210> SEQ ID NO 86
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105
```

<210> SEQ ID NO 87
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 88
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Glu Val Gln Leu Val Glu Ser Gly Gly Gly Leu Val Gln Pro Gly Gly
1               5                   10                  15

Ser Leu Lys Leu Ser Cys Ala Ala Ser
            20                  25
```

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Trp Val Arg Gln Ala Ser Gly Lys Gly Leu Glu Trp Val Gly
1               5                   10
```

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Trp Val Arg Gln Ala Ser Gly Lys Gly Leu Glu Trp Val Ala
1               5                   10
```

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Trp Val Arg Gln Ala Pro Gly Lys Gly Leu Glu Trp Val Gly
1               5                   10
```

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Trp Val Arg Gln Ala Pro Gly Lys Gly Leu Glu Trp Val Ala
1               5                   10
```

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Val Arg
            20                  25                  30
```

<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Arg Phe Thr Ile Ser Arg Asp Asp Ser Lys Asn Thr Leu Tyr Leu Gln
1               5                   10                  15

Met Asn Ser Leu Lys Ala Glu Asp Thr Ala Val Tyr Tyr Cys Val Arg
            20                  25                  30
```

<210> SEQ ID NO 95
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Arg Phe Thr Ile Ser Arg Asp Asp Ser Lys Asn Thr Leu Tyr Leu Gln
1               5                   10                  15

Met Asn Ser Leu Arg Thr Glu Asp Thr Ala Val Tyr Tyr Cys Val Arg
            20                  25                  30
```

<210> SEQ ID NO 96
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Arg Phe Thr Ile Ser Arg Asp Asp Ser Lys Asn Thr Leu Tyr Leu Gln
1               5                   10                  15

Met Asn Ser Leu Arg Ala Glu Asp Thr Ala Val Tyr Tyr Cys Val Arg
            20                  25                  30

<210> SEQ ID NO 97
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Ala Val Val Thr Gln Glu Pro Ser Leu Thr Val Ser Pro Gly Gly
1               5                   10                  15

Thr Val Thr Leu Thr Cys
            20

<210> SEQ ID NO 98
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: P-acetylphenylalanine

<400> SEQUENCE: 98

Ala Ser Thr Lys Gly Pro Ser Val Phe Pro Leu Ala Pro Ser Ser Phe
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Ser Thr Lys Gly Pro Ser Val Phe Pro Leu Ala Pro Ser Ser
1               5                   10                  15

<210> SEQ ID NO 100
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 100

Ser Thr Ser Gly Gly Thr Ala Ala Leu Gly
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Leu Val Lys Asp Tyr Phe Pro Glu Pro
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Val Thr Val Ser Trp Asn Ser Gly Ala Leu
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Ser Gly Val His Thr Phe Pro Ala Val
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Gln Ser Ser Gly Leu Tyr Ser Leu Ser
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Val Val Thr Val Pro Ser Ser Ser Leu
1               5                   10
```

```
<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Thr Gln Thr Tyr Ile Cys Asn Val Asn
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

His Lys Pro Ser Asn Thr Lys Val Asp Lys
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Lys Val Glu Pro Lys Ser Cys Asp Lys Thr His Thr
1               5                   10

<210> SEQ ID NO 109
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ser Thr Ser Gly Gly Thr Ala Ala Leu Gly Cys Leu Val Lys Asp Tyr
1               5                   10                  15

Phe Pro Glu Pro Val Thr Val Ser Trp Asn Ser Gly Ala Leu Thr Ser
            20                  25                  30

Gly Val His Thr Phe Pro Ala Val Leu Gln Ser Ser Gly Leu Tyr Ser
        35                  40                  45

Leu Ser Ser Val Val Thr Val Pro Ser Ser Ser Leu Gly Thr Gln Thr
    50                  55                  60

Tyr Ile Cys Asn Val Asn His Lys Pro Ser Asn Thr Lys Val Asp Lys
65                  70                  75                  80

Lys Val Glu Pro Lys Ser Cys Asp Lys Thr His Thr
                85                  90

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 110

Phe Gly Gly Gly Thr Lys Leu Thr Val Leu
1               5                   10

<210> SEQ ID NO 111
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 112
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (96)..(96)
<223> OTHER INFORMATION: P-acetylphenylalanine

<400> SEQUENCE: 112

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Phe
                85                  90                  95

Ser Pro Val Thr Lys Ser Phe Asn Arg Gly Glu Cys
            100                 105

<210> SEQ ID NO 113
<211> LENGTH: 95
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 113

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
                20                  25                  30

Phe Tyr Pro Arg Glu Ala Lys Val Gln Trp Lys Val Asp Asn Ala Leu
            35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu
                85                  90                  95

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Pro Val Thr Lys Ser Phe Asn Arg Gly Glu Cys
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Lys Arg Thr Val Ala Ala Pro Ser Val Phe
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ile Phe Pro Pro Ser Asp Glu Gln Leu Lys
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Gly Thr Ala Ser Val Val Cys Leu Leu
1               5                   10
```

```
<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asn Asn Phe Tyr Pro Arg Glu Ala Lys Val
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Trp Lys Val Asp Asn Ala Leu Gln Ser
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Asn Ser Gln Glu Ser Val Thr Glu Gln
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Ser Lys Asp Ser Thr Tyr Ser Leu Ser
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Thr Leu Thr Leu Ser Lys Ala Asp Tyr
1               5                   10

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 123

Glu Lys His Lys Val Tyr Ala Cys Glu Val Thr His Gln Gly Leu
1               5                   10                  15

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Trp Gly Gln Gly Thr Leu Val Thr Val Ser Ser
1               5                   10

<210> SEQ ID NO 125
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 126
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Ala

-continued

```
        65                  70                  75                  80
Gln Pro Glu Asp Glu Ala Glu Tyr Tyr Cys Ala Leu Trp Tyr Ser Asn
                    85                  90                  95
Leu Trp Val
```

HUMANIZED ANTI-CD3 ANTIBODIES, CONJUGATES AND USES THEREOF

CROSS-REFERENCE

This application is a 371 of international application PCT/US17/16407 filed Feb. 3, 2017, which claims the benefit of U.S. Provisional Application No. 62/291,143 filed Feb. 4, 2016, both of which are incorporated by reference in its entirety.

SEQUENCE LISTING

The instant application contains a Sequence Listing which has been submitted electronically in ASCII format and is hereby incorporated by reference in its entirety. Said ASCII copy, created on May 16, 2017, is named 41135-759_601_SL.txt and is 95,476 bytes in size.

BACKGROUND OF THE INVENTION

Antibody drug conjugates (ADCs) are a promising class of therapeutics that leverage the unique properties of both biologics and small molecule drugs. By tethering antibodies to drugs through a linker, these conjugates may gain high target specificity, increased serum stability, or improved cell permeability relative to their unconjugated forms. Key variables for tuning the properties and efficacy of these conjugates include the chemical site of linker attachment (both on the antibody and the drug), the antibody structure, and the linker composition/length.

In some cancers, overexpression of specific cell surface receptors can allow selective targeting of cancerous cells with small molecule drugs, while minimizing effects on healthy cells. For example, prostate cancer-specific membrane antigen (PMSA)-targeting 2-[3-(1,3-dicarboxy propyl)-ureido] pentanedioic acid (DUPA) can be conjugated to a T-cell surface antigen (αCD3) binding antibody to selectively recruit cytotoxic T-cells to kill prostate cancer cells. N-(4-{[(2-amino-4-oxo-1,4-dihydropteridin-6-yl)methyl]amino}benzoyl)-L-glutamic acid (folic acid) can also be used as a targeting agent to bind to the folate receptor (FR) antigen, which is overexpressed on FR+ cancer cell lines.

SUMMARY OF THE INVENTION

In one aspect of the disclosure, provided are antibody drug conjugates (ADCs) that target cancerous cells expressing cell surface receptors, such as PSMA and FR antigen, with a small molecule. Further provided are antibodies specific for the cluster of differentiation 3 (CD3) T-cell co-receptor, which may be used in an ADC to target T-cell mediated lysis to cancerous cells expressing particular cell surface receptors. Exemplary ADCs provided herein comprise an anti-CD3 antibody conjugated to a PMSA targeting molecule. Such ADCs may be useful for the treatment of prostate cancer. Other exemplary ADCs comprise an anti-CD3 antibody conjugated to folic acid, and are thus useful in the treatment of cancers having overexpression of FR+.

In one aspect, provided herein is an antibody comprising: a first amino acid sequence comprising SEQ ID NO: 74, and a second amino acid sequence comprising one or more of SEQ ID NOS: 54-56. In some embodiments, the first amino acid sequence comprises one or more of SEQ ID NOS: 51-53. In some embodiments, the first amino acid sequence comprises one or more of SEQ ID NOS: 97, 59, or 110. In some embodiments, the first amino acid sequence comprises SEQ ID NO: 32. In some embodiments, the first amino acid sequence comprises one or more of SEQ ID NOS: 114-123. In some embodiments, the first amino acid sequence comprises SEQ ID NO: 111 or 112. In some embodiments, the second amino acid sequence comprises one or more of SEQ ID NOS: 87, 92, 96, or 124. In some embodiments, the second amino acid sequence comprises SEQ ID NO: 27. In some embodiments, the second amino acid sequence comprises one or more of SEQ ID NOS: 99-108. In some embodiments, the second amino acid sequence comprises SEQ ID NO: 86 or 98. In some embodiments, the first amino acid sequence comprises a light chain constant domain sequence, the second amino acid sequence comprises a light chain constant domain sequence, or both the first and the second amino acid sequence each comprises a light chain constant domain sequence. In some embodiments, the first amino acid sequence comprises a heavy chain constant domain sequence, the second amino acid sequence comprises a heavy chain constant domain sequence, or both the first and the second amino acid sequence each comprises a heavy chain constant domain sequence. In some embodiments, a composition is provided comprising: a first portion comprising the antibody and a second portion comprising a second antibody or antibody fragment.

In some embodiments: (a) one or more amino acid of the first amino acid sequence is an unnatural amino acid; (b) one or more amino acid of the second amino acid sequence is an unnatural amino acid; or (c) one or more amino acid of the first amino acid sequence is an unnatural amino acid, and one or more amino acid of the second amino acid sequence is an unnatural amino acid. In some embodiments, the antibody comprises an unnatural amino acid located within: a light chain constant domain sequence of the first amino acid sequence, a heavy chain constant domain sequence of the second amino acid sequence, or the light chain constant domain sequence of the first amino acid sequence and the heavy chain constant domain sequence of the first amino acid sequence. In some embodiments, the heavy chain constant domain sequence comprises: (a) an amino acid sequence selected from SEQ ID NOS: 86 and 98; or (b) an amino acid sequence selected from one or more of SEQ ID NOS: 99-109. In some embodiments, the light chain constant domain sequence comprises an amino acid selected from: SEQ ID NOS: 111 and 112; or (b) an amino acid sequence selected from one or more of SEQ ID NOS: 113-123. In some embodiments, the unnatural amino acid is para-acetylphenylalanine. In some embodiments, a composition is provided comprising the antibody and a cell-targeting molecule. In some embodiments, a composition is provided comprising a cell-targeting molecule connected to the antibody via the unnatural amino acid. In some embodiments, the cell-targeting molecule interacts with prostate-specific membrane antigen (PSMA) or folate receptor. In some embodiments, the composition comprises a compound of Formula (III):

Formula (III)

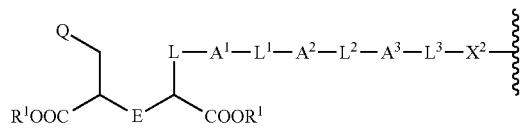

wherein:

L is

[structure: chain with $(R^2)(R^2)$ repeating $k$ times, ending in Z]

$A^1$ is selected from the group consisting of an aryl, a 5- to 6-membered heteroaryl, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

$L^1$ is

[structure with $R^{21}$ groups, O, repeating $m^1$ and $k^1$ times, ending in $Z^1$]

$A^2$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

$L^2$ is

[structure with $R^{22}$ groups, O, repeating $m^2$ and $k^2$ times, ending in $Z^2$]

$A^3$ is a bond

[structure: phenyl with $G^1$ substituents and $(R^3)_p$]

, or

[structure: phenyl with $G^2$ substituents and $(R^3)_p$];

$L^3$

[structure with $R^{23}$ groups, O, repeating $m^3$ and $k^3$ times, ending in $Z^3$]

$X^2$ is

[structure with $R^{24}$ groups, $A^4$, repeating $k^4$ times, $Z^4$—$X^3$—$L^4$];

$A^4$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

each R$^1$ is independently selected from H, alkyl, and haloalkyl;

each R$^2$, R$^{21}$, R$^{22}$, R$^{23}$, and R$^{24}$ is independently selected from H, halo, —OR$^1$, —CN, —SR$^1$, alkyl, cycloalkyl, haloalkyl, arylalkyl, and heteroarylalkyl;

each R$^3$ is independently selected from halo, —OR$^1$, —CN, —SR$^1$, alkyl, cycloalkyl, haloalkyl, arylalkyl, heteroarylalkyl, —NO$_2$, and NR$^1$R$^1$;

each G$^1$ and G$^2$ is independently selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

each Z, Z$^1$, Z$^2$, and Z$^3$ is independently selected from the group consisting of a bond, —O—, and —N(R$^1$)—;

Z$^4$ is selected from a bond, aryl, and a 5- to 6-membered heteroaryl;

k, k$^1$, k$^2$, k$^3$, and k$^4$ are each independently selected from 0, 1, 2, 3, 4, 5, 6, 7, 8, 9, and 10;

m$^1$, m$^2$, and m$^3$ are each independently selected from 0, 1, 2, 3, 4, 5, 6, 7, 8, 9, and 10;

p is 0, 1, 2, 3 or 4;

X$^3$ is [oxime structure], [oxime-H structure], [triazole], [triazole isomer], [phenyl-fused bicyclic pyridazine], [hydrazone], [hydrazone-H], or —S—;

L$^4$ is a bond directly attached to a modified amino acid, or a linker bound to a modified amino acid, wherein the modified amino acid is part of the antibody;

Q is selected from the group consisting of:

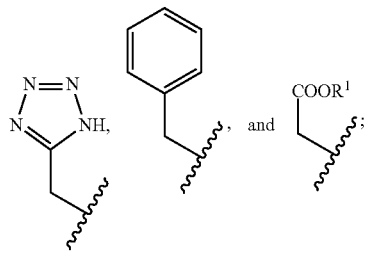

and

E is selected from the group consisting of:

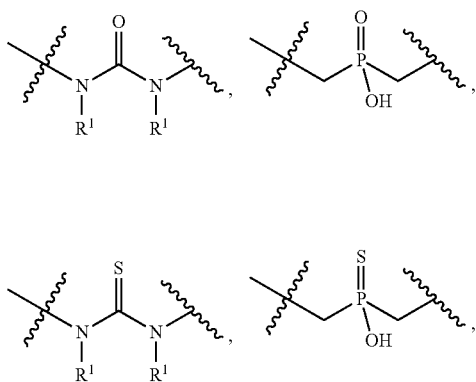

and a stereoisomer thereof.

In another aspect, provided herein is an antibody comprising a first amino acid sequence comprising: (a) one or more of SEQ ID NOS: 54-56; and (b) SEQ ID NO: 86, SEQ ID NO: 98, or an amino acid sequence having an unnatural amino acid replacing one or more amino acid residues of SEQ ID NO: 86. In some embodiments, the first amino acid sequence comprises one or more of SEQ ID NOS: 87, 92, 96, or 124. In some embodiments, the antibody further comprising a second amino acid sequence comprising: (a) one or more of SEQ ID NOS: 51-53, (b) one or more of SEQ ID NOS: 97, 59, 74, 110, or (c) a combination of (a) and (b). In some embodiments, provided is a composition comprising the antibody and a cell-targeting molecule. In some embodiments, the cell-targeting molecule interacts with prostate-specific membrane antigen (PSMA) or a folate receptor. In some embodiments, provided is a composition comprising the antibody, the composition comprising a compound of Formula (III):

Formula (III)

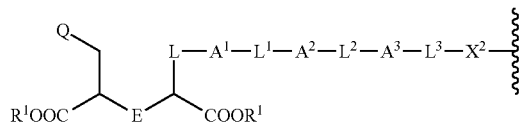

wherein:

L is

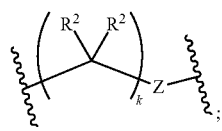

$A^1$ is selected from the group consisting of an aryl, a 5- to 6-membered heteroaryl, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

$L^1$ is

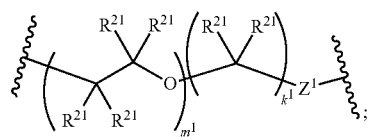

$A^2$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

$L^2$ is

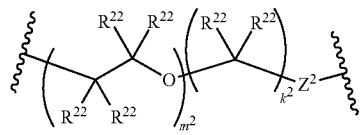

$A^3$ is a bond,

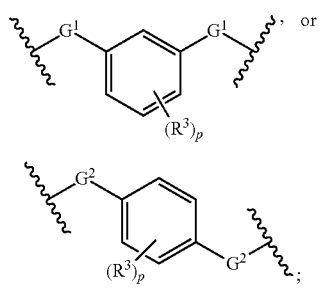

$L^3$ is

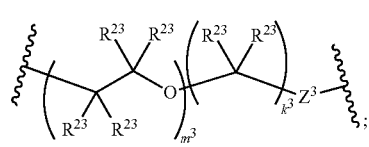

$X^2$ is

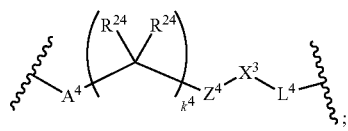

$A^4$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

each R$^1$ is independently selected from H, alkyl, and haloalkyl;

each R$^2$, R$^{21}$, R$^{22}$, R$^{23}$, and R$^{24}$ is independently selected from H, halo, —OR$^1$, —CN, —SR$^1$, alkyl, cycloalkyl, haloalkyl, arylalkyl, and heteroarylalkyl;

each R$^3$ is independently selected from halo, —OR$^1$, —CN, —SR$^1$, alkyl, cycloalkyl, haloalkyl, arylalkyl, heteroarylalkyl, —NO$_2$, and NR$^1$R$^1$;

each G$^1$ and G$^2$ is independently selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

each Z, Z$^1$, Z$^2$, and Z$^3$ is independently selected from the group consisting of a bond, —O—, and —N(R$^1$)—;

Z$^4$ is selected from a bond, aryl, and a 5- to 6-membered heteroaryl;

k, k$^1$, k$^2$, k$^3$, and k$^4$ are each independently selected from 0, 1, 2, 3, 4, 5, 6, 7, 8, 9, and 10;

m$^1$, m$^2$, and m$^3$ are each independently selected from 0, 1, 2, 3, 4, 5, 6, 7, 8, 9, and 10;

p is 0, 1, 2, 3, or 4;

$X^3$ is

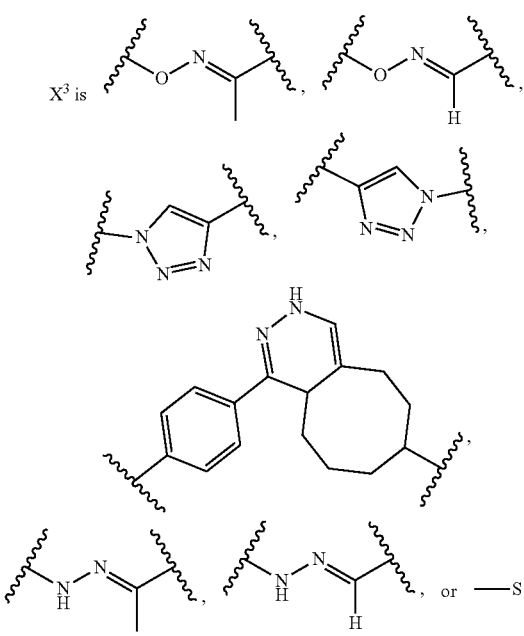

$L^4$ is a bond directly attached to a modified amino acid, or a linker bound to a modified amino acid, wherein the modified amino acid is part of the antibody;

Q is selected from the group consisting of:

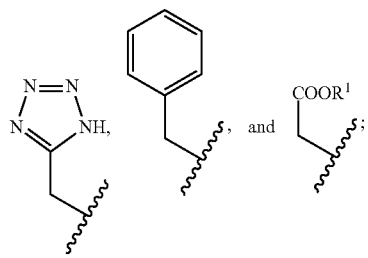

and

E is selected from the group consisting of:

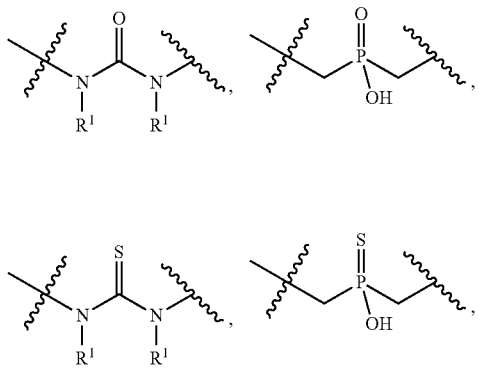

and a stereoisomer thereof.

In another aspect, provided herein is an antibody comprising: (a) a first amino acid sequence comprising one or more of SEQ ID NOS: 54-56; and (b) an unnatural amino acid. In some embodiments, the first amino acid sequence comprises one or more of SEQ ID NOS: 87, 92, 96, or 124. In some embodiments, the first amino acid sequence comprises one or more of SEQ ID NOS: 99-108. In some embodiments, the first amino acid sequence comprises SEQ ID 98. In some embodiments, the first amino acid sequence comprises the unnatural amino acid. In some embodiments, the antibody further comprises a second amino acid sequence comprising: (a) one or more of SEQ ID NOS: 51-53, (b) one or more of SEQ ID NOS: 97, 59, 74, or 110, or (c) a combination of (a) and (b). In some embodiments, provided is a composition comprising the antibody and a cell-targeting molecule. In some embodiments, the cell-targeting molecule interacts with prostate-specific membrane antigen (PSMA) or a folate receptor. In some embodiments, a composition is provided comprising the antibody, comprising a compound of Formula (III):

Formula (III)

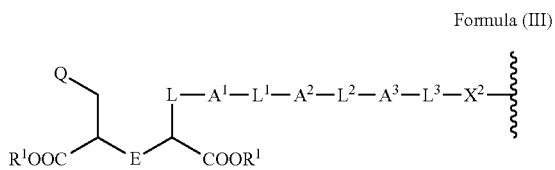

wherein:

L is

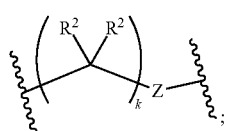

A¹ is selected from the group consisting of an aryl, a 5- to 6-membered heteroaryl, —C(O)—, —N(R¹)—, —O—, —C(O)N(R¹)—, —N(R¹)C(O)—, —S(O)$_{1,2}$N(R¹)—, and —N(R¹)S(O)$_{1,2}$—;

L¹ is

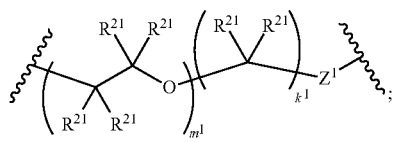

A² is selected from the group consisting of a bond, —C(O)—, —N(R¹)—, —O—, —C(O)N(R¹)—, —N(R¹)C(O)—, —S(O)$_{1,2}$N(R¹)—, and —N(R¹)S(O)$_{1,2}$—;

L² is

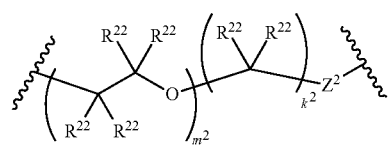

A³ is a bond,

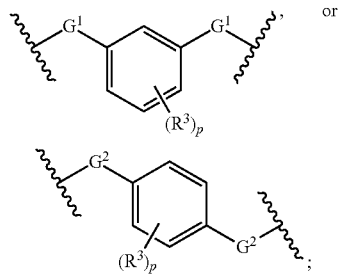 or

L³ is

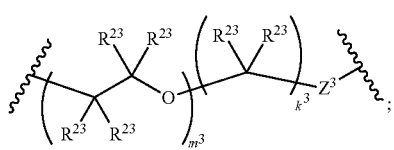

X² is

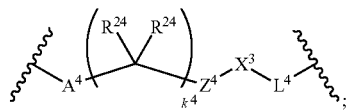

A⁴ is selected from the group consisting of a bond, —C(O)—, —N(R¹)—, —O—, —C(O)N(R¹)—, —N(R¹)C(O)—, —S(O)$_{1,2}$N(R¹)—, and —N(R¹)S(O)$_{1,2}$—;

each R¹ is independently selected from H, alkyl, and haloalkyl;

each R², R²¹, R²², R²³ and R²⁴ is independently selected from H, halo, —OR¹, —CN, —SR¹, alkyl, cycloalkyl, haloalkyl, arylalkyl, and heteroarylalkyl;

each R³ is independently selected from halo, —OR¹, —CN, —SR¹, alkyl, cycloalkyl, haloalkyl, arylalkyl, or heteroarylalkyl, —NO₂, and NR¹R¹;

each G¹ and G² is independently selected from the group consisting of a bond, —C(O)—, —N(R¹)—, —O—, —C(O)N(R¹)—, —N(R¹)C(O)—, —S(O)$_{1,2}$N(R¹)—, and —N(R¹)S(O)$_{1,2}$—;

each Z, Z¹, Z², and Z³ is independently selected from the group consisting of a bond, —O—, and —N(R¹)—;

Z⁴ is selected from a bond, aryl, and a 5- to 6-membered heteroaryl;

k, k¹, k², k³, and k⁴ are each independently selected from 0, 1, 2, 3, 4, 5, 6, 7, 8, 9, and 10;

m¹, m² and m³ are each independently selected from 0, 1, 2, 3, 4, 5, 6, 7, 8, 9, and 10;

p is 0, 1, 2, 3 or 4;

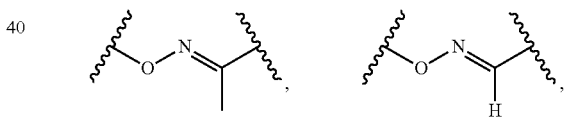

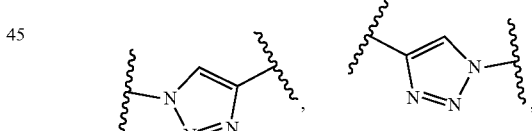

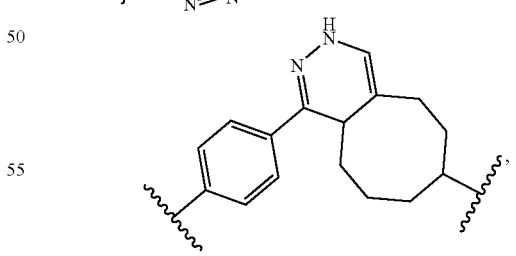

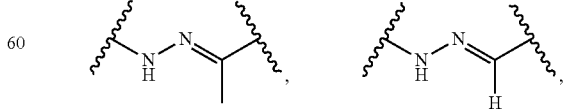

L⁴ is a bond directly attached to a modified amino acid, or a linker bound to a modified amino acid, wherein the modified amino acid is part of the antibody;

Q is selected from the group consisting of:

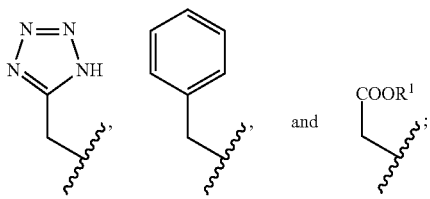

and

E is selected from the group consisting of:

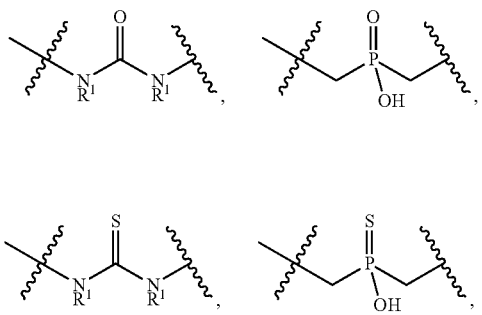

and a stereoisomer thereof.

In another aspect, provided is a composition comprising: (a) an amino acid sequence comprising one or more of SEQ ID NOS: 51-56 and an unnatural amino acid; and (b) a cell-targeting molecule linked to the amino acid sequence via the unnatural amino acid. In some embodiments, the unnatural amino acid is located within a heavy chain constant domain sequence of the amino acid sequence. In some embodiments, the amino acid sequence comprises one or more of SEQ ID NOS: 87, 92, 96, or 124. In some embodiments, the amino acid sequence comprises: one or more of SEQ ID NOS: 99-108. In some embodiments, the amino acid sequence comprises: SEQ ID NO: 86, SEQ ID NO: 98, or an amino acid sequence having the unnatural amino acid replace one or more amino acid residues of SEQ ID NO: 86. In some embodiments, the antibody comprises a second amino acid sequence comprising: (a) one or more of SEQ ID NOS: 51-53; (b) one or more of SEQ ID NOS: 97, 59, 74, 110; or (c) a combination of (a) and (b). In some embodiments, the unnatural amino acid is para-acetylphenylalanine. In some embodiments, the cell-targeting molecule interacts with prostate-specific membrane antigen (PSMA) or folate receptor.

BRIEF DESCRIPTION OF THE DRAWINGS

FIG. 2 shows alignments of anti-CD3 variable heavy chain and light chain amino acid sequences, where the hypervariable regions are denoted by LCDR1, LCDR2, LCDR3, HCDR1, HCDR2, and HCDR3, corresponding to SEQ ID NOS: 51-56, respectively. VH hu1 and VH hu2 correspond to SEQ ID NOS: 25 and 26, respectively. VL hu1 through VL hu 10 correspond to SEQ ID NOS: 28-37, respectively. Nucleic acid sequences encoding these sequences were individually cloned into the pFUSE vector under the IL2 signal peptide sequence. FIG. 2 discloses murine anti-CD3 VH and VL as SEQ ID NOS: 24 and 23, respectively, in order of appearance, IGHV3-73 as SEQ ID NO: 125, and IGLV7-46 as SEQ ID NO: 126.

FIG. 20C shows chemical structure of N-(4-{[(2-amino-4-oxo-1,4-dihydropteridin-6-yl)methyl]amino}benzoyl)-L-glutamic acid (folic acid/folate).

FIG. 20D shows exemplary analogs of chemical structure of N-(4-{[(2-amino-4-oxo-1,4-dihydropteridin-6-yl)methyl] amino}benzoyl)-L-glutamic acid (folic acid/folate), such as (4-((1-(2,4-diaminopteridin-6-yl)ethyl)(methyl)amino)benzoyl)glutamic acid (denopterin), and (4-(((2,4-diaminopteridin-6-yl)methyl)(methyl)amino)benzoyl)glutamic acid (methotrexate).

FIG. 26 shows huL5H2_DI-1×DUPA and huL5H2_DI-2×DUPA demonstrated dose-dependent cytotoxicity across VCaP, C4-2, and LNCaP cells lines.

FIG. 42 shows huL5H2_DI-1×DUPA demonstrated dose-dependent in vivo anti-tumor activity in the NSG mouse model reconstituted with human PBLs, with a slight delay in anti-tumor activity relative to experiments using PBMCs in the C4-2 xenograft mouse model.

FIG. 43 shows weight loss was caused by tumor burden. PBL and huL5H2_DI-1×DUPA did not demonstrate significant weight loss in the absence of tumor.

DETAILED DESCRIPTION OF THE INVENTION

Figure 1A:
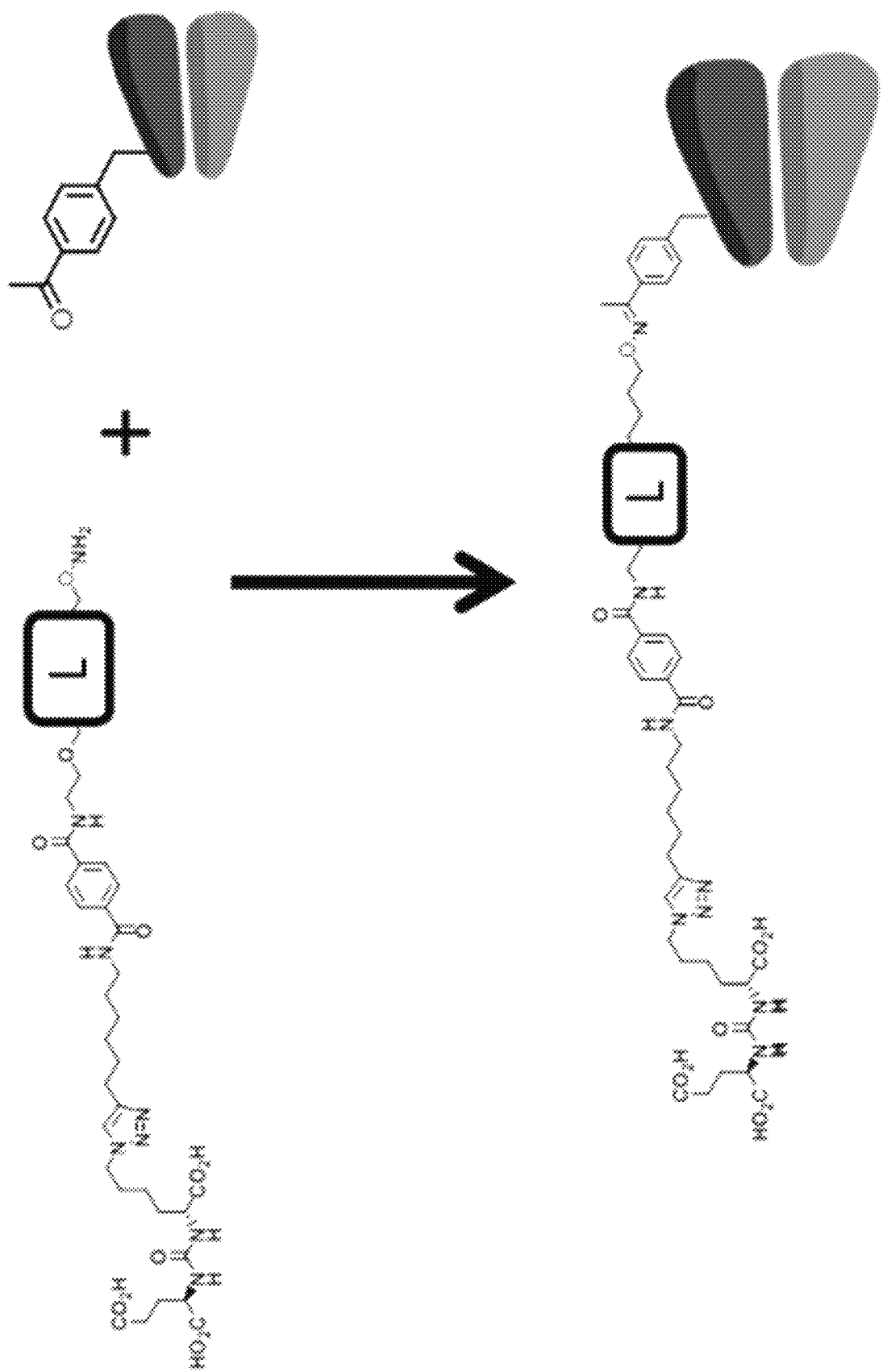
FIG. 1A shows a schematic synthesis of an anti-CD3 antibody (e.g., huL5H2) single mutant DUPA conjugate attached via a linker (L) to the heavy chain.
Figure 1B:
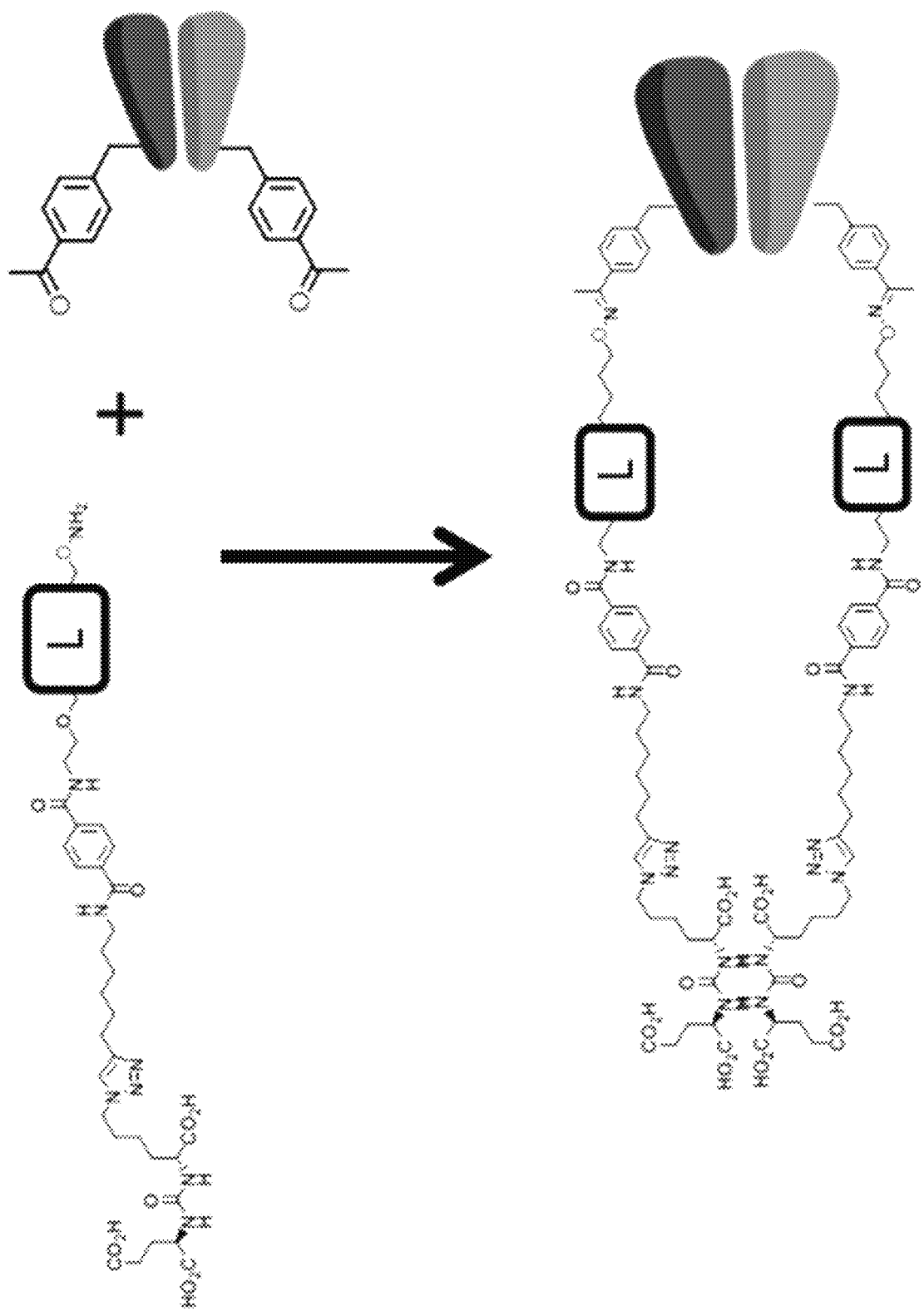
FIG. 1B shows a schematic synthesis of an anti-CD3 antibody (e.g., huL5H2) double mutant DUPA conjugate attached via two linkers (L) to both the heavy and light chains.

Disclosed herein are humanized anti-CD3 antibodies and their respective targeting agent antibody conjugates. These antibodies are humanized with additional mutations introduced to reduce potential immunogenicity in humans and optimize binding to T cells. Examples provided herein demonstrate humanization, optimization of binding, and reduction of immunogenicity of a murine cross-species reactive anti-CD3 antibody. Examples provided herein also demonstrate conjugation of the resulting humanized antibody to 2-[3-(1,3-dicarboxypropyl)ureido]pentanedioic acid (DUPA), which binds prostate-specific membrane antigen (PSMA). Exemplary schematics of DUPA conjugations are shown in FIG. 1A and FIG. 1B. The humanized anti-CD3 antibody DUPA conjugate can bind both T cells and PSMA-positive cells, directing T cells and their cytotoxic activity to PSMA positive cells, as demonstrated in xenograft models herein. This indicates these conjugates may be useful in the treatment of prostate cancer in humans. In addition, these humanized anti-CD3 antibodies may be conjugated to other targeting agents (e.g., folic acid) to be used for the treatment of other cancers or conditions.

In one aspect, humanized anti-CD3 antibody sequences are provided having CDRs from a murine anti-CD3 antibody (e.g., SEQ ID NOS: 51-56). For example, the humanized antibody clone with light chain variant 5 and heavy chain variant 2, referred to herein as "huL5H2" (SEQ ID NOS: 39, 41) demonstrated binding activity to both human and cynomolgus monkey T cells that was comparable with that of the murine antibody. In addition, introducing four point mutations within the framework region of the heavy chain of HuL5H2, referred to herein as "huL5H2_DI" or "DI-huL5H2" (SEQ ID NOS: 39, 43) significantly reduced its in-silico immunogenicity score (K19R, S41P K89R, T90A). These mutations did not affect the antibody's expression levels, binding affinity to human and cynomolgus monkey T cells, or in vitro activity. huL5H2_DI conjugated with a single DUPA molecule ("huL5H2_DI-1×DUPA", SEQ ID NOS: 39, 44) demonstrated similar biophysical and pharmacological properties when compared with the double conjugate (huL5H2_DI-2×DUPA, SEQ ID NOS: 40, 44).

I. Antibodies

In one aspect, provided herein are antibodies and conjugates and/or fusions thereof. In a non-limiting example, an antibody is an anti-CD3 antibody, and further provided are conjugates and fusions of the anti-CD3 antibody. Exemplary antibody conjugates comprise an anti-CD3 antibody and a cell targeting molecule. Exemplary antibody fusions comprise an anti-CD3 antibody and a second amino acid molecule, such as another antibody or portion thereof. In some embodiments, an antibody fusion comprises at least one chain of the anti-CD3 antibody linked to the second amino acid molecule via a peptide linker.

Antibodies include functional domains or other fragments of an antibody, including: antigen binding (Fab) region, Fab', F(ab')2, F(ab')3, Fab', fragment crystallizable (Fc) region, single chain variable fragment (scFv), di-scFv, single domain immunoglobulin, trifunctional immunoglobulin, chemically linked F(ab')2, and combinations thereof. In some cases, reference to an antibody includes an antibody fragment thereof. In some cases, an antibody fragment is referred to as an antibody, for example, a Fab or scFv may be referred to as an antibody or antibody fragment. An antibody fragment further includes a complementarity determining regions (CDR), framework regions, heavy chain constant domain (e.g., CH1, CH2, CH3), light chain constant domain (CL), or any combination thereof. Non-limiting examples of heavy chain constant domain sequences of antibodies provided herein include SEQ ID NOS: 86 and 98-109. Non-limiting examples of light chain constant domain sequences of antibodies provided herein include SEQ ID NOS: 111-123. An antibody fragment includes an antigen binding fragment of an antibody.

In some instances, the antibody is a mammalian antibody or derived or modified from a mammalian antibody. The antibody may be a chimeric antibody. The antibody may be an engineered antibody. The antibody may be a recombinant antibody. The antibody may be selected from a humanized, human engineered, or fully human antibody.

As used herein, antibody and immunoglobulin may be interchangeable. The immunoglobulin may be selected from an IgA, IgD, IgE, IgG, IgM, IgY, and IgW.

Provided herein are humanized antibodies. The humanized antibody may comprise a human antibody, wherein at least one CDR of the human antibody is replaced or modified with a CDR from an antibody produced in a non-human species. The humanized antibody may comprise a human antibody, wherein at least one CDR of the human antibody is at least partially replaced or modified with a CDR from an antibody produced in a non-human species. The humanized antibody may comprise a human antibody, wherein between 1 CDR and 6 CDRs of the human antibody are at least partially replaced or modified with between 1 CDR and 6 CDRs from an antibody produced in a non-human species. The humanized antibody may comprise a human antibody, wherein at least one CDR of the human antibody is at least partially replaced or modified with a CDR from an antibody that binds an antigen in a non-human species. The antibody that binds an antigen in a non-human species or the antibody produced in a non-human species may be referred to herein as a "donor antibody." The CDR of the human antibody and/or the donor antibody may be a light chain CDR (CDRL). The CDR of the human antibody and/or the donor antibody may be a heavy chain CDR (CDRH). The CDR of the human antibody and/or the donor antibody may be selected from CDRL1 (e.g., SEQ ID NO: 51), CDRL2 (e.g., SEQ ID NO: 52), CDRL3 (e.g., SEQ ID NO: 53), CDRH1 (e.g., SEQ ID NO: 54), CDRH2 (e.g., SEQ ID NO: 55), and CDRH3 (e.g., SEQ ID NO: 56). The CDR of the human antibody may be a CDR of a human lambda light chain variable domain. The donor antibody may be cross-species reactive. The donor antibody may be cross-species reactive with two or more species selected from, by way of non-limiting example, human, mouse, monkey (e.g., cynomolgus monkey), rabbit, sheep, rat, guinea pig, goat, donkey, chicken, and hamster. The non-human species may be cross-species reactive with mouse, human, and cynomolgus monkey.

The antibodies and fragments thereof disclosed herein may comprise a lambda light chain or portion thereof. The antibodies and antibody fragments disclosed herein may comprise a kappa light chain or portion thereof. In some cases, a portion thereof includes between about 5 amino acids and about 10 amino acids, between about 5 amino acids and about 10 amino acids, or between 5 amino acids and about 15 amino acids. In some cases, a portion thereof includes at least 5 amino acids, at least about 10 amino acids, at least about 15 amino acids, at least about 20 amino acids, at least about 25 amino acids, at least about 30 amino acids, at least about 35 amino acids, at least about 40 amino acids, and at least about 50 amino acids. The antibodies and antibody fragments disclosed herein may comprise a heavy chain selected from a gamma heavy chain, a delta heavy chain, an alpha heavy chain, a mu heavy chain, an epsilon heavy chain, and portions thereof. The antibodies and antibody fragments disclosed herein may comprise a combination of a portion of the lambda light chain and a portion of the kappa light chain. The antibodies and antibody fragments disclosed herein may comprise a human kappa light chain variable domain and a human lambda light chain constant domain. The antibodies and antibody fragments disclosed herein may comprise a human lambda light chain variable domain and a human kappa light chain constant domain. The antibodies and antibody fragments disclosed herein may comprise at least a portion of a light chain lambda variable domain and/or at least a portion of a light chain kappa constant domain. In some cases, at least a portion of the antibody fragment includes at least 5 amino acids, at least about 10 amino acids, at least about 15 amino acids, at least about 20 amino acids, at least about 25 amino acids, at least about 30 amino acids, at least about 35 amino acids, at least about 40 amino acids, and at least about 50 amino acids.

An antibody or antibody fragment provided herein may comprise two or more amino acid sequences. A first amino acid sequence may make up a first antibody chain and a second amino acid sequence may make up a second antibody chain. A first antibody chain may comprise a first amino acid sequence, and a second antibody chain may comprise a second amino acid sequence. A chain of an antibody may refer to an antibody heavy chain, an antibody light chain, or a combination of a region or all of an antibody heavy chain and a region or all of an antibody light chain. As a non-limiting example, an antibody provided herein comprises a heavy chain or fragment thereof, and a light chain or fragment thereof. Two amino acid sequences of an antibody, including two antibody chains, may be connected by one or more disulfide bonds, a chemical linker, a peptide linker, or a combination thereof. A chemical linker includes a linker via an unnatural amino acid. A chemical linker includes a chemical conjugate. A peptide linker includes any amino acid sequence joining the two amino acid sequences. In some cases, a peptide linker comprises at least about 1, 3, 5, 10, 15, 20, 25, 30, 35, 40, 45, 50, 60, 70, 80, 90, 100 or more amino acids. In some cases, a peptide linker may be a portion of any antibody, including a domain of an antibody, such as a variable domain, CH1, CH2, CH3, and/or CL domain. In some cases, a heavy and a light chain are connected, for example, via a peptide linker to make a single chain variable fragment (scFv). In some cases, a heavy chain and a light chain are connected, for example, by one or more disulfide bonds.

The antibodies and antibody fragments may be reactive with an antigen on an effector cell. For example, the effector cell is an immune cell. However, cells not traditionally categorized as immune cells (e.g. fibroblasts, pluripotent stem cells, adipocytes) are optionally (genetically) modified to have immune cell activity (e.g. cytotoxic activity). The immune cell may be capable of exerting a cytotoxic activity on another cell. The immune cell may be a leukocyte. The immune cell may be a lymphocyte. The immune cell may be selected from a macrophage, an erythrocyte, a thrombocyte, a neutrophil, a monocyte, a macrophage, an eosinophil, a basophil, a mast cell, a NK cell, a B-cell, or a T-cell. The immune cell may be a T cell. The T cell may be a cytotoxic T cell. The T cell may be a natural killer T cell. The effector cell may be a genetically modified cell. The effector cell may be genetically modified to have cytotoxic activity. The effector cell may be genetically modified to have enhanced cytotoxic activity. The effector cell may be modified to have decreased cytotoxic activity.

The antibody or antibody fragment may interact with a receptor on a T-cell. The receptor may be a T-cell receptor (TCR). The TCR may comprise TCR alpha, TCR beta, TCR gamma, and/or TCR delta. The receptor may be a T-cell receptor zeta.

The antibody or antibody fragment may bind to a receptor on a lymphocyte, dendritic cell, B-cell, macrophage, monocytes, neutrophils and/or NK cells. The receptor may be an Fc receptor. The Fc receptor may be an Fc-gamma receptor, Fc-alpha receptor, and/or Fc-epsilon receptor. Fc-gamma receptors include, but are not limited to, FcγRI (CD64), FcγRIIA (CD32), FcγRIIB (CD32), FcγRIIIA (CD16a), and FcγRIIIB (CD16b). Fc-alpha receptors include, but are not limited to, FcαRI. Fc-epsilon receptors include, but are not limited to, FcεRI and FcεRII. The receptor may be CD89 (Fc fragment of IgA receptor or FCAR). The targeting agent may be selected from an anti-viral drug, an antibiotic, and an anti-parasitic drug. For example, the targeting agent antibody conjugate may bind specifically to pathogenic bacteria or fungi when the targeting agent antibody conjugate comprises a Fc receptor-binding antibody.

The antibody or antibody fragment may interact with a cluster of differentiation protein (CD) on a T cell. The CD may be selected from, by way of non-limiting example, CD3, CD8, CD25, CD45, and CD154.

The antibody or antibody fragment may interact with a co-receptor on a T-cell. The co-receptor may be selected from CD3, CD4, and CD8. CD8 may comprise CD8-alpha and/or CD8-beta chains. The antibody or antibody fragment may interact with a CD3 co-receptor. The CD3 co-receptor may be selected from CD3-gamma, CD3-delta and CD3-epsilon.

The antibody or antibody fragment may bind a cluster of differentiation 3 protein (CD3). Thus, the antibody or antibody fragment may be an anti-CD3 antibody or anti-CD3 antibody fragment. The anti-CD3 antibody or anti-CD3 antibody fragment may be a humanized anti-CD3 antibody or a humanized anti-CD3 antibody fragment. The humanized anti-CD3 antibody fragment may be a humanized anti-CD3 Fab. In mammals, CD3 is a protein complex of four distinct chains, one CD3 gamma chain, one CD3 delta chain, and two CD3 epsilon chains. Unless otherwise noted, CD3 includes any one or combination of these distinct chains. Thus, the anti-CD3 antibody or anti-CD3 antibody fragment may bind a CD3 selected from a CD3 gamma, a CD3 delta, and a CD3 epsilon. The CD3 may be a non-human CD3. The CD3 may be selected from a murine CD3, a simian CD3, and a human CD3. The anti-CD3 antibody or anti-CD3 antibody fragment may be cross-species reactive. For example, the anti-CD3 antibody or anti-CD3 antibody fragment may bind a human CD3, as well as a CD3 expressed in another species.

The antibody or antibody fragment may comprise a light chain, wherein the light chain is encoded by a nucleotide sequence selected from SEQ ID NOS: 16-18. The antibody or antibody fragment may comprise a light chain, wherein the light chain is encoded by a nucleotide sequence having at least 20 consecutive nucleotides, at least 50 consecutive nucleotides, at least 100 consecutive nucleotides, at least 200 consecutive nucleotides, at least 300 consecutive nucleotides, at least 400 consecutive nucleotides, at least 500 consecutive nucleotides, or at least 600 consecutive nucleotides, wherein the consecutive nucleotides have a sequence found in a sequence selected from SEQ ID NOS: 16-18.

The antibody or antibody fragment may comprise a light chain, wherein the light chain has an amino acid sequence selected from SEQ ID NOS: 38-40. The antibody or antibody fragment may comprise a light chain, wherein the light chain is encoded by an amino acid sequence selected from SEQ ID NOS: 38-40, wherein about 1 to about 5, about 1 to about 10, or about 1 to about 20 amino acids of SEQ ID NOS: 38-40 have been substituted with an alternate amino acid.

The antibody or antibody fragment may comprise a light chain variable domain, wherein the light chain variable domain is represented by an amino acid sequence selected from SEQ ID NOS: 28-37. The antibody or antibody fragment may comprise a light chain variable domain, wherein the light chain variable domain is represented by an amino acid of SEQ ID NO: 32. The antibody or antibody fragment may comprise a light chain variable domain, wherein the light chain variable domain is represented by an amino acid sequence selected from SEQ ID NOS: 28-37, and wherein about 1 to about 5, about 1 to about 10, or about 1 to about 20 amino acids of SEQ ID NOS: 28-37 have been substituted with an alternate amino acid. The antibody or antibody fragment may comprise a light chain variable domain, wherein the light chain variable domain is represented by an amino acid of SEQ ID NO: 32, and wherein about 1 to about 5, about 1 to about 10, or about 1 to about 20 amino acids of SEQ ID NO: 32 have been substituted with an alternate amino acid.

The antibody or antibody fragment may comprise a heavy chain, wherein the heavy chain is encoded by a nucleotide sequence selected from SEQ ID NOS: 19-22. The antibody or antibody fragment may comprise a heavy chain, wherein the heavy chain is encoded by a nucleotide sequence having at least 20 consecutive nucleotides, at least 50 consecutive nucleotides, at least 100 consecutive nucleotides, at least 200 consecutive nucleotides, at least 300 consecutive nucleotides, at least 400 consecutive nucleotides, at least 500 consecutive nucleotides, or at least 600 consecutive nucleotides, wherein the consecutive nucleotides have a sequence found in a sequence selected from SEQ ID NOS: 19-22.

The antibody or antibody fragment may comprise a heavy chain, wherein the heavy chain has an amino acid sequence selected from SEQ ID NOS: 41-44. The antibody or antibody fragment may comprise a heavy chain, wherein the heavy chain is encoded by an amino acid sequence selected from SEQ ID NOS: 41-44, wherein about 1 to about 5, about 1 to about 10, or about 1 to about 20 amino acids of SEQ ID NOS: 41-44 have been substituted with an alternate amino acid. The antibody or antibody fragment may comprise a heavy chain, wherein the heavy chain is represented by an amino acid sequence of SEQ ID NO: 41. The heavy chain may be represented by SEQ ID NO:41, wherein at least one amino acid is replaced with an alternate amino acid. The at least one amino acid may be selected from lysine at position 19 (K19), serine at position 41 (S41), lysine at position 89 (K89), and threonine at position 90 (T90). K19 may be replaced with an arginine (K19R). S41 may be replaced with a proline (S41P). K89 may be replaced with an arginine (K89R). T90 may be replaced with an alanine (T90A). The heavy chain may be represented by SEQ ID NO: 41, wherein any combination of these replacements may be made. The heavy chain may be represented by an amino acid sequence selected from SEQ ID NOS: 45-48. The heavy chain may comprise an amino acid sequence selected from SEQ ID NOS: 49-50.

The antibody or antibody fragment may comprise a heavy chain variable domain, wherein the heavy chain variable domain is represented by an amino acid sequence selected from SEQ ID NOS: 25-27. The antibody or antibody fragment may comprise a heavy chain variable domain, wherein the heavy chain variable domain is represented by an amino acid of SEQ ID NO: 27. The antibody or antibody fragment may comprise a heavy chain variable domain, wherein the heavy chain variable domain is represented by an amino acid sequence selected from SEQ ID NOS: 25-27, and wherein about 1 to about 5, about 1 to about 10, or about 1 to about 20 amino acids of SEQ ID NOS: 25-27 have been substituted with an alternate amino acid. The antibody or antibody fragment may comprise a heavy chain variable domain, wherein the heavy chain variable domain is represented by an amino acid of SEQ ID NO: 27, and wherein about 1 to about 5, about 1 to about 10, or about 1 to about 20 amino acids of SEQ ID NO: 27 have been substituted with an alternate amino acid.

The antibody or antibody fragment may comprise a light chain, wherein the light chain comprises a variable domain. The variable domain may comprise a CDR1, a CDR2, and a CDR3, and any combination thereof. The variable domain may comprise a region between two CDRs. The region between two CDRs may be a region between the CDR1 and the CDR2, referred to herein as "LC Inter-CDR1/2 Region." The LC Inter-CDR1/2 Region may be represented by a sequence selected from SEQ ID NOS: 57-61. The LC Inter-CDR1/2 Region may be represented by a sequence of SEQ ID NO. 59. The LC Inter-CDR1/2 Region may comprise a peptide represented by SEQ ID NO. 64. The LC Inter-CDR1/2 Region may comprise a peptide represented by a sequence selected from SEQ ID NOS: 62-68. The region between two CDRs may be a region between the CDR2 and the CDR3, referred to herein as "LC Inter-CDR2/3 Region." The LC Inter-CDR2/3 Region may be represented by a sequence selected from SEQ ID NOS: 72-77.

The LC Inter-CDR1/2 Region may comprise a peptide represented by the amino acid sequence QKPDHLFR (SEQ ID NO. 64). The LC Inter-CDR1/2 Region may comprise a peptide represented by the amino acid sequence $QX_1X_2DHLFR$ (SEQ ID NO. 65), wherein $X_1$ is lysine. The LC Inter-CDR1/2 Region may comprise a peptide represented by the amino acid sequence $QX_1X_2DHLFR$ (SEQ ID NO. 65), wherein $X_1$ is selected from a polar amino acid and a basic amino acid. The LC Inter-CDR1/2 Region may comprise a peptide represented by the amino acid sequence $QX_1X_2DHLFR$ (SEQ ID NO. 65), wherein $X_1$ is selected from a histidine and an arginine. The LC Inter-CDR1/2 Region may comprise a peptide represented by the amino acid sequence $QX_1X_2DHLFR$ (SEQ ID NO. 65), wherein $X_2$ is proline. The LC Inter-CDR1/2 Region may comprise a peptide represented by the amino acid sequence $QX_1X_2DHLFR$ (SEQ ID NO. 65), wherein $X_2$ is a polar amino acid. The LC Inter-CDR1/2 Region may comprise a peptide represented by the amino acid sequence $QX_1X_2DHLFR$ (SEQ ID NO. 65), wherein $X_2$ is selected from a serine, a threonine, a cysteine, an asparagine and a glutamine.

The LC Inter-CDR1/2 Region may be represented by SEQ ID NO. 66 ($X_1VX_2X_3X_4X_5DHLFRGX_6X_7G$). $X_1$ may be tryptophan. $X_2$ may be glutamine. $X_3$ may be selected from glutamine and glutamic acid. $X_4$ may be lysine. $X_5$ may be proline. $X_6$ may be leucine. $X_7$ may be isoleucine. The LC Inter-CDR1/2 Region may be represented by SEQ ID NO. 67 ($X_1VX_2Q\ X_3X_4DHLFX_5GX_6X_7G$). $X_1$ may be tryptophan. $X_2$ may be glutamine. $X_3$ may be lysine. $X_4$ may be proline. $X_5$ may be selected from arginine and threonine. $X_6$ may be leucine. $X_7$ may be isoleucine. The LC Inter-CDR1/2 Region may be represented by SEQ ID NO. 68 ($X_1VX_2X_3X_4X_5DHLFX_6GX_7X_8G$). $X_1$ may be tryptophan. $X_2$ may be glutamine. $X_3$ may be selected from glutamine and glutamic acid. $X_4$ may be lysine. $X_5$ may be proline. $X_5$ may be selected from arginine and threonine. $X_7$ may be leucine. $X_8$ may be isoleucine. In some cases, the valine in position 2 of a sequence selected from SEQ ID NO. 66-68 is substituted with a phenylalanine.

The antibody or antibody fragment may comprise a combination of two or more peptides or polypeptides represented by the sequences disclosed herein. One of skill in the art would readily understand that a few amino acids may be substituted with alternate amino acids while maintaining the properties of the antibody or antibody fragment. A few amino acids may be about 1 to about 5 amino acids, about 1 to about 10 amino acids, or about 1 to about 20 amino acids. The next several paragraphs describe, by way of non-limiting example, the antibodies or antibody fragments disclosed herein that may comprise the combination of two or more peptides or polypeptides represented by the sequences disclosed herein.

The antibody or antibody fragment may comprise a LC Inter-CDR1/2 Region represented by a sequence selected from SEQ ID NOS: 57-61, and a heavy chain represented by an amino acid sequence selected from SEQ ID NOS: 41-44. The antibody or antibody fragment may comprise a LC Inter-CDR1/2 Region, wherein the LC Inter-CDR1/2 Region comprises a peptide represented by a sequence selected from SEQ ID NOS: 62-68, and a heavy chain represented by an amino acid sequence selected from SEQ ID NOS: 41-44. The antibody or antibody fragment may comprise a LC Inter-CDR1/2 Region represented by SEQ ID NO: 59, and a heavy chain represented by an amino acid sequence selected from SEQ ID NOS: 41-44. The antibody or antibody fragment may comprise a LC Inter-CDR1/2 Region comprising a peptide represented by SEQ ID NO: 64, and a heavy chain represented by an amino acid sequence selected from SEQ ID NOS: 41-44.

The antibody or antibody fragment may comprise a LC Inter-CDR1/2 Region represented by a sequence selected from SEQ ID NOS: 57-61; and a heavy chain variable domain represented by an amino acid sequence selected from SEQ ID NOS: 25-27. The antibody or antibody fragment may comprise a LC Inter-CDR1/2 Region, wherein the LC Inter-CDR1/2 Region comprises a peptide represented by a sequence selected from SEQ ID NOS: 62-68, and a heavy chain variable domain represented by an amino acid sequence selected from SEQ ID NOS: 25-27. The antibody or antibody fragment may comprise a LC Inter-CDR1/2 Region represented by SEQ ID NO: 59, and a heavy chain variable domain represented by an amino acid sequence selected from SEQ ID NOS: 25-27. The antibody or antibody fragment may comprise a LC Inter-CDR1/2 Region comprising a peptide represented by SEQ ID NO: 64, and a heavy chain variable domain represented by an amino acid sequence selected from SEQ ID NOS: 25-27. The heavy chain variable domain may be represented by amino acid sequence of SEQ ID NO: 27.

The antibody or antibody fragment may comprise a LC Inter-CDR1/2 Region represented by a sequence selected from SEQ ID NOS: 57-61; and a CDR represented by an amino acid sequence selected from SEQ ID NOS: 51-56. The antibody or antibody fragment may comprise a LC Inter-CDR1/2 Region, wherein the LC Inter-CDR1/2 Region comprises a peptide represented by a sequence selected from SEQ ID NOS: 62-68; and a CDR represented by an amino acid sequence selected from SEQ ID NOS: 51-56. The antibody or antibody fragment may comprise a LC Inter-CDR1/2 Region represented by SEQ ID NO: 59; and a CDR represented by an amino acid sequence selected from SEQ ID NOS: 51-56. The antibody or antibody fragment may comprise a LC Inter-CDR1/2 Region comprising a peptide represented by SEQ ID NO: 64; and a CDR represented by an amino acid sequence selected from SEQ ID NOS: 51-56.

The antibody or antibody fragment may comprise a heavy chain, wherein the heavy chain comprises a variable domain. The variable domain may comprise a CDR1, a CDR2, a CDR3, and any combination thereof. The variable domain may comprise a region between two CDRs. The region between two CDRs may be a region between the CDR1 and the CDR2, referred to herein as "HC Inter-CDR1/2 Region." The HC Inter-CDR1/2 Region may be represented by a sequence selected from SEQ ID NOS: 70-71. The region between two CDRs may be a region between the CDR2 and the CDR3, referred to herein as "HC Inter-CDR2/3 Region." The HC Inter-CDR2/3 Region may be represented by a sequence selected from SEQ ID NOS: 78-79. The variable domain may comprise a region next to a CDR. The region next to the CDR may be a region N-terminal to CDR1, referred to herein as "HC Pre-CDR1." The HC Pre-CDR1 Region may be represented by SEQ ID NO. 69.

The antibody or antibody fragment may comprise a LC Inter-CDR1/2 Region represented by a sequence selected from SEQ ID NOS: 57-61, and a LC Inter-CDR2/3 Region represented by a sequence selected from SEQ ID NOS: 72-77. The antibody or antibody fragment may comprise a LC Inter-CDR1/2 Region, wherein the LC Inter-CDR1/2 Region comprises a peptide represented by a sequence selected from SEQ ID NOS: 62-68, and a LC Inter-CDR2/3 Region represented by a sequence selected from SEQ ID NOS: 72-77. The antibody or antibody fragment may comprise a LC Inter-CDR1/2 Region represented by SEQ ID NO: 59, and a LC Inter-CDR2/3 Region represented by a sequence selected from SEQ ID NOS: 72-77. The antibody or antibody fragment may comprise a LC Inter-CDR1/2 Region comprising a peptide represented by SEQ ID NO: 64, and a LC Inter-CDR2/3 Region represented by a sequence selected from SEQ ID NOS: 72-77.

The antibody or antibody fragment may comprise a LC Inter-CDR1/2 Region represented by a sequence selected from SEQ ID NOS: 57-61, and a HC Inter-CDR1/2 Region may be represented by a sequence selected from SEQ ID NOS: 70-71. The antibody or antibody fragment may comprise a LC Inter-CDR1/2 Region represented by a sequence selected from SEQ ID NOS: 57-61, and a HC Inter-CDR2/3 Region may be represented by a sequence selected from SEQ ID NOS: 78-79. The antibody or antibody fragment may comprise a LC Inter-CDR1/2 Region represented by a sequence selected from SEQ ID NOS: 57-61, and a HC Pre-CDR1 Region may be represented by SEQ ID NO. 69.

The antibody or antibody fragment may comprise a LC Inter-CDR1/2 Region, wherein the LC Inter-CDR1/2 Region comprises a peptide represented by a sequence selected from SEQ ID NOS: 62-68, and a HC Inter-CDR2/3 Region may be represented by a sequence selected from SEQ ID NOS: 78-79. The antibody or antibody fragment may comprise a LC Inter-CDR1/2 Region, wherein the LC Inter-CDR1/2 Region comprises a peptide represented by a sequence selected from SEQ ID NOS: 62-68, and a HC Inter-CDR1/2 Region may be represented by a sequence selected from SEQ ID NOS: 70-71. The antibody or antibody fragment may comprise a LC Inter-CDR1/2 Region, wherein the LC Inter-CDR1/2 Region comprises a peptide represented by a sequence selected from SEQ ID NOS: 62-68, and a HC Pre-CDR1 Region may be represented by SEQ ID NO. 69.

The antibody or antibody fragment may comprise a LC Inter-CDR1/2 Region represented by SEQ ID NO: 59, and a HC Inter-CDR1/2 Region may be represented by a sequence selected from SEQ ID NOS: 70-71. The antibody or antibody fragment may comprise a LC Inter-CDR1/2 Region represented by SEQ ID NO: 59, and a HC Inter-CDR2/3 Region may be represented by a sequence selected from SEQ ID NOS: 78-79. The antibody or antibody fragment may comprise a LC Inter-CDR1/2 Region represented by SEQ ID NO: 59 and a HC Pre-CDR1 Region may be represented by SEQ ID NO. 69.

The antibody or antibody fragment may comprise a LC Inter-CDR1/2 Region comprising a peptide represented by SEQ ID NO: 64, and a HC Inter-CDR1/2 Region may be represented by a sequence selected from SEQ ID NOS: 70-71. The antibody or antibody fragment may comprise a LC Inter-CDR1/2 Region comprising a peptide represented by SEQ ID NO: 64, and a HC Inter-CDR2/3 Region may be represented by a sequence selected from SEQ ID NOS: 78-79. The antibody or antibody fragment may comprise a LC Inter-CDR1/2 Region comprising a peptide represented by SEQ ID NO: 64 and a HC Pre-CDR1 Region may be represented by SEQ ID NO: 69.

Humanized Anti-CD3 Antibodies and Fragments Thereof

The antibody or antibody fragment may be a humanized anti-CD3 antibody or humanized anti-CD3 antibody fragment. The humanized anti-CD3 antibody or humanized anti-CD3 antibody fragment may comprise a lambda light chain or portion thereof. The humanized anti-CD3 antibody or humanized anti-CD3 antibody fragment may comprise a kappa light chain or portion thereof. The humanized anti-CD3 antibody or humanized anti-CD3 antibody fragment may comprise a heavy chain selected from a gamma heavy chain, a delta heavy chain, an alpha heavy chain, a mu heavy chain, and an epsilon heavy chain. The humanized anti-CD3 antibody or humanized anti-CD3 antibody fragment may comprise a combination of a portion of the lambda light chain and a portion of the kappa light chain. The humanized anti-CD3 antibody or humanized anti-CD3 antibody fragment may comprise a human kappa light chain variable domain and a human lambda light chain constant domain. The humanized anti-CD3 antibody or humanized anti-CD3 antibody fragment may comprise a human lambda light chain variable domain and a human kappa light chain constant domain.

The humanized anti-CD3 antibody or humanized anti-CD3 antibody fragment may have a heavy chain variable region (VH) encoded by a nucleotide sequence selected from SEQ ID NOS: 3-5. The VH may be encoded by at least about 50, about 100, about 150, about 200, about 250, or about 300 consecutive nucleotides of SEQ ID NOS: 3-5. The VH may be encoded by a nucleotide sequence similar to SEQ ID NOS: 3-5. The nucleotide sequence similar to SEQ ID NOS: 3-5 may be SEQ ID NOS: 3-5 with about 1 to about 5, about 1 to about 10, about 1 to about 20, or about 1 to about 30 nucleotide substitutions. The substitutions may be an alternative nucleotide for the nucleotide in SEQ ID NOS: 3-5.

The humanized anti-CD3 antibody or humanized anti-CD3 antibody fragment may have a heavy chain variable region (VH) encoded by an amino acid sequence selected from SEQ ID NOS: 25-27. The antibody or antibody fragment may comprise a VH, wherein the VH is encoded by an amino acid sequence selected from SEQ ID NOS: 25-27, wherein SEQ ID NOS: 25-27 have 1 to about 10 amino acids substituted with an alternate amino acid.

The humanized anti-CD3 antibody or humanized anti-CD3 antibody fragment may have a light chain variable region (VL) encoded by a nucleotide sequence selected from SEQ ID NOS: 6-15. The VL may be encoded by at least about 50, about 100, about 150, about 200, about 250, or about 300 consecutive nucleotides of SEQ ID NOS: 6-15. The VL may be encoded by a nucleotide sequence similar to SEQ ID NOS: 6-15. The nucleotide sequence similar to SEQ ID NOS: 6-15 may be SEQ ID NOS: 6-15 with about 1 to about 5, about 1 to about 10, about 1 to about 20, or about 1 to about 30 nucleotide substitutions. The substitutions may be an alternative nucleotide for the nucleotide in SEQ ID NOS: 6-15.

The humanized anti-CD3 antibody or humanized anti-CD3 antibody fragment may have a light chain variable region (VL) encoded by an amino acid sequence selected from SEQ ID NOS: 28-37. The antibody or antibody fragment may comprise a VL, wherein the VL is encoded by an amino acid sequence selected from SEQ ID NOS: 28-37, wherein SEQ ID NOS: 28-37 have about 1 to about 10 amino acids substituted with an alternate amino acid.

The humanized anti-CD3 antibody or humanized anti-CD3 antibody fragment may have a light chain (LC) encoded by a nucleotide sequence selected from SEQ ID NOS: 16-18. The LC may be encoded by at least about 20 consecutive nucleotides, at least 50 consecutive nucleotides, at least 100 consecutive nucleotides, at least 200 consecutive nucleotides, at least 300 consecutive nucleotides, at least 400 consecutive nucleotides, at least 500 consecutive nucleotides, or at least 600 consecutive nucleotides of SEQ ID NOS: 16-18. The LC may be encoded by a nucleotide sequence similar to SEQ ID NOS: 16-18. The nucleotide sequence similar to SEQ ID NOS: 16-18 may be SEQ ID NOS: 16-18 with about 1 to about 10, about 1 to about 20, about 1 to about 30, about 1 to about 40, about 1 to about 50, or about 1 to about 60 substitutions. The substitutions may be an alternative nucleotide for the nucleotide in SEQ ID NOS: 16-18.

The humanized anti-CD3 antibody or humanized anti-CD3 antibody fragment may have a light chain (LC) encoded by an amino acid sequence selected from SEQ ID NOS: 38-40. The antibody or antibody fragment may comprise a LC, wherein the LC is encoded by an amino acid sequence selected from SEQ ID NOS: 38-40, wherein SEQ ID NOS: 38-40 have about 1 to about 5, about 1 to about 10, or about 1 to about 20 amino acids substituted with an alternate amino acid.

The humanized anti-CD3 antibody or humanized anti-CD3 antibody fragment may have a heavy chain (HC) encoded by a nucleotide sequence selected from SEQ ID NOS: 19-22. The HC may be encoded by at least about 20 consecutive nucleotides, at least 50 consecutive nucleotides, at least 100 consecutive nucleotides, at least 200 consecutive nucleotides, at least 300 consecutive nucleotides, at least 400 consecutive nucleotides, at least 500 consecutive nucleotides, or at least 600 consecutive nucleotides of SEQ ID NOS: 19-22. The HC may be encoded by a nucleotide sequence similar to SEQ ID NOS: 19-22. The nucleotide sequence similar to SEQ ID NOS: 19-22 may be SEQ ID NOS: 19-22 with about 1 to about 10, about 1 to about 20, about 1 to about 30, about 1 to about 40, about 1 to about 50, or about 1 to about 60 substitutions. The substitutions may be an alternative nucleotide for the nucleotide in SEQ ID NOS: 19-22.

The humanized anti-CD3 antibody or humanized anti-CD3 antibody fragment may have a heavy chain (HC) encoded by an amino acid sequence selected from SEQ ID NOS: 41-44. The antibody or antibody fragment may comprise a HC, wherein the HC is encoded by an amino acid sequence selected from SEQ ID NOS: 41-44, wherein SEQ ID NOS: 41-44 have about 1 to about 5, about 1 to about 10, or about 1 to about 20 amino acids substituted with an alternate amino acid.

The humanized anti-CD3 antibody or humanized anti-CD3 antibody fragment may have a light chain encoded by a nucleotide sequence selected from SEQ ID NOS: 17 and 18 and a heavy chain encoded by a nucleotide sequence selected from SEQ ID NOS: 21 and 22. The humanized anti-CD3 antibody or humanized anti-CD3 antibody fragment has a light chain encoded by SEQ ID NO: 17 and a heavy chain encoded by SEQ ID NO: 21. The humanized anti-CD3 antibody or humanized anti-CD3 antibody fragment has a light chain encoded by SEQ ID NO: 17 and a heavy chain encoded by SEQ ID NO: 22. The humanized anti-CD3 antibody or humanized anti-CD3 antibody fragment has a light chain encoded by SEQ ID NO: 18 and a heavy chain encoded by SEQ ID NO: 21. The humanized anti-CD3 antibody or humanized anti-CD3 antibody fragment has a light chain encoded by SEQ ID NO: 18 and a heavy chain encoded by SEQ ID NO: 22.

The light chain may be encoded by a nucleotide sequence similar to SEQ ID NOS: 17 and 18. The nucleotide sequence similar to SEQ ID NOS: 17 and 18 may be SEQ ID NOS: 17 and 18 with about 1 to about 10, about 1 to about 20, about 1 to about 30, about 1 to about 40, about 1 to about 50, or about 1 to about 60 substitutions. The substitutions may be an alternative nucleotide for the nucleotide in SEQ ID NOS: 17 and 18. The heavy chain may be encoded by a nucleotide sequence similar to SEQ ID NOS: 21 and 22. The nucleotide sequence similar to SEQ ID NOS: 21 and 22 may be SEQ ID NOS: 21 and 22 with about 1 to about 10, about 1 to about 20, about 1 to about 30, about 1 to about 40, about 1 to about 50, or about 1 to about 60 substitutions. The substitutions may be an alternative nucleotide for the nucleotide in SEQ ID NOS: 21 and 22.

In one aspect, disclosed herein is an antibody comprising an amino acid sequence comprising SEQ ID NOS: 55 and 96. In some embodiments, the amino acid sequence is a first amino acid sequence, wherein the antibody further comprises a second amino acid sequence. In some embodiments, the first amino acid sequence comprises SEQ ID NO: 54. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising an amino acid sequence comprising SEQ ID NOS: 54 and 55, and one or more of SEQ ID NOS: 87 and 96. In some embodiments, the amino acid sequence is a first amino acid sequence, wherein the antibody further comprises a second amino acid sequence. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) a first amino acid sequence comprising SEQ ID NO: 96; and (b) a second amino acid sequence comprising SEQ ID NO: 51, and one or more of SEQ ID NOS: 97, 59, and 74. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) a first amino acid sequence comprising SEQ ID NO: 96; and (b) a second amino acid sequence comprising one or more of SEQ ID NOS: 59 and 74. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) a first amino acid sequence comprising SEQ ID NO: 54; and (b) a second amino acid sequence comprising SEQ ID NO: 51 and one or more of SEQ ID NOS: 97, 59, and 74. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) a first amino acid sequence comprising SEQ ID NO: 54; and (b) a second amino acid sequence comprising one or more of SEQ ID NOS: 59 and 74. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) a first amino acid sequence comprising SEQ ID NOS: 54 and 55; and (b) a second amino acid sequence comprising one or more of SEQ ID NOS: 97, 59, and 74. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) a first amino acid sequence comprising SEQ ID NOS: 54 and 92; and (b) a second amino acid sequence comprising one or more of SEQ ID NOS: 97, 59, and 74. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) a first amino acid sequence comprising SEQ ID NO: 55; and (b) a second amino acid sequence comprising one or more of SEQ ID NOS: 59 and 74. In some embodiments, the first amino acid sequence comprises SEQ ID NO: 54. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) a first amino acid sequence comprising SEQ ID NOS: 92 and 96; and (b) a second amino acid sequence comprising one or more of SEQ ID NOS: 97, 59, and 74. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) a first amino acid sequence comprising one or more of SEQ ID NOS: 54, 55, 56, and 96; and (b) a second amino acid sequence comprising one or more of SEQ ID NOS: 59 and 74. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: an amino acid sequence comprising one or more of SEQ ID NOS: 51, 52, and 53, and one or more of SEQ ID NOS: 59 and 74. In some embodiments, the amino acid sequence is a first amino acid sequence, wherein the antibody further comprises a second amino acid sequence. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 97. In some embodiments, the first amino acid sequence comprises SEQ ID NO: 59. In some embodiments, the first amino acid sequence comprises SEQ ID NO: 74. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 87. In some embodiments, the second amino acid sequence comprises SEQ ID NO: 92. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the antibody comprises an unnatural amino acid. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: an amino acid sequence comprising SEQ ID NO: 74. In some embodiments, the amino acid sequence is a first amino acid sequence, wherein the antibody further comprises a second amino acid sequence. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 97. In some embodiments, the first amino acid sequence comprises SEQ ID NO: 59. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 87. In some embodiments, the second amino acid sequence comprises SEQ ID NO: 92. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the antibody comprises an unnatural amino acid. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) a first amino acid sequence comprising SEQ ID NOS: 54, 55, 56, 87, 92, and 96; and (b) a second amino acid sequence comprising SEQ ID NOS: 51, 52, 53, 97, 59, and 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: an amino acid sequence comprising one or more of SEQ ID NOS: 54-56, 69-71, 78, 79, and 87-96. In some embodiments, the amino acid sequence is a first amino acid sequence, wherein the antibody further comprises a second amino acid sequence. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 69. In some embodiments, the first amino acid sequence comprises SEQ ID NO: 70. In some embodiments, the first amino acid sequence comprises SEQ ID NO: 71. In some embodiments, the first amino acid sequence comprises SEQ ID NO: 78. In some embodiments, the first amino acid sequence comprises SEQ ID NO: 79. In some embodiments, the first amino acid sequence comprises SEQ ID NO: 87. In some embodiments, the first amino acid sequence comprises SEQ ID NO: 88. In some embodiments, the first amino acid sequence comprises SEQ ID NO: 89. In some embodiments, the first amino acid sequence comprises SEQ ID NO: 90. In some embodiments, the first amino acid sequence comprises SEQ ID NO: 91. In some embodiments, the first amino acid sequence comprises SEQ ID NO: 92. In some embodiments, the first amino acid sequence comprises SEQ ID NO: 93. In some embodiments, the first amino acid sequence comprises SEQ ID NO: 94. In some embodiments, the first amino acid sequence comprises SEQ ID NO: 95. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 57. In some embodiments, the second amino acid sequence comprises SEQ ID NO: 58. In some embodiments, the second amino acid sequence comprises SEQ ID NO: 59. In some embodiments, the second amino acid sequence comprises SEQ ID NO: 60. In some embodiments, the second amino acid sequence comprises SEQ ID NO: 61. In some embodiments, the second amino acid sequence comprises SEQ ID NO: 62. In some embodiments, the second amino acid sequence comprises SEQ ID NO: 63. In some embodiments, the second amino acid sequence comprises SEQ ID NO: 64. In some embodiments, the second amino acid sequence comprises SEQ ID NO: 65. In some embodiments, the second amino acid sequence comprises SEQ ID NO: 66. In some embodiments, the second amino acid sequence comprises SEQ ID NO: 67. In some embodiments, the second amino acid sequence comprises SEQ ID NO: 68. In some embodiments, the second amino acid sequence comprises SEQ ID NO: 72. In some embodiments, the second amino acid sequence comprises SEQ ID NO: 73. In some embodiments, the second amino acid sequence comprises SEQ ID NO: 74. In some embodiments, the second amino acid sequence comprises SEQ ID NO: 75. In some embodiments, the second amino acid sequence comprises SEQ ID NO: 76. In some embodiments, the second amino acid sequence comprises SEQ ID NO: 77. In some embodiments, the second amino acid sequence comprises SEQ ID NO: 97. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the antibody comprises an unnatural amino acid. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: an amino acid sequence comprising one or more of SEQ ID NOS: 51-53, 57-68, 72-77, and 97. In some embodiments, the amino acid sequence is a first amino acid sequence, wherein the antibody further comprises a second amino acid sequence. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 57. In some embodiments, the first amino acid sequence comprises SEQ ID NO: 58. In some embodiments, the first amino acid sequence comprises SEQ ID NO: 59. In some embodiments, the first amino acid sequence comprises SEQ ID NO: 60. In some embodiments, the first amino acid sequence comprises SEQ ID NO: 61. In some embodiments, the first amino acid sequence comprises SEQ ID NO: 62. In some embodiments, the first amino acid sequence comprises SEQ ID NO: 63. In some embodiments, the first amino acid sequence comprises SEQ ID NO: 64. In some embodiments, the first amino acid sequence comprises SEQ ID NO: 65. In some embodiments, the first amino acid sequence comprises SEQ ID NO: 66. In some embodiments, the first amino acid sequence comprises SEQ ID NO: 67. In some embodiments, the first amino acid sequence comprises SEQ ID NO: 68. In some embodiments, the first amino acid sequence comprises SEQ ID NO: 72. In some embodiments, the first amino acid sequence comprises SEQ ID NO: 73. In some embodiments, the first amino acid sequence comprises SEQ ID NO: 74. In some embodiments, the first amino acid sequence comprises SEQ ID NO: 75. In some embodiments, the first amino acid sequence comprises SEQ ID NO: 76. In some embodiments, the first amino acid sequence comprises SEQ ID NO: 77. In some embodiments, the first amino acid sequence comprises SEQ ID NO: 97. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 69. In some embodiments, the second amino acid sequence comprises SEQ ID NO: 70. In some embodiments, the second amino acid sequence comprises SEQ ID NO: 71. In some embodiments, the second amino acid sequence comprises SEQ ID NO: 78. In some embodiments, the second amino acid sequence comprises SEQ ID NO: 79. In some embodiments, the second amino acid sequence comprises SEQ ID NO: 87. In some embodiments, the second amino acid sequence comprises SEQ ID NO: 88. In some embodiments, the second amino acid sequence comprises SEQ ID NO: 89. In some embodiments, the second amino acid sequence comprises SEQ ID NO: 90. In some embodiments, the second amino acid sequence comprises SEQ ID NO: 91. In some embodiments, the second amino acid sequence comprises SEQ ID NO: 92. In some embodiments, the second amino acid sequence comprises SEQ ID NO: 93. In some embodiments, the second amino acid sequence comprises SEQ ID NO: 94. In some embodiments, the second amino acid sequence comprises SEQ ID NO: 95. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the antibody comprises an unnatural amino acid. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) an amino acid sequence comprising one or more of SEQ ID NOS: 54, 55, and 56; and (b) an unnatural amino acid. In some embodiments, the amino acid sequence is a first amino acid sequence, wherein the antibody further comprises a second amino acid sequence. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) an amino acid sequence comprising SEQ ID NO: 96; and (b) an unnatural amino acid. In some embodiments, the amino acid sequence is a first amino acid sequence, wherein the antibody further comprises a second amino acid sequence. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) an amino acid sequence comprising one or more of SEQ ID NOS: 54, 55, 56, and 96; and (b) an unnatural amino acid. In some embodiments, the amino acid sequence is a first amino acid sequence, wherein the antibody further comprises a second amino acid sequence. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) an amino acid sequence comprising one or more of SEQ ID NOS: 51, 52, and 53; and (b) an unnatural amino acid. In some embodiments, the amino acid sequence is a first amino acid sequence, wherein the antibody further comprises a second amino acid sequence. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 97. In some embodiments, the first amino acid sequence comprises SEQ ID NO: 59. In some embodiments, the first amino acid sequence comprises SEQ ID NO: 74. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 87. In some embodiments, the second amino acid sequence comprises SEQ ID NO: 92. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) an amino acid sequence comprising one or more of SEQ ID NOS: 97, 59, and 74; and (b) an unnatural amino acid. In some embodiments, the amino acid sequence is a first amino acid sequence, wherein the antibody further comprises a second amino acid sequence. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 97. In some embodiments, the first amino acid sequence comprises SEQ ID NO: 59. In some embodiments, the first amino acid sequence comprises SEQ ID NO: 74. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 87. In some embodiments, the second amino acid sequence comprises SEQ ID NO: 92. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) an amino acid sequence comprising one or more of SEQ ID NOS: 51, 52, 53, 97, 59, and 74; and (b) an unnatural amino acid. In some embodiments, the amino acid sequence is a first amino acid sequence, wherein the antibody further comprises a second amino acid sequence. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 97. In some embodiments, the first amino acid sequence comprises SEQ ID NO: 59. In some embodiments, the first amino acid sequence comprises SEQ ID NO: 74. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 87. In some embodiments, the second amino acid sequence comprises SEQ ID NO: 92. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) one or more of SEQ ID NOS: 54, 55, 56, 96, 51, 52, 53, 97, 59, and 74; and (b) an unnatural amino acid. In some embodiments, the antibody comprises a first amino acid sequence and a second amino acid sequence. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) an amino acid sequence comprising one or more of SEQ ID NOS: 54-56, 69-71, 78, 79, and 87-96; and (b) an unnatural amino acid. In some embodiments, the amino acid sequence is a first amino acid sequence, wherein the antibody further comprises a second amino acid sequence. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 69. In some embodiments, the first amino acid sequence comprises SEQ ID NO: 70. In some embodiments, the first amino acid sequence comprises SEQ ID NO: 71. In some embodiments, the first amino acid sequence comprises SEQ ID NO: 78. In some embodiments, the first amino acid sequence comprises SEQ ID NO: 79. In some embodiments, the first amino acid sequence comprises SEQ ID NO: 87. In some embodiments, the first amino acid sequence comprises SEQ ID NO: 88. In some embodiments, the first amino acid sequence comprises SEQ ID NO: 89. In some embodiments, the first amino acid sequence comprises SEQ ID NO: 90. In some embodiments, the first amino acid sequence comprises SEQ ID NO: 91. In some embodiments, the first amino acid sequence comprises SEQ ID NO: 92. In some embodiments, the first amino acid sequence comprises SEQ ID NO: 93. In some embodiments, the first amino acid sequence comprises SEQ ID NO: 94. In some embodiments, the first amino acid sequence comprises SEQ ID NO: 95. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 57. In some embodiments, the second amino acid sequence comprises SEQ ID NO: 58. In some embodiments, the second amino acid sequence comprises SEQ ID NO: 59. In some embodiments, the second amino acid sequence comprises SEQ ID NO: 60. In some embodiments, the second amino acid sequence comprises SEQ ID NO: 61. In some embodiments, the second amino acid sequence comprises SEQ ID NO: 62. In some embodiments, the second amino acid sequence comprises SEQ ID NO: 63. In some embodiments, the second amino acid sequence comprises SEQ ID NO: 64. In some embodiments, the second amino acid sequence comprises SEQ ID NO: 65. In some embodiments, the second amino acid sequence comprises SEQ ID NO: 66. In some embodiments, the second amino acid sequence comprises SEQ ID NO: 67. In some embodiments, the second amino acid sequence comprises SEQ ID NO: 68. In some embodiments, the second amino acid sequence comprises SEQ ID NO: 72. In some embodiments, the second amino acid sequence comprises SEQ ID NO: 73. In some embodiments, the second amino acid sequence comprises SEQ ID NO: 74. In some embodiments, the second amino acid sequence comprises SEQ ID NO: 75. In some embodiments, the second amino acid sequence comprises SEQ ID NO: 76. In some embodiments, the second amino acid sequence comprises SEQ ID NO: 77. In some embodiments, the second amino acid sequence comprises SEQ ID NO: 97. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is an antibody comprising: (a) an amino acid sequence comprising one or more of SEQ ID NOS: 51-53, 57-68, 72-77, and 97; and (b) an unnatural amino acid. In some embodiments, the amino acid sequence is a first amino acid sequence, wherein the antibody further comprises a second amino acid sequence. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 57. In some embodiments, the first amino acid sequence comprises SEQ ID NO: 58. In some embodiments, the first amino acid sequence comprises SEQ ID NO: 59. In some embodiments, the first amino acid sequence comprises SEQ ID NO: 60. In some embodiments, the first amino acid sequence comprises SEQ ID NO: 61. In some embodiments, the first amino acid sequence comprises SEQ ID NO: 62. In some embodiments, the first amino acid sequence comprises SEQ ID NO: 63. In some embodiments, the first amino acid sequence comprises SEQ ID NO: 64. In some embodiments, the first amino acid sequence comprises SEQ ID NO: 65. In some embodiments, the first amino acid sequence comprises SEQ ID NO: 66. In some embodiments, the first amino acid sequence comprises SEQ ID NO: 67. In some embodiments, the first amino acid sequence comprises SEQ ID NO: 68. In some embodiments, the first amino acid sequence comprises SEQ ID NO: 72. In some embodiments, the first amino acid sequence comprises SEQ ID NO: 73. In some embodiments, the first amino acid sequence comprises SEQ ID NO: 74. In some embodiments, the first amino acid sequence comprises SEQ ID NO: 75. In some embodiments, the first amino acid sequence comprises SEQ ID NO: 76. In some embodiments, the first amino acid sequence comprises SEQ ID NO: 77. In some embodiments, the first amino acid sequence comprises SEQ ID NO: 97. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 69. In some embodiments, the second amino acid sequence comprises SEQ ID NO: 70. In some embodiments, the second amino acid sequence comprises SEQ ID NO: 71. In some embodiments, the second amino acid sequence comprises SEQ ID NO: 78. In some embodiments, the second amino acid sequence comprises SEQ ID NO: 79. In some embodiments, the second amino acid sequence comprises SEQ ID NO: 87. In some embodiments, the second amino acid sequence comprises SEQ ID NO: 88. In some embodiments, the second amino acid sequence comprises SEQ ID NO: 89. In some embodiments, the second amino acid sequence comprises SEQ ID NO: 90. In some embodiments, the second amino acid sequence comprises SEQ ID NO: 91. In some embodiments, the second amino acid sequence comprises SEQ ID NO: 92. In some embodiments, the second amino acid sequence comprises SEQ ID NO: 93. In some embodiments, the second amino acid sequence comprises SEQ ID NO: 94. In some embodiments, the second amino acid sequence comprises SEQ ID NO: 95. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the antibody comprises a cell-targeting molecule linked to the antibody via the unnatural amino acid. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the antibody specifically binds CD3. In some embodiments, the antibody is cross-species reactive. In some embodiments, the antibody is cross-species reactive with human and monkey antigens. In some embodiments, the antibody comprises a cross-species reactive CDR. In some embodiments, the antibody is a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the antibody of any of the preceding embodiments and at least a portion of another antibody. In some embodiments, the fusion antibody is a bispecific antibody comprising an Fab domain of the antibody of any of the preceding claims and an Fab domain of another antibody. In some embodiments, disclosed herein is a method for treating a disease by administering the antibody of any of the preceding embodiments to a patient. In some embodiments, disclosed herein is a method for treating cancer by administering the antibody of any of the preceding embodiments to a patient.

In another aspect, disclosed herein is a composition comprising: (a) an amino acid sequence comprising one or more of SEQ ID NOS: 54, 55, and 56, and an unnatural amino acid; and (b) a cell-targeting molecule linked to the amino acid sequence via the unnatural amino acid. In some embodiments, the amino acid sequence is a first amino acid sequence, wherein the composition further comprises a second amino acid sequence. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 51.

In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the composition specifically binds CD3. In some embodiments, the composition is cross-species reactive. In some embodiments, the composition is cross-species reactive with human and monkey antigens. In some embodiments, the composition comprises a cross-species reactive CDR. In some embodiments, the composition comprises a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the composition of any of the preceding embodiments and at least a portion of another antibody. In some embodiments, the fusion antibody is a bispecific antibody comprising an Fab domain of the composition of any of the preceding claims and an Fab domain of another antibody. In some embodiments, disclosed herein is a method for treating a disease by administering the composition of any of the preceding embodiments to a patient. In some embodiments, disclosed herein is a method for treating cancer by administering the composition of any of the preceding embodiments to a patient.

In another aspect, disclosed herein is a composition comprising: (a) an amino acid sequence comprising SEQ ID NO: 96, and an unnatural amino acid; and (b) a cell-targeting molecule linked to the amino acid sequence via the unnatural amino acid. In some embodiments, the amino acid sequence is a first amino acid sequence, wherein the antibody further comprises a second amino acid sequence. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the composition specifically binds CD3. In some embodiments, the composition is cross-species reactive. In some embodiments, the composition is cross-species reactive with human and monkey antigens. In some embodiments, the composition comprises a cross-species reactive CDR. In some embodiments, the composition comprises a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the composition of any of the preceding embodiments and at least a portion of another antibody. In some embodiments, the fusion antibody is a bispecific antibody comprising an Fab domain of the composition of any of the preceding claims and an Fab domain of another antibody. In some embodiments, disclosed herein is a method for treating a disease by administering the composition of any of the preceding embodiments to a patient. In some embodiments, disclosed herein is a method for treating cancer by administering the composition of any of the preceding embodiments to a patient.

In another aspect, disclosed herein is a composition comprising: (a) an amino acid sequence comprising one or more of SEQ ID NOS: 54, 55, 56, and 96, and an unnatural amino acid; and (b) a cell-targeting molecule linked to the amino acid sequence via the unnatural amino acid. In some embodiments, the amino acid sequence is a first amino acid sequence, wherein the composition further comprises a second amino acid sequence. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 87. In some embodiments, the first amino acid sequence comprises SEQ ID NO: 92. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 97. In some embodiments, the second amino acid sequence comprises SEQ ID NO: 59. In some embodiments, the second amino acid sequence comprises SEQ ID NO: 74. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the composition specifically binds CD3. In some embodiments, the composition is cross-species reactive. In some embodiments, the composition is cross-species reactive with human and monkey antigens. In some embodiments, the composition comprises a cross-species reactive CDR. In some embodiments, the composition comprises a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the composition of any of the preceding embodiments and at least a portion of another antibody. In some embodiments, the fusion antibody is a bispecific antibody comprising an Fab domain of the composition of any of the preceding claims and an Fab domain of another antibody. In some embodiments, disclosed herein is a method for treating a disease by administering the composition of any of the preceding embodiments to a patient. In some embodiments, disclosed herein is a method for treating cancer by administering the composition of any of the preceding embodiments to a patient.

In another aspect, disclosed herein is a composition comprising: (a) a first amino acid sequence comprising one or more of SEQ ID NOS: 51, 52, and 53; (b) a second amino acid sequence comprising an unnatural amino acid; and (c) a cell-targeting molecule linked to the second amino acid sequence via the unnatural amino acid. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 97. In some embodiments, the first amino acid sequence comprises SEQ ID NO: 59. In some embodiments, the first amino acid sequence comprises SEQ ID NO: 74. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 87. In some embodiments, the second amino acid sequence comprises SEQ ID NO: 92. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the composition specifically binds CD3. In some embodiments, the composition is cross-species reactive. In some embodiments, the composition is cross-species reactive with human and monkey antigens. In some embodiments, the composition comprises a cross-species reactive CDR. In some embodiments, the composition comprises a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the composition of any of the preceding embodiments and at least a portion of another antibody. In some embodiments, the fusion antibody is a bispecific antibody comprising an Fab domain of the composition of any of the preceding claims and an Fab domain of another antibody. In some embodiments, disclosed herein is a method for treating a disease by administering the composition of any of the preceding embodiments to a patient. In some embodiments, disclosed herein is a method for treating cancer by administering the composition of any of the preceding embodiments to a patient.

In another aspect, disclosed herein is a composition comprising: (a) a first amino acid sequence comprising one or more of SEQ ID NOS: 97, 59, and 74; (b) a second amino acid sequence comprising an unnatural amino acid; and (c) a cell-targeting molecule linked to the second amino acid sequence via the unnatural amino acid. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 97. In some embodiments, the first amino acid sequence comprises SEQ ID NO: 59. In some embodiments, the first amino acid sequence comprises SEQ ID NO: 74. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 87. In some embodiments, the second amino acid sequence comprises SEQ ID NO: 92. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the composition specifically binds CD3. In some embodiments, the composition is cross-species reactive. In some embodiments, the composition is cross-species reactive with human and monkey antigens. In some embodiments, the composition comprises a cross-species reactive CDR. In some embodiments, the composition comprises a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the composition of any of the preceding embodiments and at least a portion of another antibody. In some embodiments, the fusion antibody is a bispecific antibody comprising an Fab domain of the composition of any of the preceding claims and an Fab domain of another antibody. In some embodiments, disclosed herein is a method for treating a disease by administering the composition of any of the preceding embodiments to a patient. In some embodiments, disclosed herein is a method for treating cancer by administering the composition of any of the preceding embodiments to a patient.

In another aspect, disclosed herein is a composition comprising: (a) a first amino acid sequence comprising one or more of SEQ ID NOS: 51, 52, 53, 97, 59, and 74; (b) a second amino acid sequence comprising an unnatural amino acid; and (c) a cell-targeting molecule linked to the second amino acid sequence via the unnatural amino acid. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 97. In some embodiments, the first amino acid sequence comprises SEQ ID NO: 59. In some embodiments, the first amino acid sequence comprises SEQ ID NO: 74. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 87. In some embodiments, the second amino acid sequence comprises SEQ ID NO: 92. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the composition specifically binds CD3. In some embodiments, the composition is cross-species reactive. In some embodiments, the composition is cross-species reactive with human and monkey antigens. In some embodiments, the composition comprises a cross-species reactive CDR. In some embodiments, the composition comprises a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the composition of any of the preceding embodiments and at least a portion of another antibody. In some embodiments, the fusion antibody is a bispecific antibody comprising an Fab domain of the composition of any of the preceding claims and an Fab domain of another antibody. In some embodiments, disclosed herein is a method for treating a disease by administering the composition of any of the preceding embodiments to a patient. In some embodiments, disclosed herein is a method for treating cancer by administering the composition of any of the preceding embodiments to a patient.

In another aspect, disclosed herein is an composition comprising: (a) an amino acid sequence comprising one or more of SEQ ID NOS: 54-56, 69-71, 78, 79, and 87-96, and an unnatural amino acid; and (b) a cell-targeting molecule linked to the amino acid sequence via the unnatural amino acid. In some embodiments, the amino acid sequence is a first amino acid sequence, wherein the antibody further comprises a second amino acid sequence. In some embodiments, the first amino acid sequence comprises SEQ ID NO: 54. In some embodiments, the first amino acid sequence comprises SEQ ID NO: 55. In some embodiments, the first amino acid sequence comprises SEQ ID NO: 56. In some embodiments, the first amino acid sequence comprises SEQ ID NO: 69. In some embodiments, the first amino acid sequence comprises SEQ ID NO: 70. In some embodiments, the first amino acid sequence comprises SEQ ID NO: 71. In some embodiments, the first amino acid sequence comprises SEQ ID NO: 78. In some embodiments, the first amino acid sequence comprises SEQ ID NO: 79. In some embodiments, the first amino acid sequence comprises SEQ ID NO: 87. In some embodiments, the first amino acid sequence comprises SEQ ID NO: 88. In some embodiments, the first amino acid sequence comprises SEQ ID NO: 89. In some embodiments, the first amino acid sequence comprises SEQ ID NO: 90. In some embodiments, the first amino acid sequence comprises SEQ ID NO: 91. In some embodiments, the first amino acid sequence comprises SEQ ID NO: 92. In some embodiments, the first amino acid sequence comprises SEQ ID NO: 93. In some embodiments, the first amino acid sequence comprises SEQ ID NO: 94. In some embodiments, the first amino acid sequence comprises SEQ ID NO: 95. In some embodiments, the first amino acid sequence comprises SEQ ID NO: 96. In some embodiments, the second amino acid sequence comprises SEQ ID NO: 51. In some embodiments, the second amino acid sequence comprises SEQ ID NO: 52. In some embodiments, the second amino acid sequence comprises SEQ ID NO: 53. In some embodiments, the second amino acid sequence comprises SEQ ID NO: 57. In some embodiments, the second amino acid sequence comprises SEQ ID NO: 58. In some embodiments, the second amino acid sequence comprises SEQ ID NO: 59. In some embodiments, the second amino acid sequence comprises SEQ ID NO: 60. In some embodiments, the second amino acid sequence comprises SEQ ID NO: 61. In some embodiments, the second amino acid sequence comprises SEQ ID NO: 62. In some embodiments, the second amino acid sequence comprises SEQ ID NO: 63. In some embodiments, the second amino acid sequence comprises SEQ ID NO: 64. In some embodiments, the second amino acid sequence comprises SEQ ID NO: 65. In some embodiments, the second amino acid sequence comprises SEQ ID NO: 66. In some embodiments, the second amino acid sequence comprises SEQ ID NO: 67. In some embodiments, the second amino acid sequence comprises SEQ ID NO: 68. In some embodiments, the second amino acid sequence comprises SEQ ID NO: 72. In some embodiments, the second amino acid sequence comprises SEQ ID NO: 73. In some embodiments, the second amino acid sequence comprises SEQ ID NO: 74. In some embodiments, the second amino acid sequence comprises SEQ ID NO: 75. In some embodiments, the second amino acid sequence comprises SEQ ID NO: 76. In some embodiments, the second amino acid sequence comprises SEQ ID NO: 77. In some embodiments, the second amino acid sequence comprises SEQ ID NO: 97. In some embodiments, the first amino acid sequence comprises at least 95% sequence identity with SEQ ID NO: 44. In some embodiments, the second amino acid sequence comprises at least 95% sequence identity with SEQ ID NO: 39. In some embodiments, the unnatural amino acid is para-acetylphenylalanine. In some embodiments, the unnatural amino acid is located within a CH1 sequence of the first amino acid sequence. In some embodiments, the CH1 sequence comprises SEQ ID NO: 86. In some embodiments, the cell-targeting molecule is a non-peptide compound. In some embodiments, the cell-targeting molecule interacts with prostate-specific membrane antigen (PSMA). In some embodiments, the cell-targeting molecule is DUPA, or a derivative there. In some embodiments, the cell-targeting molecule is folate, or a derivative thereof. In some embodiments, the composition specifically binds CD3. In some embodiments, the composition is cross-species reactive. In some embodiments, the composition is cross-species reactive with human and monkey antigens. In some embodiments, the composition comprises a cross-species reactive CDR. In some embodiments, the composition comprises a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the composition of any of the preceding embodiments and at least a portion of another antibody. In some embodiments, the fusion antibody is a bispecific antibody comprising an Fab domain of the composition of any of the preceding claims and an Fab domain of another antibody. In some embodiments, disclosed herein is a method for treating a disease by administering the composition of any of the preceding embodiments to a patient. In some embodiments, disclosed herein is a method for treating cancer by administering the composition of any of the preceding embodiments to a patient.

In another aspect, disclosed herein is a composition comprising: (a) an amino acid sequence comprising one or more of SEQ ID NOS: 51-53, 57-68, 72-77, and 97, and an unnatural amino acid; and (b) a cell-targeting molecule linked to the amino acid sequence via the unnatural amino acid. In some embodiments, the amino acid sequence is a first amino acid sequence, wherein the antibody further comprises a second amino acid sequence. In some embodiments, the first amino acid sequence comprises SEQ ID NO: 51. In some embodiments, the first amino acid sequence comprises SEQ ID NO: 52. In some embodiments, the first amino acid sequence comprises SEQ ID NO: 53. In some embodiments, the first amino acid sequence comprises SEQ ID NO: 57. In some embodiments, the first amino acid sequence comprises SEQ ID NO: 58. In some embodiments, the first amino acid sequence comprises SEQ ID NO: 59. In some embodiments, the first amino acid sequence comprises SEQ ID NO: 60. In some embodiments, the first amino acid sequence comprises SEQ ID NO: 61. In some embodiments, the first amino acid sequence comprises SEQ ID NO: 62. In some embodiments, the first amino acid sequence comprises SEQ ID NO: 63. In some embodiments, the first amino acid sequence comprises SEQ ID NO: 64. In some embodiments, the first amino acid sequence comprises SEQ ID NO: 65. In some embodiments, the first amino acid sequence comprises SEQ ID NO: 66. In some embodiments, the first amino acid sequence comprises SEQ ID NO: 67. In some embodiments, the first amino acid sequence comprises SEQ ID NO: 68. In some embodiments, the first amino acid sequence comprises SEQ ID NO: 72. In some embodiments, the first amino acid sequence comprises SEQ ID NO: 73. In some embodiments, the first amino acid sequence comprises SEQ ID NO: 74. In some embodiments, the first amino acid sequence comprises SEQ ID NO: 75. In some embodiments, the first amino acid sequence comprises SEQ ID NO: 76. In some embodiments, the first amino acid sequence comprises SEQ ID NO: 77. In some embodiments, the first amino acid sequence comprises SEQ ID NO: 97. In some embodiments, the second amino acid sequence comprises SEQ ID NO: 54. In some embodiments, the second amino acid sequence comprises SEQ ID NO: 55. In some embodiments, the second amino acid sequence comprises SEQ ID NO: 56. In some embodiments, the second amino acid sequence comprises SEQ ID NO: 69. In some embodiments, the second amino acid sequence comprises SEQ ID NO: 70. In some embodiments, the second amino acid sequence comprises SEQ ID NO: 71. In some embodiments, the second amino acid sequence comprises SEQ ID NO: 78. In some embodiments, the second amino acid sequence comprises SEQ ID NO: 79. In some embodiments, the second amino acid sequence comprises SEQ ID NO: 87. In some embodiments, the second amino acid sequence comprises SEQ ID NO: 88. In some embodiments, the second amino acid sequence comprises SEQ ID NO: 89. In some embodiments, the second amino acid sequence comprises SEQ ID NO: 90. In some embodiments, the second amino acid sequence comprises SEQ ID NO: 91. In some embodiments, the second amino acid sequence comprises SEQ ID NO: 92. In some embodiments, the second amino acid sequence comprises SEQ ID NO: 93. In some embodiments, the second amino acid sequence comprises SEQ ID NO: 94. In some embodiments, the second amino acid sequence comprises SEQ ID NO: 95. In some embodiments, the second amino acid sequence comprises SEQ ID NO: 96. In some embodiments, the first amino acid sequence comprises at least 95% sequence identity with SEQ ID NO: 39. In some embodiments, the second amino acid sequence comprises at least 95% sequence identity with SEQ ID NO: 44. In some embodiments, the unnatural amino acid is para-acetylphenylalanine. In some embodiments, the unnatural amino acid is located within a CH1 sequence of the second amino acid sequence. In some embodiments, the CH1 sequence comprises SEQ ID NO: 86. In some embodiments, the cell-targeting molecule is a non-peptide compound. In some embodiments, the cell-targeting molecule interacts with prostate-specific membrane antigen (PSMA). In some embodiments, the cell-targeting molecule is DUPA. In some embodiments, the composition specifically binds CD3, or a derivative there. In some embodiments, the cell-targeting molecule is folate, or a derivative thereof. In some embodiments, the composition is cross-species reactive. In some embodiments, the composition is cross-species reactive with human and monkey antigens. In some embodiments, the composition comprises a cross-species reactive CDR. In some embodiments, the composition comprises a humanized antibody. In some embodiments, the first and second amino acid sequences are linked. In some embodiments, the first and second amino acid sequences are linked as a single fusion sequence. In some embodiments, the first and second amino acid sequences are linked by a chemical bond. In some embodiments, the first and second amino acid sequences are linked by a disulfide bond. In some embodiments, disclosed herein is a fusion antibody comprising at least a portion of the composition of any of the preceding embodiments and at least a portion of another antibody. In some embodiments, the fusion antibody is a bispecific antibody comprising an Fab domain of the composition of any of the preceding claims and an Fab domain of another antibody. In some embodiments, disclosed herein is a method for treating a disease by administering the composition of any of the preceding embodiments to a patient. In some embodiments, disclosed herein is a method for treating cancer by administering the composition of any of the preceding embodiments to a patient.

The anti-CD3 antibody may comprise a heavy chain region selected from SEQ ID NOS: 24-27, 42-50,54-56, 69-71, and 78-81 and a light chain region selected from SEQ ID NOS: 23, 28-40, 51-53, 57, 58-68, 72-77, and 82-83. As a non-limiting example, an antibody may comprise heavy chain SEQ ID NO: 44, and light chain SEQ ID NO: 39.

The anti-CD3 antibody may comprise any combination of sequences selected from those presented in Tables 35-39 herein.

Sites for Conjugation

The antibody or antibody fragment may comprise one or more sites for conjugation to another molecule, for example, a non-immunoglobulin peptide, an additional antibody or additional antibody fragment, a targeting agent, a non-peptide structure, or a therapeutic compound. The one or more sites may comprise a lysine or a cysteine. In one embodiment, the one or more sites may comprise one or more unnatural amino acids. In one embodiment, the one or more unnatural amino acids of the antibody or antibody fragment consist of p-acetylphenylalanine (pAcF). Optionally, the one or more unnatural amino acids of the antibody or antibody fragment consist of selenocysteine. Optionally, the one or more unnatural amino acids consist of (a) various substituted tyrosine and phenylalanine analogues such as O-methyl-L-tyrosine, p-amino-L-phenylalanine, 3-nitro-L-tyrosine, p-nitro-L-phenylalanine, m-methoxy-L-phenylalanine and p-isopropyl-L-phenylalanine; (b) amino acids with aryl azide and benzophenone groups that may be photo-cross-linked; (c) amino acids that have unique chemical reactivity including acetyl-L-phenylalanine, m-acetyl-L-phenylalanine, O-allyl-L-tyrosine, O-(2-propynyl)-L-tyrosine, p-ethylthiocarbonyl-L-phenylalanine, and p-(3-oxobutanoyl)-L-phenylalanine; (d) heavy-atom-containing amino acids for phasing in X-ray crystallography including p-iodo and p-bromo-L-phenylalanine; (e) the redox-active amino acid dihydroxy-L-phenylalanine; (f) glycosylated amino acids including b-N-acetylglucosamine-O-serine and a-N-acetylgalactosamine-O-threonine; (g) fluorescent amino acids with naphthyl, dansyl, and 7-aminocoumarin side chains; (h) photocleavable and photoisomerizable amino acids with azobenzene and nitrobenzyl Cys, Ser, and Tyr side chains; (i) the phosphotyrosine mimetic p-carboxymethyl-L-phenylalanine; (j) the glutamine homologue homoglutamine; (k) 2-aminooctanoic acid; (l) and any combination of (a)-(k) thereof. Optionally, the one or more unnatural amino acids consist of at least one oxime, carbonyl, dicarbonyl, hydroxylamine, cyclooctyne, aryl/alkyl azides, norbornene, cyclopropene, trans-cyclooctene, tetrazine group, and any combination thereof. The one or more unnatural amino acids may be genetically encoded. The one or more unnatural amino acids may be incorporated into the antibody or antibody fragment. The one or more unnatural amino acids may be site-specifically incorporated the antibody or antibody fragment. The targeting agent antibody conjugate may comprise two or more unnatural amino acids. The targeting agent antibody conjugate may comprise three or more unnatural amino acids. The targeting agent antibody conjugate may comprise four or more unnatural amino acids. The one or more unnatural amino acids may replace one or more amino acid residues in the antibody or antibody fragment. The one or more unnatural amino acids may replace an amino acid residue in a heavy chain of the antibody or antibody fragment. The one or more unnatural amino acids of the antibody or antibody fragment replace an amino acid residue in a light chain of the antibody or antibody fragment. The one or more unnatural amino acids of the antibody or antibody fragment replace an amino acid residue in a variable region of the antibody or antibody fragment.

II. Targeting Agents

In another aspect, provided herein are antibody conjugates and antibody fusions comprising an antibody or antibody fragment disclosed herein, or an antibody or antibody fragment derived or otherwise modified from an antibody or antibody fragment disclosed herein. As a non-limiting example, provided are targeting agent antibody conjugates comprising an antibody or antibody fragment disclosed herein conjugated to a targeting agent. It should be understood that the targeting agents described herein may be slightly modified by conjugation to the antibody or antibody fragment or to a linker that connects the targeting agent to the antibody or antibody fragment, and that targeting agents as disclosed herein include these slightly modified forms, but otherwise remain structurally and functionally similar to the therapeutic agent as known in the art. The targeting agent may be selected from a small molecule, a cell-targeting molecule, a ligand, a protein, a peptide, a peptoid, a DNA aptamer, a peptide nucleic acid (PNA), a vitamin, a substrate, or a substrate analog. The peptide may comprise a cyclic peptide or a linear peptide. The targeting agent may comprise a ligand. The targeting agent may comprise at least a portion of a ligand. The ligand may be a chemical ligand. The ligand may be a hormonal ligand. The ligand may be a peptide ligand. The ligand may be a protein ligand. The targeting agent may be derivatized (e.g. with a naturally occurring protein or peptide). The targeting agent may be a compound. The targeting agent may be a (non-peptidic) small molecule. The targeting agent may bind a target cell. The targeting agent may bind a cell surface protein or a cell surface marker on a cell. The targeting agent may bind a protein, a peptide, or a biomolecule, wherein the protein, the peptide, or the biomolecule is not bound to a cell. The protein, peptide or biomolecule may be circulating in a bloodstream. The protein, peptide, or biomolecule may be a component of extracellular matrix. The protein may be an enzyme. The enzyme may have enzymatic activity. A biomolecule, by non-limiting example, may be selected from a fiber, a biopolymer (e.g. collagen), a glycan, a proteoglycan, a lipid, a sterol, a carbohydrate, a nucleic acid, and a cellular fragment.

The targeting agent of the targeting agent antibody conjugate may have a therapeutic effect because it brings a cytotoxic effector cell in proximity of a target cell. The therapeutic effect on the intended indication of the targeting agent antibody conjugate may be due to the targeting agent antibody conjugate recruiting a cytotoxic effector cell to the target cell. The therapeutic effect on the intended indication of the targeting agent antibody conjugate may be wholly due to the targeting agent antibody conjugate recruiting a cytotoxic effector cell to the target cell. The therapeutic effect on the intended indication of the targeting agent antibody construct may be predominantly due to the targeting agent antibody conjugate recruiting a cytotoxic effector cell to the target cell.

The therapeutic effect of the intended indication may be due to the targeting agent antibody conjugate recruiting a protein, peptide, or biomolecule to the target cell. The therapeutic effect of the intended indication may wholly due to the targeting agent antibody conjugate recruiting a protein, peptide, or biomolecule to the target cell. The therapeutic effect on the intended indication may be at least partially due to the targeting agent antibody conjugate recruiting a protein, peptide or biomolecule to the target cell.

The targeting agent alone may be a targeting agent that has a therapeutic effect (e.g., a drug). The targeting agent alone may not be a targeting agent that has any therapeutic effect. The targeting agent alone may or may not have any therapeutic effect towards an intended indication of the targeting agent antibody conjugate. The targeting agent may or may not have a therapeutic effect towards the intended indication of the targeting agent antibody conjugate without being conjugated to the anti-CD3 antibody or antibody fragment. The dose of the therapeutic agent when administered as part of the targeting agent antibody conjugate to provide a therapeutic effect may or may not have a therapeutic effect when the therapeutic agent is administered alone at that dose. The targeting agent of the targeting agent antibody conjugate may or may not be intended to have any therapeutic effect besides recruiting the cytotoxic effector cell to the target cell. The targeting agent of the targeting agent antibody conjugate may or may not have a therapeutic effect on the target cell, wherein the therapeutic effect is negligible relative to the therapeutic effect of recruiting the cytotoxic effector cell, protein, peptide or biomolecule to the target cell. The targeting agent of the targeting agent antibody conjugate may or may not have a therapeutic effect on the target cell, wherein the therapeutic effect is less than the therapeutic effect of recruiting the cytotoxic effector cell, protein, peptide, or biomolecule to the target cell. The binding of the targeting agent to the target cell may induce an unintentional response from the target cell. The binding of the targeting agent to the target cell may induce an unintentional therapeutic effect in addition to the therapeutic effect of recruiting the cytotoxic effector cell, protein, peptide, or biomolecule to the target cell.

The targeting agent may bind a cell surface molecule on a cancer cell. The cancer cell may be selected from, by way of non-limiting example, a breast cancer cell, a brain cancer cell, a pancreatic cancer cell, a skin cancer cell, a lung cancer cell, a liver cancer cell, a gall bladder cancer cell, a colon cancer cell, an ovarian cancer cell, a prostate cancer cell, a uterine cancer cell, a bone cancer cell, and a blood cancer (leukemic) cancer cell. The cell surface molecule may be selected from, by way of non-limiting example, a G protein coupled receptor (GPCR), a kinase receptor, a cytokine receptor, and a chemokine receptor. The cell surface molecule may be selected from, by way of non-limiting example, a CD20, a CD19, a CD22, a CS1, a BCMA, a CD123, a CD33, a CLL-1, a GD-2, a EGFR, a EGRF vIII, a mesothelin, a CD38, a Her2/ErbB2, a Patched receptor (PTCH), a Smoothened receptor (SMO), a FKBP-12, an estrogen receptor, a vascular endothelial growth factor (VEGFR1, VEGFR2), an epidermal growth factor receptor, a fibroblast growth factor receptor (FGFR), a folate receptor, a cholecystokinin B receptor, a gonadotropin-releasing hormone receptor, a somatostatin receptor, a gastrin-releasing peptide receptor, a neurokinin receptor, a melanocortin receptor, a neurotensin receptor, a neuropeptide Y receptor, and an integrin.

Figure 20A:
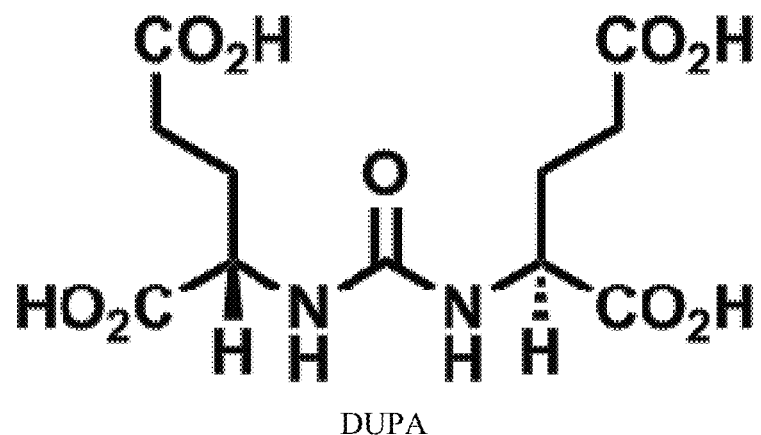
FIG. 20A shows chemical structure of 2-[3-(1,3-dicarboxypropyl)ureido]pentanedioic acid (DUPA).
Figure 20B:
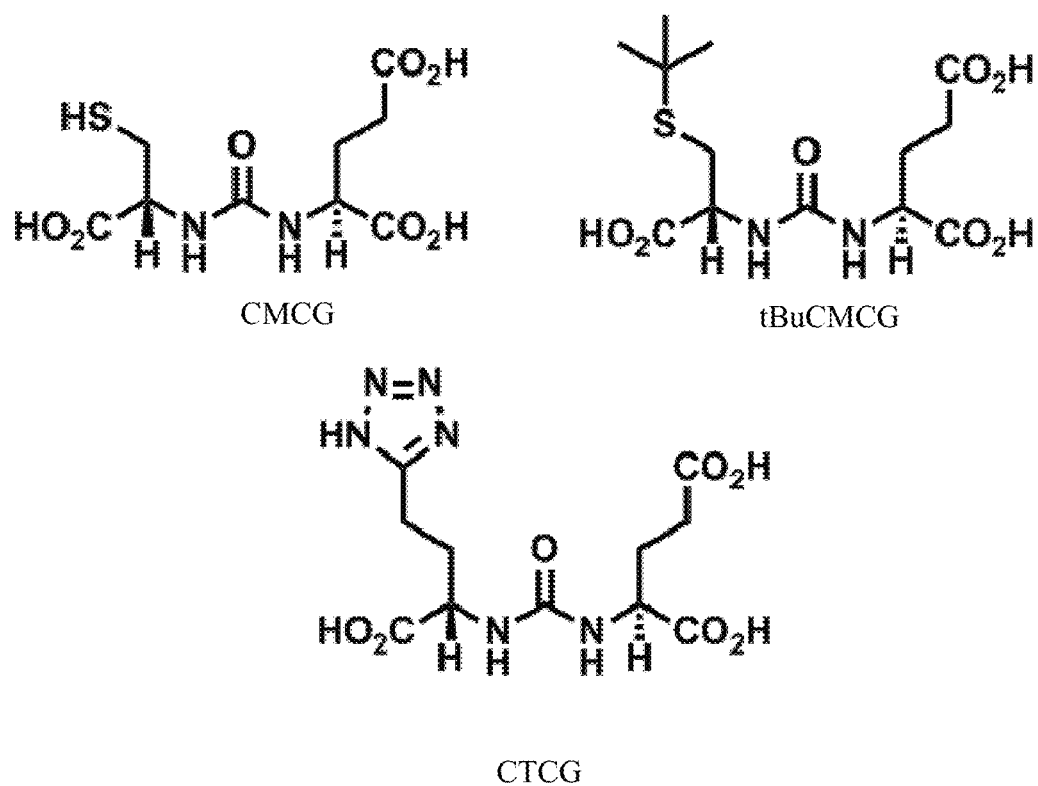
FIG. 20B shows exemplary analogs of chemical structure of 2-[3-(1,3-dicarboxypropyl)ureido]pentanedioic acid (DUPA), such as ((1-carboxy-2-mercaptoethyl)carbamoyl) glutamic acid (CMCG), ((2-(tert-butylthio)-1-carboxyethyl) carbamoyl)glutamic acid (tBuCMCG), and ((1-carboxy-3-(1H-tetrazol-5-yl)propyl)carbamoyl)glutamic acid (CTCG).

The targeting agent may bind a prostate-specific membrane antigen (PSMA). The targeting agent that binds PSMA may be 2-[3-(1,3-dicarboxypropyl)ureido]pentanedioic acid (DUPA), or an analog thereof (see, e.g., FIGS. 20A and 20B). An analog thereof may be a moiety that is based on DUPA and preserves PSMA binding. The DUPA analog may preserve a significant portion of the structure of DUPA. Moreover, the DUPA analog may be a slightly modified form of DUPA because of its conjugation to a linker or an antibody/antibody fragment. For example, the DUPA analog may be slightly modified due to conjugation of a DUPA carboxyl group to the linker or antibody/antibody fragment. In addition, DUPA may be slightly modified because of its conjugation to a linker or an antibody/antibody fragment, but maintain its PSMA binding properties. As used herein, the term "DUPA" comprises 2-[3-(1,3-dicarboxypropyl)ureido]pentanedioic acid, analogs, and stereoisomers thereof as described above.

The targeting agent may bind a folate receptor protein (FR). The targeting agent that binds FR may be N-(4-{[(2-amino-4-oxo-1,4-dihydropteridin-6-yl)methyl]amino}benzoyl)-L-glutamic acid (folic acid), or an analog thereof (see, e.g., FIGS. 20C and 20D). An analog thereof may be a moiety that is based on folic acid and preserves FR binding. The folic acid analog may preserve a significant portion of the structure of folic acid. Moreover, the folic acid analog may be a slightly modified form of folic acid because of its conjugation to a linker or an antibody/antibody fragment. For example, the folic acid analog may be slightly modified due to conjugation of a folate carboxyl group to the linker or antibody/antibody fragment. In addition, folic acid may be slightly modified because of its conjugation to a linker or an antibody/antibody fragment, but maintain its FR binding properties. As used herein, the term "folic acid" or "folate" comprises N-(4-{[(2-amino-4-oxo-1,4-dihydropteridin-6-yl)methyl]amino}benzoyl)-L-glutamic acid and analogs thereof as described above.

III. Targeting Agent Antibody Conjugates

Figure 1C:
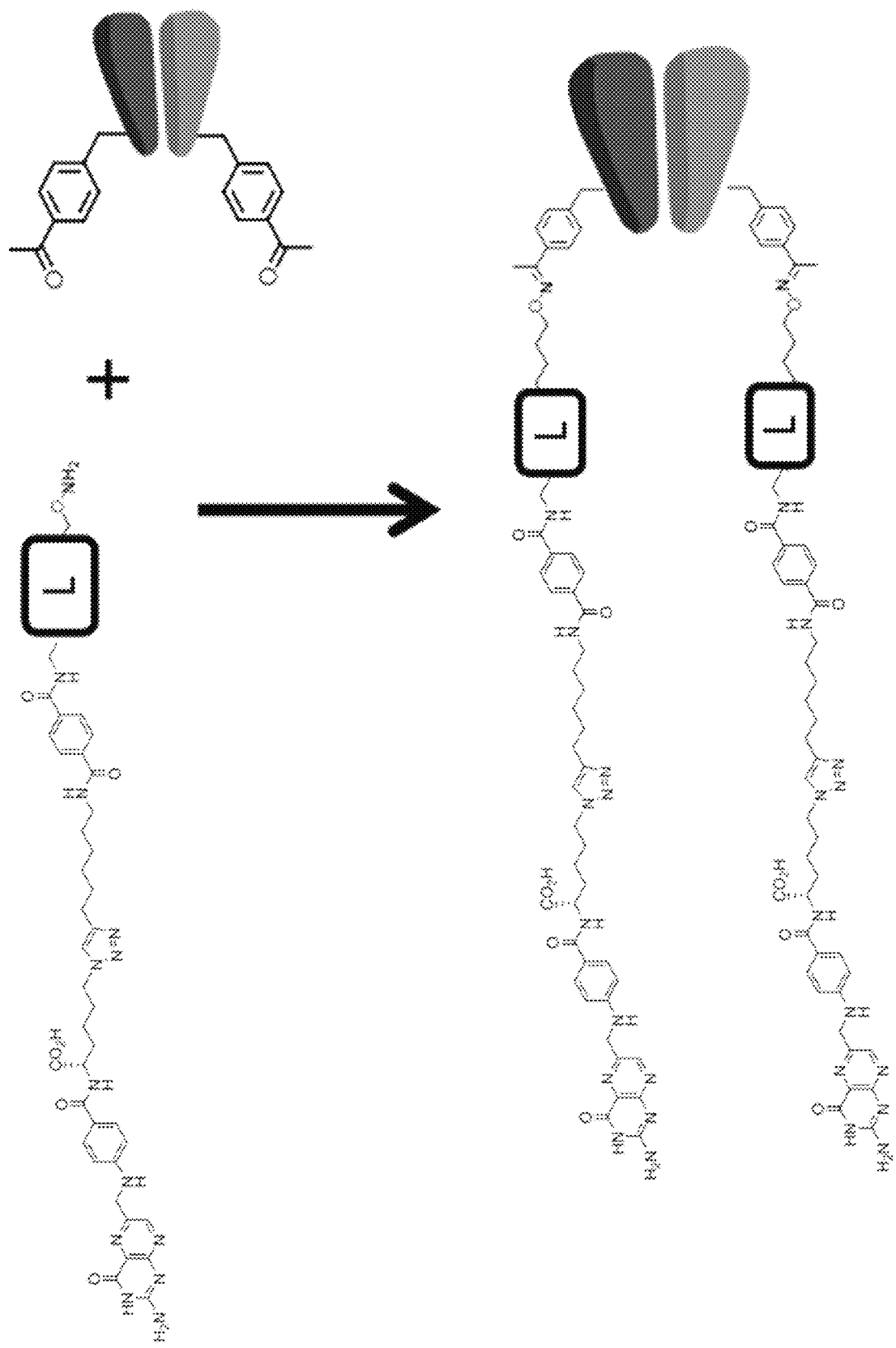
FIG. 1C shows a schematic synthesis of an anti-CD3 antibody (e.g., huL5H2) double mutant folate conjugate attached via linker (L) to both heavy and light chains.
Figure 1D:
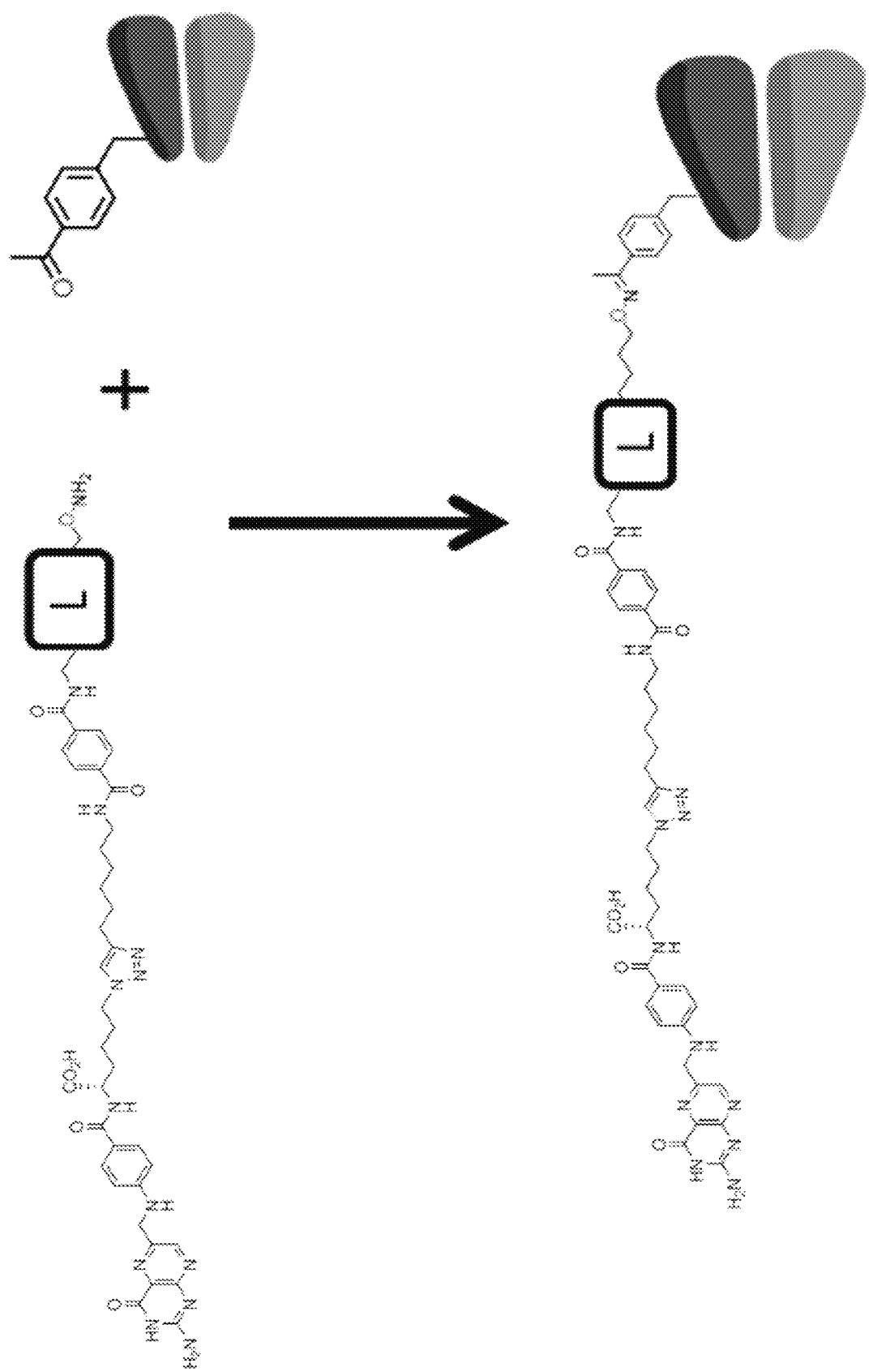
FIG. 1D shows a schematic synthesis of an anti-CD3 antibody (e.g., huL5H2) single mutant folate conjugate attached via linker (L) to the heavy chain.

In another aspect, provided herein are targeting agent antibody conjugates comprising antibodies and antibody fragments disclosed herein conjugated to one or more targeting agents. The targeting agent antibody conjugates disclosed herein may comprise one or more antibodies or antibody fragments. The targeting agent antibody conjugates disclosed herein may comprise one or more targeting agents, which may be referred to herein as multivalent targeting agent antibody conjugates. For example, the targeting agent antibody conjugate may comprise an antibody or antibody fragment with a first targeting agent conjugated to the light chain and a second targeting agent conjugated to the heavy chain (see, e.g., FIG. 1A, FIG. 1C). The targeting agent antibody conjugate may comprise an antibody or antibody fragment with a first targeting agent conjugated to the light chain and a second targeting agent conjugated to the light chain. The targeting agent antibody conjugate may comprise an antibody or antibody fragment with a first targeting agent conjugated to the heavy chain and a second targeting agent conjugated to the heavy chain. The targeting agent antibody may comprise an antibody or antibody fragment with only a first targeting agent conjugated to the heavy chain, and an unconjugated light chain (see, e.g., FIG. 1B, FIG. 1D).

The targeting agent antibody conjugates disclosed herein may comprise one or more natural amino acids, wherein the one or more targeting agents are conjugated to the one or more natural amino acids. The one or more natural amino acids, by way of non-limiting example, may be selected from a lysine and a cysteine. The targeting agent antibody conjugates disclosed herein may comprise one or more unnatural amino acids, wherein the one or more targeting agents are conjugated to the one or more unnatural amino acids. The one or more targeting agents may be conjugated to the one or more natural or unnatural amino acids via a linker.

The targeting agent antibody conjugates may bring the effector cell in proximity of a target cell, such that the effector cell may have cytotoxic activity towards the target cell. The targeting agent antibody conjugates may comprise a humanized anti-CD3 antibody or humanized anti-CD3 antibody fragment conjugated to a targeting agent. The humanized anti-CD3 antibody fragment may be a humanized anti-CD3 Fab. The humanized anti-CD3 antibody or humanized anti-CD3 antibody fragment may comprise a peptide or polypeptide represented by a sequence selected from SEQ ID NOS: 23-79, and combinations thereof.

Figure 19A:
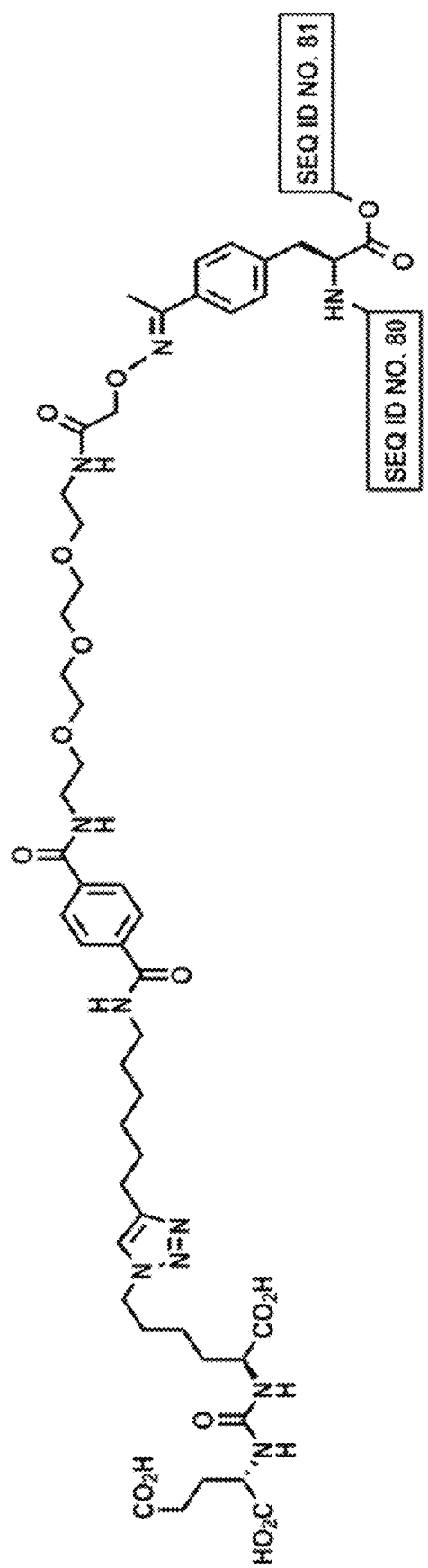
FIG. 19A and FIG. 19B show a representative heavy chain and light chain, respectively, of exemplary DUPA conjugates described herein. The N-terminal (SEQ ID NO:80) and C-terminal (SEQ ID NO: 81) of the heavy chain are connected by a non-canonical amino acid (pAcF) which is conjugated to DUPA via a linker. The N-terminal (SEQ ID NO:82) and C-terminal (SEQ ID NO: 83) of the light chain are connected by an unnatural amino acid which is conjugated to DUPA via a linker. The targeting agent antibody conjugates may comprise only a conjugated light chain, only a conjugated heavy chain, or both a conjugated light chain and a conjugated heavy chain.
Figure 19B:
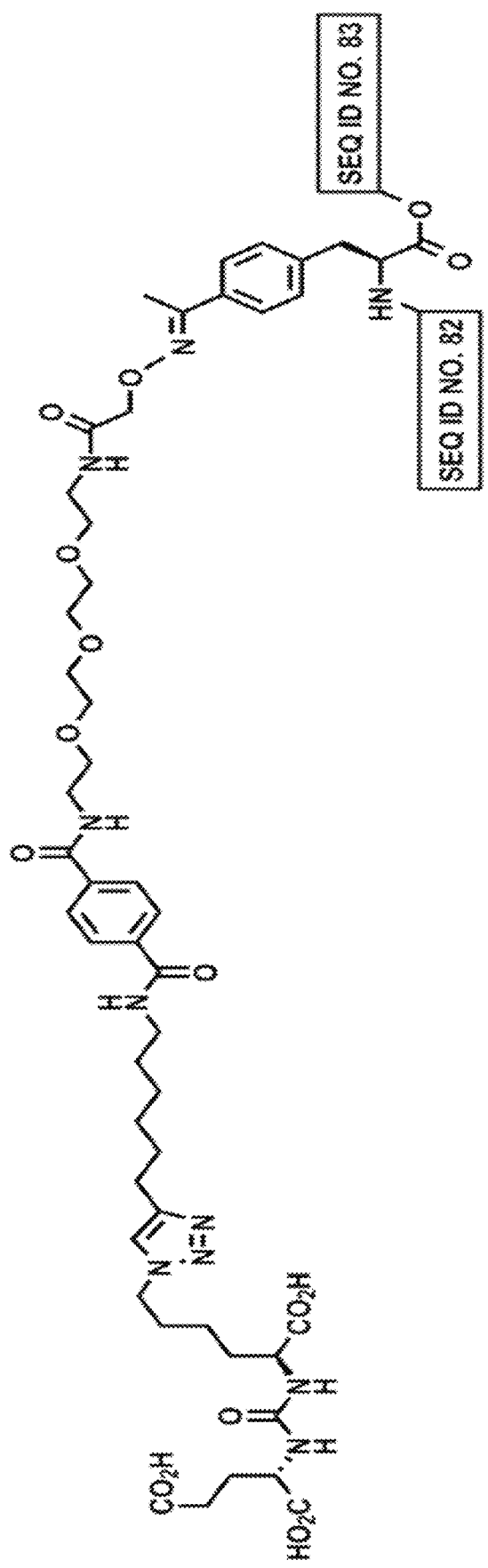

The targeting agent antibody conjugates may bring a T cell in proximity of a prostate cancer cell. The targeting agent antibody conjugates may comprise a humanized anti-CD3 antibody or humanized anti-CD3 antibody fragment conjugated to a compound that binds prostate-specific membrane antigen (PSMA). The targeting agent antibody conjugates may comprise a humanized anti-CD3 antibody or humanized anti-CD3 antibody fragment conjugated to a peptide that binds prostate-specific membrane antigen (PSMA). The targeting agent antibody conjugates may comprise a humanized anti-CD3 antibody or humanized anti-CD3 antibody fragment conjugated to 2-[3-(1,3-dicarboxypropyl)ureido]pentane dioic acid (DUPA). The targeting agent antibody conjugates may comprise a humanized anti-CD3 antibody or humanized anti-CD3 antibody or humanized anti-CD3 Fab conjugated to DUPA. The targeting agent antibody conjugates may comprise a humanized anti-CD3 antibody or humanized anti-CD3 Fab conjugated to more than one DUPA. The targeting agent antibody conjugates may comprise a humanized anti-CD3 antibody or humanized anti-CD3 Fab conjugated to two DUPAs, wherein a first DUPA is conjugated to a light chain of the humanized anti-CD3 antibody or humanized anti-CD3 Fab and the second DUPA is conjugated to a heavy chain of the humanized anti-CD3 antibody or humanized anti-CD3 Fab. The targeting agent antibody conjugates may comprise a humanized anti-CD3 antibody or humanized anti-CD3 Fab conjugated to more than one DUPA and a peptide or protein represented by an amino acid sequence selected from SEQ ID NOS. 80-83. The targeting agent antibody conjugate may be depicted in FIG. 1A and FIG. 1B. Portions of the targeting agent antibody conjugate may be depicted in FIG. 19A or FIG. 19B.

Figure 19C:
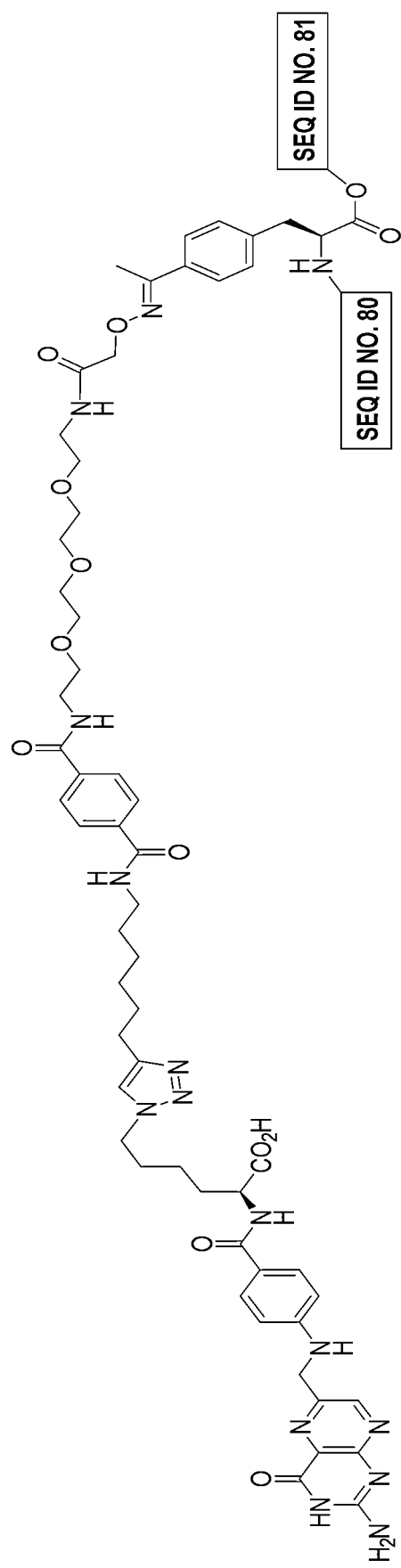
FIG. 19C and FIG. 19D show a representative heavy chain and light chain, respectively, of exemplary folate conjugates described herein. The N-terminal (SEQ ID NO:80) and C-terminal (SEQ ID NO: 81) of the heavy chain are connected by an unnatural amino acid which is conjugated to folate via a linker. The N-terminal (SEQ ID NO:82) and C-terminal (SEQ ID NO: 83) of the light chain are connected by an unnatural amino acid which is conjugated to folate via a linker. The targeting agent antibody conjugates may comprise only a conjugated light chain, only a conjugated heavy chain, or both a conjugated light chain and a conjugated heavy chain.
Figure 19D:
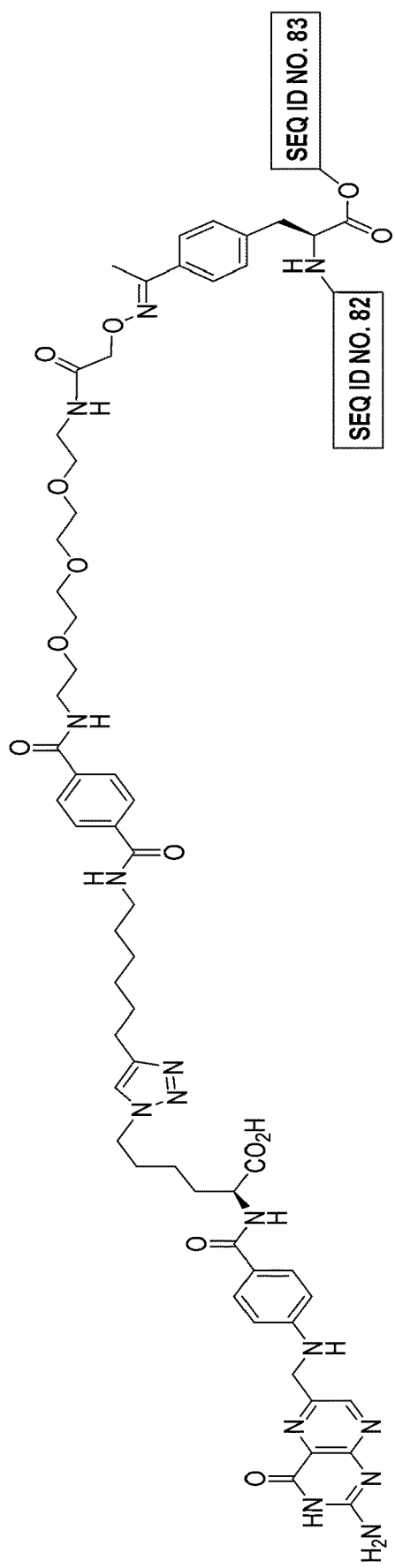

The targeting agent antibody conjugates may comprise a humanized anti-CD3 antibody or humanized anti-CD3 antibody fragment conjugated to a compound that binds folate receptor protein (FR). The targeting agent antibody conjugates may comprise a humanized anti-CD3 antibody or humanized anti-CD3 antibody fragment conjugated to a peptide that binds folate receptor protein. The targeting agent antibody conjugates may comprise a humanized anti-CD3 antibody or humanized anti-CD3 antibody fragment conjugated to N-(4-{[(2-amino-4-oxo-1,4-dihydropteridin-6-yl)methyl]amino}benzoyl)-L-glutamic acid. The targeting agent antibody conjugates may comprise a humanized anti-CD3 antibody or humanized anti-CD3 Fab conjugated to folic acid. The targeting agent antibody conjugates may comprise a humanized anti-CD3 antibody or humanized anti-CD3 Fab conjugated to more than one folic acid molecule. The targeting agent antibody conjugates may comprise a humanized anti-CD3 antibody or humanized anti-CD3 Fab conjugated to two folic acids, wherein a first folic acid is conjugated to a light chain of the humanized anti-CD3 antibody or humanized anti-CD3 Fab and the second folic acid is conjugated to a heavy chain of the humanized anti-CD3 antibody or humanized anti-CD3 Fab. The targeting agent antibody conjugates may comprise a humanized anti-CD3 antibody or humanized anti-CD3 Fab conjugated to more than one folic acid and a peptide or protein represented by an amino acid sequence selected from SEQ ID NOS. 80-83. The targeting agent antibody conjugate may be depicted in FIG. 1C and FIG. 1D. Portions of the targeting agent antibody conjugate may be depicted in FIG. 19C or FIG. 19D.

DUPA may be conjugated to the humanized anti-CD3 antibody or humanized anti-CD3 antibody fragment via a linker. DUPA and the linker together may be a compound of Formula (VI):

Formula (VI)

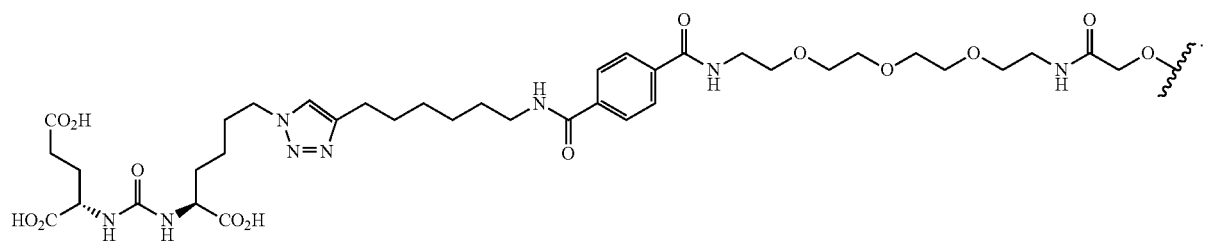

Folic acid may be conjugated to the humanized anti-CD3 antibody or humanized anti-CD3 antibody fragment via a linker. Folic acid and the linker together may be a compound of Formula (VII):

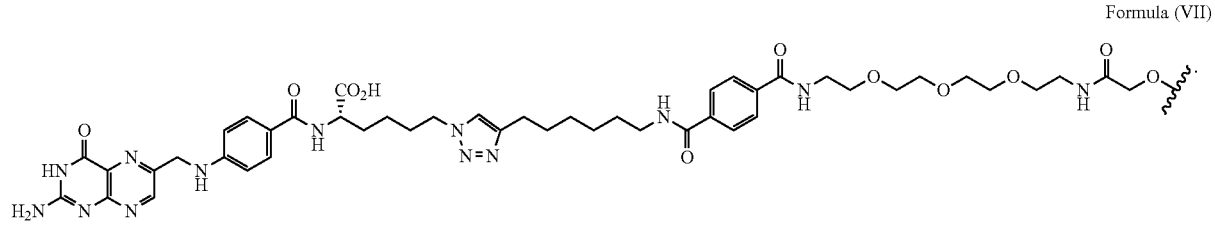 [SMILES: *OCC(=O)NCCOCCOCCOCCNC(=O)c1ccc(C(=O)NCCCCCCc2cn(CCCC[C@H](NC(=O)c3ccc(NCc4cnc5nc(N)[nH]c(=O)c5n4)cc3)C(=O)O)nn2)cc1]

Formula (VII)

Formula (VI) may be referred to herein as "p-TriA" or "P-TriA." P-TriA may be conjugated to an antibody, e.g., a Fab, via an unnatural amino acid. The Fab may comprise a light chain encoded by a nucleotide sequence selected from SEQ ID NOS: 17 and 18 and a heavy chain encoded by a nucleotide sequence selected from SEQ ID NOS: 21 and 22 (DI-huL5H2), or selected from SEQ ID NOS: 19 and 20 (huL5H2). The resulting cross-species reactive PSMA-binding/anti-CD3 antibody conjugate is referred to herein as huL5H2-P-TriA or DI-huL5H2-P-TriA. huL5H2-P-TriA and DI-huL5H2-P-TriA showed good in vitro efficacy and selectivity, and demonstrated robust in vivo anti-tumor activity in PSMA-positive C4-2 cancer xenograft and prostate cancer patient-derived xenograft (PDX) models (see, e.g., Examples 4 and 5).

Linkers

The targeting agent antibody conjugates disclosed herein may comprise one or more linkers. The targeting agent antibody conjugates disclosed herein may comprise two or more linkers. The targeting agent antibody conjugates disclosed herein may comprise three or more linkers. The targeting agent antibody conjugates disclosed herein may comprise 4, 5, 6, 7, or more linkers.

The one or more linkers may comprise a functional group. The one or more linkers may comprise an amino acid. The one or more linkers may comprise a peptide. The one or more linkers may comprise a polymer. The polymer may be a polyethylene glycol. The one or more linkers may comprise an amide. The one or more linkers may comprise phenyl group.

One or more linkers may be formed by reaction of an amino acid on the antibody with a linker already attached to the targeting agent. One or more linkers may be formed by reaction of an amino acid or another reactive functional group on the targeting agent with a linker already attached to the antibody. One or more linkers may be formed by reaction of a linker already attached to the antibody with another linker already attached to the targeting agent. In order to form a linker already attached to the antibody or the targeting agent, a bifunctional linker, with two orthogonally reactive functional groups, may be coupled to the antibody or the targeting agent, such that one remaining reactive functional group is available for subsequent coupling. The reactive functional groups may be selected from the group consisting of azides, alkynes, alkenes, dienes, nitrones, cyclooctyne, cyclopropene, trans-cyclooctene, norborene, tetrazine, and any combination thereof.

The one or more linkers may be the product of a bioorthogonal reaction between the linker already attached to the antibody and the linker already attached to the targeting agent, non-limiting examples of which are reviewed in Kim et al., Curr Opin Chem Bio 17:412-419 (2013).

The linker already attached to the antibody and the linker already attached to the targeting agent may be reacted to form a linker via cycloaddition, metathesis, metal-mediated cross-coupling reaction, radical polymerization, oxidative coupling, acyl-transfer reaction, and click chemistry. The cycloaddition may be a Huisgen-cycloaddition. The cycloaddition may be a copper-free [3+2] Huisgen-cycloaddition. The cycloaddition may be a Diels-Alder reaction. The cycloaddition may be a hetero Diels-Alder reaction. The linker may be the product of an enzyme-mediated reaction between the linker already attached to the antibody and the linker already attached to the targeting agent. The linker may be a product of a transglutaminase-mediated reaction between the linker already attached to the antibody and the linker already attached to the targeting agent, non-limiting examples of which are described in Lin et al., J. Am. Chem. Soc. 128:4542-4543 (2006) and WO 2013/093809.

The one or more linkers may comprise a disulfide bridge that connects two cysteine residues, such as ThioBridge™ technology by PolyTherics. The one or more linkers may comprise a maleimide bridge that connects two amino acid residues. The one or more linkers may comprise a maleimide bridge that connects two cysteine residues.

The one or more linkers may comprise a cleavable linker. The one or more linkers may comprise a non-cleavable linker. The one or more linkers may comprise a flexible linker. The one or more linkers may comprise an inflexible linker.

Targeting agent antibody conjugates may be optimized by adjusting linker length. The one or more linkers may be relatively short. The one or more linkers may be relatively long. The one or more linkers may be between about 1 angstroms (Å) to about 120 angstroms (Å) in length. The one or more linkers may be between about 5 angstroms (Å) to about 105 angstroms (Å) in length. The one or more linkers may be between about 10 angstroms (Å) to about 100 angstroms (Å) in length. The one or more linkers may be between about 10 angstroms (Å) to about 90 angstroms (Å) in length. The one or more linkers may be between about 10 angstroms (Å) to about 80 angstroms (Å) in length. The one or more linkers may be between about 10 angstroms (Å) to about 70 angstroms (Å) in length. The one or more linkers may be between about 15 angstroms (Å) to about 45 angstroms (Å) in length. The one or more linkers may be equal to or greater than about 4, 5, 6, 7, 8, 9, 10, 11, 12, 13, 14, 15, 16, 17, 18, 19, 20, 25, 27, 30, or more angstroms in length. The one or more linkers may be equal to or greater than about 10 angstroms in length. The one or more linkers may be equal to or greater than about 15 angstroms in length. The one or more linkers may be equal to or greater than about 20 angstroms in length. The one or more linkers may be equal to or less than about 110, 100, 90, 85, 80, 75, 70, 65, 60, 55, 50, 45, 43, 42, 41, 40, 39, 38, 37, 36, 35, 34, 33, 32, 31, 30, or fewer angstroms in length. The one or more linkers may be equal to or less than about 100 angstroms in length. The one or more linkers may be equal to or less than about 80 angstroms in length. The one or more linkers may be equal to or less than about 60 angstroms in length. The one or more linkers may be equal to or less than about 40 angstroms in length.

The one or more linkers disclosed herein may comprise a compound of Formula (II):

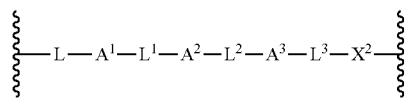

Formula (II)

wherein:

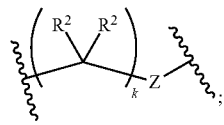

L is $A^1$ is selected from the group consisting of an aryl, a 5- to 6-membered heteroaryl, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

$L^1$ is

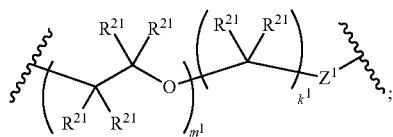

$A^2$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

$L^2$ is

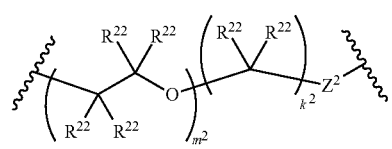

$A^3$ is a bond,

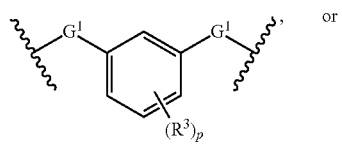

or

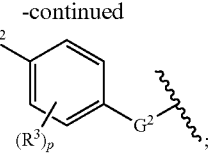

$L^3$ is

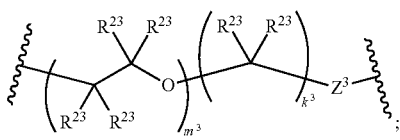

$X^2$ is

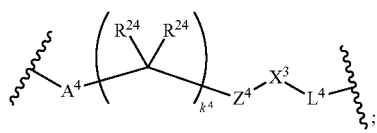

$A^4$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

each $R^1$ is independently selected from H, alkyl, and haloalkyl;

each $R^2$, $R^{21}$, $R^{22}$, $R^{23}$ and $R^{24}$ is independently selected from H, halo, —OR$^1$, —CN, —SR$^1$, alkyl, cycloalkyl, haloalkyl, arylalkyl, and heteroarylalkyl;

each $R^3$ is independently selected from halo, —OR$^1$, —CN, —SR$^1$, alkyl, cycloalkyl, haloalkyl, arylalkyl, heteroarylalkyl, —NO$_2$, and NR$^1$R$^1$;

each $G^1$ and $G^2$ is independently selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

each Z, $Z^1$, $Z^2$, and $Z^3$ is independently selected from the group consisting of a bond, —O—, and —N(R$^1$)—;

$Z^4$ is selected from a bond, aryl, and a 5- to 6-membered heteroaryl;

k, $k^1$, $k^2$, $k^3$, and $k^4$ are each independently selected from 0, 1, 2, 3, 4, 5, 6, 7, 8, 9, and 10;

$m^1$, $m^2$ and $m^3$ are each independently selected from 0, 1, 2, 3, 4, 5, 6, 7, 8, 9, and 10;

p is 0, 1, 2, 3 or 4;

$X^3$ is

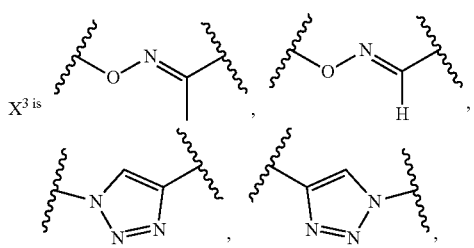

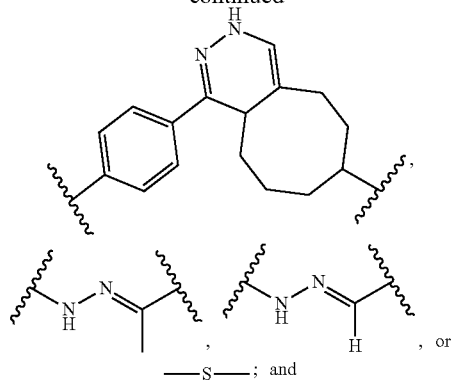
, 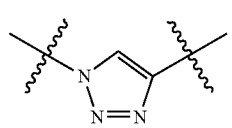; and

L⁴ is a bond directly attached to a modified amino acid; a linker bound to a modified amino acid, wherein the modified amino acid is part of the antibody; or a stereoisomer thereof.

The one or more linkers disclosed herein may comprise a compound of Formula (IIa):

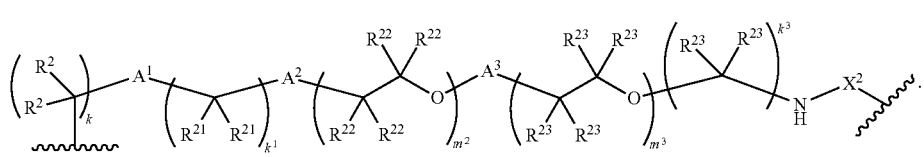

Formula (IIa)

The one or more linkers disclosed herein may comprise a compound of Formula (IIb):

Formula (IIb)

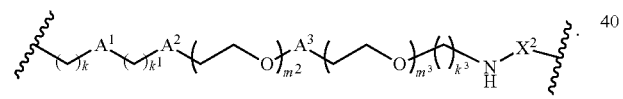

In some embodiments described above or below of a compound of Formula (II), (IIa), or (IIb), k is 1, 2, 3, or 4; and Z is a bond.

In some embodiments described above or below of a compound of Formula (II), (IIa), or (IIb), k is 4; and Z is a bond.

In some embodiments described above or below of a compound of Formula (II), (IIa), or (IIb), $A^1$ is —C(O)N($R^1$)—, a 6-membered aryl, or a 5-membered heteroaryl.

In some embodiments described above or below of a compound of Formula (II), (IIa), or (IIb), $A^1$ is —C(O)N(H)—.

In some embodiments described above or below of a compound of Formula (II), (IIa), or (IIb), $A^1$ is

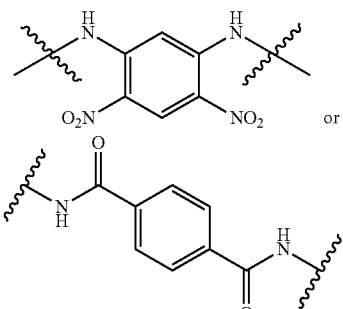

In some embodiments described above or below of a compound of Formula (II), (IIa), or (IIb), $m^1$ is 0; $k^1$ is 6 or 7; and $Z^1$ is a bond.

In some embodiments described above or below of a compound of Formula (II), (IIa), or (IIb), $A^2$ is —C(O)N(H)—; $m^2$ is 2; $k^2$ is 2; and $Z^2$ is a bond.

In some embodiments described above or below of a compound of (II), (IIa), or (IIb), $A^2$ is —C(O)N(H)—; $m^2$ is 3; $k^2$ is 2; and $Z^2$ is a bond.

In some embodiments described above or below of a compound of Formula (II), (IIa), or (IIb), $A^2$ is —C(O)N(H)—; $m^2$ is 10; $k^2$ is 2; and $Z^2$ is a bond.

In some embodiments described above or below of a compound of Formula (II), (IIa), or (IIb), $A^3$ is

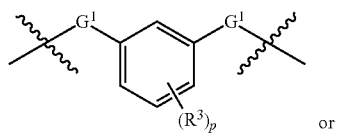

or

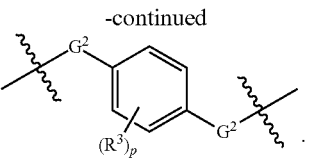

In some embodiments described above or below of a compound of Formula (II), (IIa), or (IIb), $R^3$ is —NO₂; and p is 2.

In some embodiments described above or below of a compound of Formula (II), (IIa), or (IIb), each $G^1$ and $G^2$ are independently selected from the group consisting of —C(O)—, —N(H)—, —C(O)N(H)—, and —N(H)C(O)—.

In some embodiments described above or below of a compound of Formula (II), (IIa), or (IIb), $A^3$ is In some embodiments described above or below of a compound of Formula (II), (IIa), or (IIb), $A^3$ is a bond.

In some embodiments described above or below of a compound of Formula (II), (IIa), or (IIb), $m^3$ is 0, 1, 2, or 3; $k^3$ is 2; and $Z^3$ is —NH—.

In some embodiments described above or below of a compound of Formula (II), (IIa), or (IIb), each $R^2$, $R^{21}$, $R^{22}$, $R^{23}$, and $R^{24}$ is independently selected from H, F, —CH$_3$, or —CF$_3$.

In some embodiments described above or below of a compound of Formula (II), (IIa), or (IIb), each $R^2$, $R^{21}$, $R^{22}$, $R^{23}$, and $R^{24}$ is H.

In some embodiments described above or below of a compound of Formula (II), (IIa), or (IIb), $X^2$ is

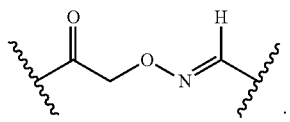 [SMILES: */C=N/OCC(*)=O]

IV. Targeting Agent Antibody Conjugate Production Methods

In another aspect, provided herein are methods of producing targeting agent antibody conjugates. The method may comprise conjugating an antibody or antibody fragment disclosed herein to a targeting agent disclosed herein. The method may comprise conjugating the targeting agent to an unnatural amino acid of the antibody or antibody fragment. The method may comprise incorporating one or more unnatural amino acids into the antibody or antibody fragment.

Incorporation of Unnatural Amino Acids

Incorporating one or more unnatural amino acids into the antibody or antibody fragment may comprise modifying one or more amino acid residues in the antibody or antibody fragment. Modifying the one or more amino acid residues in the antibody or antibody fragment may comprise mutating one or more nucleotides in the nucleotide sequence encoding the targeting agent. Mutating the one or more nucleotides in the nucleotide sequence encoding the targeting agent may comprise altering a codon encoding an amino acid to a nonsense codon.

Incorporating one or more unnatural amino acids into the antibody or antibody fragment may comprise modifying one or more amino acid residues in the antibody or antibody fragment to produce one or more amber codons in the antibody or antibody fragment.

The one or more unnatural amino acids may be incorporated into the antibody or antibody fragment in response to an amber codon. The one or more unnatural amino acids may be site-specifically incorporated into the antibody or antibody fragment.

Incorporating one or more unnatural amino acids into the antibody or antibody fragment may comprise use of one or more genetically encoded unnatural amino acids with orthogonal chemical reactivity relative to the canonical twenty amino acids to site-specifically modify the targeting agent. Incorporating the one or more unnatural amino acids may comprise use of an evolved tRNA/aminoacyl-tRNA synthetase pair to site-specifically incorporate one or more unnatural amino acids at defined sites in the targeting agent in response to one or more amber nonsense codon.

Incorporating one or more unnatural amino acids into a targeting agent may comprise modifying one or more amino acid residues in a targeting agent. Modifying the one or more amino acid residues in a targeting agent may comprise mutating one or more nucleotides in the nucleotide sequence encoding the targeting agent. Mutating the one or more nucleotides in the nucleotide sequence encoding the targeting agent may comprise altering a codon encoding an amino acid to a nonsense codon.

Incorporating one or more unnatural amino acids into a targeting agent may comprise modifying one or more amino acid residues in a targeting agent to produce one or more amber codons in a targeting agent.

The one or more unnatural amino acids may be incorporated into a targeting agent in response to an amber codon. The one or more unnatural amino acids may be site-specifically incorporated into a targeting agent.

Incorporating one or more unnatural amino acids into a targeting agent may comprise use of one or more genetically encoded unnatural amino acids with orthogonal chemical reactivity relative to the canonical twenty amino acids to site-specifically modify the targeting agent. Incorporating the one or more unnatural amino acids may comprise use of an evolved tRNA/aminoacyl-tRNA synthetase pair to site-specifically incorporate one or more unnatural amino acids at defined sites in the targeting agent in response to one or more amber nonsense codon.

Additional methods for incorporating unnatural amino acids include, but are not limited to, methods disclosed in Chatterjee et al. (A Versatile Platform for Single- and Multiple-Unnatural Amino Acid Mutagenesis in *Escherichia coli*, Biochemistry, 2013), Kazane et al. (*J Am Chem Soc*, 135(1):340-6, 2013), Kim et al. (*J Am Chem Soc*, 134(24): 9918-21, 2012), Johnson et al. (*Nat Chem Biol*, 7(11):779-86, 2011), and Hutchins et al. (*J Mol Biol*, 406(4):595-603, 2011).

Linking Antibodies, Antibody Fragments, and/or Targeting Agents

The methods may comprise linking the antibody, antibody fragment, targeting agent or intermediates thereof to produce a targeting agent antibody conjugate comprising (a) an antibody or antibody fragment; (b) one or more linkers; and (c) a targeting agent, wherein the one or more linkers link the first antibody or antibody fragment to the targeting agent. The method may further comprise conjugating the one or more linkers to a targeting agent to produce a targeting agent-linker intermediate and coupling the targeting agent-linker intermediate to the antibody or antibody fragment. The method may further comprise conjugating the one or more linkers to the antibody or antibody fragment to produce an antibody-linker intermediate or antibody fragment-linker intermediate and coupling the antibody-linker intermediate or antibody-fragment-linker intermediate to the targeting agent. Coupling an intermediate to an antibody, antibody fragment or targeting agent may comprise formation of an oxime. Coupling an intermediate to an antibody, antibody fragment or targeting agent may comprise formation of the oxime in an acidic solution. Coupling an intermediate to an antibody, antibody fragment or targeting agent may comprise formation of the oxime in a slightly acidic solution. Coupling an intermediate to an antibody, antibody fragment or targeting agent may comprise formation of the oxime in a slightly neutral solution. The antibody or antibody fragment may comprise an unnatural amino acid. Linking the antibody or antibody fragment to the targeting agent-linker intermediate may comprise forming an oxime between the unnatural amino acid and the targeting agent-linker intermediate. The targeting agent may comprise an unnatural amino acid. Linking the targeting agent to the antibody-linker intermediate or antibody fragment-linker intermediate may comprise forming an oxime between the unnatural amino acid and the antibody-linker intermediate or the antibody fragment-linker intermediate.

The method of producing a targeting agent antibody conjugate may comprise (a) conjugating a first linker to the antibody or antibody fragment to produce an antibody-linker intermediate or antibody fragment-linker intermediate; (b) conjugating a second linker to the targeting agent to produce a targeting agent-linker intermediate; and (c) linking the two intermediates together to produce the targeting agent antibody conjugate. Conjugating the linker to the antibody, antibody fragment, or targeting agent may comprise production of an ionic bond, a covalent bond, a non-covalent bond, or a combination thereof between the linker and the antibody, antibody fragment, or targeting agent. Conjugating the linker to the antibody, antibody fragment or targeting agent may be performed as described in Roberts et al., Advanced Drug Delivery Reviews 54:459-476 (2002).

The methods disclosed herein may comprise coupling one or more linkers to one or more antibodies, antibody fragments, targeting agents, or combinations thereof to produce one or more intermediates such as an antibody-linker intermediate, an antibody fragment-linker intermediate and/or a targeting agent antibody conjugate-linker intermediate. The methods may comprise coupling a first linker to an antibody or antibody fragment to produce an antibody-linker intermediate or antibody fragment-linker intermediate. The methods may comprise coupling a linker to a targeting agent to produce a targeting agent-linker intermediate.

Coupling of the one or more linkers to the antibody, antibody fragment, or targeting agent may occur simultaneously. Coupling of the one or more linkers to the antibody, antibody fragment, or targeting molecule may occur sequentially. Coupling of the one or more linkers to the antibody, antibody fragment, or targeting molecule may occur in a single reaction volume. Coupling of the one or more linkers to the antibody, antibody fragment, or targeting molecule may occur in two or more reaction volumes.

Coupling one or more linkers to the antibody, antibody fragment and/or targeting molecule may comprise forming one or more oximes between the linker and the antibody, antibody fragment or targeting molecule. Coupling one or more linkers to the antibody, antibody fragment and/or targeting agent may comprise forming one or more stable bonds between linker and the antibody, antibody fragment or targeting agent. Coupling one or more linkers to the antibody, antibody fragment and/or targeting agent may comprise forming one or more covalent bonds between linker and the antibody, antibody fragment or targeting agent. Coupling one or more linkers to the antibody, antibody fragment and/or targeting agent may comprise forming one or more non-covalent bonds between linker and the antibody, antibody fragment or targeting agent. Coupling one or more linkers to the antibody, antibody fragment and/or ligand may comprise forming one or more ionic bonds between linker and the antibody, antibody fragment or targeting agent.

Coupling one or more linkers to the antibody or antibody fragment may comprise site specifically coupling one or more linkers to the antibody or antibody fragment. Site-specific coupling may comprise linking the one or more linkers to the unnatural amino acid of the antibody or antibody fragment. Linking the one or more linkers to the unnatural amino acid of the antibody or antibody fragment may comprise formation of an oxime. Linking the one or more linkers to the unnatural amino acid of the antibody or antibody fragment may comprise formation of a sulfide. Linking the one or more linkers to the unnatural amino acid of the antibody or antibody fragment may comprise, by way of non-limiting example, reacting a hydroxylamine of the one or more linkers with an aldehyde or ketone of an amino acid. The amino acid may be an unnatural amino acid. Linking the one or more linkers to the unnatural amino acid of the antibody or antibody fragment may comprise, by way of non-limiting example, reacting a bromo derivative of the one or more linkers with thiol of an amino acid. The amino acid may be an unnatural amino acid.

The targeting agent antibody conjugate may be of Formula (I): X-L-Y or Formula (IA): Y-L-X, wherein:

a. X comprises the antibody or antibody fragment;

b. L comprises the one or more linkers; and c. Y comprises one or more DUPA molecules.

The targeting agent antibody conjugate may comprise a compound of Formula (III):

Formula (III)

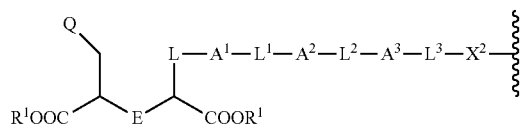

wherein:

L is

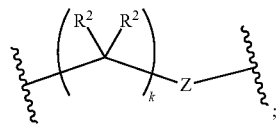

$A^1$ is selected from the group consisting of an aryl, a 5- to 6-membered heteroaryl, —C(O)—, —N($R^1$)—, —O—, —C(O)N($R^1$)—, —N($R^1$)C(O)—, —S(O)$_{1,2}$N($R^1$)—, and —N($R^1$)S(O)$_{1,2}$—;

$L^1$ is

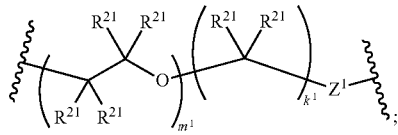

$A^2$ is selected from the group consisting of a bond, —C(O)—, —N($R^1$)—, —O—, —C(O)N($R^1$)—, —N($R^1$)C(O)—, —S(O)$_{1,2}$N($R^1$)—, and —N($R^1$)S(O)$_{1,2}$—;

$L^2$ is

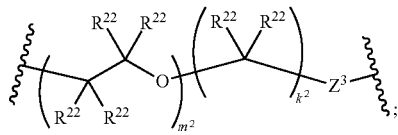

$A^3$ is a bond,

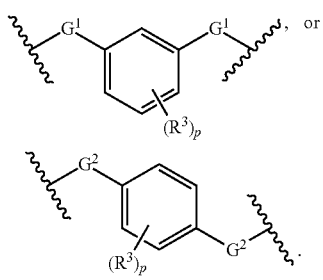, or $L^3$ is

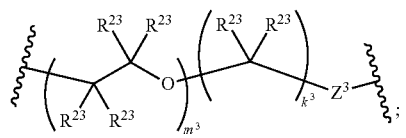;

$X^2$ is

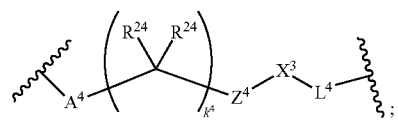;

$A^4$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

each R$^1$ is independently selected from H, alkyl, and haloalkyl;

each R$^2$, R$^{21}$, R$^{22}$, R$^{23}$, and R$^{24}$ is independently selected from H, halo, —OR$^1$, —CN, —SR$^1$, alkyl, cycloalkyl, haloalkyl, arylalkyl, and heteroarylalkyl;

each R$^3$ is independently selected from halo, —OR$^1$, —CN, —SR$^1$, alkyl, cycloalkyl, haloalkyl, arylalkyl, heteroarylalkyl, —NO$_2$, and NR$^1$R$^1$;

each G$^1$ and G$^2$ is independently selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

each Z, Z$^1$, Z$^2$, and Z$^3$ is independently selected from the group consisting of a bond, —O—, and —N(R$^1$)—;

Z$^4$ is selected from a bond, aryl, and a 5- to 6-membered heteroaryl;

k, k$^1$, k$^2$, k$^3$, and k$^4$ are each independently selected from 0, 1, 2, 3, 4, 5, 6, 7, 8, 9, and 10;

m$^1$, m$^2$ and m$^3$ are each independently selected from 0, 1, 2, 3, 4, 5, 6, 7, 8, 9, and 10;

p is 0, 1, 2, 3 or 4;

$X^3$ is

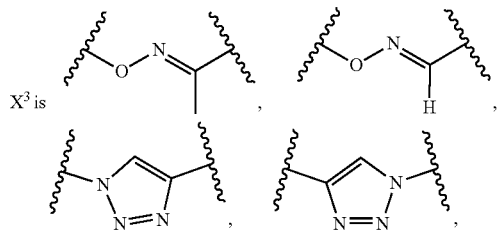,

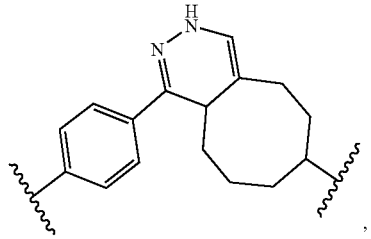,

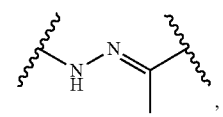,

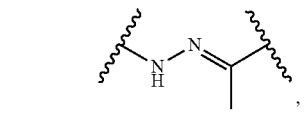, or —S—;

$L^4$ is a bond directly attached to a modified amino acid, or a linker bound to a modified amino acid, wherein the modified amino acid is part of the antibody;

Q is selected from the group consisting of:

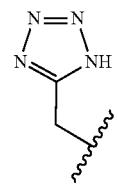,

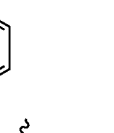, and ;

E is selected from the group consisting of:

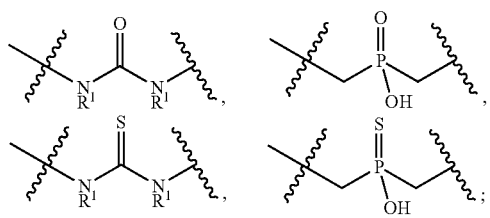

and a stereoisomer thereof.

The targeting agent antibody conjugate may comprise a compound of Formula (IIIa):

Formula (IIIa)

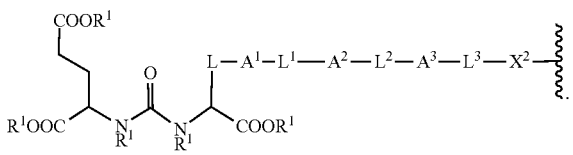

The targeting agent antibody conjugate may comprise a compound of Formula (IIIb):

Formula (IIIb)

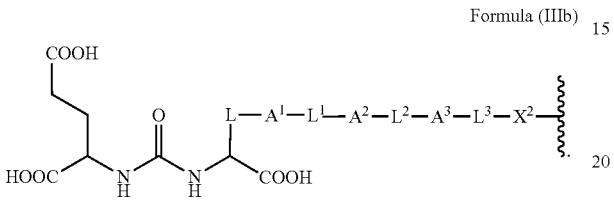

The targeting agent antibody conjugate may comprise a compound of Formula (IIIc):

Formula (IIIc)

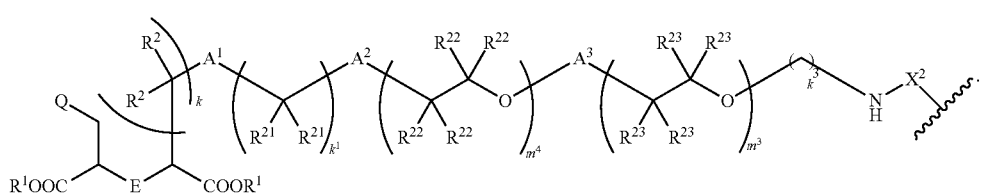

The targeting agent antibody conjugate may comprise a compound of Formula (IIId):

Formula (IIId)

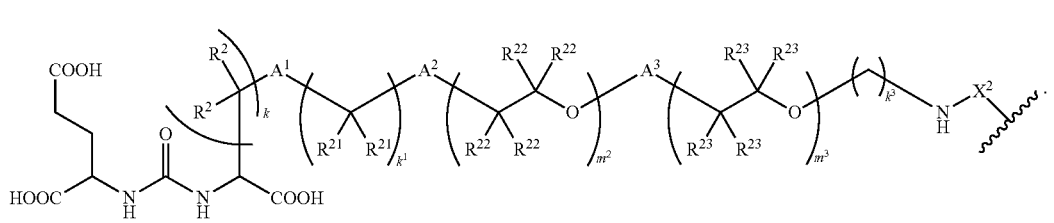

The targeting agent antibody conjugate may comprise a compound of Formula (IIIe):

Formula (IIIe)

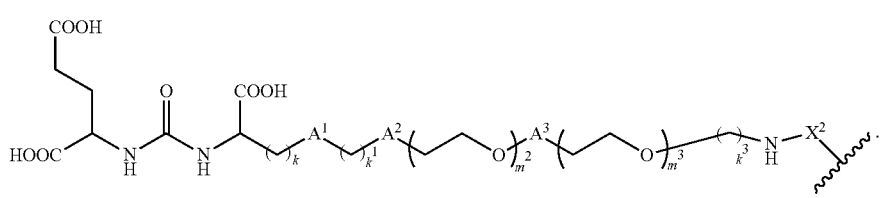

In some embodiments described above or below of a compound of Formula (III), (IIIa), (IIIb), (IIIc), (IIId), or (IIIe), k is 1, 2, 3, or 4; and Z is a bond.

In some embodiments described above or below of a compound of Formula (III), (IIIa), (IIIb), (IIIc), (IIId), or (IIIe), k is 4; and Z is a bond.

In some embodiments described above or below of a compound of Formula (III), (IIIa), (IIIb), (IIIc), (IIId), or (IIIe), $A^1$ is —C(O)N($R^1$)—, a 6-membered aryl, or a 5-membered heteroaryl.

In some embodiments described above or below of a compound of Formula (III), (IIIa), (IIIb), (IIIc), (IIId), or (IIIe), $A^1$ is —C(O)N(H)—.

In some embodiments described above or below of a compound of Formula (III), (IIIa), (IIIb), (IIIc), (IIId), or (IIIe), $A^1$ is

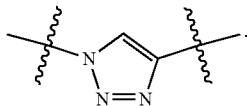 [SMILES: *c1cn(*)nn1]

In some embodiments described above or below of a compound of Formula (III), (IIIa), (IIIb), (IIIc), (IIId), or (IIIe), $m^1$ is 0; $k^1$ is 6 or 7; and $Z^1$ is a bond.

In some embodiments described above or below of a compound of Formula (III), (IIIa), (IIIb), (IIIc), (IIId), or (IIIe), $A^2$ is —C(O)N(H)—; $m^2$ is 2; $k^2$ is 2; and $Z^2$ is a bond.

In some embodiments described above or below of a compound of Formula (III), (IIIa), (IIIb), (IIIc), (IIId), or (IIIe), $A^2$ is —C(O)N(H)—; $m^2$ is 3; $k^2$ is 2; and $Z^2$ is a bond.

In some embodiments described above or below of a compound of Formula (III), (IIIa), (IIIb), (IIIc), (IIId), or (IIIe), $A^2$ is —C(O)N(H)—; $m^2$ is 10; $k^2$ is 2; and $Z^2$ is a bond.

In some embodiments described above or below of a compound of Formula (III), (IIIa), (IIIb), (IIIc), (IIId), or (IIIe), $A^3$ is

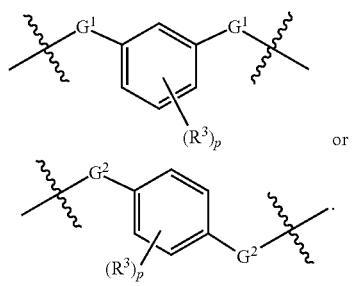

or

In some embodiments described above or below of a compound of Formula (III), (IIIa), (IIIb), (IIIc), (IIId), or (IIIe), $R^3$ is —NO$_2$; and p is 2.

In some embodiments described above or below of a compound of Formula (III), (IIIa), (IIIb), (IIIc), (IIId), or (IIIe), each $G^1$ and $G^2$ are independently selected from the group consisting of —C(O)—, —N(H)—, —C(O)N(H)—, and —N(H)C(O)—.

In some embodiments described above or below of a compound of Formula (III), (IIIa), (IIIb), (IIIc), (IIId), or (IIIe), $A^3$ is

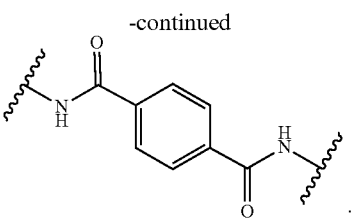

or

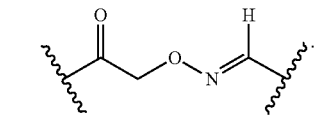 [SMILES: */C=N/OCC(*)=O]

In some embodiments described above or below of a compound of Formula (III), (IIIa), (IIIb), (IIIc), (IIId), or (IIIe), $A^3$ is a bond.

In some embodiments described above or below of a compound of Formula (III), (IIIa), (IIIb), (IIIc), (IIId), or (IIIe), $m^3$ is 0, 1, 2, or 3; $k^3$ is 2; and $Z^3$ is —NH—.

In some embodiments described above or below of a compound of Formula (III), (IIIa), (IIIb), (IIIc), (IIId), or (IIIe), each $R^2$, $R^{21}$, $R^{22}$, $R^{23}$, and $R^{24}$ is independently selected from H, F, —CH$_3$, and —CF$_3$.

In some embodiments described above or below of a compound of Formula (III), (IIIa), (IIIb), (IIIc), (IIId), or (IIIe), each $R^2$, $R^{21}$, $R^{22}$, $R^{23}$, and $R^{24}$ is H.

In some embodiments described above or below of a compound of Formula (III), (IIIa), (IIIb), (IIIc), (IIId), or (IIIe), $X^2$ is In some embodiments described above or below of a compound of Formula (III), the compound is selected from:

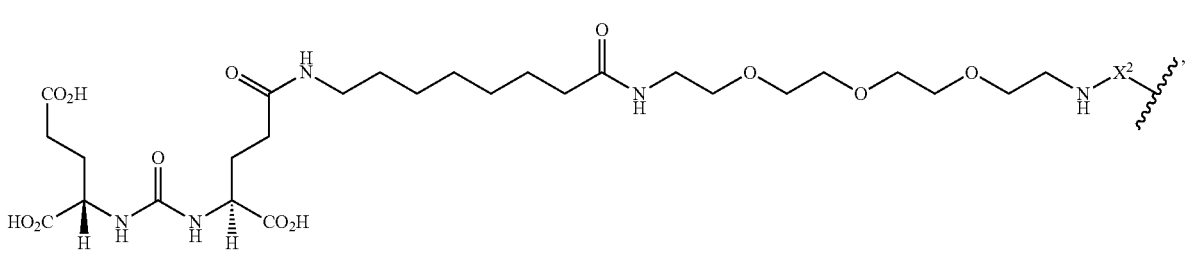

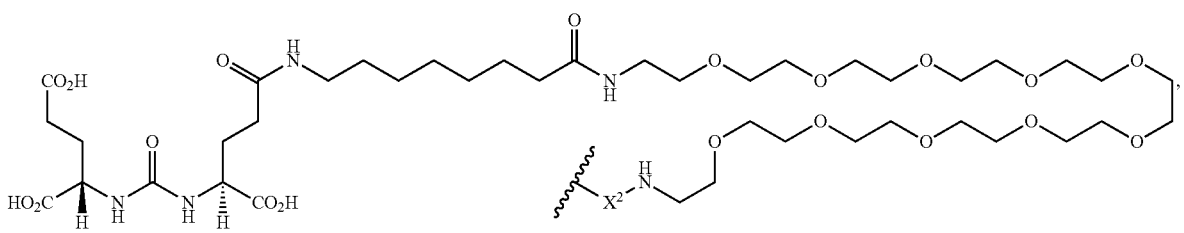

-continued

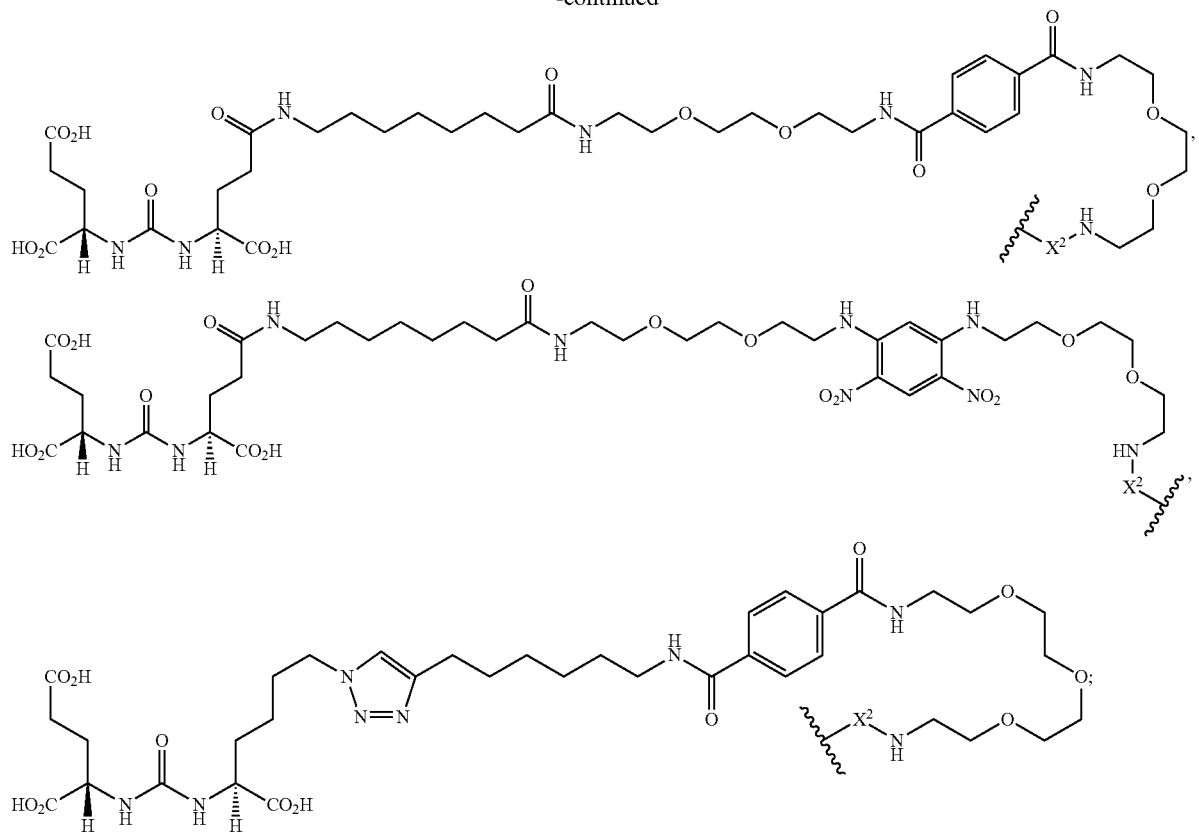

and a stereoisomer thereof.

The targeting agent antibody conjugate may comprise a compound of Formula (IV):

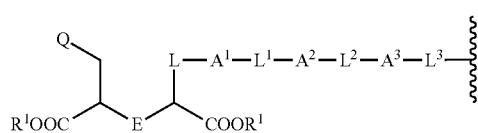

Formula (IV)

wherein:

L is

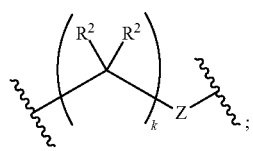

$A^1$ is selected from the group consisting of an aryl, a 5- to 6-membered heteroaryl, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

$L^1$ is

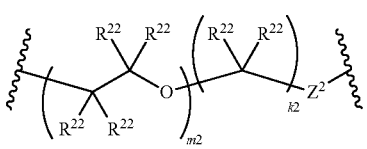

$A^2$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

$L^2$ is

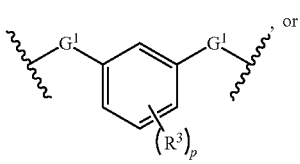

$A^3$ is a bond,

, or

-continued

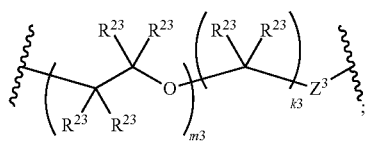

$L^3$ is

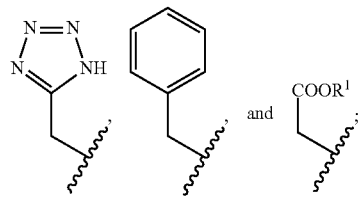

each $R^1$ is independently selected from H, alkyl, and haloalkyl;

each $R^2$, $R^{21}$, $R^{22}$, and $R^{23}$ is independently selected from H, halo, —$OR^1$, —CN, —$SR^1$, alkyl, cycloalkyl, haloalkyl, arylalkyl, and heteroarylalkyl;

each $R^3$ is independently selected from halo, —$OR^1$, —CN, —$SR^1$, alkyl, cycloalkyl, haloalkyl, arylalkyl, heteroarylalkyl, —$NO_2$, and $NR^1R^1$;

each $G^1$ and $G^2$ is independently selected from the group consisting of a bond, —C(O)—, —N($R^1$)—, —O—, —C(O)N($R^1$)—, —N($R^1$)C(O)—, —S(O)$_{1,2}$N($R^1$)—, and —N($R^1$)S(O)$_{1,2}$—;

each Z, $Z^1$, $Z^2$, and $Z^3$ is independently selected from the group consisting of a bond, —O—, and —N($R^1$)—;

k, $k^1$, $k^2$, and $k^3$ are each independently selected from 0, 1, 2, 3, 4, 5, 6, 7, 8, 9, and 10;

$m^1$, $m^2$ and $m^3$ are each independently selected from 0, 1, 2, 3, 4, 5, 6, 7, 8, 9, and 10;

p is 0, 1, 2, 3 or 4;

Q is selected from the group consisting of:

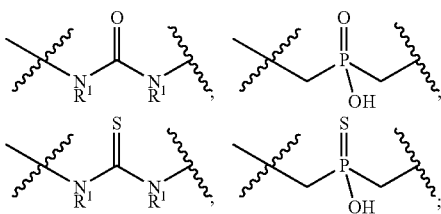

E is selected from the group consisting of:

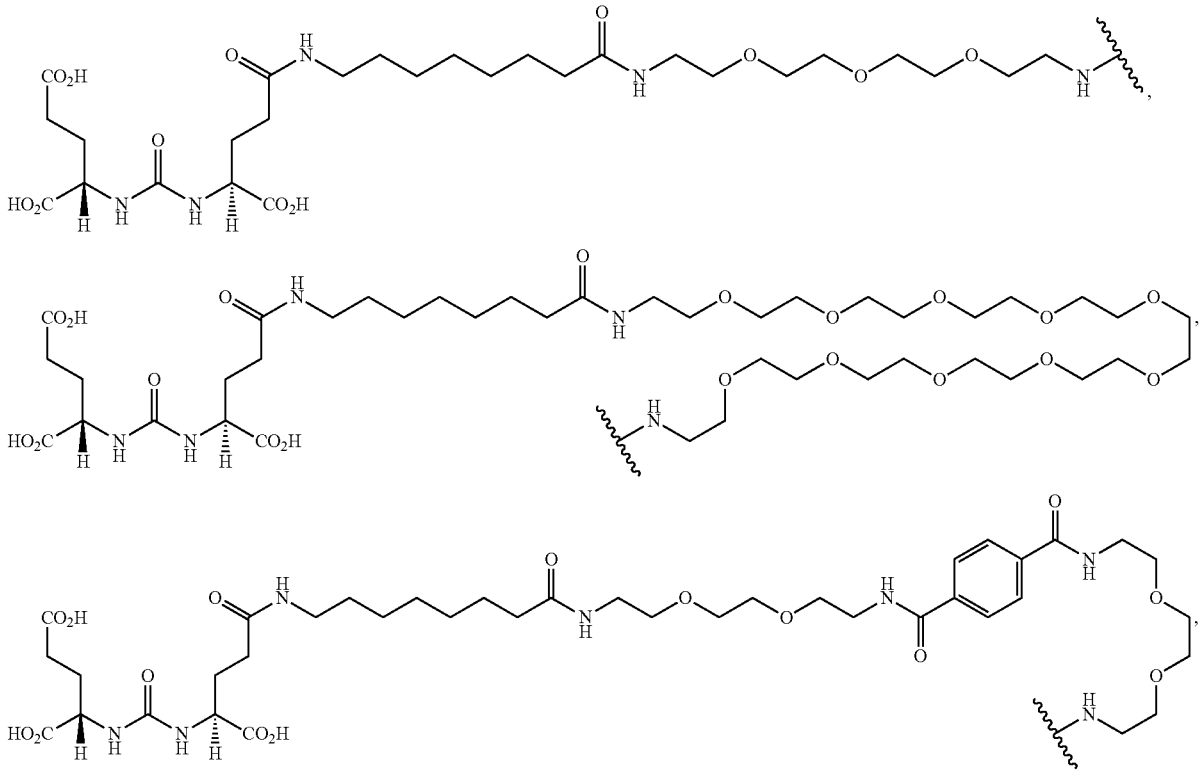

and a stereoisomer thereof.

In some embodiments described above or below of a compound of Formula (IV), the compound is selected from:

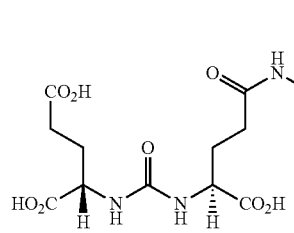
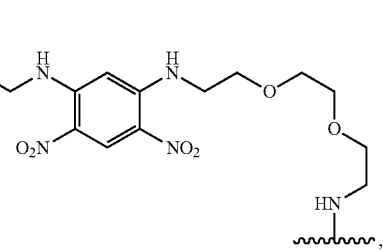

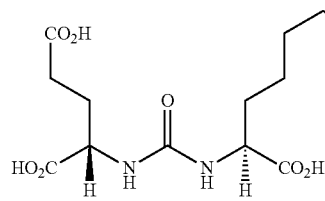
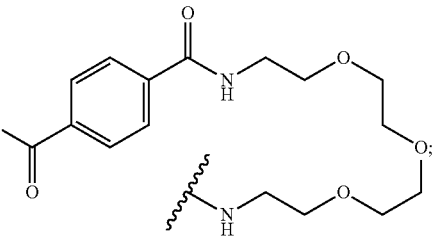

and a stereoisomer thereof.

The targeting agent antibody conjugate may comprise a compound of Formula (V):

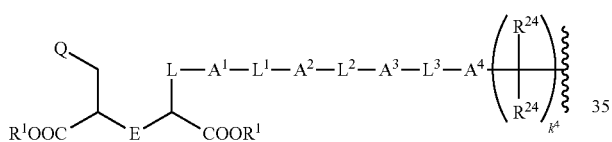

Formula (V)

wherein:

L is

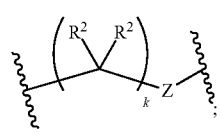

$A^1$ is selected from the group consisting of an aryl, a 5- to 6-membered heteroaryl, —C(O)—, —N($R^1$)—, —O—, —C(O)N($R^1$)—, —N($R^1$)C(O)—, —S(O)$_{1,2}$N($R^1$)—, and —N($R^1$)S(O)$_{1,2}$—;

$L^1$ is

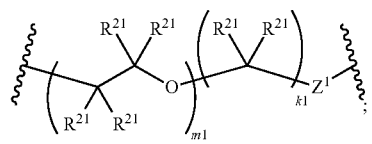

$A^2$ is selected from the group consisting of a bond, —C(O)—, —N($R^1$)—, —O—, —C(O)N($R^1$)—, —N($R^1$)C(O)—, —S(O)$_{1,2}$N($R^1$)—, and —N($R^1$)S(O)$_{1,2}$—;

$L^2$ is

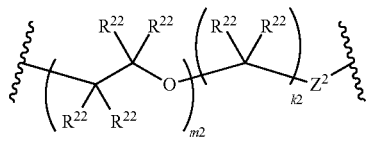

$A^3$ is a bond,

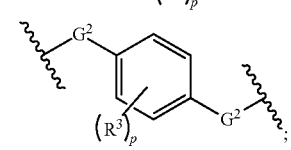

$L^3$ is

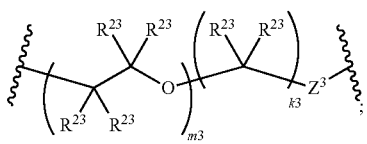

$A^4$ is selected from the group consisting of a bond, —C(O)—, —N($R^1$)—, —O—, —C(O)N($R^1$)—, —N($R^1$)C(O)—, —S(O)$_{1,2}$N($R^1$)—, and —N($R^1$)S(O)$_{1,2}$—;

each $R^1$ is independently selected from H, alkyl, and haloalkyl;

each $R^2$, $R^{21}$, $R^{22}$, $R^{23}$, and $R^{24}$ is independently selected from H, halo, —$OR^1$, —CN, —$SR^1$, alkyl, cycloalkyl, haloalkyl, arylalkyl, and heteroarylalkyl;

each R³ is independently selected from halo, —OR¹, —CN, —SR¹, alkyl, cycloalkyl, haloalkyl, arylalkyl, heteroarylalkyl, —NO₂, and NR¹R¹;

each G¹ and G² is independently selected from the group consisting of a bond, —C(O)—, —N(R¹)—, —O—, —C(O)N(R¹)—, —N(R¹)C(O)—, —S(O)₁,₂N(R¹)—, and —N(R¹)S(O)₁,₂—;

each Z, Z¹, Z², and Z³ is independently selected from the group consisting of a bond, —O—, and —N(R¹)—;

k, k¹, k², k³, and k⁴ are each independently selected from 0, 1, 2, 3, 4, 5, 6, 7, 8, 9, and 10;

m¹, m² and m³ are each independently selected from 0, 1, 2, 3, 4, 5, 6, 7, 8, 9, and 10;

p is 0, 1, 2, 3 or 4;

Q is selected from the group consisting of:

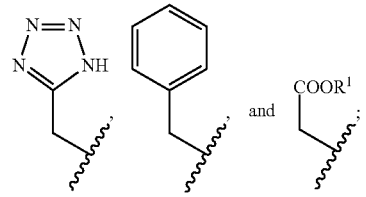

E is selected from the group consisting of:

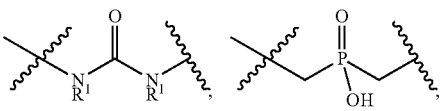

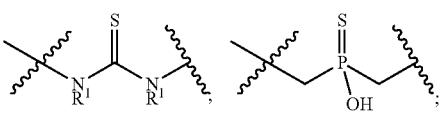

and a stereoisomer thereof.

In some embodiments described above or below of a compound of Formula (V), the compound is selected from:

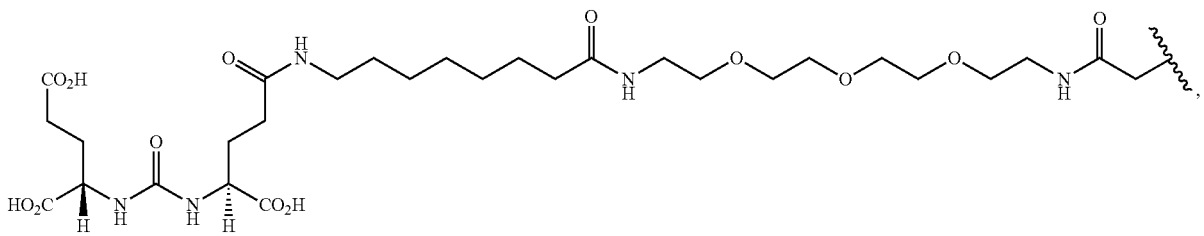

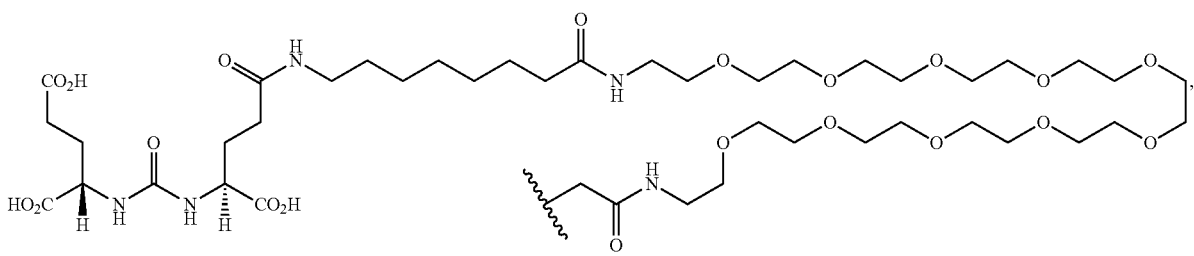

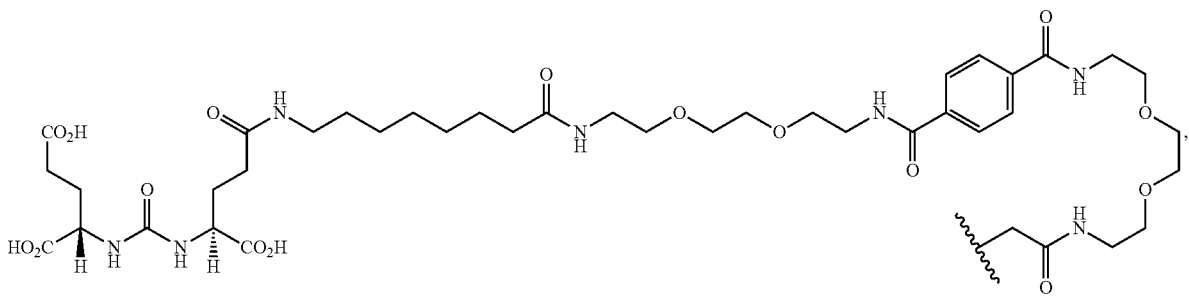

-continued
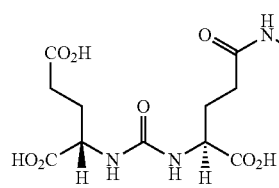 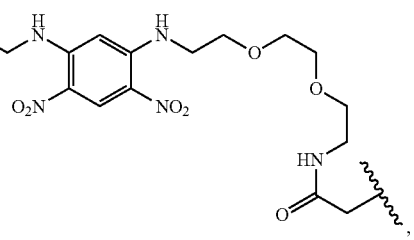
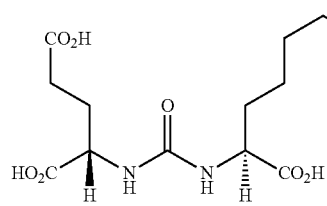 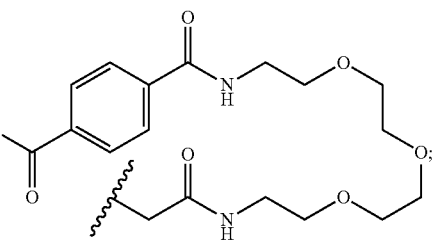
and a stereoisomer thereof.
In some embodiments, the targeting agent-linker comprises a compound selected from:
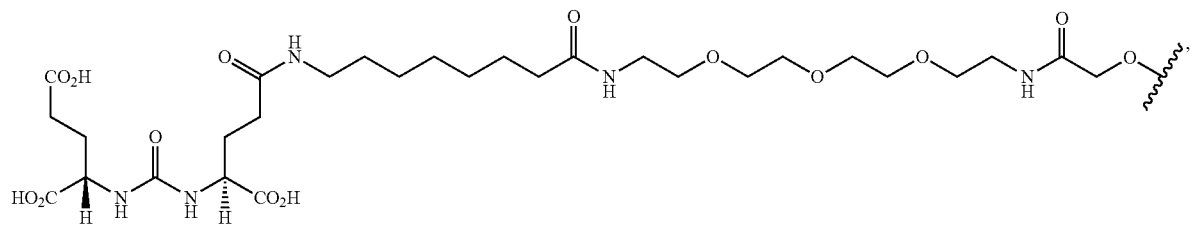
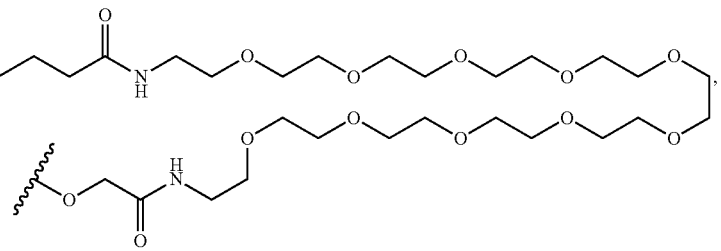
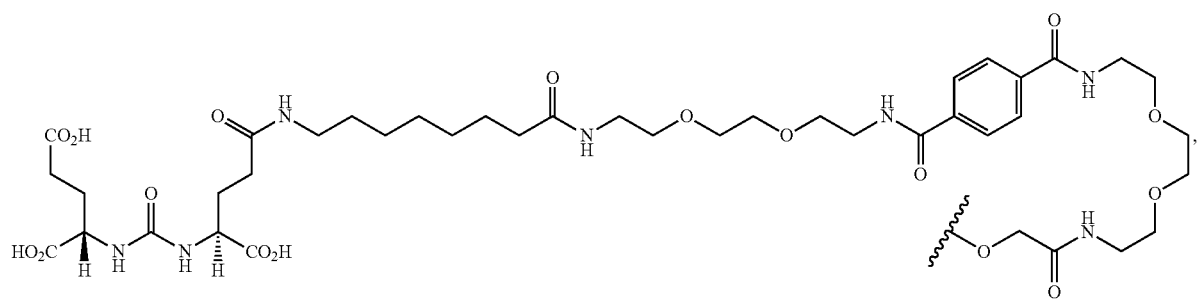

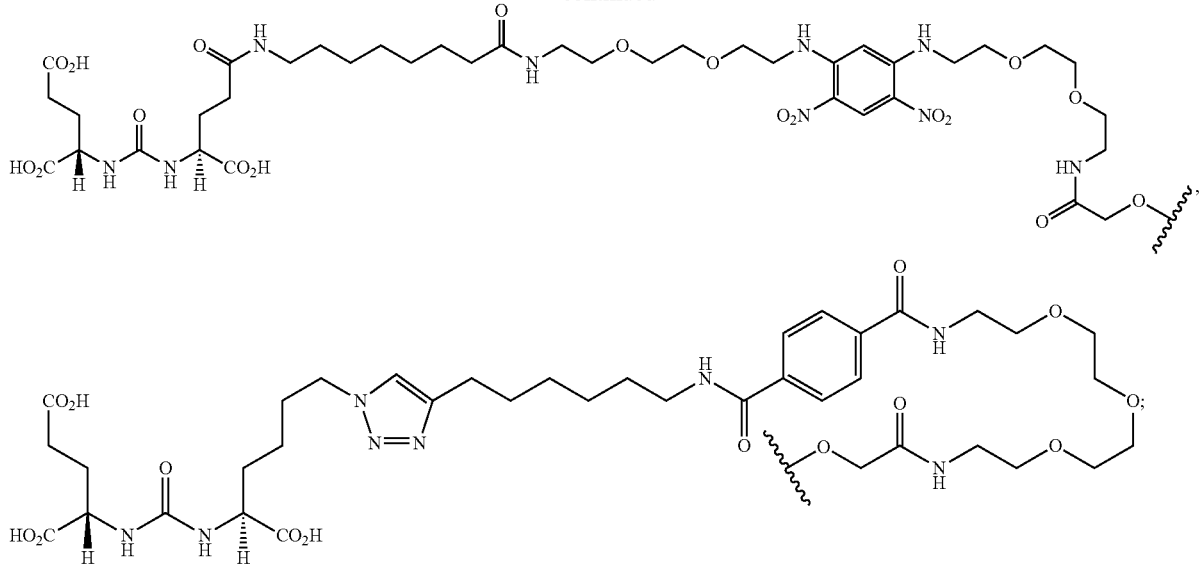

and a stereoisomer thereof.

In some embodiments, the targeting agent-linker comprises a compound selected from:

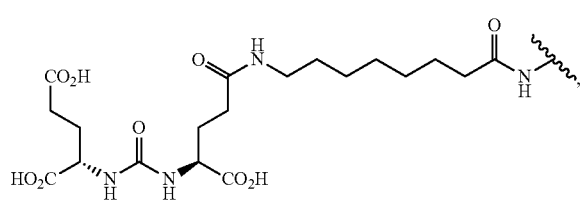

and a stereoisomer thereof.

IV. Pharmaceutical Compositions

Disclosed herein are pharmaceutical compositions that comprise an antibody and/or targeting agent antibody conjugates disclosed herein and a pharmaceutically acceptable carrier or excipient. The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

Pharmaceutical compositions herein may be formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

A pharmaceutical composition disclosed herein may further comprise a pharmaceutically acceptable diluent(s), excipient(s), or carrier(s). The pharmaceutical compositions may include other medicinal or pharmaceutical agents; carriers; adjuvants; preserving, stabilizing, wetting or emulsifying agents; solution promoters; salts for regulating the osmotic pressure; and/or buffers. In addition, the pharmaceutical compositions also contain other therapeutically valuable substances.

A pharmaceutical composition disclosed herein may be administered to a subject by any suitable administration route, including but not limited to, parenteral (intravenous, subcutaneous, intraperitoneal, intramuscular, intravascular, intrathecal, intravitreal, infusion, or local), topical, oral, or nasal administration. A suitable administration route may comprise a microneedle device.

Formulations suitable for intramuscular, subcutaneous, peritumoral, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor, and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent may be optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi-dose containers, with an added preservative. The pharmaceutical compositions described herein may be in a form suitable for parenteral injection as sterile suspension, solution or emulsion in oily or aqueous vehicle, and contain formulatory agents such as suspending, stabilizing, and/or dispersing agents. Pharmaceutical formulations for parenteral administration include aqueous solutions of an active agent in water soluble form. Additionally, suspensions are optionally prepared as appropriate oily injection suspensions.

The pharmaceutical composition described herein may be in unit dosage forms suitable for single administration of precise dosages. In unit dosage form, the formulation may be divided into unit doses containing appropriate quantities of an active agent disclosed herein. The unit dosage may be in the form of a package containing discrete quantities of the formulation. Non-limiting examples are packaged tablets or capsules, and powders in vials or ampoules. Aqueous suspension compositions may be packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

The pharmaceutical composition may be administered once daily, twice daily, three times daily or more. The pharmaceutical composition may be administered once weekly, twice weekly, three times weekly or more. The pharmaceutical composition may be administered bi-weekly. The pharmaceutical composition may be administered monthly. The pharmaceutical composition may be administered as needed.

The pharmaceutical composition may be co-administered with a therapeutic treatment (e.g., anti-inflammatory treatment, antibiotic, anti-viral drug, chemotherapy, radiation). The therapeutic treatment may comprise an additional targeting agent antibody conjugate.

V. Therapeutic Uses

Disclosed herein are methods of treating a subject for a condition with a targeting agent antibody conjugate or pharmaceutical composition disclosed herein.

The condition, by way of non-limiting example, may be a cancer. The cancer, by way of non-limiting example, may be selected from prostate cancer, breast cancer, brain cancer, pancreatic cancer, skin cancer, lung cancer, liver cancer, colon cancer, bladder cancer, ovarian cancer, uterine cancer, leukemia, lymphoma, and testicular cancer. The cancer may be a prostate cancer. The cancer may comprise a recurrent and/or refractory cancer. Examples of cancers include, but are not limited to, sarcomas, carcinomas, lymphomas, or leukemias.

The cancer may comprise a neuroendocrine cancer. The cancer may comprise a pancreatic cancer. The cancer may comprise an exocrine pancreatic cancer. The cancer may comprise a thyroid cancer. The thyroid cancer may comprise a medullary thyroid cancer.

The cancer may comprise a prostate cancer. The prostate cancer may be a PSMA-positive prostate cancer. PSMA expression may be highly upregulated and restricted to cancer cells in some or all stages of the prostate cancer. The cancer may be hormone-refractory prostate cancer.

The cancer may comprise an epithelial cancer. The cancer may comprise a breast cancer. The cancer may comprise an endometrial cancer. The cancer may comprise an ovarian cancer. The ovarian cancer may comprise a stromal ovarian cancer. The cancer may comprise a cervical cancer.

The cancer may comprise a skin cancer. The skin cancer may comprise a neo-angiogenic skin cancer. The skin cancer may comprise a melanoma.

The cancer may comprise a kidney cancer.

The cancer may comprise a lung cancer. The lung cancer may comprise a small cell lung cancer. The lung cancer may comprise a non-small cell lung cancer.

The cancer may comprise a colorectal cancer. The cancer may comprise a gastric cancer. The cancer may comprise a colon cancer.

The cancer may comprise a brain cancer. The brain cancer may comprise a brain tumor. The cancer may comprise a glioblastoma. The cancer may comprise an astrocytoma.

The cancer may comprise a blood cancer. The blood cancer may comprise a leukemia. The leukemia may comprise a myeloid leukemia. The cancer may comprise a lymphoma. The lymphoma may comprise a non-Hodgkin's lymphoma.

The cancer may comprise a sarcoma. The sarcoma may comprise an Ewing's sarcoma.

Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis.

In some instances, the cancer is a lung cancer. Lung cancer may start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendrioglomas. Nongliomas include meningiomas, pituitary adenomas, primary CNS lymphomas, and medulloblastomas. In some instances, the cancer is a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

The one or more diseases or conditions may be a pathogenic infection. The targeting agent may interact with a cell surface molecule on an infected cell. The targeting agent may interact with a molecule on a bacterium, a virus, or a parasite. Pathogenic infections may be caused by one or more pathogens. In some instances, the pathogen is a bacterium, fungi, virus, or protozoan.

Exemplary pathogens include but are not limited to: *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* or *Yersinia*. In some cases, the disease or condition caused by the pathogen is tuberculosis and the heterogeneous sample comprises foreign molecules derived from the bacterium *Mycobacterium tuberculosis* and molecules derived from the subject. In some instances, the disease or condition caused by a bacterium is tuberculosis; pneumonia, which may be caused by bacteria such as *Streptococcus* and *Pseudomonas*; a foodborne illness, which may be caused by bacteria such as *Shigella, Campylobacter* and *Salmonella*; or an infection such as tetanus, typhoid fever, diphtheria, syphilis and leprosy. The disease or condition may be bacterial vaginosis, a disease of the vagina caused by an imbalance of naturally occurring bacterial flora. Alternatively, the disease or condition is a bacterial meningitis, a bacterial inflammation of the meninges (e.g., the protective membranes covering the brain and spinal cord). Other diseases or conditions caused by bacteria include, but are not limited to, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a *streptococcus* bacterial infection of the deep epidermis with lymphatic spread; and cellulitis which may be caused by normal skin flora or by exogenous bacteria.

The pathogen may be a fungus, such as, but not limited to, *Candida, Aspergillus, Cryptococcus, Histoplasma, Pneumocystis,* and *Stachybotrys*. Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as, but not limited to *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g, *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

The disease or condition may be an autoimmune disease or autoimmune related disease. An autoimmune disorder may be a malfunction of the body's immune system that causes the body to attack its own tissues. Examples of autoimmune diseases and autoimmune related diseases include, but are not limited to, Addison's disease, alopecia areata, ankylosing spondylitis, antiphospholipid syndrome (APS), autoimmune aplastic anemia, autoimmune hemolytic anemia, autoimmune hepatitis, autoimmune myocarditis, Behcet's disease, celiac sprue, Crohn's disease, dermatomyositis, eosinophilic fasciitis, erythema nodosum, giant cell arteritis (temporal arteritis), Goodpasture's syndrome, Graves' disease, Hashimoto's disease, idiopathic thrombocytopenic purpura (ITP), IgA nephropathy, juvenile arthritis, diabetes, juvenile diabetes, Kawasaki syndrome, Lambert-Eaton syndrome, lupus (SLE), mixed connective tissue disease (MCTD), multiple sclerosis, myasthenia gravis, pemphigus, polyarteritis nodosa, type I, II, & III autoimmune polyglandular syndromes, polymyalgia rheumatica, polymyositis, psoriasis, psoriatic arthritis, Reiter's syndrome, relapsing polychondritis, rheumatoid arthritis, sarcoidosis, scleroderma, Sjogren's syndrome, sperm & testicular autoimmunity, stiff person syndrome, Takayasu's arteritis, temporal arteritis/giant cell arteritis, ulcerative colitis, uveitis, vasculitis, vitiligo, and Wegener's granulomatosis.

The disease or condition may be an inflammatory disease. Examples of inflammatory diseases include, but are not limited to, alveolitis, amyloidosis, angiitis, ankylosing spondylitis, avascular necrosis, Basedow's disease, Bell's palsy, bursitis, carpal tunnel syndrome, celiac disease, cholangitis, chondromalacia patella, chronic active hepatitis, chronic fatigue syndrome, Cogan's syndrome, congenital hip dysplasia, costochondritis, Crohn's Disease, cystic fibrosis, De Quervain's tendinitis, diabetes associated arthritis, diffuse idiopathic skeletal hyperostosis, discoid lupus, Ehlers-Danlos syndrome, familial mediterranean fever, fascitis, fibrositis/fibromyalgia, frozen shoulder, ganglion cysts, giant cell arteritis, gout, Graves' Disease, HIV-associated rheumatic disease syndromes, hyperparathyroid associated arthritis, infectious arthritis, inflammatory bowel syndrome/irritable bowel syndrome, juvenile rheumatoid arthritis, lyme disease, Marfan's Syndrome, Mikulicz's Disease, mixed connective tissue disease, multiple sclerosis, myofascial pain syndrome, osteoarthritis, osteomalacia, osteoporosis and corticosteroid-induced osteoporosis, Paget's Disease, palindromic rheumatism, Parkinson's Disease, Plummer's Disease, polymyalgia rheumatica, polymyositis, pseudogout, psoriatic arthritis, Raynaud's Phenomenon/Syndrome, Reiter's Syndrome, rheumatic fever, rheumatoid arthritis, sarcoidosis, sciatica (lumbar radiculopathy), scleroderma, scurvy, sickle cell arthritis, Sjogren's Syndrome, spinal stenosis, spondyloisthesis, Still's Disease, systemic lupus erythematosis, Takayasu's (Pulseless) Disease, Tendinitis, tennis elbow/golf elbow, thyroid associated arthritis, trigger finger, ulcerative colitis, Wegener's Granulomatosis, and Whipple's Disease.

EXAMPLES

Example 1. Expression and Test of Humanized CD3 Antibody Candidates

Figure 3:
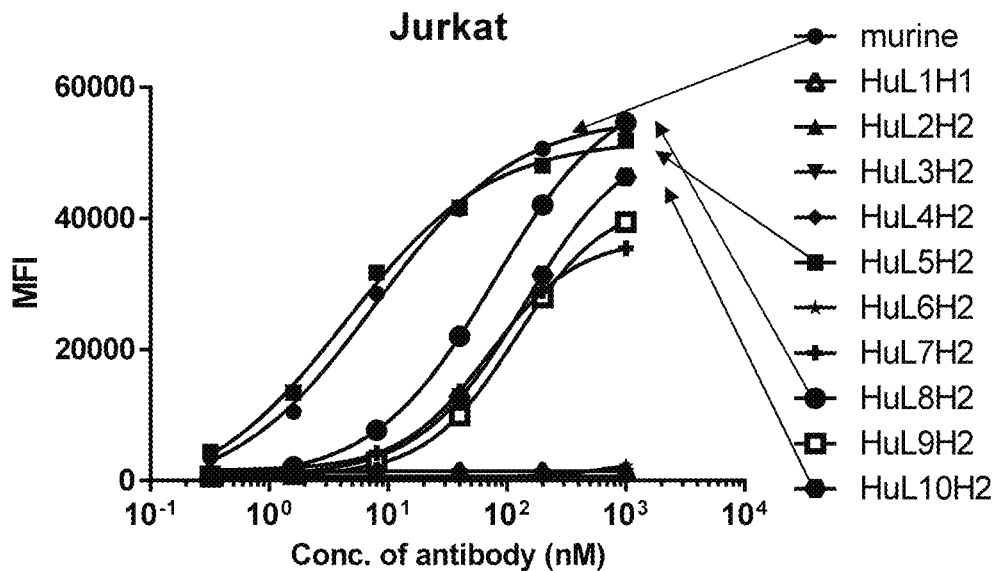
FIG. 3 shows superior binding of antibody huL5H2 (heavy chain SEQ ID NO: 41 and light chain SEQ ID NO: 39) to human CD3, which was comparable to murine anti-CD3 on human T cells in a fluorescence-based flow cytometry assay.
Figure 4:
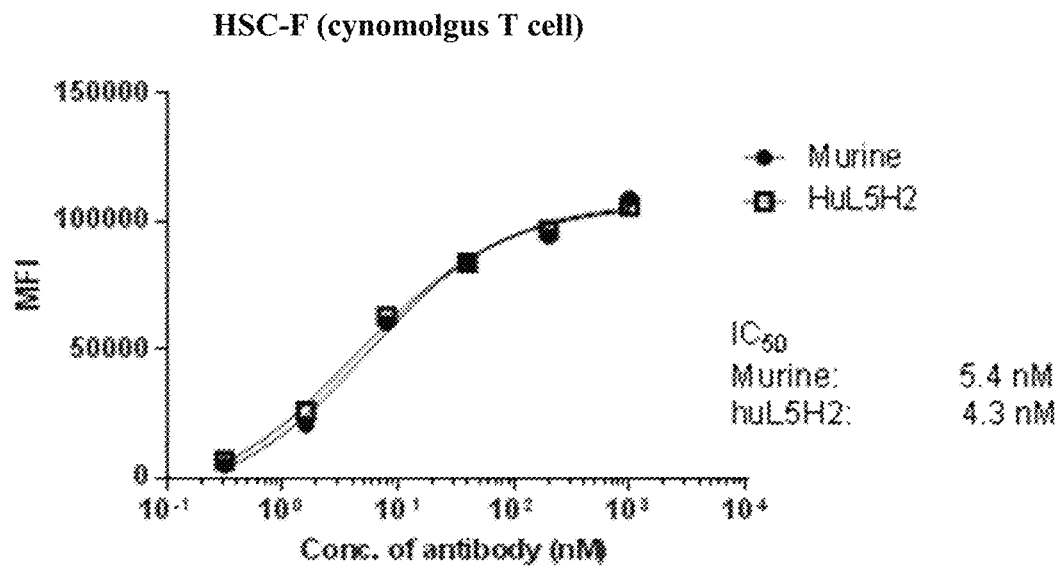
FIG. 4 shows antibody huL5H2 (heavy chain SEQ ID NO: 41 and light chain SEQ ID NO: 39) binding to human CD3 was comparable to murine anti-CD3 binding to cynomolgus T cells in a fluorescence-based flow cytometry assay.

To express humanized Fabs in mammalian cells, VH genes (VH1 and VH2) and VL genes (VL1~VL10) shown in FIG. 2 were individually cloned into the pFUSE vector under the IL2 signal peptide sequence. Light and heavy chains expression vectors were used to co-transfect Expi293F cells according to manufacturer's protocol. On day 3 or 4, cultured media was harvested and secreted Fabs were purified by Protein G chromatography. Binding affinity of humanized candidates for human and cynomolgus T cells were evaluated by flow cytometry. Briefly, cells were incubated with humanized Fabs at 4° C. for 30 min and washed twice with staining buffer (1% BSA in PBS). Bound antibodies were revealed with R-phycoethrin (PE)-conjugated anti-human kappa secondary antibodies (Southern Biotech). After several washes, samples were acquired on a BD LSR II or BD Accuri C6 and analyzed using FlowJo 7.6.2 software. In each study, cells were incubated with secondary antibody alone and the observed mean fluorescence intensity (MFI) was used to subtract for background and non-specific staining. As shown in FIG. 3 and Tables 1 and 2, huL5H2 demonstrated comparable binding affinity to human CD3 as murine anti-CD3 on human T cells (Jurkat). Moreover, huL5H2 also demonstrated good binding to cynomolgus T cells (HSC-F, FIG. 4, Table 3)

TABLE 1

| Antibody | IC50 (nM) |
| --- | --- |
| Murine (SEQ ID NOS: 23, 24) | 7.732 |
| HuL1H1 (SEQ ID NOS: 25, 28) | ~9.227 e−009 |
| HuL2H2 (SEQ ID NOS: 26, 29) | ~9.227 e−009 |
| HuL3H2 (SEQ ID NOS: 26, 30) | 17.68 |
| Hul4H2 (SEQ ID NOS: 26, 31) | ~1.294e+010 |
| HuL5H2 (SEQ ID NOS: 26, 32) | 4.462 |
| HuL6H2 (SEQ ID NOS: 26, 33) | 676.7 |
| HuL7H2 (SEQ ID NOS: 26, 34) | 70.42 |
| HuL8H2 (SEQ ID NOS: 26, 35) | 77.99 |
| HuL9H2 (SEQ ID NOS: 26, 36) | 118.8 |
| HuL10H2 (SEQ ID NOS: 26, 37) | 138.9 |

TABLE 2

| Concentration (nM) | Murine | HuL1H1 | HuL2H2 | HuL3H2 | HuL4H2 | HuL5H2 | HuL6H2 | HuL7H2 | HuL8H2 | HuL9H2 | HuL10H2 |
| --- | --- | --- | --- | --- | --- | --- | --- | --- | --- | --- | --- |
| 1000.000 | 54400 | 1470 | 1470 | 666 | 650 | 51800 | 2203 | 35400 | 54600 | 39400 | 46300 |
| 200.000 | 50600 | 1460 | 1460 | 643 | 620 | 48000 | 835 | 28900 | 42000 | 27900 | 31300 |
| 40.000 | 41400 | 1450 | 1450 | 650 | 620 | 41600 | 598 | 13600 | 22000 | 9946 | 12700 |
| 8.000 | 28500 | 1450 | 1450 | 610 | 620 | 31700 | 573 | 4241 | 7673 | 2756 | 3274 |
| 1.600 | 10500 | 1440 | 1440 | 610 | 615 | 13400 | 597 | 2040 | 2117 | 986 | 1608 |
| 0.320 | 3563 | 1400 | 1400 | 600 | 599 | 4432 | 572 | 1574 | 837 | 637 | 688 |
| 0.000 | 1397 | 1397 | 1397 | 559 | 559 | 1397 | 559 | 1252 | 559 | 559 | 559 |

TABLE 3

| Concentration (nM) | Murine | HuL5H2 |
| --- | --- | --- |
| 1000.000 | 109000 | 106000 |
| 200.000 | 94400 | 96900 |
| 40.000 | 84800 | 84000 |
| 8.000 | 60700 | 63200 |
| 1.600 | 21100 | 26300 |
| 0.320 | 5328 | 7074 |
| 0.000 | 1209 | 1209 |

Figure 5:
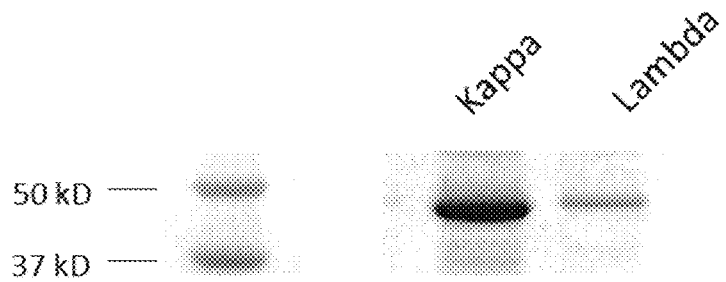
FIG. 5 shows an SDS-PAGE gel of purified anti-CD3 antibodies (kappa=SEQ ID NOS: 39, 41) lambda=SEQ ID NOS: 38, 41) containing the pAcF non-canonical amino acid. The anti-CD3 antibody having a Fab with a kappa constant region yielded approximately 4-fold higher expression levels than the Fab composed of a lambda constant region.

Example 2. Expression of HuL5H2 Fab in *E. coli* (Comparison of Kappa Vs Lambda Light Chain)

huL5H2 Fab with kappa or lambda light chain constant region was cloned into the pBAD vector and expressed using TOP10 *Escherichia coli* (*E. coli*) competent cells. Briefly, colonies were picked, inoculated into Terrific Broth (TB, 12.00 g Casein Peptone, 4.00 (mL) Glyerol, 2.31 g $K_2HPO_4$, 12.54 g $K_2HPO_4$, 24.00 g Yeastolate), and grown overnight at 37° C. (200 rpm). The next day, the cells were used to inoculate 500 mL TB expression medium in 2 L flasks and was further cultured at 37° C. (200 rpm). At an O.D. of 0.8-1, arabinose was supplemented to the growth medium (final: 0.2% m/v) and the cells were grown at 26° C. (130 rpm) for 48 hours. The cells were then pelleted, suspended in lysis buffer (30 mM Tris-HCl pH 8.0, 1 mM EDTA, 20% sucrose, lysozyme 4 mg/g of cell pellet) at 10 mL/g of cell pellet, and lysed at 37° C. (200 rpm). After 30 minutes, the lysate was removed of debris by centrifugation (15000×g, 20 min) and by filtration (0.22 um). Fabs were purified from the lysate by Protein G chromatography, and confirmed by SDS-PAGE. Using this approach, the Fab consisting of a kappa constant region yielded approximately 4-fold higher expression levels than the Fab composed of a lambda constant region (FIG. 5).

Figure 6A:
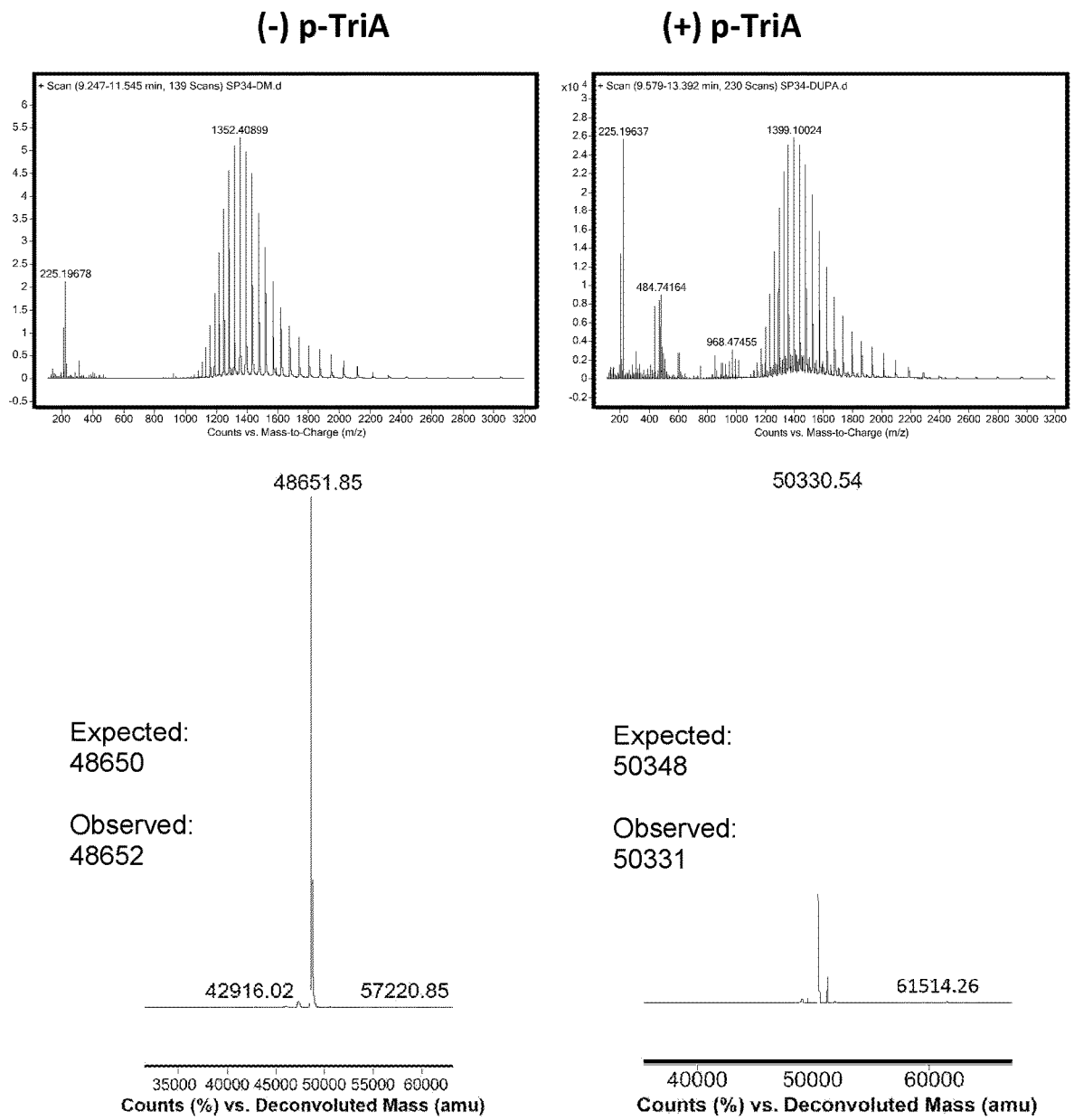
FIG. 6A shows completion of the conjugation reaction of huL5H2 (SEQ ID NOS: 40, 42) with p-TriA to as confirmed by QTOF mass spectrometry after excess linkers were removed by size filtration (Amicon, 10K and 30K). huL5H2-pTriA has two DUPA molecules (2×DUPA), one conjugated to each light chain and one conjugated to each heavy chain.
Figure 6B:
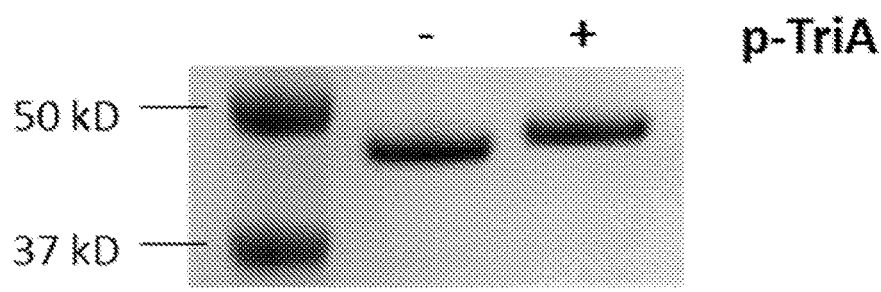
FIG. 6B shows an SDS-PAGE gel of purified anti-CD3 Fab (SEQ ID NOS: 40, 42), before and after conjugation with p-TriA at the heavy and light chain to generate huL5H2 (2×DUPA) double mutant.

Example 3. Expression and Generation of Cynomolgus Cross-Reactive Anti-CD3-Double-p-TriA Antibody Heavy and light chains of CD3-binding Fabs (clone UCHT-1, SEQ ID NOS: 84,85; or huL5H2, (SEQ ID NOS: 4, 10) including kappa constant regions on the respective light chains (SEQ ID NO: 17) and heavy chain Fab (SEQ ID NO: 19) were cloned into a bicistronic pBAD vector, and site-specific mutations to introduce TAG amber nonsense codon at two different positions (resulting in light chain S205TAG (SEQ ID NO: 18) and heavy chain K141TAG (SEQ ID NO: 20)) were performed using the Quikchange Site-directed Mutagenesis Kit (Stratagene). Antibodies were expressed in Escherichia coli (E. coli) with an orthogonal Methanococcus jannaschii tRNA/aminoacyl-tRNA synthetase specific for p-acetyl phenylalanine (pAcF) and purified. Purity and incorporation of pAcF was confirmed by SDS-PAGE and mass spectrometry using a quadrupole time of flight (QTOF) mass spectrometer. The mutant antibody with the pAcF residue incorporated (SEQ ID NOS: 40, 42) was conjugated with 30-fold molar excess of p-TriA in NaOAc (pH 4.5) buffer at 37° C. for ≥14 days. Completion of the conjugation reaction was confirmed by QTOF. Excess unreacted p-TriA was removed by size filtration using an Amicon filter having a 10K and 30K cut-of (FIG. 6A), and the size and purity of the final products were confirmed by SDS-PAGE (FIG. 6B).

Figure 7:
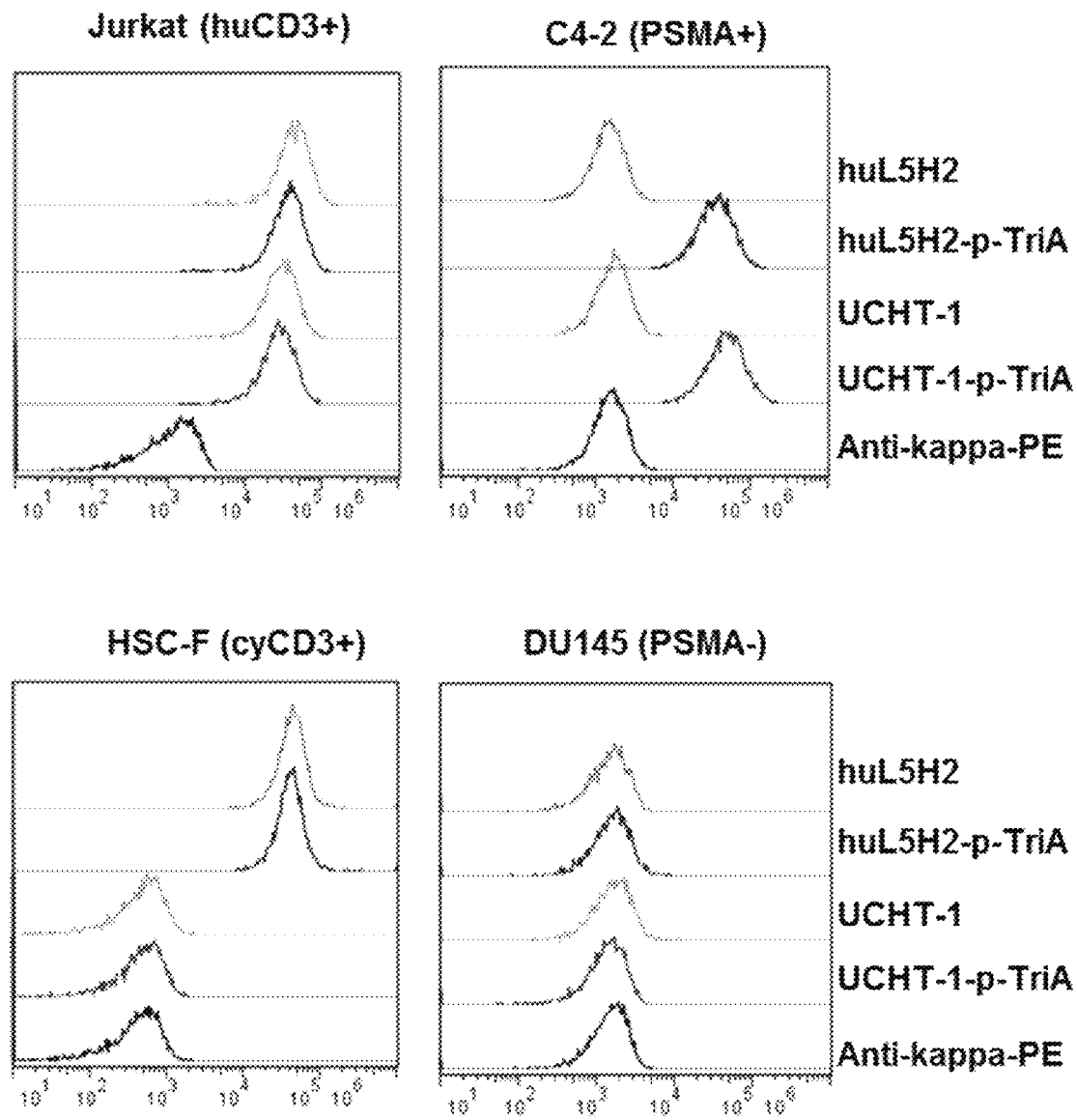
FIG. 7 shows a flow cytometry fluorescence assay where huL5H2 (SEQ ID NOS: 40, 42) and UCHT-1 (SEQ ID NOS: 84, 85) antibodies and p-TriA (2×DUPA) conjugates (SEQ ID NOS: 40, 42 conjugated to p-TriA, "huL5H2-p-TriA (2×DUPA)") demonstrated comparable cell-surface binding to Jurkat (human) T cells and C4-2 (PSMA-positive) cells, respectively, with minimal non-specific binding to DU145 (PSMA-negative) cells.

Flow cytometry was used to test binding of conjugates to cell surface CD3 on human (Jurkat) and cynomolgus (HSC-F) T cells or PSMA on C4-2 cells. Briefly, cells were incubated with UCHT-1 or huL5H2 antibodies (or corresponding p-TriA conjugates), and bound antibodies were revealed with PE-conjugated anti-human kappa secondary antibodies (Southern Biotech). In each study, cells were incubated with secondary antibody alone and the observed mean fluorescence intensity (MFI) was used to subtract for background and non-specific staining. As shown in FIG. 7, huL5H2 and UCHT-1 antibodies and conjugates demonstrated comparable binding to Jurkat (human) T cells and C4-2 (PSMA-positive) cells, respectively, with minimal non-specific binding to DU145 (PSMA-negative) cells. Notably, only antibodies consisting of huL5H2 Fab bound to cynomogous T cells, HSC-F.

Example 4. In Vitro Studies

Cytotoxicity Assay

Figure 8A:
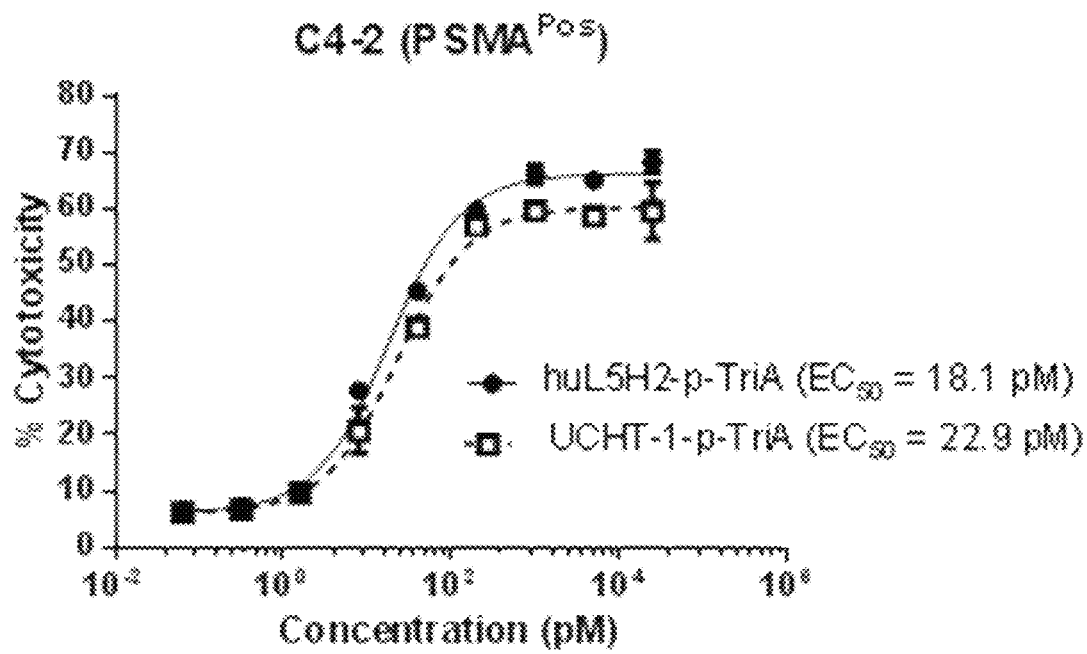
FIG. 8A shows huL5H2-p-TriA (2×DUPA) and UCHT-1-p-TriA (2×DUPA) antibody conjugates selectively redirected human PBMCs against C4-2 (PSMA-positive) cells with comparable potency in a cytotoxicity assay.
Figure 8B:
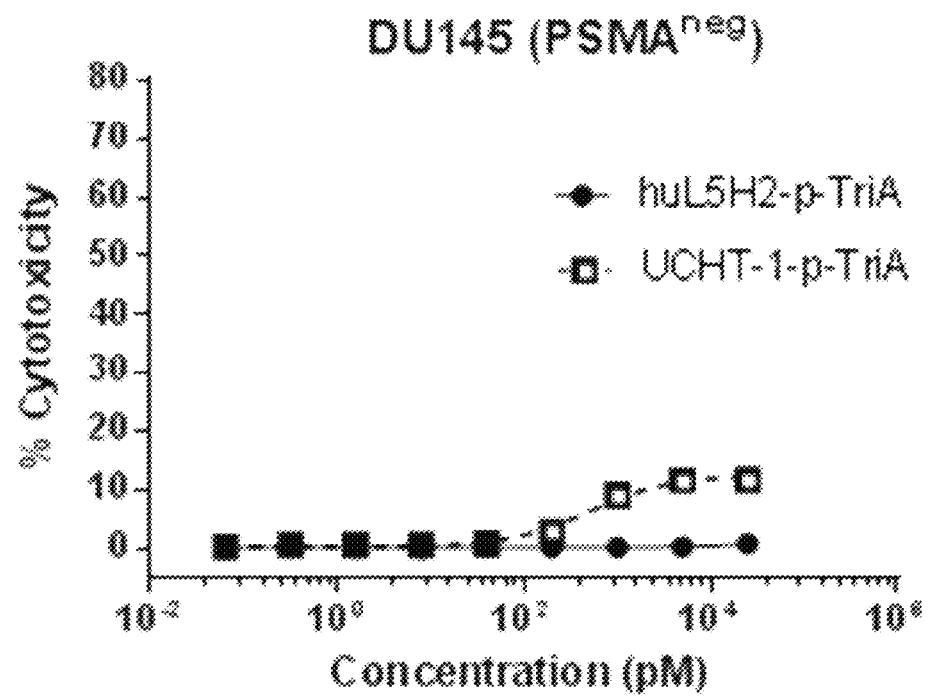
FIG. 8B shows huL5H2- and UCHT-1-p-TriA (2×DUPA) antibody conjugates induced minimal non-specific killing of DU145 (PSMA-negative) cells.
Figure 9:
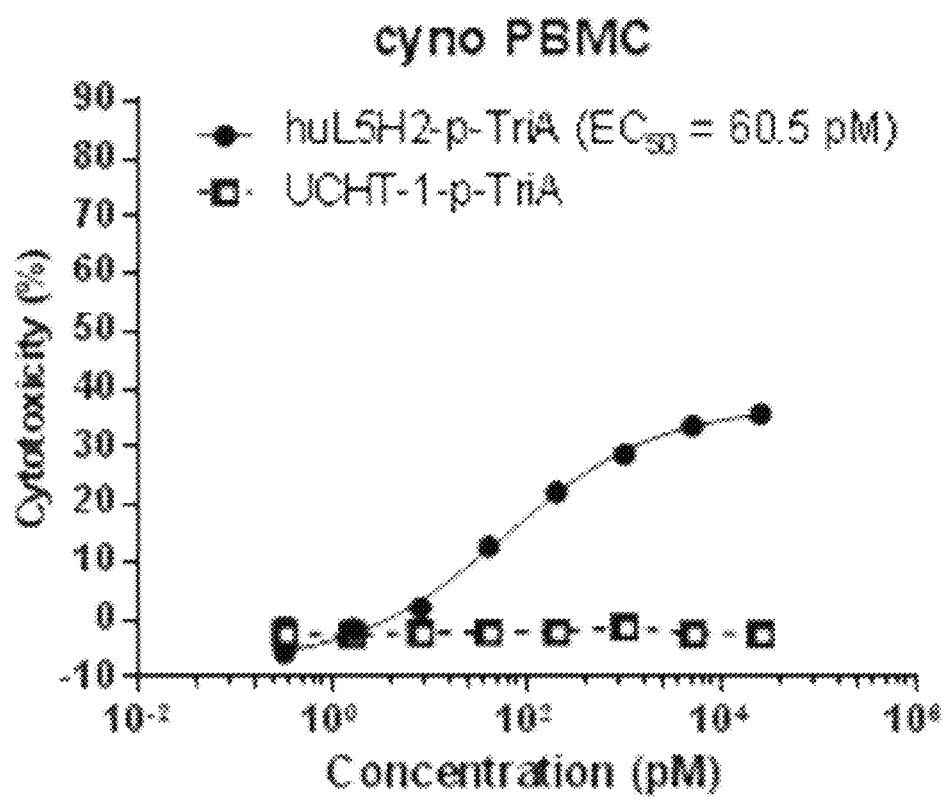
FIG. 9 shows only huL5H2-p-TriA (2×DUPA) induced lysis of C4-2 cells with cynomolgus PBMCs, with an $EC_{50}$=60.5 pM.

In vitro cytotoxicity was next performed to determine whether the anti-CD3-double-p-TriA antibody conjugates induced antigen-specific target cell killing. In brief, $1\times10^5$ PBMCs (human) and $1\times10^4$ target cells (C4-2 or DU145) were co-cultured with indicated concentrations of antibody conjugates for 24 hours. Cytotoxicity was measured using the Cytotox-96 Nonradioactive cytotoxicity assay kit (Promega), which quantifies the amount of lactate dehydrogenase (LDH) released from lysed cells into the supernatant. The percent lytic activity was calculated with the following formula: (values used represent absorbance at 490 nM) % Cytotoxicity=100×[((Target cells+Effector cells+Switch)−(Target cells+Effector cells only))/((Maximum target cell lysis)−(Target cells only))]. As shown in FIGS. 8A and 8B, and respective Tables 4 and 5, huL5H2- and UCHT-1-p-TriA antibody conjugates selectively redirected human PBMCs against C4-2 (PSMA-positive) cells with comparable potency (huL5H2-p-TriA, $EC_{50}=18.1$ pM; UCHT-1-p-TriA, $EC_{50}=22.9$ pM). Minimal non-specific killing of DU145 (PSMA-negative) cells was observed. Only huL5H2-p-TriA induced lysis of C4-2 cells with cynomolgus PBMCs (huL5H2-p-TriA, $EC_{50}=60.5$ pM) (FIG. 9, Table 6).

TABLE 4

| Concentration | Percent Cytotoxicity | | | |
|---|---|---|---|---|
| (pM) | huL5H2-p-TriA | | UCHT-1-p-TriA | |
| 25000 | 69.61369 | 66.99644 | 63.16478 | 55.97257 |
| 5000 | 65.71922 | 64.40013 | 58.80967 | 58.71545 |
| 1000 | 67.31051 | 64.8817 | 60.06595 | 59.33312 |
| 200 | 59.74142 | 59.96126 | 56.67399 | 57.48011 |
| 40 | 46.33061 | 44.43572 | 39.51528 | 38.61495 |
| 8 | 26.75356 | 28.85783 | 17.81302 | 23.59192 |
| 1.6 | 9.375 | 9.563442 | 9.06093 | 10.09736 |
| 0.32 | 7.354481 | 6.977596 | 6.642588 | 6.736809 |
| 0.064 | 6.527429 | 6.370394 | 6.778685 | 5.501466 |
| 0 | 5.606156 | 7.459171 | 8.903894 | 5.888819 |

TABLE 5

| Concentration | Percent Cytotoxicity | | | |
|---|---|---|---|---|
| (pM) | huL5H2-p-TriA | | UCHT-1-p-TriA | |
| 25000 | 1.181365 | 0.476798 | 12.01105 | 11.36723 |
| 5000 | 0.094145 | 0.476798 | 12.28438 | 10.92383 |
| 1000 | 0.46465 | 0.009111 | 9.350705 | 8.797983 |
| 200 | 0.397838 | −0.11844 | 3.319363 | 2.523688 |
| 40 | 0.1974 | 0.1974 | 0.871599 | 0.57398 |
| 8 | 0.009111 | 0.112366 | 0.689383 | 0.391764 |
| 1.6 | 0.282434 | −0.082 | 0.318878 | 0.762269 |
| 0.32 | 0.11844 | 0.264213 | 0.586127 | 0.476798 |
| 0.064 | 0.173105 | −0.08807 | 0.555758 | 0.045554 |
| 0 | 0.094145 | −0.14881 | 0.482872 | 0.1974 |

TABLE 6

| Concentration | pos Percent Cytotoxicity against C4-2 ($PSMA^{pos}$) | | | |
|---|---|---|---|---|
| (pM) | huL5H2-p-TriA | | UCHT-1-p-TriA | |
| 25000 | 37.00233 | 34.55063 | −2.59718 | −2.443147 |
| 5000 | 33.51732 | 33.94091 | −2.69345 | −1.987463 |
| 1000 | 28.60107 | 28.89631 | −0.29309 | −2.192842 |
| 200 | 23.08795 | 21.28447 | −1.57671 | −2.513745 |
| 40 | 11.97185 | 13.49293 | −1.17237 | −3.059282 |
| 8 | 2.184284 | 2.100849 | −1.03117 | −3.527801 |
| 1.6 | −0.90281 | −1.98105 | −1.7885 | −3.579145 |
| 0.32 | −5.69711 | −5.74204 | −0.67818 | −3.989902 |

Activation Markers Upregulation and Proliferation Assay

Figure 10A:
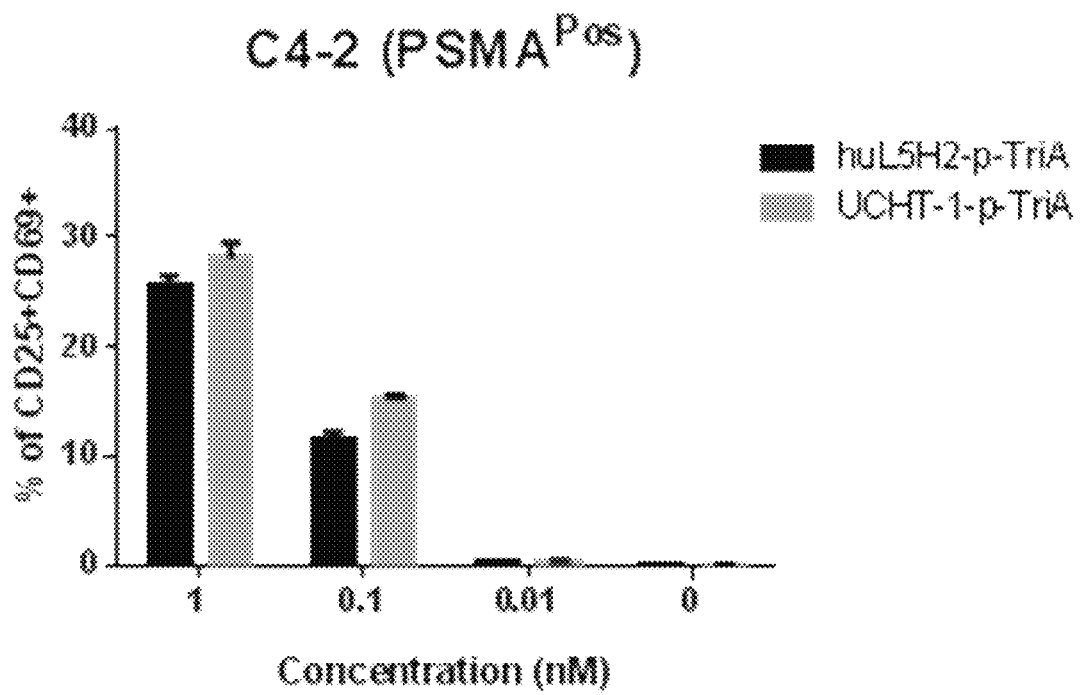
FIG. 10A shows both p-TriA conjugates of huL5H2 and UCHT-1 (2×DUPA) induced a similar level of T cell activation in PSMA-positive cells.
Figure 10B:
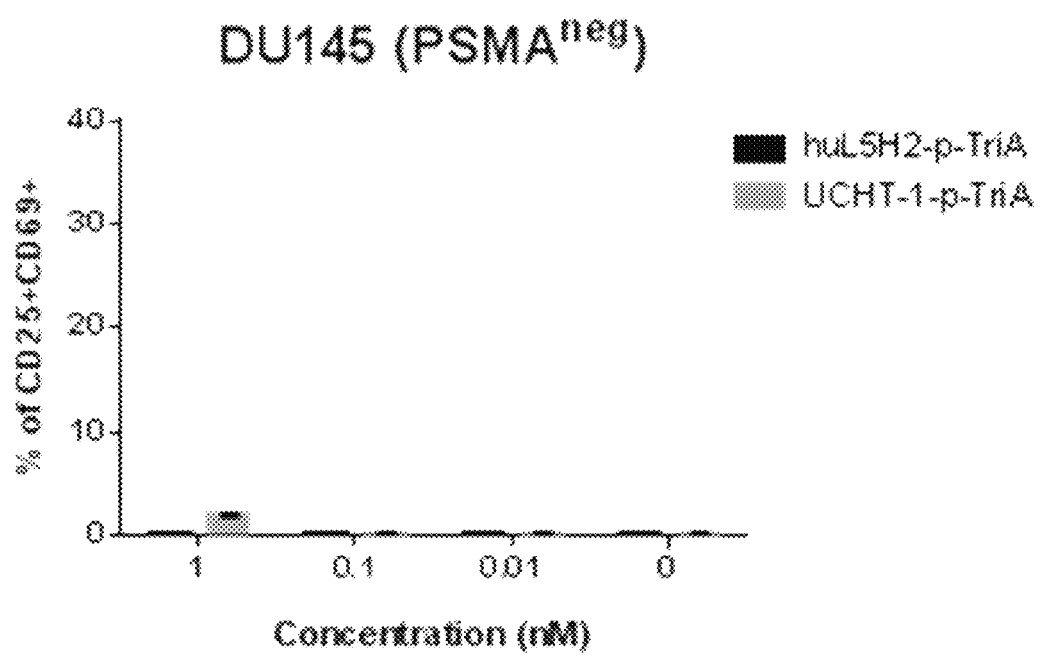
FIG. 10B shows p-TriA of huL5H2 and UCHT-1 (2×DUPA) conjugates induced minimal T cell activation in PSMA-negative cells.

Upregulation of activation markers on human T cells by the anti-CD3-double-p-TriA antibody conjugates was assessed in the presence of target cells. In these studies, equal number ($1\times10^5$) of human PBMC and C4-2 (PSMA-positive) or human PBMC and DU145 (PSMA-negative) cells were co-cultured in the presence of 1, 0.1, 0.01, or 0 nM antibody conjugates in 96 well round bottom plates at 37° C. for 24 hours. The next day, cultures were labeled with PE-conjugated anti-CD3 (OKT3), AlexaFluor 488-conjugated CD25 (BC96) and allophycocyanin (APC)-conjugated CD69 (FN50) antibodies (all purchased from Biolegend). Appropriate isotype controls were included in each study to determine background and exclude non-specific staining. Unstained and single color controls were acquired and used for compensation. Data is shown in FIGS. 10A and 10B, and Tables 7 and 8.

Figure 11A:
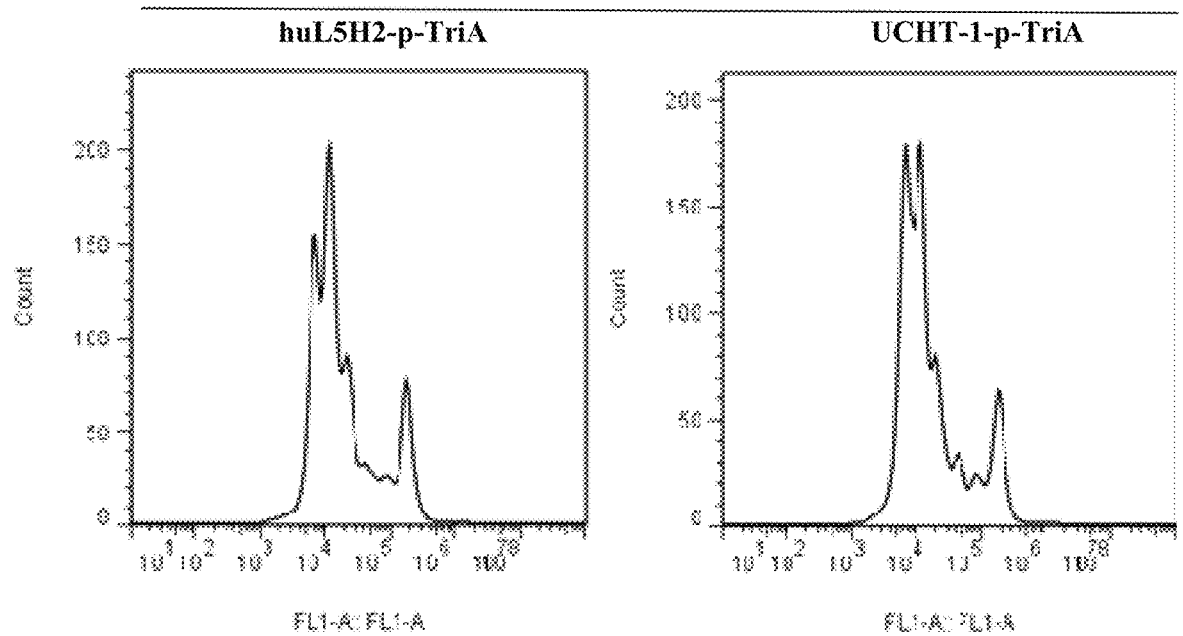
FIG. 11A shows both p-TriA huL5H2 and UCHT-1 (2×DUPA) conjugates induced similar T cell proliferation in PSMA-positive cells in a flow cytometry assay.
Figure 11B:
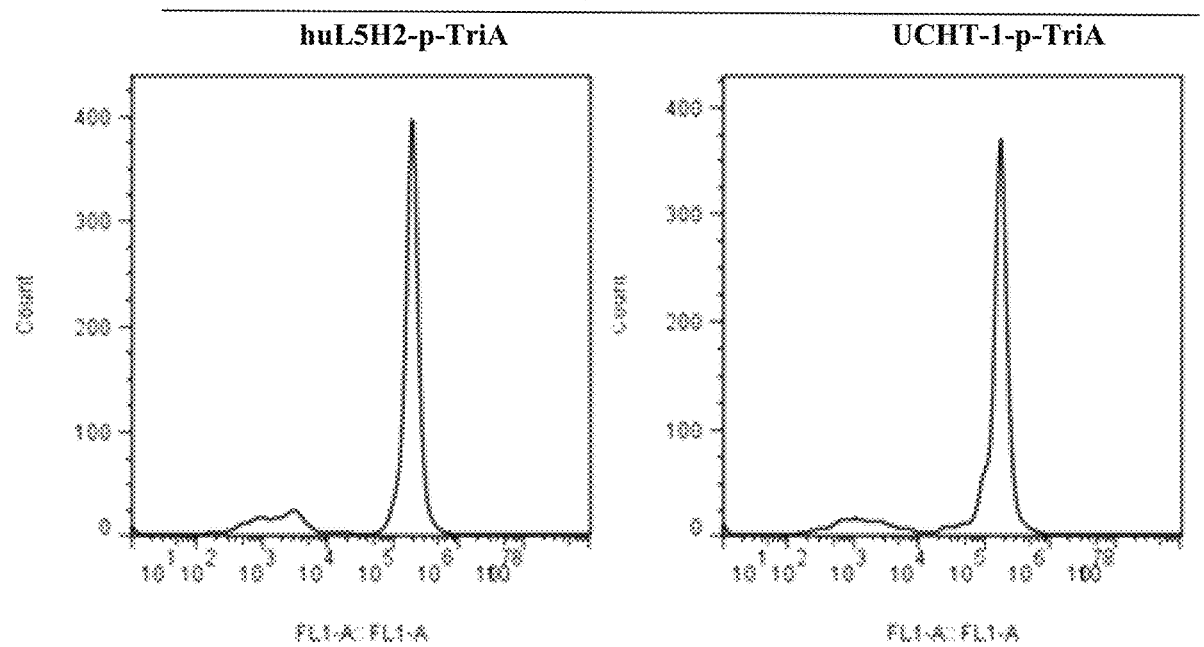
FIG. 11B shows both p-TriA huL5H2 and UCHT-1 (2×DUPA) conjugates induced minimal T cell proliferation in PSMA-negative cells in a flow cytometry assay.

The effect of anti-CD3-double-p-TriA antibody conjugates on T cell proliferation was also assessed. $1 \times 10^5$ carboxyfluorescein succinimidyl ester (CFSE)-labeled human PBMC and $1 \times 10^5$ target cells were co-cultured in the presence 1 nM antibody conjugates for 72 hours. All experiments were acquired on a BD Accuri C6 and analyzed using FlowJo 7.6.2 software. As shown in FIG. 11A and FIG. 11B, both p-TriA conjugates induced similar capacity of T cell activation and proliferation, respectively, in a PSMA-dependent manner.

TABLE 7

| Target Cell | Percent CD69- and CD25-positive C4-2 (PSMA-positive) | | | | | |
|---|---|---|---|---|---|---|
| Concentration (nM) | huL5H2-p-TriA | | | UCHT-1-p-TriA | | |
| 1 | 27.2 | 25.2 | 25 | 30.6 | 28.2 | 25.8 |
| 0.1 | 12.4 | 12.2 | 9.99 | 15.4 | 14.8 | 15.8 |
| 0.01 | 0.266 | 0.438 | 0.375 | 0.456 | 0.531 | 0.511 |
| 0 | 0.02 | 0.02 | 0.079 | 0.079 | 0.079 | 0.02 |

TABLE 8

| Target Cell | Percent CD69- and CD25-positive DU145 (PSMA-negative) | | | | | |
|---|---|---|---|---|---|---|
| Concentration (nM) | huL5H2-p-TriA | | | UCHT-1-p-TriA | | |
| 1 | 0.16 | 0.08 | 0.06 | 2.09 | 1.43 | 1.85 |
| 0.1 | 0.06 | 0.08 | 0.16 | 0.12 | 0.16 | 0.06 |
| 0.01 | 0.14 | 0.12 | 0.179 | 0.16 | 0.139 | 0.1 |
| 0 | 0.1 | 0.06 | 0.08 | 0.119 | 0.159 | 0.14 |

Cytokine Release Assay

Figure 12A:
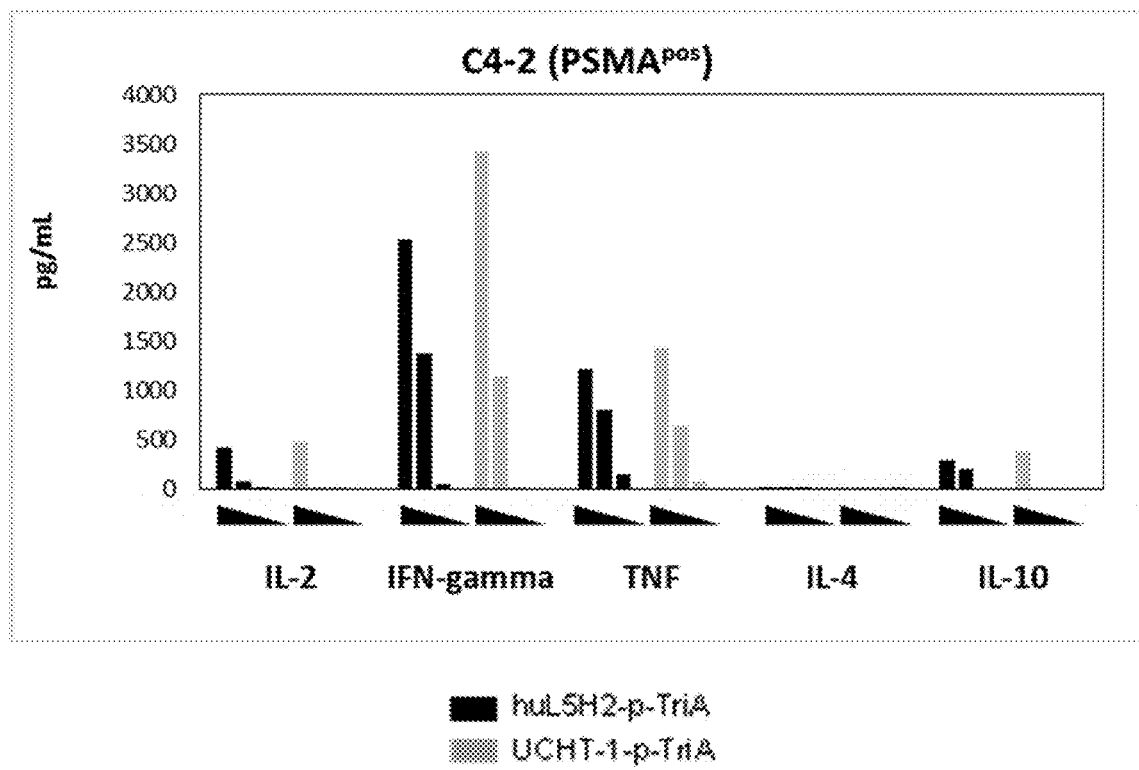
FIG. 12A shows both p-TriA huL5H2 and UCHT-1 (2×DUPA) conjugates induced comparable levels of inflammatory cytokines from human T cells in the presence of PSMA-positive C4-2 cells.
Figure 12B:
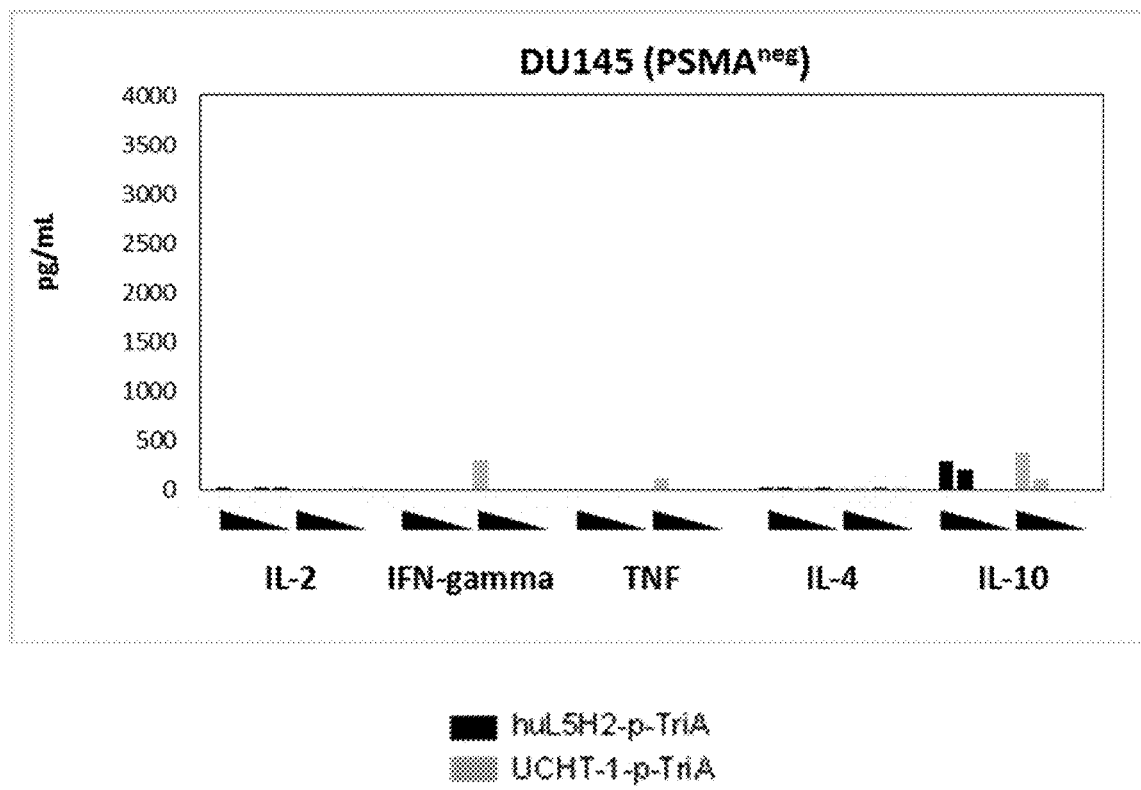
FIG. 12B shows both p-TriA huL5H2 and UCHT-1 (2×DUPA) conjugates induced minimal levels of inflammatory cytokines from human T cells in the presence of PSMA-negative DU145 cells.

Cytokines in cultured media from activation studies described above were quantified using BD CBA Human Th1/Th2 Kit II (BD Biosciences). Samples were acquired on a BD Accuri C6 and analyzed using FCAP Array software. As shown in FIGS. 12A and 121B, and Tables 9 and 10, both p-TriA conjugates induced comparable levels of inflammatory cytokines from human T cells in the presence of PSMA-positive C4-2 cells.

TABLE 9

| | C4-2 (PSMA-positive) | | | | | | | |
|---|---|---|---|---|---|---|---|---|
| | huL5H2-p-TriA | | | | UCHT-1-p-TriA | | | |
| Concentration (nM) Cytokines | 1 | 0.1 | 0.01 | 0 | 1 | 0.1 | 0.01 | 0 |
| IL-2 | 425.33 | 71.31 | 6.51 | 0 | 470.16 | 27.81 | 4.03 | 0 |
| IFN-gamma | 2524.56 | 1372.34 | 51.99 | 0 | 3408.74 | 1146.9 | 21.3 | 0 |
| TNF | 1212.52 | 805.51 | 150.64 | 0 | 1427.27 | 630 | 73.93 | 0 |
| IL-4 | 12.75 | 8.82 | 2.37 | 2.14 | 15.67 | 6.97 | 2.74 | 1.7 |
| IL-10 | 289.48 | 206.09 | 0 | 0 | 372.16 | 101.46 | 0 | 0 |

TABLE 10

| | DU145 (PSMA-negative) | | | | | | | |
|---|---|---|---|---|---|---|---|---|
| | huL5H2-p-TriA | | | | UCHT-1-p-TriA | | | |
| Concentration (nM) Cytokines | 1 | 0.1 | 0.01 | 0 | 1 | 0.1 | 0.01 | 0 |
| IL-2 | 18.32 | 0 | 7.57 | 9.65 | 0 | 0 | 0 | 5.84 |
| IFN-gamma | 0 | 0 | 0 | 0 | 310.48 | 0 | 0 | 0 |

TABLE 10-continued

| | DU145 (PSMA-negative) | | | | | | | |
|---|---|---|---|---|---|---|---|---|
| | huL5H2-p-TriA | | | | UCHT-1-p-TriA | | | |
| TNF | 0 | 0 | 0 | 0 | 124.6 | 0 | 0 | 0 |
| IL-4 | 2.41 | 2.24 | 2.52 | 2.15 | 1.92 | 2.02 | 2.41 | 2.02 |
| IL-10 | 0 | 0 | 0 | 0 | 9.16 | 0 | 0 | 0 |

Example 5. In Vivo Studies

Xenograft

Figure 13A:
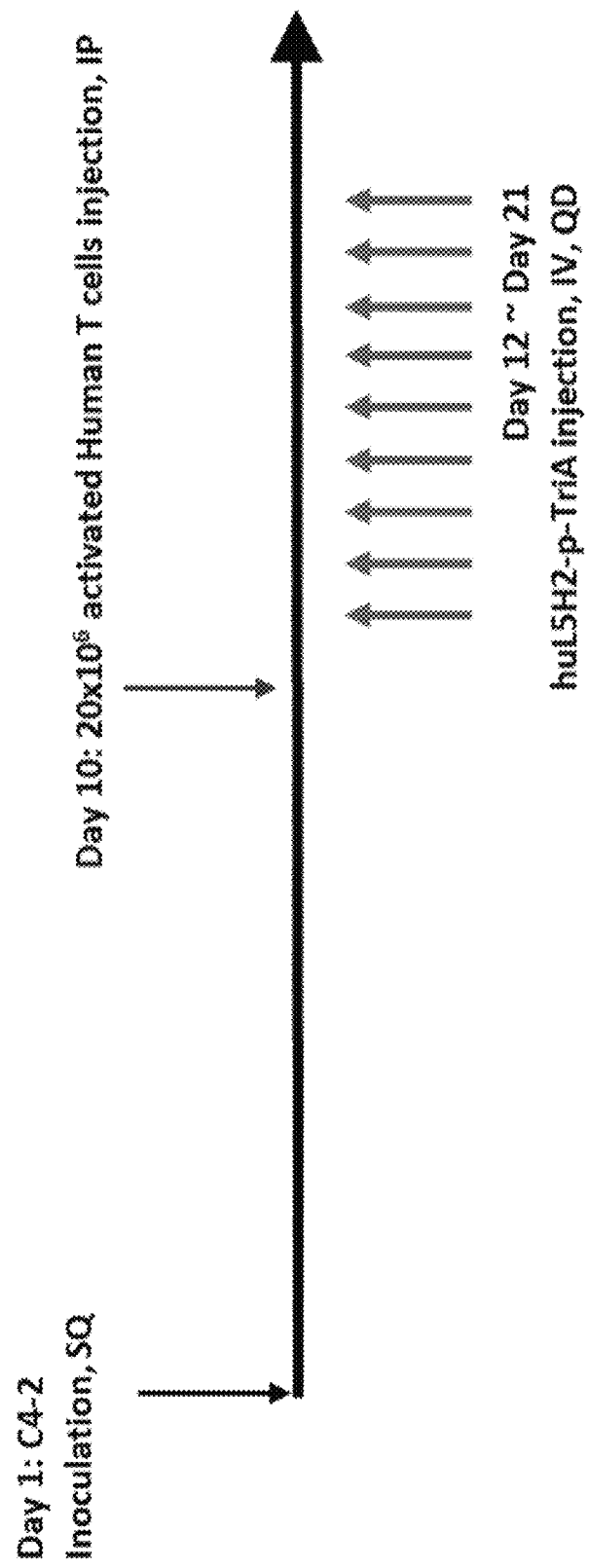
FIG. 13A shows an experimental setup for the treatment of C4-2 xenografts in mice with huL5H2-p-TriA (2×DUPA).
Figure 13B:
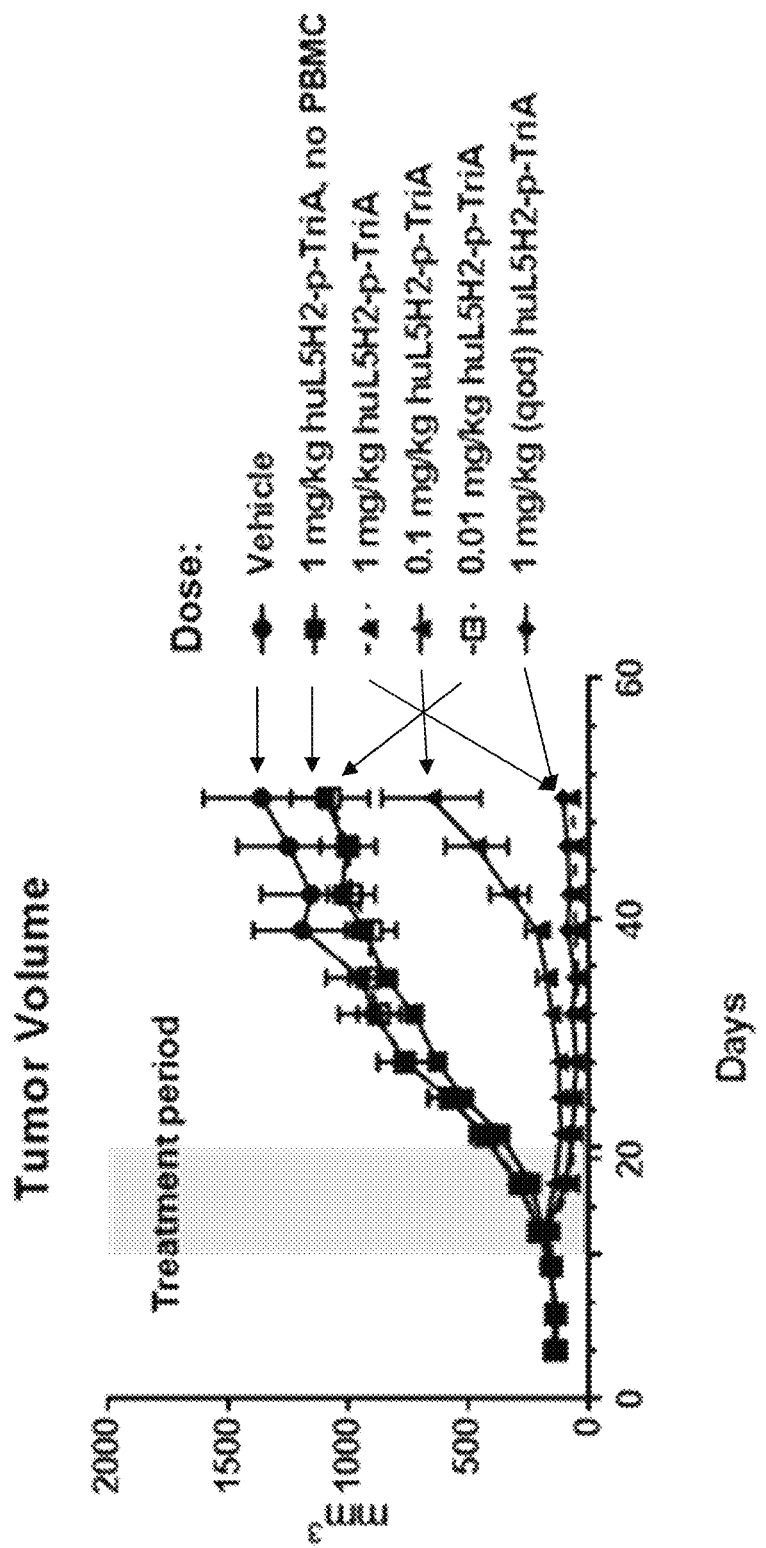
FIG. 13B shows huL5H2-p-TriA (2×DUPA) demonstrated dose-dependent in vivo anti-tumor activity against C4-2 xenografts in a NSG mouse model reconstituted with human T cells.

The in vivo efficacy of huL51H2-p-TriA was established in a C4-2 xenograft model. Six to eight weeks old male NOD. Cg-Prkdc$^{scid}$ Il2rg$^{tm1Wjl}$/SzJ (NSG) mice were implanted subcutaneously with 1×10$^6$ C4-2 cells in Matrigel (Corning). Once tumors were approximately 150-200 mm$^3$ in size, 20×10$^6$ activated T cells were infused via intraperitoneal and on the next day, daily intravenous treatment with indicated dose of huL51H2-p-TriA was carried out for 10 days. In parallel, a control group (tumor only) consisting of mice injected daily with PBS were included. Tumor growth was monitored biweekly using external calipers and calculated using the formula: (l×w×h)/2. As shown in FIGS. 13A and 13B, and Tables 11-16, huL51H2-p-TriA demonstrated dose-dependent in vivo anti-tumor activity in the NSG mouse model reconstituted with human T cells. Moreover, daily and every other day treatments were observed to be equally effective in eradicating C4-2 tumors.

TABLE 11

| Treatment Days | Tumor Volume (mm3) Vehicle | | | | |
|---|---|---|---|---|---|
| 0 | | | | | |
| 4 | 92.383 | 125.126 | 162.17 | 176.448 | 148.903 |
| 7 | 129.386 | 126.511 | 143.868 | 139.514 | 164.488 |
| 11 | 132.9602 | 149.7841 | 190.1222 | 152.8505 | 194.4304 |
| 14 | 171.77 | 163.085 | 195.765 | 197.452 | 266.497 |
| 18 | 262.926 | 329.476 | 282.933 | 232.695 | 364.021 |
| 22 | 357.874 | 453.907 | 514.18 | 265.011 | 587.627 |
| 25 | 456.548 | 683.349 | 666.83 | 340.556 | 782.714 |
| 28 | 704.318 | 931.33 | 774.096 | 357.961 | 1048.348 |
| 32 | 800.775 | 1198.76 | 955.653 | 376.124 | 1140.723 |
| 35 | 932.385 | 1238.736 | 887.041 | 439.676 | 1239.037 |
| 39 | 1268.09 | 1561.976 | 1154.103 | 431.296 | 1546.235 |
| 42 | 1257.107 | 1464.272 | 981.121 | 441.02 | 1631.606 |
| 46 | 1175.51 | 1612.388 | 1267.491 | 487.822 | 1699.22 |
| 50 | 1404.576 | 1969.644 | 1097.821 | 600.271 | 1738.931 |

TABLE 12

| Treatment Days | Tumor Volume (mm3) huL5H2 DI-2xDUPA 1 mg/kg, no PBMC | | | | |
|---|---|---|---|---|---|
| 0 | | | | | |
| 4 | 146.311 | 175.579 | 138.154 | 130.337 | 152.875 |
| 7 | 127.092 | 141.343 | 128.933 | 142.711 | 175.271 |
| 11 | 125.961 | 187.973 | 134.537 | 151.132 | 176.831 |
| 14 | 174.67 | 226.785 | 175.471 | 173.263 | 190.23 |
| 18 | 263.621 | 260.446 | 157.4 | 229.606 | 288.194 |
| 22 | 347.527 | 409.022 | 193.643 | 484.903 | 397.567 |
| 25 | 654.71 | 605.685 | 279.441 | 601.698 | 459.315 |
| 28 | 696.459 | 731.026 | 385.881 | 777.722 | 562.675 |
| 32 | 769.484 | 824.674 | 467.48 | 935.881 | 638.843 |
| 35 | 871.458 | 889.715 | 635.774 | 1068.018 | 762.314 |
| 39 | 885.889 | 914.236 | 726.983 | 1080.212 | 1073.046 |

TABLE 12-continued

| Treatment Days | Tumor Volume (mm3) huL5H2 DI-2xDUPA 1 mg/kg, no PBMC | | | | |
|---|---|---|---|---|---|
| 42 | 995.221 | 957.272 | 788.294 | 1228.208 | 1162.943 |
| 46 | 866.77 | 1073.114 | 731.529 | 1165.54 | 1220.265 |
| 50 | 920.34 | 1036.848 | 951.114 | 1215.678 | 1360.944 |

TABLE 13

| Treatment Days | Tumor Volume (mm3) huL5H2_DI-2xDUPA 1 mg/kg | | | | |
|---|---|---|---|---|---|
| 0 | | | | | |
| 4 | 119.745 | 151.946 | 129.252 | 122.107 | 134.167 |
| 7 | 138.711 | 143.926 | 121.815 | 129.486 | 159.216 |
| 11 | 142.1008 | 143.7369 | 148.0319 | 164.6003 | 151.8278 |
| 14 | 135.943 | 172.439 | 152.596 | 190.116 | 152.417 |
| 18 | 69.732 | 75.611 | 75.24 | 93.575 | 67.709 |
| 22 | 53.724 | 54.004 | 78.817 | 61.947 | 59.459 |
| 25 | 54.76 | 52.362 | 83.641 | 68.407 | 47.685 |
| 28 | 44.341 | 51.414 | 90.731 | 59.844 | 45.328 |
| 32 | 39.236 | 47.24 | 77.336 | 61.814 | 54.213 |
| 35 | 33.123 | 48.011 | 56.683 | 53.165 | 39.249 |
| 39 | 48.399 | 44.63 | 77.121 | 64.964 | 42.305 |
| 42 | 50.017 | 46.581 | 71.445 | 67.944 | 48.805 |
| 46 | 47.685 | 49.317 | 76.261 | 67.46 | 49.359 |
| 50 | 82.591 | 54.341 | 84.279 | 82.953 | 65.75 |

TABLE 14

| Treatment Days | Tumor Volume (mm3) huL5H2_DI-2xDUPA 0.1 mg/kg | | | | |
|---|---|---|---|---|---|
| 0 | | | | | |
| 4 | 155.309 | 113.827 | 138.675 | 138.761 | 130.847 |
| 7 | 145.413 | 121.06 | 154.499 | 138.481 | 130.569 |
| 11 | 185.5239 | 159.4957 | 164.9136 | 125.4246 | 181.5284 |
| 14 | 230.52 | 149.2 | 188.607 | 144.861 | 193.634 |
| 18 | 219.892 | 129.965 | 129.517 | 95.282 | 117.032 |
| 22 | 167.636 | 103.128 | 105.863 | 99.383 | 101.899 |
| 25 | 166.383 | 126.692 | 93.621 | 89.752 | 133.334 |
| 28 | 173.912 | 153.353 | 102.111 | 101.125 | 102.174 |
| 32 | 166.445 | 270.662 | 108.015 | 104 | 119.2 |
| 35 | 223.386 | 311.363 | 141.26 | 111.124 | 89.05 |
| 39 | 184.142 | 374.221 | 281.788 | 103.964 | 122.728 |
| 42 | 300.629 | 501.91 | 538.11 | 129.219 | 181.543 |
| 46 | 458.553 | 611.132 | 870.141 | 118.985 | 278.419 |
| 50 | 638.688 | 674.049 | 1382.693 | 125.465 | 457.966 |

TABLE 15

| Treatment Days | Tumor Volume (mm3) huL5H2_DI-2xDUPA 0.01 mg/kg | | | | |
|---|---|---|---|---|---|
| 0 | | | | | |
| 4 | 128.359 | 136.876 | 125.019 | 153.676 | 145.595 |
| 7 | 146.067 | 137.62 | 130.654 | 119.173 | 154.354 |
| 11 | 164.2142 | 147.8484 | 142.4045 | 159.3286 | 166.5676 |
| 14 | 168.815 | 233.591 | 185.52 | 221.558 | 218.653 |
| 18 | 208.076 | 350.684 | 323.69 | 334.596 | 193.371 |
| 22 | 284.866 | 532.256 | 529.668 | 503.61 | 280.309 |

TABLE 15-continued

| Treatment Days | Tumor Volume (mm3) huL5H2_DI-2xDUPA 0.01 mg/kg | | | | |
|---|---|---|---|---|---|
| 25 | 313.219 | 731.491 | 743.735 | 710.57 | 393.878 |
| 28 | 465.763 | 958.391 | 1026.034 | 821.939 | 555.945 |
| 32 | 583.188 | 1061.614 | 1038.919 | 914.388 | 769.382 |
| 35 | 624.773 | 1105.795 | 980.013 | 973.353 | 914.341 |
| 39 | 568.327 | 1152.805 | 891.729 | 815.426 | 1100.677 |
| 42 | 646.524 | 1158.8 | 997.195 | 933.189 | 1212.134 |
| 46 | 581.986 | 1168.856 | 1047.78 | 969.494 | 1243.452 |
| 50 | 574.358 | 1245.395 | 975.512 | 1029.648 | 1562.498 |

TABLE 16

| Treatment Days | Tumor Volume (mm3) huL5H2_DI-2xDUPA 1 mg/kg (qod) | | | | |
|---|---|---|---|---|---|
| 0 | | | | | |
| 4 | 117.598 | 129.579 | 157.769 | 129.106 | 149.626 |
| 7 | 132.124 | 151.005 | 136.636 | 116.148 | 118.534 |
| 11 | 152.7356 | 143.4742 | 189.7295 | 166.1541 | 181.2077 |
| 14 | 172.411 | 156.371 | 207.959 | 208.469 | 151.423 |
| 18 | 70.619 | 89.479 | 112.859 | 95.388 | 85.421 |
| 22 | 54.138 | 61.084 | 87.967 | 78.081 | 58.076 |
| 25 | 48.889 | 45.474 | 76.68 | 66.582 | 55.171 |
| 28 | 52.419 | 36.023 | 68.693 | 58.217 | 48.691 |
| 32 | 57.584 | 44.727 | 93.237 | 70.926 | 70.737 |
| 35 | 46.818 | 51.959 | 89.682 | 39.326 | 54.995 |

TABLE 16-continued

| Treatment Days | Tumor Volume (mm3) huL5H2_DI-2xDUPA 1 mg/kg (qod) | | | | |
|---|---|---|---|---|---|
| 39 | 76.485 | 60.434 | 161.469 | 73.506 | 71.292 |
| 42 | 77.774 | 53.135 | 138.62 | 77.48 | 47.641 |
| 46 | 104.46 | 55.969 | 145.498 | 94.773 | 44.032 |
| 50 | 129.085 | 67.366 | 193.971 | 86.057 | 62.449 |

Example 6. Patient-Derived Xenograft

Figure 14A:
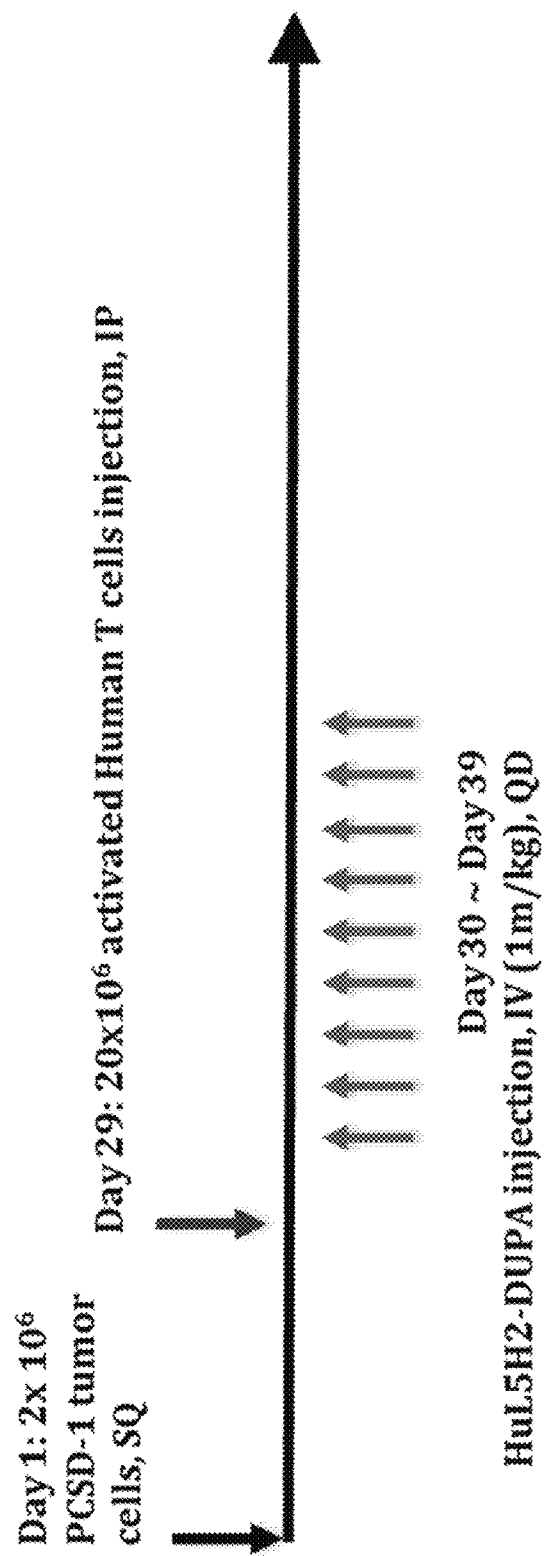
FIG. 14A shows an experimental setup for the treatment of a tumor in a PCSD1 PDX (patient-derived xenograft) model with HuL5H2-DUPA (2×DUPA) and activated T cells.
Figure 14B:
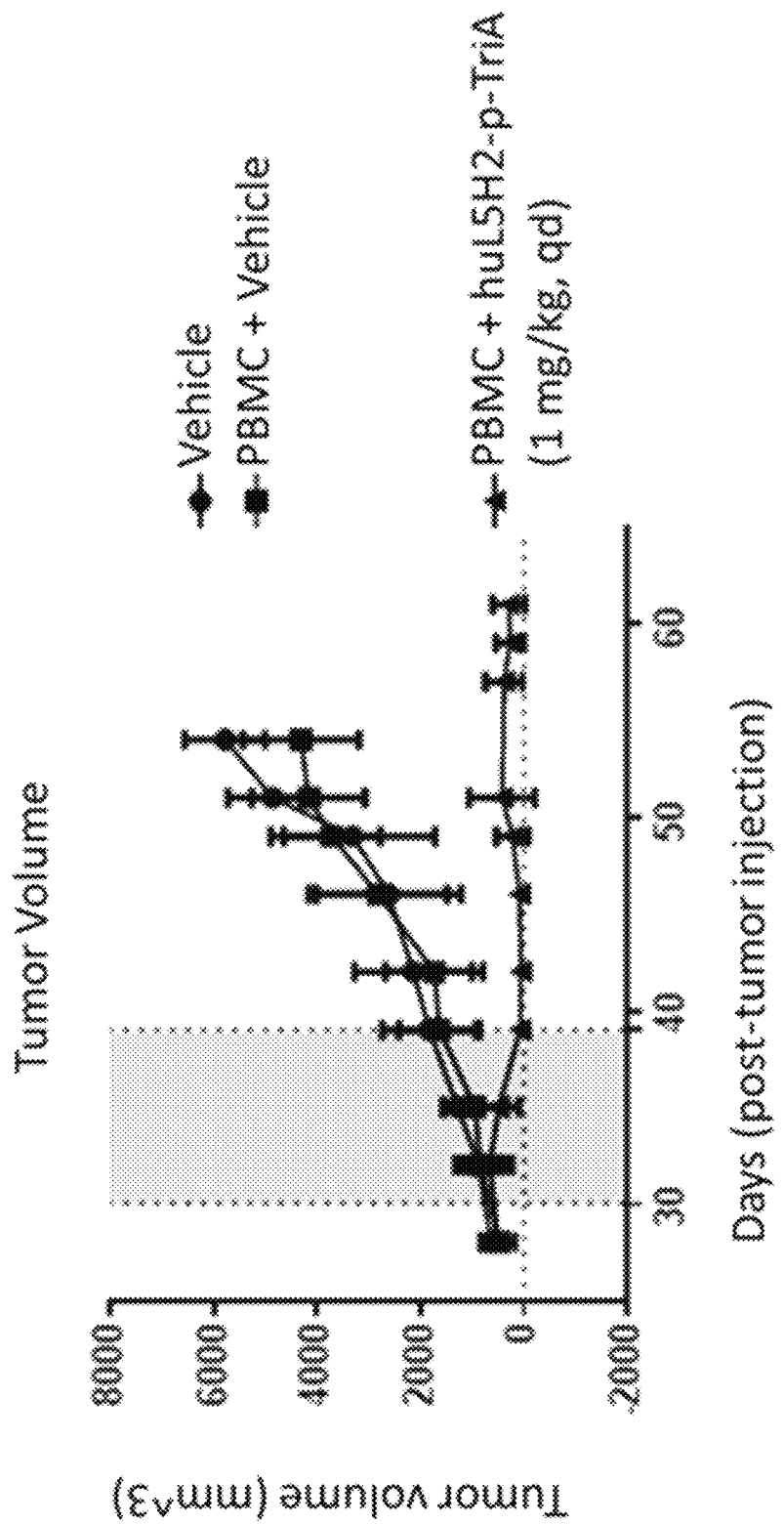
FIG. 14B shows huL5H2-p-TriA (2×DUPA) in combination with PBMCs demonstrated a reduction in tumor volume for the PDX mouse model.

Results in the C4-2 xenograft model were next validated in a patient-derived xenograft (PDX) model using primary cells from a human prostate cancer femoral metastasis, PCSD1 (2). Six to eight weeks old male NOD.Cg-Prkdc$^{scid}$ Il2rg$^{tm1Wjl}$/SzJ (NSG) mice were implanted subcutaneously with $2 \times 10^6$ PCSD1 tumor cells. Once a palpable tumor is established, approximately 500 mm$^3$, $20 \times 10^6$ activated T cells were infused via the intraperitoneal and on the next day, daily intravenous treatment with 1 mg/kg of huL51H2-p-TriA was carried out for 10 days. In parallel, a control group (tumor only) where mice were injected daily with PBS were included. Tumor growth was monitored biweekly using external calipers and calculated using the formula: (l×w2)/2. As shown in FIGS. 14A and 14B, and Tables 17-19, huL51H2-p-TriA demonstrated promising efficacy in the PDX model.

TABLE 17

| Treatment Days | Tumor Volume (mm3) Vehicle | | | | | | | | |
|---|---|---|---|---|---|---|---|---|---|
| 28. | 650.4750 | 247.0090 | 729.0000 | 0.0000* | 677.6000 | 789.5680 | 786.5000 | 686.8160 | 104.4300 |
| 32. | 734.8320 | 652.8640 | 1420.0940 | 0.0000* | 703.8690 | 1125.0000 | 571.2560 | 997.2480 | 1232.0070 |
| 35. | 1310.7880 | 905.5935 | 1223.1140 | 0.0000* | 1372.8800 | 1766.2500 | 1130.1360 | 1818.6620 | 1255.7070 |
| 39. | 1835.4800 | 1550.7360 | 2152.0080 | 0.0000 | 2407.1920 | 2898.9410 | 1990.0980 | 1392.6400 | 2321.8240 |
| 42. | 2645.3760 | 1273.7670 | 2419.2000 | 0.0000 | 2683.4690 | 3444.8960 | 2573.2080 | 2094.8400 | 1909.7000 |
| 46. | 1993.2640 | 2179.4480 | 3495.6160 | 0.0000 | 3610.0000 | 2844.1130 | 4206.5520 | 3550.0800 | 2995.2000 |
| 49. | 3285.6000 | 3170.2710 | 3927.2960 | 0.0000 | 4243.6160 | 3604.0640 | 5013.2750 | 4458.5480 | 3507.1080 |
| 51. | 3999.7010 | 4231.2490 | 4620.8000 | | 5285.4880 | 6394.0320 | 4704.4800 | 4371.1250 | 4750.8930 |
| 54. | 5272.1280 | 4855.0440 | 5191.5280 | | 6231.2720 | 6650.4020 | 6597.9250 | 3927.2960 | 6067.4400 |
| 57. | | | | | | | | | |
| 59. | | | | | | | | | |
| 61. | | | | | | | | | |
| 28. | 1257.107 | | | | 1464.272 | 981.121 | 441.02 | 1631.606 | |
| 32. | 1175.51 | | | | 1612.388 | 1267.491 | 487.822 | 1699.22 | |
| 35. | 1404.576 | | | | 1969.644 | 1097.821 | 600.271 | 1738.931 | |

*These values were not used for calculating the final average tumor volume. Each column represents the data for an individual mouse.

TABLE 18

| Treatment Days | Tumor Volume (mm3) PBMC + Vehicle | | | | | |
|---|---|---|---|---|---|---|
| 28. | 744.8760 | 509.9125 | 563.5575 | 826.8750 | 0.0000 | 506.250 |
| 32. | 1636.8960 | 609.7545 | 777.7280 | 443.7600 | 243.6820 | 1173.600 |
| 35. | 1460.7200 | 567.2480 | 730.0800 | 722.1375 | 103.9680 | 722.000 |
| 39. | 2721.7050 | 1500.0000 | 1861.8400 | 1399.3620 | 278.6630 | 0.000 |
| 42. | 2928.3450 | 898.5600 | 2681.6630 | 1314.5140 | 309.3040 | 0.000 |
| 46. | 5049.4500 | 2598.4000 | 3146.7800 | 1141.6680 | 1302.5280 | 0.000 |
| 49. | 5163.3050 | 2861.5260 | 4240.0000 | 2513.8960 | 3325.2420 | 0.000 |
| 51. | 6171.6480 | 3772.0890 | 4180.0000 | 2872.2380 | 3142.8000 | 0.000 |
| 54. | 2967.0480 | 4808.1250 | 4863.3610 | 4686.7520 | 2936.7720 | |
| 57. | | | | | | 693.668 |
| 59. | | | | | | 443.576 |
| 61. | | | | | | 419.813 |
| 28. | 995.221 | 957.272 | 788.294 | 1228.208 | 1162.943 | |
| 32. | 866.77 | 1073.114 | 731.529 | 1165.54 | 1220.265 | |
| 35. | 920.34 | 1036.848 | 951.114 | 1215.678 | 1360.944 | |

*These values were not used for calculating the final average tumor volume. Each column represents the data for an individual mouse.

TABLE 19

| Treatment Days | Tumor Volume (mm3) PBMC + huL5H2_DI-2xDUPA (1 mg/kg, qd) | | | | | |
|---|---|---|---|---|---|---|
| 28. | 711.504 | 437.1125 | 592.012 | 402.040 | 337.561 | 774.400* |
| 32. | 1238.400 | 425.250 | 587.250 | 306.5605 | 252.6523 | 1381.203* |
| 35. | 1137.150 | 207.1035 | 235.468 | 514.425 | 107.648 | 208.088* |
| 39. | 105.966 | 0.000 | 0.000 | 295.074 | 0.000 | |
| 42. | 112.0905 | 0.000 | 0.000 | 271.472 | 0.000 | |
| 46. | 184.049 | 0.000 | 0.000 | 332.838 | 0.000 | |
| 49. | 725.000 | 0.000 | 107.217 | 473.984 | 0.000 | |
| 51. | 1609.699 | 0.000 | 0.000 | 188.356 | 718.8005 | |
| 54. | | | | | | |
| 57. | 404.9415 | 0.000 | 337.500 | 898.128 | 0.000 | |
| 59. | 173.400 | 0.000 | 321.408 | 681.462 | 0.000 | |
| 61. | 105.5925 | 0.000 | 369.820 | 816.480 | 0.000 | |
| 28. | 50.017 | 46.581 | 71.445 | 67.944 | 48.805 | |
| 32. | 47.685 | 49.317 | 76.261 | 67.46 | 49.359 | |
| 35. | 82.591 | 54.341 | 84.279 | 82.953 | 65.75 | |

*These values were not used for calculating the final average tumor volume.

Figure 15:
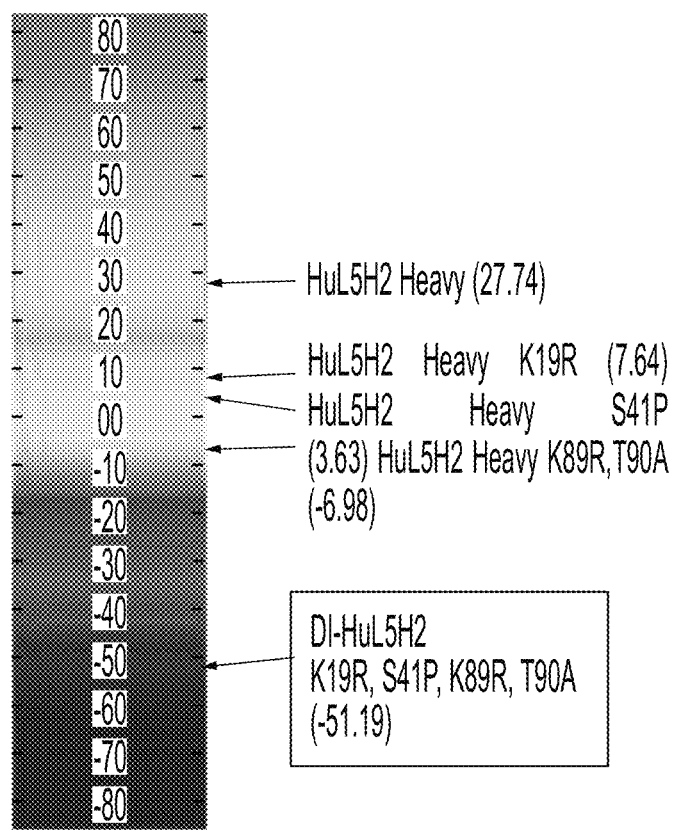
FIG. 15 shows introduction of four de-immunizing mutations in the variable heavy chain of SEQ ID NO: 41 predicted in-silico by Epivax software that resulted in a significantly reduced immunogenicity score. The resulting antibody heavy chain has SEQ ID NO: 43, and SEQ ID NO: 44 when configured to conjugate via pAcF.
Figure 16:
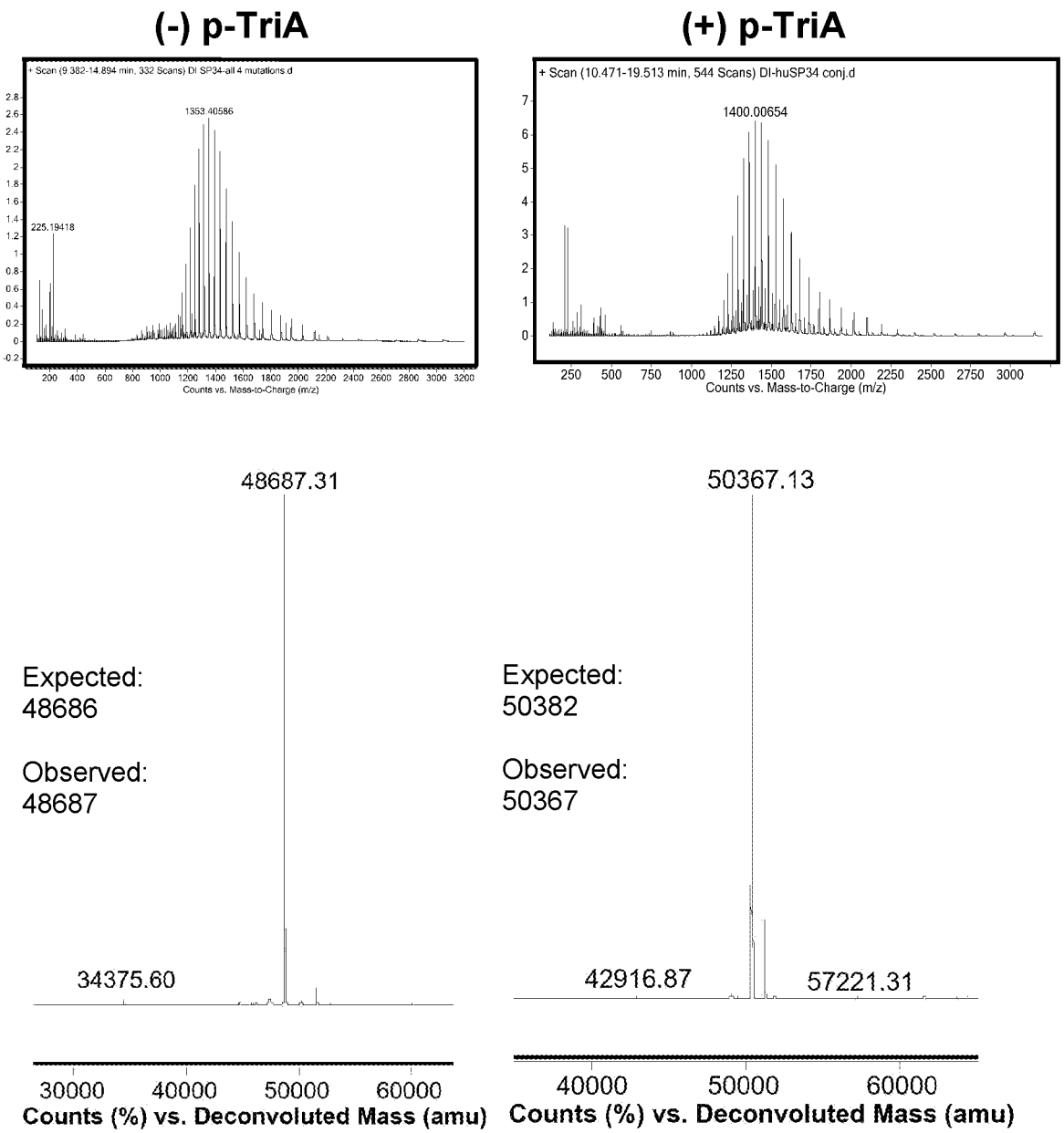
FIG. 16 shows completion of the conjugation reaction of de-immunized (DI) DI-HuL5H2 (SEQ ID NOS: 40, 44) with p-TriA as confirmed by QTOF mass spectrometry after excess linkers were removed by size filtration (Amicon, 10K and 30K) to generate huL5H2_DI-2×DUPA.

Example 7. Expression, Generation, and Characterization of De-Immunized huL5H2_DI-2xDUPA Antibody Conjugate In silico immunogenicity analysis (EpiVax) of HuL5H2 antibody predicted the antibody to be potentially immunogenic (immunogenicity score=27.74), due to the potential T cell epitopes found within the heavy chain sequence. Four de-immunizing mutations (K19R, S41P, K89R, and T90A) were introduced to generate a de-immunized (DI) version of HuL5H2 antibody (DI-HuL5H2) with a significantly reduced immunogenicity score (−51.19) as shown in FIG. 15. Site-specific point mutations at positions K 19, 541, K89, and T90 on the heavy chain were introduced in the HuL5H2 using the Quikchange Site-directed Mutagenesis Kit (Stratagene) and expressed as described above. The pAcF mutant DI-HuL5H2 was further conjugated with 30-fold molar excess of p-TriA in NaOAc (pH 4.5) buffer at 37° C. for ≥14 days. Excess p-TriA was removed by size filtration (Amicon, 10K and 30K) and completion of conjugation reaction was confirmed by QTOF (FIG. 16).

Figure 17A:
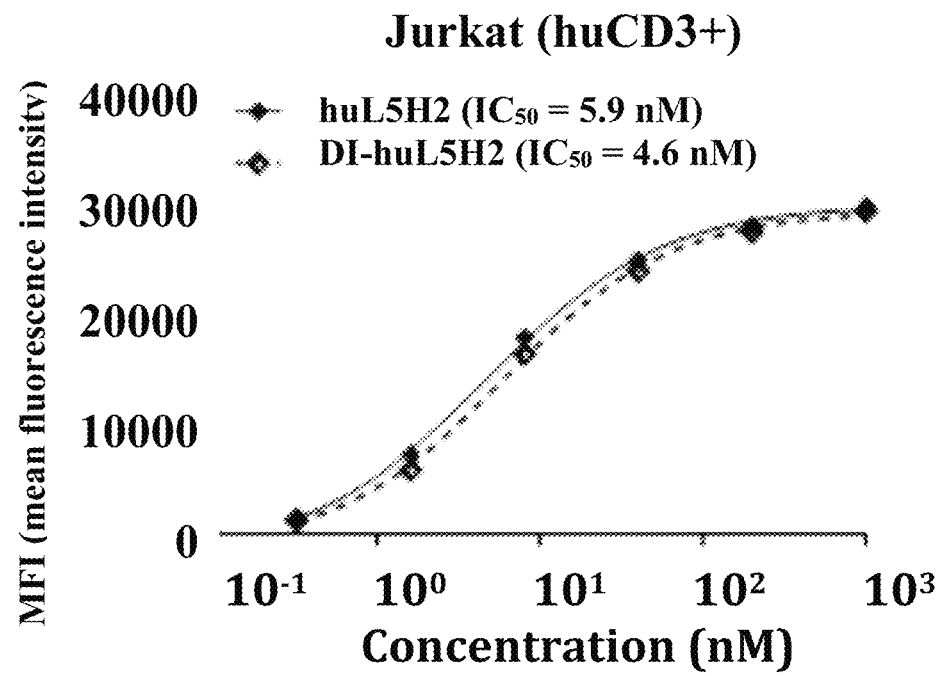
FIG. 17A shows similar binding profiles to human T cells were observed with huL5H2 (SEQ ID NOS: 40, 42) and DI-huL5H2 (SEQ ID NOS: 40, 44), which suggest that cross-reactivity to human CD3 was retained even after introducing de-immunizing mutations.
Figure 17B:
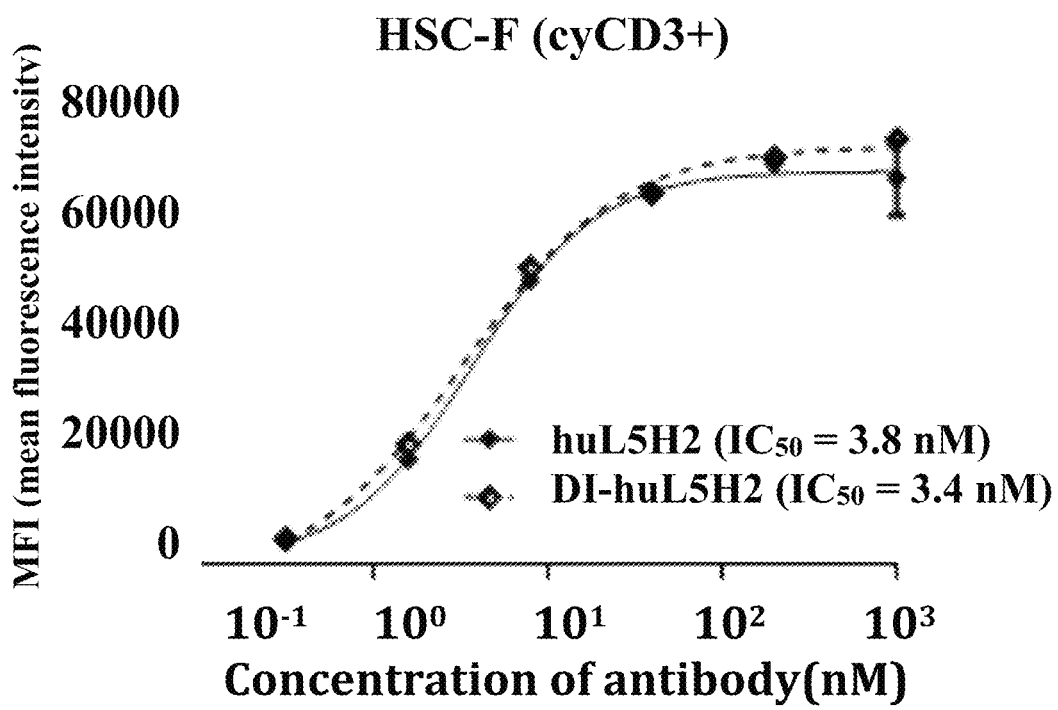
FIG. 17B shows similar binding profiles to cynomolgus T cells were observed with huL5H2 (SEQ ID NOS: 40, 42) and DI-huL5H2 (SEQ ID NOS: 40, 44), which suggest that cross-reactivity to cynomolgus CD3 was retained even after introducing de-immunizing mutations.

Flow cytometry was used to assess for potential differential binding to cell surface CD3 on human (Jurkat) and cynomolgus T cells as a result of the "de-immunization" process. As described above, cells were incubated with huL5H2 or DI-huL5H2 antibodies for 30 min and bound antibodies were revealed with R-phycoethrin (PE)-conjugated anti-human kappa secondary antibodies (Southern Biotech). After several washes, samples were acquired on a BD LSRII or BD Accuri C6 and analyzed using FlowJo software. In these studies, similar binding profiles to human and cynomolgus T cells were observed with both antibodies, which suggest that cross-reactivity to human CD3 was retained even after introducing de-immunizing mutations (FIGS. 17A and 17B, and Tables 20-21) (Jurkat: huL5H2 $IC_{50}$=5.9 nM and DI-huL5H2 $IC_{50}$=4.6 nM; HSC-F: huL5H2 $IC_{50}$=3.8 nM and DI-huL5H2 $IC_{50}$=3.4 nM).

TABLE 20

| CD3 antibody Concentration | Mean Fluorescence Intensity Jurkat (huCD3+) | | | |
|---|---|---|---|---|
| (nM) | huL5H2 | | DI-huL5H2 | |
| 1000 | 29858.33 | 29858.33 | 30058.33 | 30658.33 |
| 200 | 27858.33 | 27958.33 | 28958.33 | 28158.33 |
| 40 | 24558.33 | 24158.33 | 25658.33 | 25058.33 |

TABLE 20-continued

| CD3 antibody Concentration | Mean Fluorescence Intensity Jurkat (huCD3+) | | | |
|---|---|---|---|---|
| (nM) | huL5H2 | | DI-huL5H2 | |
| 8 | 16858.33 | 16458.33 | 18358.33 | 17858.33 |
| 1.6 | 6402.333 | 5426.333 | 7748.333 | 7030.333 |
| 0.32 | 1293.333 | 1189.333 | 1530.333 | 1558.333 |

TABLE 21

| CD3 antibody Concentration | Mean Fluorescence Intensity HSC-F(cyCD3+) | | | |
|---|---|---|---|---|
| (nM) | huL5H2 | | DI-huL5H2 | |
| 1000 | 71317.33 | 62217.33 | 73017.33 | 73917.33 |
| 200 | 69317.33 | 69417.33 | 70317.33 | 70217.33 |
| 40 | 63917.33 | 63417.33 | 64717.33 | 63917.33 |
| 8 | 49717.33 | 48617.33 | 51417.33 | 51317.33 |
| 1.6 | 18417.33 | 18017.33 | 21117.33 | 20617.33 |
| 0.32 | 4049.333 | 3968.333 | 4790.333 | 4614.333 |

Example 8. In Vitro Studies

Cytotoxicity Assay

Figure 18:
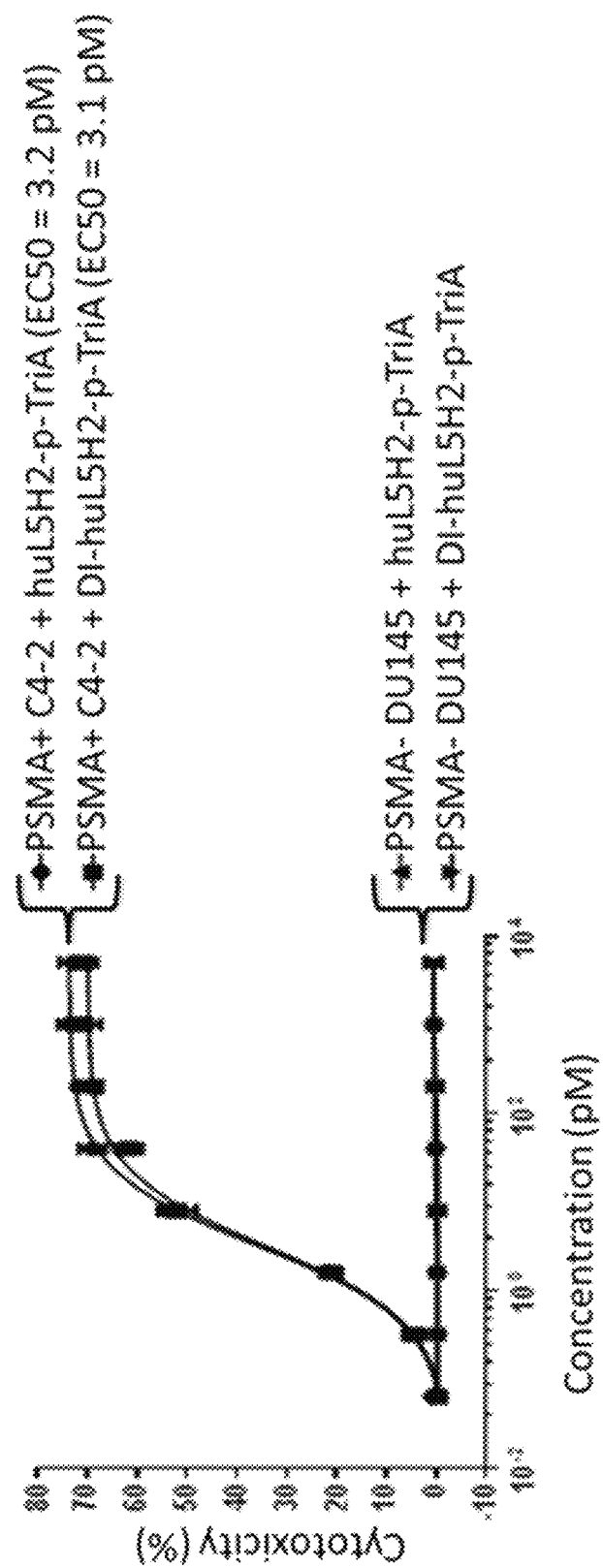
FIG. 18 shows huL5H2_DI-1×DUPA (SEQ ID NOS: 39, 44) and huL5H2_DI-2×DUPA (SEQ ID NOS: 40, 44) conjugates selectively redirected human PBMCs against C4-2 (PSMA-positive) cells with comparable potency (EC50=3.2 pM, 3.1 pM, respectively) and induced minimal non-specific killing of DU145 (PSMA-negative) cells.

The in vitro activity of the huL5H2_DJ-2xDUPA conjugate was assessed in cytotoxicity assays. As described previously in Example 4, 1×10⁵ PBMCs (human) and 1×10⁴ target cells (C4-2) were co-cultured with indicated concentrations of antibody conjugates for 24 hours. Cytotoxicity was determined by the amount of lactate dehydrogenase (LDH) released from lysed cells. As shown in FIG. 18, and Tables 22-23, huL5H2- and huL5H2_DJ-2xDUPA conjugates selectively redirected human PBMCs against C4-2 (PSMA-positive) cells with comparable potency (huL5H2-p-TriA, $EC_{50}$=3.2 pM; 1DJ-huL5H2-p-TriA, $EC_{50}$=3.1 pM) and induced minimal non-specific killing of DU145 (PSMA-negative) cells.

TABLE 22

| Target cells CD3 antibody conjugates Concentration (pM) | Percent Cytotoxicity C4-2 (PSMA-positive) | | | | | |
|---|---|---|---|---|---|---|
| | huL5H2-p-TriA | | | DI-huL5H2-p-TriA | | |
| 5000 | 72.30169 | 70.27051 | 75.91704 | 74.08192 | 69.01573 | 69.66665 |
| 1000 | 75.47786 | 74.30935 | 70.78027 | 74.6152 | 67.82368 | 69.92544 |
| 200 | 72.14484 | 70.19993 | 73.33689 | 68.26286 | 68.20796 | 68.92162 |
| 40 | 71.07044 | 66.02777 | 70.05092 | 60.45967 | 64.84357 | 59.9107 |
| 8 | 54.00537 | 53.54267 | 54.02106 | 52.63295 | 55.45622 | 47.84125 |
| 1.6 | 21.89075 | 23.37296 | 20.05563 | 22.1966 | 22.88673 | 18.72242 |
| 0.32 | 3.516009 | 6.911768 | 3.139574 | 4.637472 | 5.21781 | 3.915971 |
| 0.064 | 1.767154 | 1.367192 | −0.83652 | 0.865278 | −0.88358 | −1.07179 |
| 0 | 3.1646695 | 2.5451199 | 2.2471088 | 3.1646695 | 2.5451199 | 2.2471088 |

TABLE 23

| Target cells CD3 antibody conjugates Concentration (pM) | Percent Cytotoxicity DU145 (PSMA-negative) | | | | | |
|---|---|---|---|---|---|---|
| | huL5H2-p-TriA | | | DI-huL5H2-p-TriA | | |
| 5000 | 0.500375 | −0.10841 | 0.825619 | 0.867317 | 0.20849 | 1.000751 |
| 1000 | 1.334334 | 0.783921 | 0.708865 | 0.508715 | 0.20849 | −0.34192 |
| 200 | 0.225169 | 0.333584 | 0.60045 | 0.075056 | −0.15845 | 0.550413 |
| 40 | 0.792261 | 0.366942 | 0.567092 | 0.341923 | −0.58377 | −0.64215 |
| 8 | 0.016679 | −0.4003 | 0.20015 | 0.083396 | −0.27521 | −0.51705 |
| 1.6 | 0.333584 | −0.14177 | 0.575432 | −0.4003 | 0.083396 | −1.04245 |
| 0.32 | 0.016679 | −0.47536 | 0.583771 | −0.36694 | −0.17513 | −0.58377 |
| 0.064 | 0.241848 | −0.28355 | 0.150113 | −0.53373 | −0.52539 | −0.98407 |
| 0 | 0.4264309 | 0.1595641 | −0.0072276 | 0.4264309 | 0.1595641 | −0.0072276 |

Example 9. Synthesis and Comparison of huL5H2_DI-2×DUPA and huL5H2_DI-1×DUPA

In Vitro Binding Comparison Assay

Binding affinity was measured by Octet (ForteBio) using an in-house instrument; the interaction was tested using the DUPA-CD3 as the ligand and reversed interaction as the analyte Each ligand was prepared at 20 μg/mL, 15 ug/ml, 10 μg/mL, and 5 μg/mL in PBS. Analytes were serially diluted 1.2× from 6 μg/mL to 1 μg/mL in the 1×PBS. 100 mM glycine (pH 2.87) regeneration solution, and 1×PBS for baseline stabilization was also prepared. Biosensor, ligand and analytes pair is following: (1) CH-1-antibodies-recombinant human or cynomolgus monkey CD3 delta/epsilon complex, (2) Fc-recombinant human or cynomolgus monkey CD3 delta/epsilon complex-antibodies (3) CH-1-antibodies-recombinant human or cynomolgus monkey PSMA; and (4) Ni-NTA-recombinant human or cynomolgus monkey PSMA-antibodies. Prior to the binding measurements, the sensor tips were pre-hydrated in 1×PBS for 30 min, followed by 1 cycles of pre-conditioning with 60-sec dips in glycine (pH 2.87). The sensor tips were then transferred to the ligand-containing wells for a 180-sec loading step. After a 120-sec baseline dip in 1×PBS, the binding kinetics were measured by dipping the ligand-coated sensors into the wells containing corresponding analyte at varying concentrations. The binding interactions were monitored over a 180-sec association period and followed by a 7.5 to 15-min dissociation period in new wells containing fresh 1×PBS. Binding was comparable between huL5H2_DI-2×DUPA and huL5H2_DI-1×DUPA to CD3 with an affinity of 10 nM; huL5H2_DI-2×DUPA showed significantly higher binding when PMSA was used as the ligand, due to avidity effects (Table 24). Binding affinity of both conjugates to cynoP-SMA (cynomolgus PSMA) and cynoCD3 (cynomolgus CD3) was similar to the binding affinity of both conjugates to human PSMA and human CD3, respectively.

TABLE 24

| Binding to | Capture | Ligand | Analyte | Affinity |
|---|---|---|---|---|
| CD3 | CH1 | L5H2-DI-1X-DUPA | hu.CD3 d/e-Fc | 4.83E−09 |
| CD3 | CH1 | L5H2-DI-2X-DUPA | hu.CD3 d/e-Fc | 5.13E−09 |
| cynoCD3 | CH1 | L5H2-DI-1X-DUPA | cy.CD3 d/e-Fc | 3.29E−09 |
| CD3 | Fc | hu.CD3de-Fc | L5H2-DI-1X-DUPA | 2.12E−08 |
| CD3 | Fc | hu.CD3de-Fc | L5H2-DI-2X-DUPA | 1.10E−08 |
| cynoCD3 | Fc | cy.CD3 d/e-Fc | L5H2-DI-1X-DUPA | 1.13E−08 |
| PSMA | CH1 | L5H2-DI-1X-DUPA | hu.PSMA | 2.36E−11 |
| PSMA | CH1 | L5H2-DI-2X-DUPA | hu.PSMA | 9.03E−11 |
| cynoP SMA | CH1 | L5H2-DI-1X-DUPA | hu.PSMA | n/a |

TABLE 24-continued

| Binding to | Capture | Ligand | Analyte | Affinity |
|---|---|---|---|---|
| PSMA | Ni-NTA | hu.PSMA | L5H2-DI-1X-DUPA | 2.17E-09 |
| PSMA | Ni-NTA | hu.PSMA | L5H2-DI-2X-DUPA | <1.0E-12 |
| cynoPSMA | Ni-NTA | cyno.PSMA | L5H2-DI-1X-DUPA | 5.11E-09 |

Synthesis of huL5H2_DI-1×DUPA

Humanized anti-CD3 containing single mutant Fab format antibodies were buffer exchanged into conjugation buffer, consisting of 50 m % NaOAc (pH 4.5), 150 M R NaCl and 100 glycerol using PD-10 disposable column and concentrated to 30 mg/ml using Amicon 10K filter. The oxime ligation was conducted with 24-215 molar excess of prostate-specific membrane antigen (PSMA)-binding small molecule ligands to 10 mg/ml antibodies, and the reaction was completed within 18 hours at room temperature, as monitored by liquid chromatography-mass spectrometer. Excess small molecules were removed by size filtration (Amicon 10K) and the conjugates were buffer exchanged into PBS (pH 7.4) followed by removing potential aggregated by a millex GV 0.22 um filter before in vitro and in vivo studies. Formic acid salts of DUPA were found to be optimal for conjugation, with a 99.86% conjugation efficiency (Table 25 and Table 26).

randomly conjugated with Alexa Fluor 488 using Alexa Fluor 488 antibody labeling kit (Thermo Fisher Scientific) as per manufacturer's protocol. Corresponding antibodies that were not conjugated to DUPA (i.e. 1×TAG) served as antigen-specific controls. 25 ug of Alexa Fluor 488-labelled antibodies were incubated with 0.5×106 C4-2 (PSMA-positive) cells at 37° C. for specified durations or on ice for 30 minutes (control). Internalization was halted and excess conjugates were removed with subsequent washes using ice-cold staining buffer (200 FBS/1 mM EDTA/DPBS). For each time point, cells were incubated with or without an anti-Alexa Fluor 488 antibody (Thermo Fisher Scientific) on ice for 30 minutes. The mean fluorescence of quenched (Q) and non-quenched (NonQ) cells were assessed on a BD FACSCanto™ II and used to calculate internalization rates as described previously (Cancer Immunol Immunother.

TABLE 25

| Calibr ID | Salt | Scale | % conjugation | Recovery | Ratio |
|---|---|---|---|---|---|
| CBR-001-623-836-1 | Formic acid | 2 mg | 98.91 | 90.79 | 54 |
| CBR-001-623-840-7 | Formic acid | 2 mg | 99.48 | 0.4 | 74 |
| CBR-001-625-095-6 | Formic acid | 2 mg | 99.86 | 96.81 | 68 |
| CBR-001-625-094-5 | Formic acid | 2 mg | 99.86 | 92.45 | 81 |

TABLE 26

| Protein | Small Molec Batch | Salt | % conjugation | Ratio | Notes |
|---|---|---|---|---|---|
| huL5H2_DI-1xpAcF | CBR-001-600-008-1 | HCl | N/A | 215 | aggregation |
| huL5H2_DI-1xpAcF | CBR-001-620-049-0 | Na2CO3 | 93.48 | 40 | |
| huL5H2_DI-1xpAcF | CBR-001-620-048-9 | Li2CO3 | 74.33 | 54 | |
| huL5H2_DI-1xpAcF | WuxiDUPA | Li2CO3 | 90.29 | 96 | |
| huL5H2_DI-1xpAcF | CBR-001-623-837-2 | Li2CO3 | 90.34 | 133 | |
| huL5H2_DI-1xpAcF | CBR-001-597-963-2 | TFA | 99.56 | 31 | |
| huL5H2_DI-1xpAcF | CBR-001-593-245-3 | TFA | 99.68 | 24 | |
| huL5H2_DI-1xpAcF | TSRI | TFA | 91.16 | 57 | aggregation |
| huL5H2_DI-1xpAcF | CBR-001-623-836-1 | Formic acid | 98.91 | 27 | |
| huL5H2_DI-1xpAcF | CBR-001-623-840-7 | Formic acid | 99.48 | 37 | |
| huL5H2_DI-1xpAcF | CBR-001-624-015-6 | TFA | 99.47 | 37 | aggregation |
| huL5H2_DI-1xpAcF | CBR-001-625-095-6 | Formic acid | 99.86 | 34 | |
| huL5H2_DI-1xpAcF | CBR-001-625-094-5 | Formic acid | 99.86 | 40 | |

Comparison of PSMA-Mediated Internalization

Figure 21A:
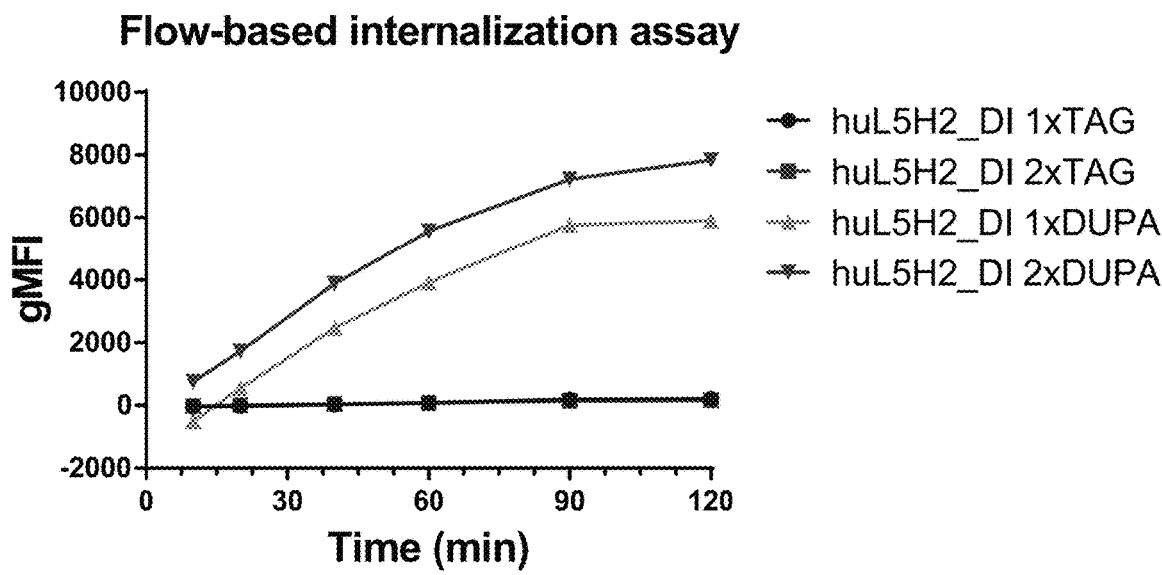
FIG. 21A shows that huL5H2_DI-1×DUPA (SEQ ID NOS: 39, 44) and huL5H2_DI-2×DUPA (SEQ ID NOS: 40, 44) conjugates are internalized into PSMA+ cells with similar rates.
Figure 21B:
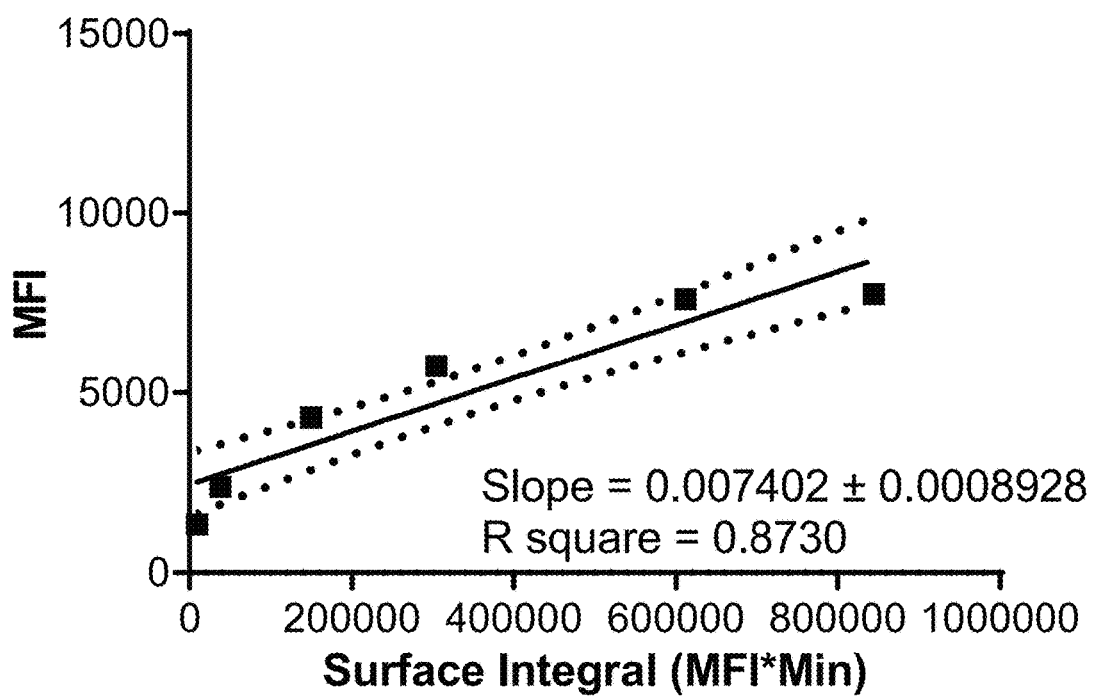
FIG. 21B and FIG. 21C show calculation of the internalization rate constants (linear-fit slopes) for L5H2_DI-1× DUPA and L5H2_DI-2×DUPA, respectively.
Figure 21C:
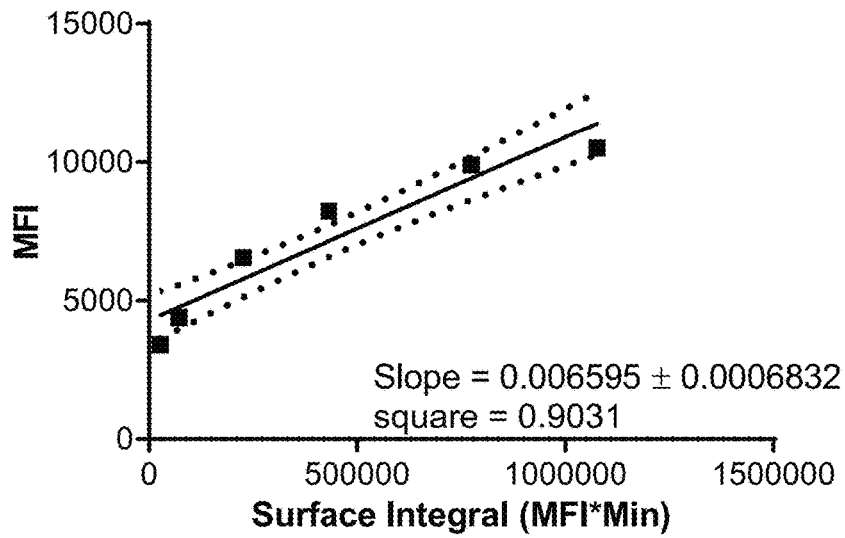

Flow cytometry was used to determine the internalization rates of huL5H2_DI-1×DUPA and -2×DUPA conjugates (FIG. 21A, FIG. 21B, FIG. 21Q). Antibody conjugates were 2008 December; 57(12):1879-90 and Mol Biol Cell. 2004 December; 15(12):5268-82). In these studies, both huL5H2_DI-1×DUPA and huL5H2_DI-2×DUPA conjugates internalized at comparable rates on PSMA-positive cells (Table 27).

TABLE 27

| JSM-6-147 | huL5H2_DI-1xDUPA | huL5H2_DI-2xDUPA |
|---|---|---|
| $K_e$ = slope | 0.007402 | 0.006595 |
| $T_{1/2} = \ln(2)/K_e$ | 96.64323 (1.6 h) | 105.1019 (1.8 h) |
| JSM-6-088 | huL5H2_DI-1xDUPA | huL5H2_DI-2xDUPA |
| $K_e$ = slope | 0.007527 | 0.006439 |
| $T_{1/2} = \ln(2)/K_e$ | 92.0881 (1.5 h) | 107.6483 (1.8 h) |

In Vitro Cytoxicity

Figure 22:
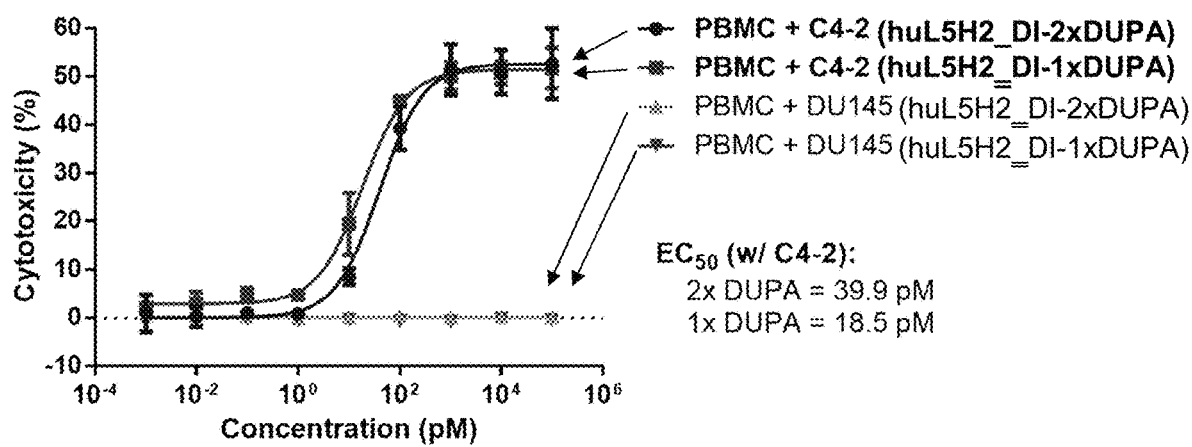
FIG. 22 shows that both huL5H2_DI 1×DUPA and huL5H2_DI 2×DUPA, in the presence of PBMCs, were cytotoxic against PSMA+C4-2 cells (10:1 ratio of PBMC: C4-2 cells).

The in vitro efficacy of huL5H2_DI-1xDUPA and -2xDUPA was assessed in cytotoxicity assays. As described previously in Example 4, $1\times10^5$ PBMCs (human) and $1\times10^4$ target cells (C4-2, PSMA-positive or DU145, PSMA-negative) were co-cultured at a 10:1 (Effector:Target cell) ratio with indicated concentrations of antibody conjugates for 24 hours. Cytotoxicity was determined by calculating the amount of lactate dehydrogenase (LDH) released from lysed target cells. As shown, both conjugates selectively redirected human PBMCs against C4-2 cells, where a slightly increased efficacy was observed with huL5H2_DI-1xDUPA (EC50=18.5 pM) in comparison to huL5H2_DI-2xDUPA (EC50=39.9 pM) (FIG. 22). No off-target killing of DU145 was observed with both conjugates.

Cytokine Release

Figure 23:
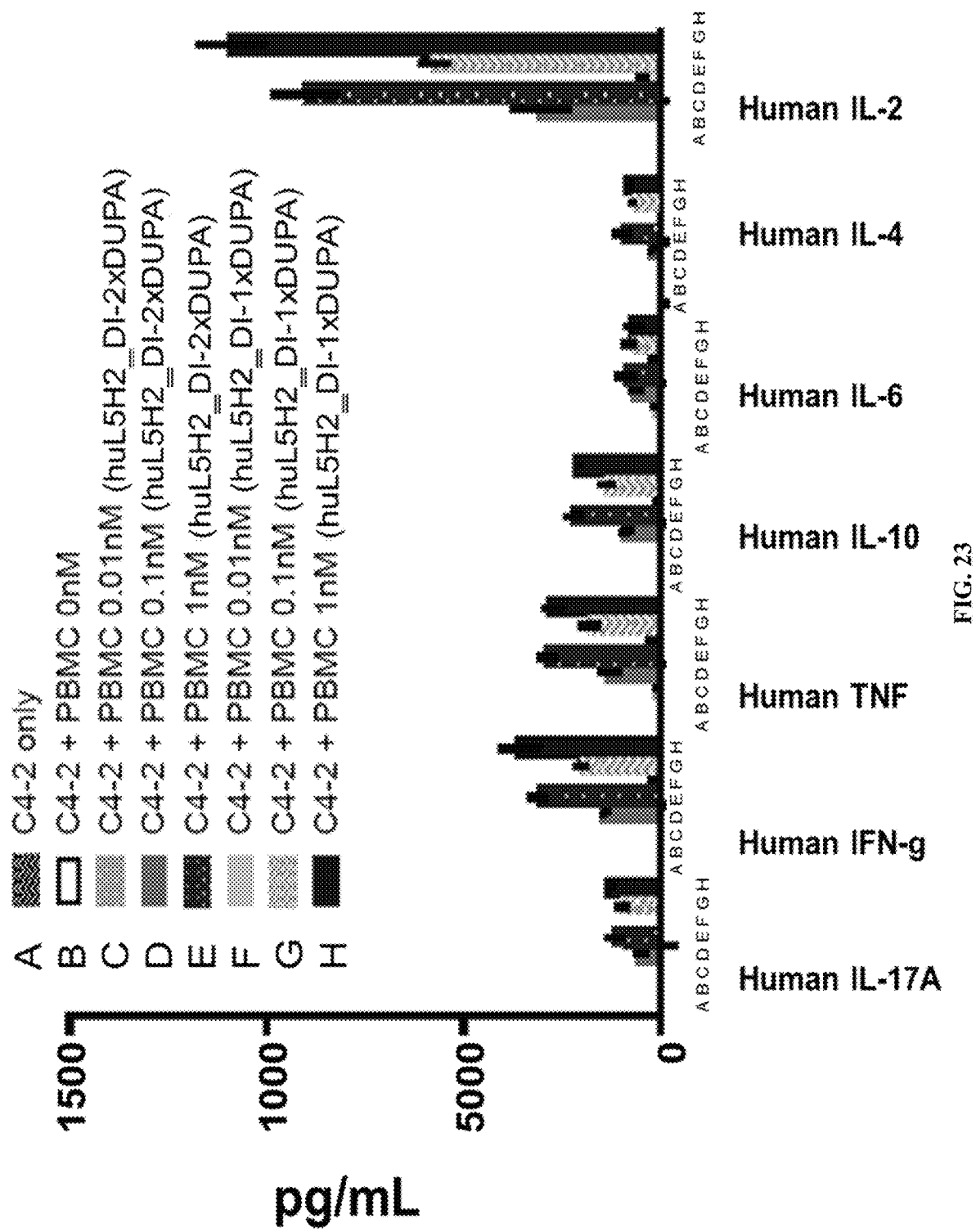
FIG. 23 shows that huL5H2_DI 1×DUPA and huL5H2_DI 2×DUPA demonstrated cytokine release levels in C4-2 cancer cells. Samples were obtained from media used in the cytotoxicity study in FIG. 22.

Cytokines in cultured media from cytotoxicity assays described above were quantified using BD CBA Human Th1/Th2 Kit II (BD Biosciences). Samples were acquired on a BD Accuri C6 and analyzed using the FCAP Array software. As shown, both huL5H2_DI-1xDUPA and huL5H2_DI-2xDUPA induced comparable antigen-specific release of human inflammatory cytokines in the presence of PSMA-positive C4-2 cells. huL5H2_DI-1xDUPA and -2xDUPA demonstrated a similar cytokine profile (FIG. 23).

In Vitro Activation and Proliferation

Figure 24:
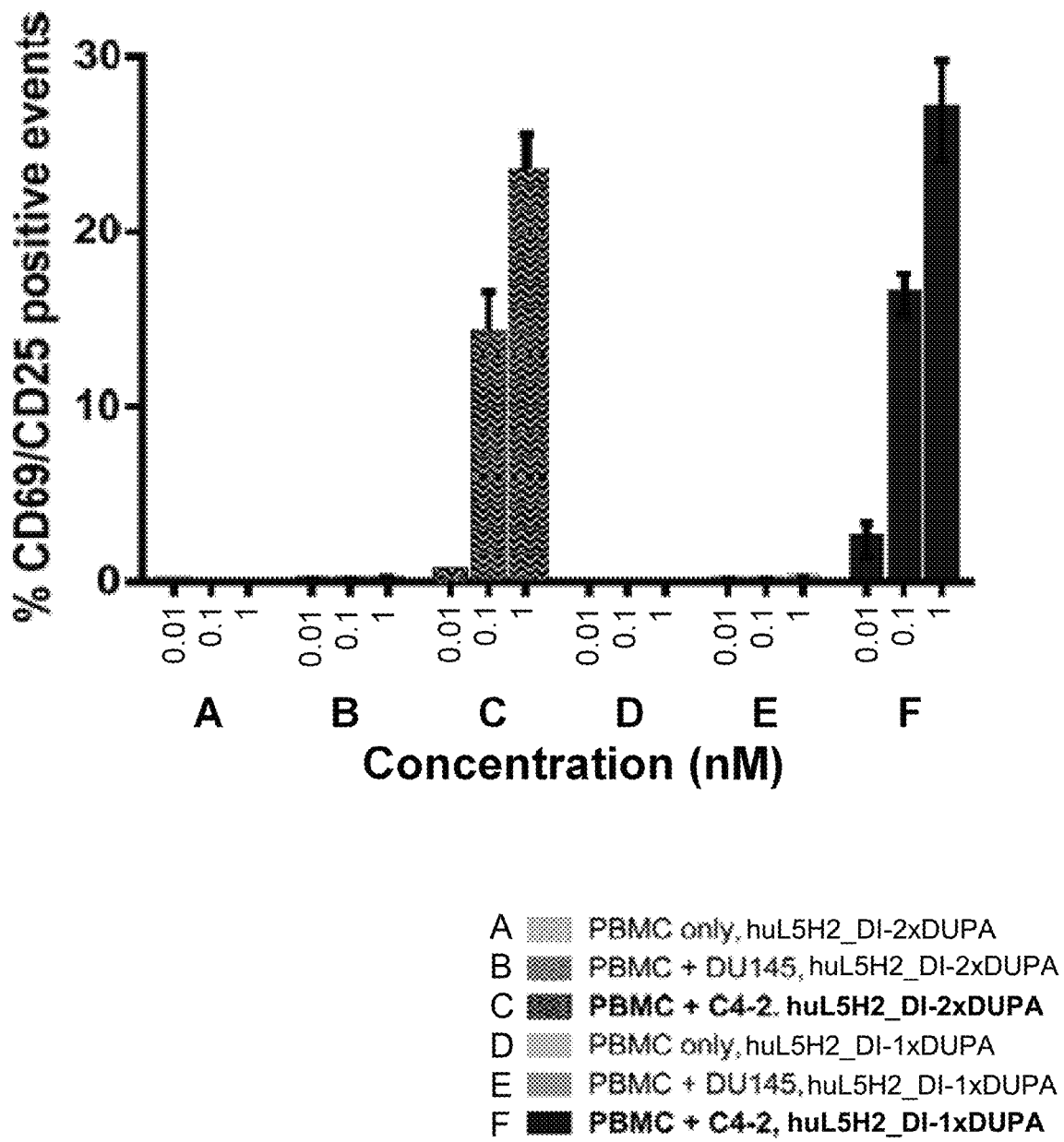
FIG. 24 shows that huL5H2_DI 1×DUPA and huL5H2_DI 2×DUPA demonstrated significant PSMA+ dependent upregulation of activation markers CD25/CD69 in human PBMCs.
Figure 25:
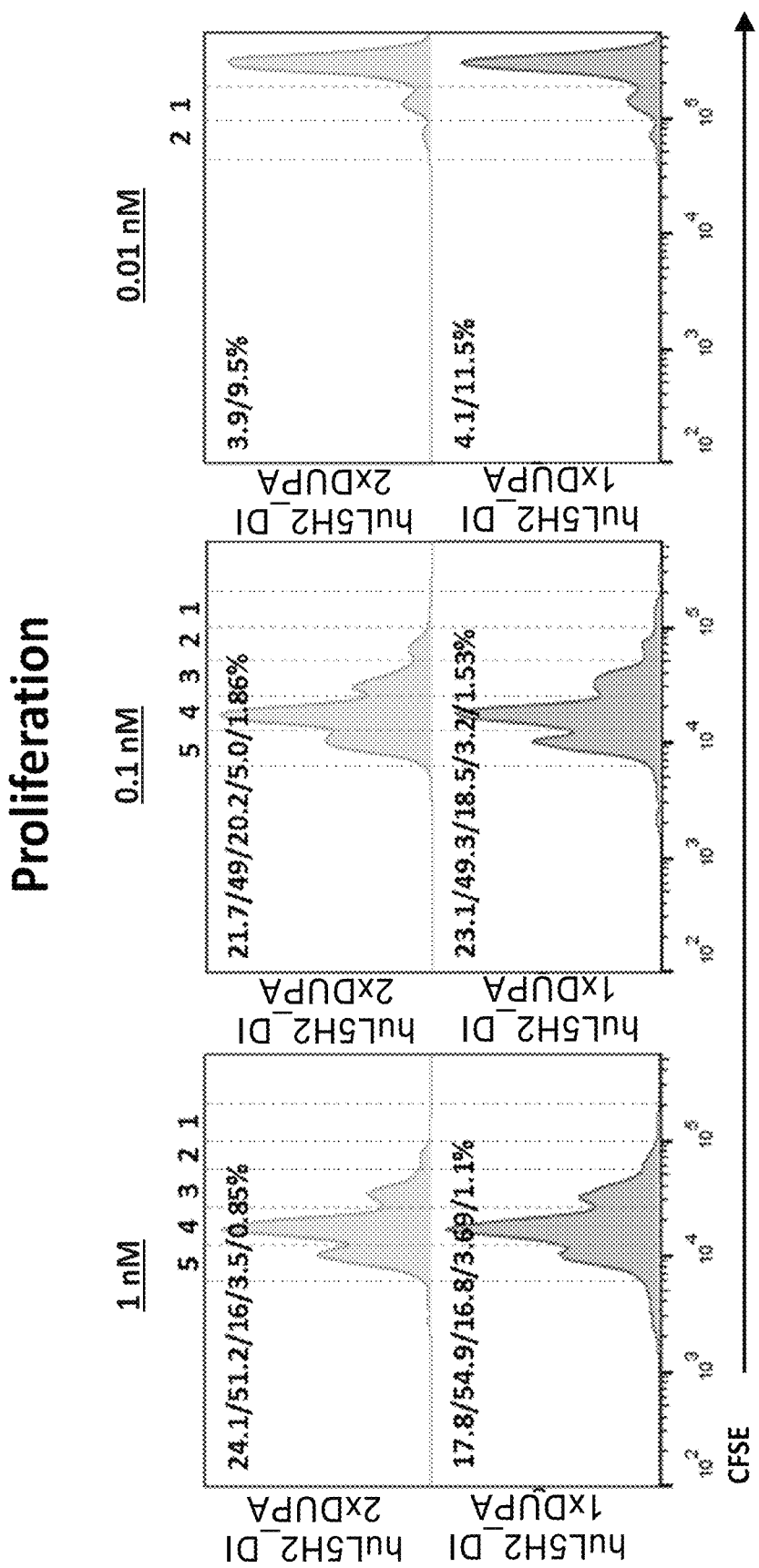
FIG. 25 shows that huL5H2_DI 1×DUPA and huL5H2_DI 2×DUPA demonstrated significant T-cell proliferation activity when using human PBMCs.

Upregulation of activation markers on human PBMC by huL5H2_DI-1xDUPA and huL5H2_DI-2xDUPA antibody conjugates was assessed in the presence of PSMA-positive and PSMA-negative target cells. In these studies, equal number ($1\times10^5$) of human PBMC and C4-2 (PSMA-positive) or DU145 (PSMA-negative) cells were co-cultured in the presence of 1, 0.1, 0.01, or 0 nM antibody conjugates in 96 well round bottom plates at 37° C. for 24 hours. The next day, cultures were labeled with PE-conjugated anti-CD3 (OKT3), AlexaFluor 488-conjugated CD25 (BC96) and allophycocyanin (APC)-conjugated CD69 (FN50) antibodies (all purchased from Biolegend). Appropriate isotype controls were included in each study to determine background and exclude non-specific staining. Unstained and single color controls were acquired and used for compensation. The effect of huL5H2_DI-1xDUPA and huL5H2_DI-2xDUPA antibody conjugates on T-cell proliferation was also assessed. $1\times10^5$ carboxyfluorescein succinimidyl ester (CFSE)-labeled human PBMC and $1\times10^5$ mitomycin-treated target cells were cocultured in the presence 1 nM antibody conjugates. After 72 hours, cultures were labeled with anti-CD3 antibody and 7-AAD dye to assess for live, dividing T-cells on the BD Accuri C6. As shown in FIG. 24 and FIG. 25, both L5H2_DI antibody conjugates induced similar capacity of T-cell activation and proliferation, respectively, in a PSMA-dependent manner.

PSMA Quantification Assay

To compare the in vitro activity of huL5H2_DI-1xDUPA and -2xDUPA antibody conjugates against different cancer cells with varying antigen densities, the relative number of cell surface PSMA per cell found on different prostate cancer cell lines was established (Table 28). Cell lines were stained with a PE-conjugated anti-human PSMA antibody (Biolegend) and acquired on a BD FACSCanto™ II or BD Accuri C6. Antigen densities were determined by extrapolating the signal intensities from a standard curve generated by using the QuantiBRITE PE Fluorescent Quantitation kit (BD Pharmingen).

TABLE 28

| Prostate Cancer Cell Lines | Rel. No. PSMA/cell | ±SD |
|---|---|---|
| LNCaP | 179620 | 85951 |
| C4-2 | 110341 | 43526 |
| VCap | 46738 | 27521 |
| 22Rv-1 (sorted) | 12217 | 2935 |
| 22Rv-1 (parent) | 3606 | 1770 |
| DU145 | 114 | 86 |

Figure 27:
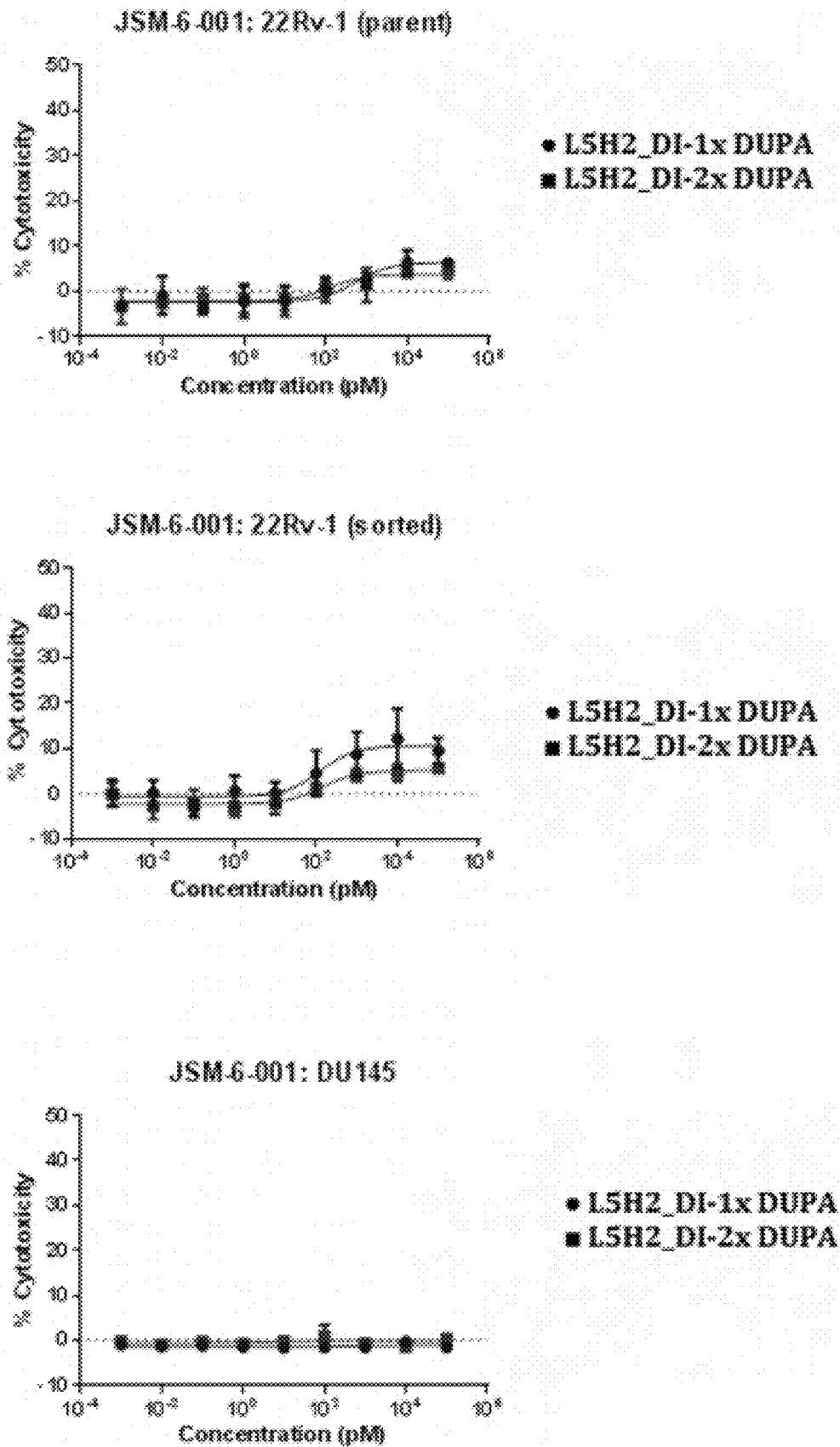
FIG. 27 shows huL5H2_DI-1×DUPA and huL5H2_DI-2×DUPA demonstrated dose-dependent cytotoxicity using the 22Rv-1 cell line.

The in vitro activity of huL5H2_DI-1xDUPA and huL5H2_DI-2xDUPA antibody conjugates against different cancer cells with varying cell surface PSMA densities was assessed in cytotoxicity assays. As described previously in Example 4, $1\times10^5$ PBMCs (human) and $1\times10^4$ target cells (C4-2) were cocultured with indicated concentrations of antibody conjugates for 24 hours. Cytotoxicity was determined by the amount of lactate dehydrogenase (LDH) released from lysed cells. In these studies, an insignificant increase in target cell killing was observed with huL5H2_DI-1xDUPA in comparison to huL5H2_DI-2xDUPA (FIG. 26 and FIG. 27).

PSMA Competition Assay

Figure 28:
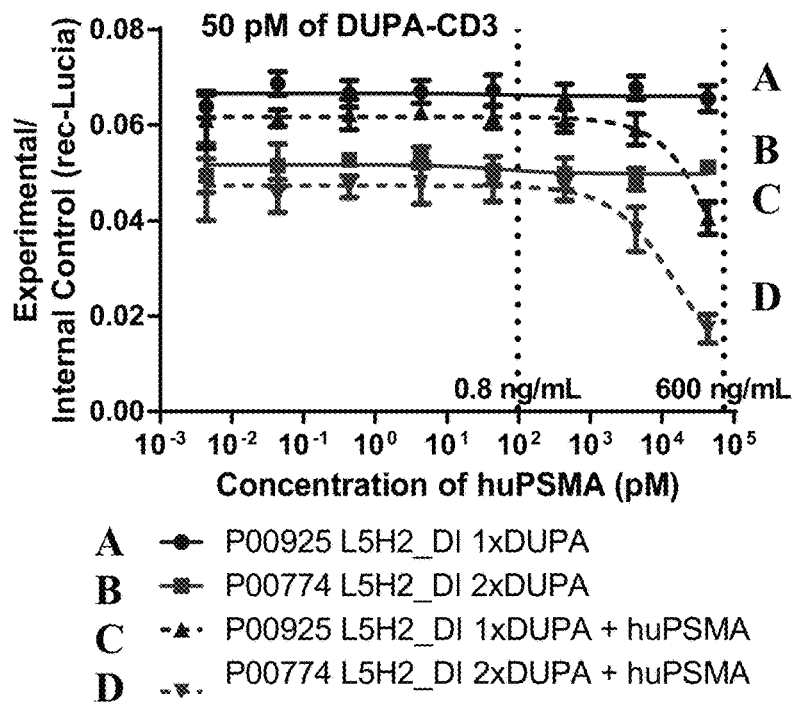
FIG. 28 shows huL5H2_DI-1×DUPA (batch ID P00925) and huL5H2_DI-2×DUPA (batch ID P00774) were not significantly inhibited from activating T-cells by unbound human PSMA in the presence of human PBMCs and C4-2 cells in a Jurkat NFAT assay.
Figure 29:
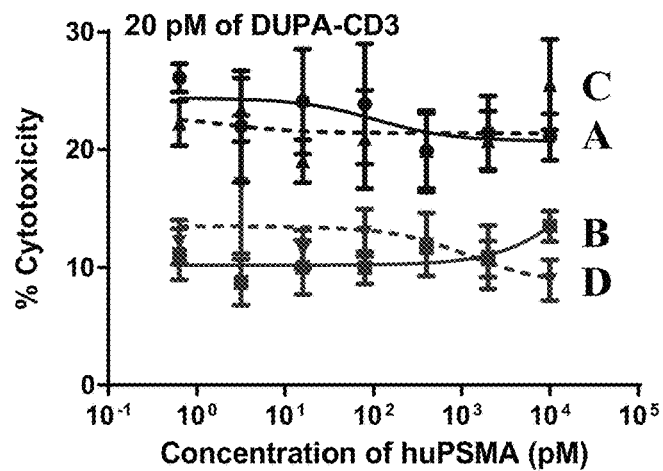
FIG. 29 shows huL5H2_DI-1×DUPA (batch ID P00925) and huL5H2_DI-2×DUPA (batch ID P00774) demonstrated no significant inhibition of cytotoxicity against C4-2 cells by unbound human PSMA using PBMC donor 5053 cells.

To determine whether soluble PSMA can negatively impact the activity of huL5H2_DI-1xDUPA and huL5H2_DI-2xDUPA antibody conjugates, competition assays were established using human PBMC or Jurkat T-cells that stably express the firefly luciferase gene driven by nuclear factor of activated T-cells (NFAT) response elements (Jurkat NFAT-Luc, Invivogen). In assays using human PBMC, $1\times10^5$ PBMCs and $1\times10^4$ target cells (C4-2) were cocultured in the presence of 20 pM huL5H2_DI antibody conjugates and varying concentrations of human PSMA (huPSMA, R&D systems). After 24 hours, target cell lysis was determined by measuring the amount of lactate dehydrogenase (LDH) released. Similarly, $2\times10^5$ Jurkat NFAT-Luc cells and $2\times10^4$ C4-2 cells were cocultured in the presence of 50 pM huL5H2_DI antibody conjugates and varying concentrations of human PSMA (huPSMA, R&D systems) for 24 hours. Luciferase production was measured using the *Gaussia* Luciferase Glow Assay kit (Pierce) as per manufacturer's instructions. In these studies, soluble huPSMA (up to 10 nM) did not interfere with both huL5H2_DI antibody conjugates in redirecting human PBMCs against PSMA-positive cells (FIG. 28 and FIG. 29) To the same extent, only higher concentrations of huPSMA (≥1 nM) was observed to inhibit T-cell activation in cultures containing either huL5H2_DI-1xDUPA or huL5H2_DI-2xDUPA.

Jurkat Activation Assay

Figure 30:
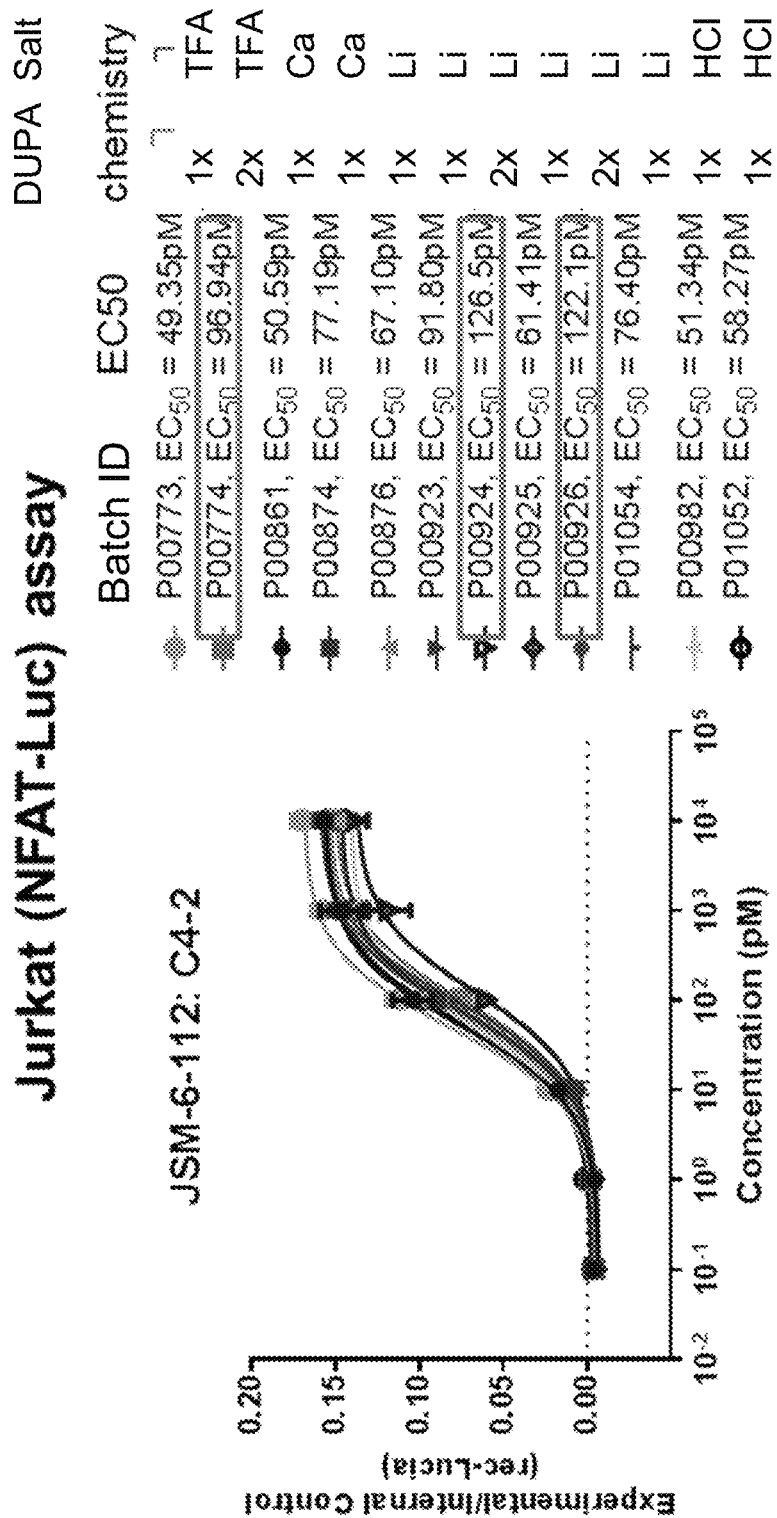
FIG. 30 shows a comparison of different batches (ID=P0####) of DUPA conjugates for T-cell activation in a fluorescence-based Jurkat (NFAT-Luc) assay, in the presence of C4-2 cells.
Figure 31A:
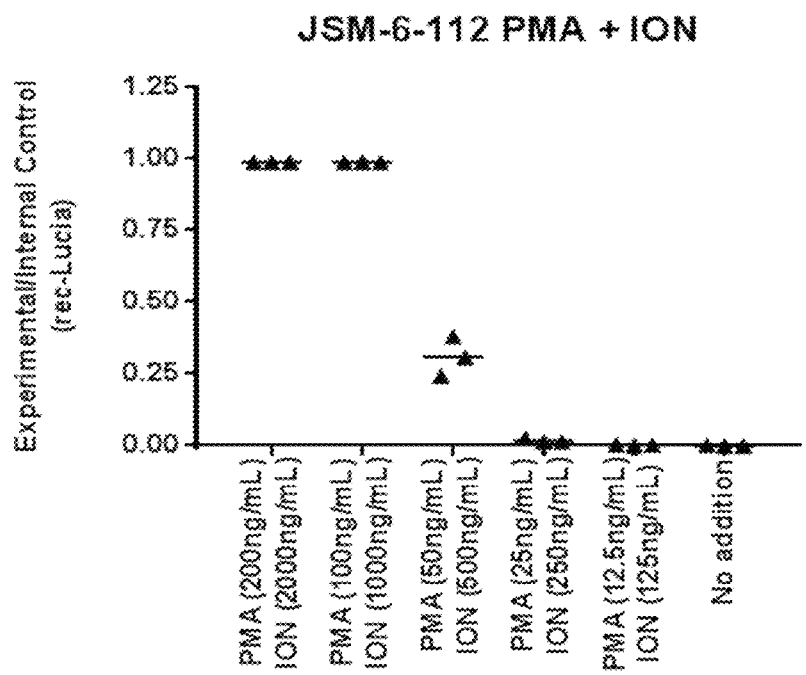
FIG. 31A shows positive controls PMA and Ionomycin activated T-cells in a fluorescence-based Jurkat (NFAT-Luc) assay.
Figure 31B:
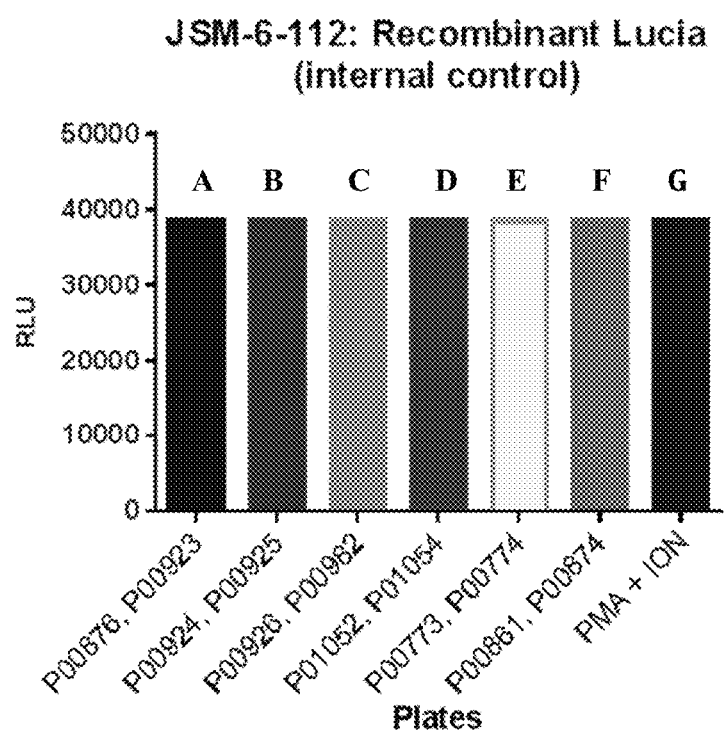
FIG. 31B shows internal positive control recombinant luciferase produced a consistent signal across batches of DUPA conjugates.

To validate the activity of different production batches (DUPA sources listed as P0####; with chemistry indicating the salt state, FIG. 30) of either huL5H2_DI-1xDUPA or huL5H2_DI-2xDUPA with minimal assay-to-assay variation, a T-cell activation assay was established using a stable Jurkat T-cell line that expresses the firefly luciferase gene driven by six NFAT response elements (Jurkat NFAT-Luc, Invivogen). As described previously in Example 4, $2\times10^5$ Jurkat NFAT-Luc cells and $2\times10^4$ target cells were cocultured in the presence of varying concentrations of antibody conjugates. Phorbol 12-myristate 13-acetate (PMA) and ionomycin (ION))-treated cells were included as controls. After 24 hours, luciferase production was measured using the *Gaussia* Luciferase Glow Assay kit (Pierce) as per manufacturer's instructions. Experimental values were normalized to the absorbance collected from PMA and ION treated cells or recombinant luciferase (recombinant Lucia, Invivogen) (FIG. 31A, and FIG. 31B). Each bar in FIG. 31B represents an average RLU value of two wells containing Recombinant Lucia on each plate containing specific treatment samples. This data demonstrate minimal plate-to-plate variation during read-out.

Serum Stability

Figure 32:
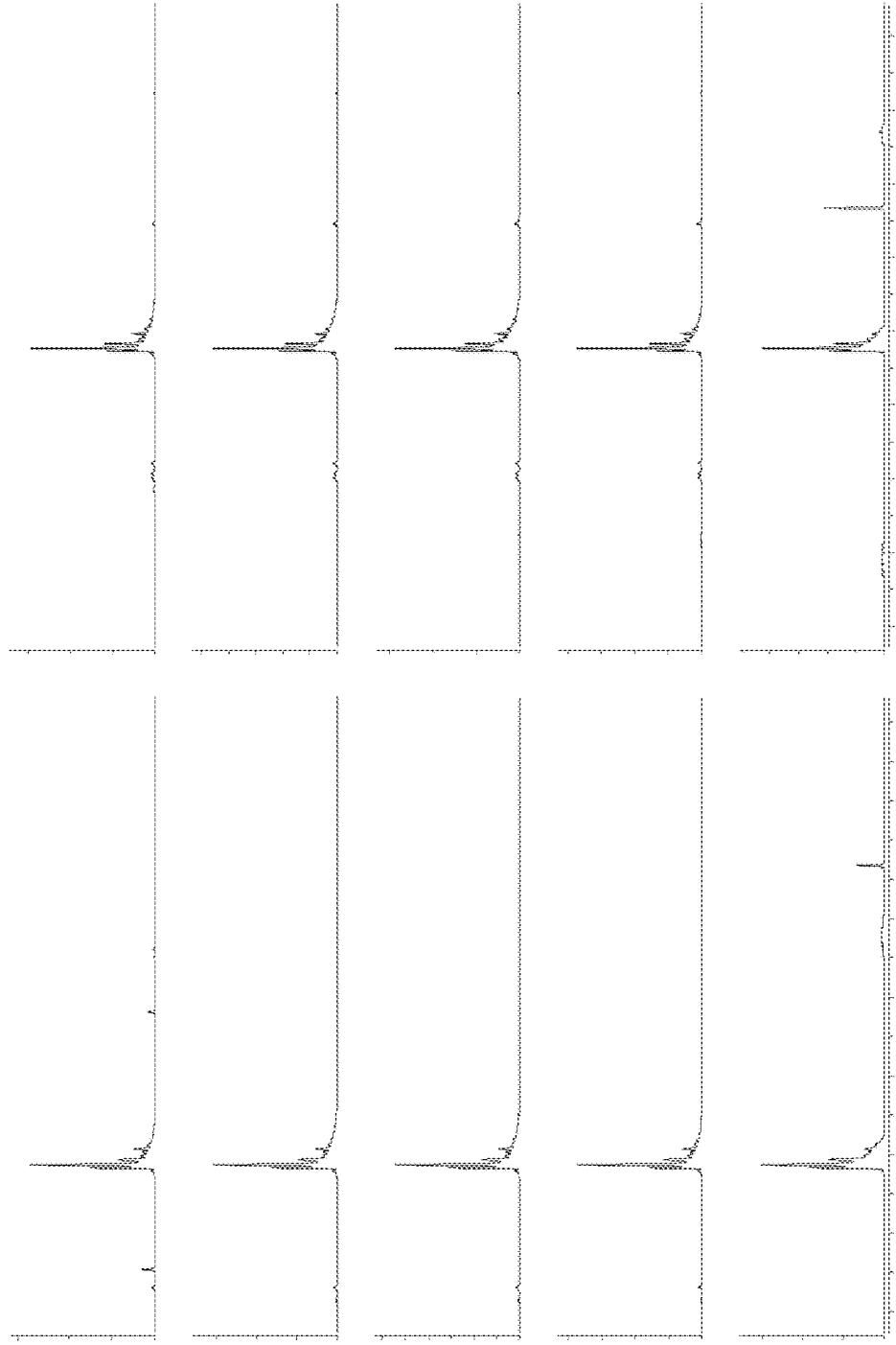
FIG. 32 shows huL5H2_DI-1×DUPA and huL5H2_DI-2×DUPA had no appreciable change in structure or mass by LCMS-QTOF mass spectrometry after 48 h incubation in different serums.
Figure 33A:
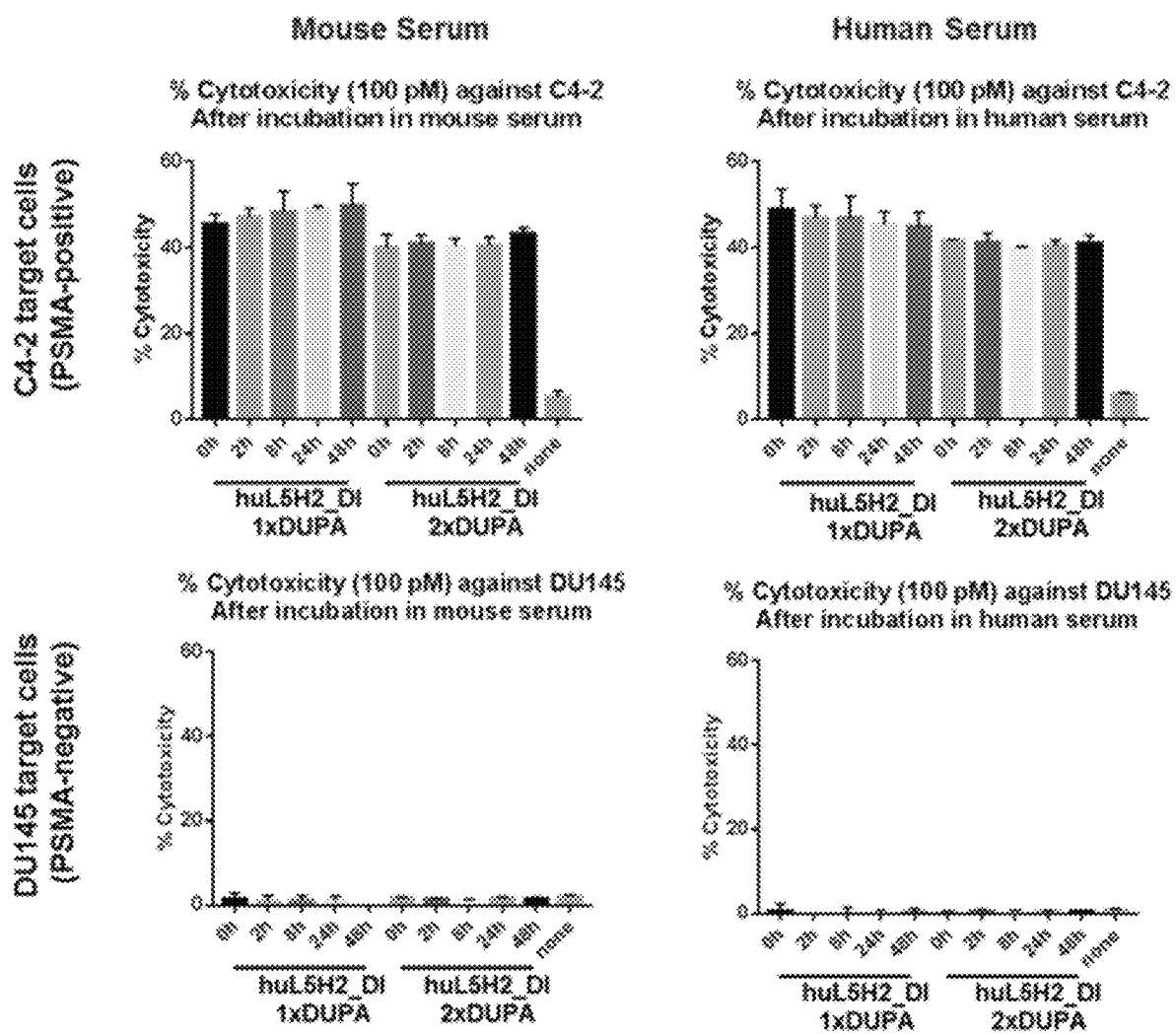
FIG. 33A shows huL5H2_DI-1×DUPA and huL5H2_DI-2×DUPA had no appreciable change in cytotoxicity against C4-2 PSMA+ cells after 48 h incubation in mouse or human serum.
Figure 33B:
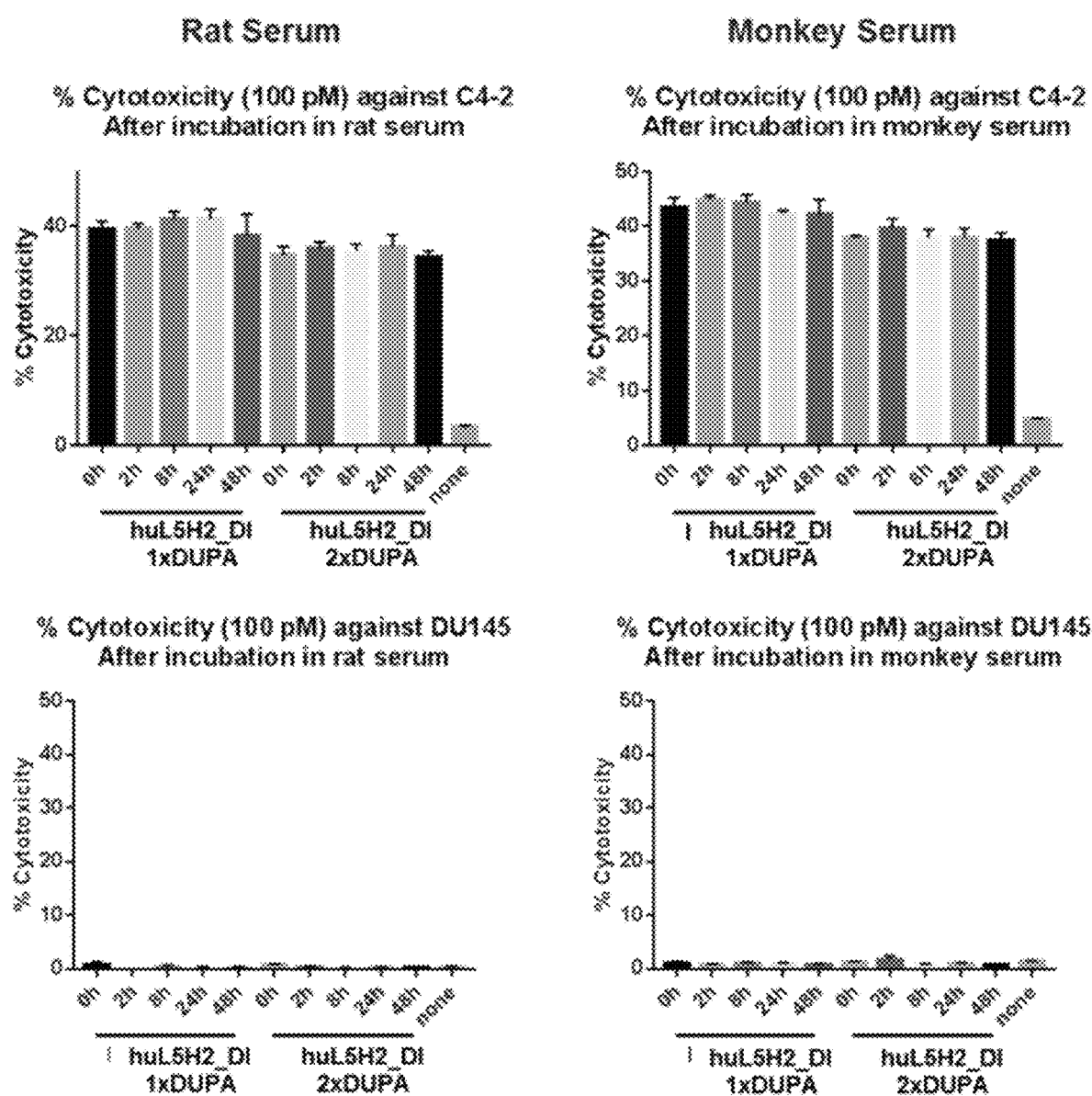
FIG. 33B shows huL5H2_DI-1×DUPA and huL5H2_DI-2×DUPA had no appreciable change in cytotoxicity against C4-2 PSMA+ cells after 48 h incubation in rat or monkey serum.
Figure 34A:
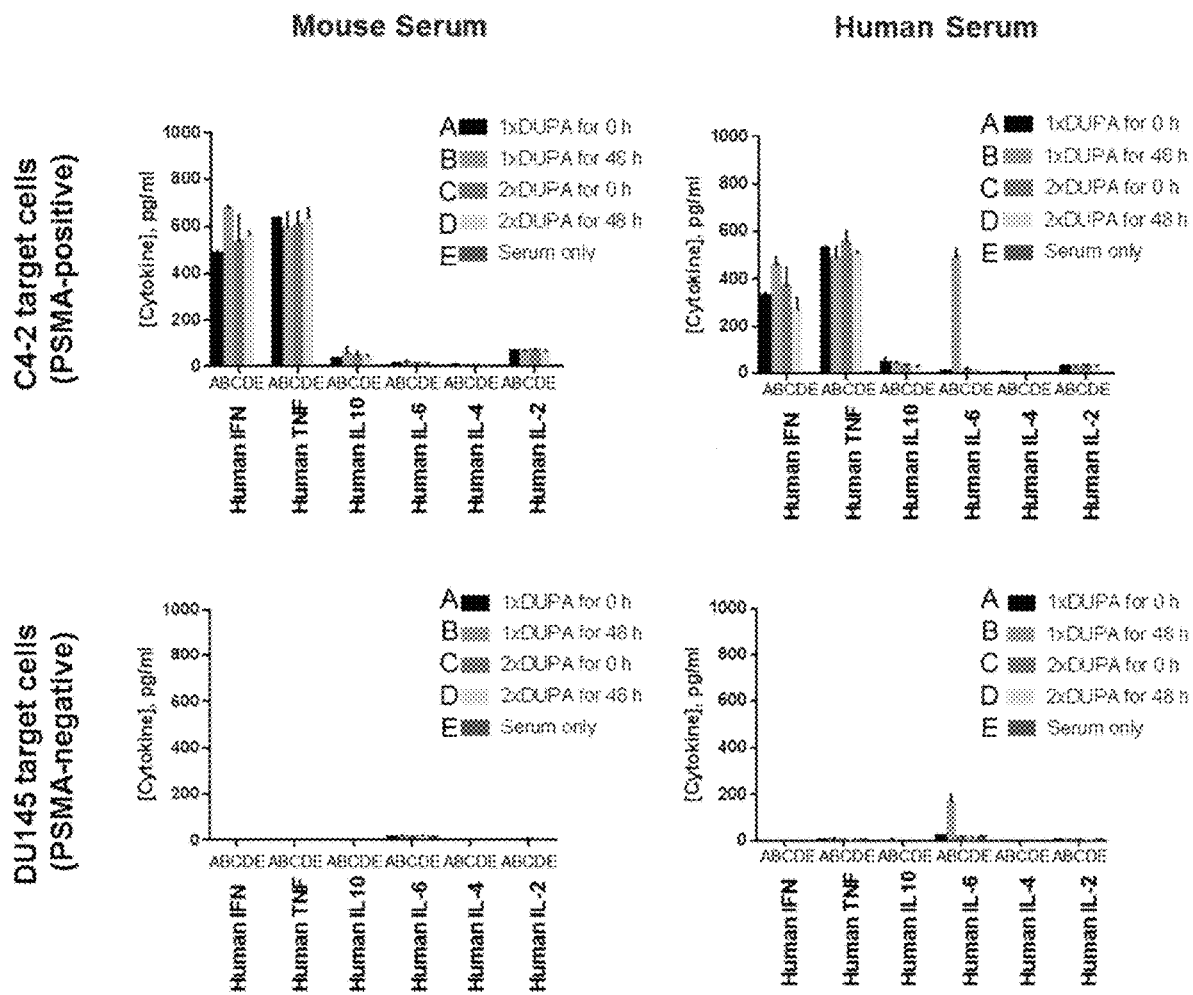
FIG. 34A shows huL5H2_DI-1×DUPA and huL5H2_DI-2×DUPA had no appreciable loss of T-cell activation in PSMA+ cells (as evidenced by cytokine release) after 48 h incubation in mouse or human serum.
Figure 34B:
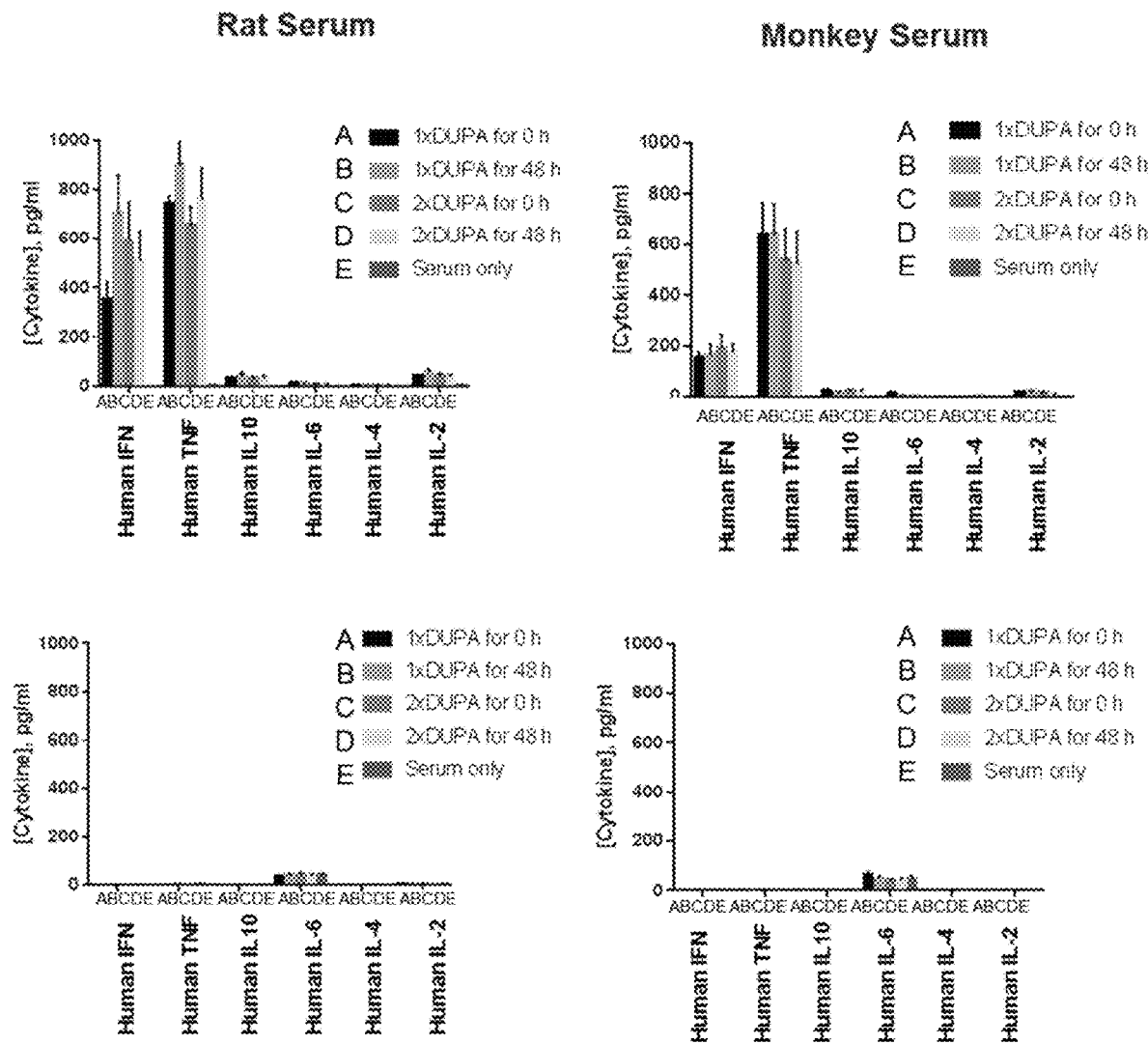
FIG. 34B shows huL5H2_DI-1×DUPA and huL5H2_DI-2×DUPA had no appreciable loss of T-cells activation in PSMA+ cells (as evidenced by cytokine release) after 48 h incubation in rat or monkey serum.

To determine degradation, loss or gain of activity in serum, 0.5 mg/ml conjugates were added to normal CD1 mouse, human (FIG. 33A), rat and cynomolgus monkey (FIG. 33B) followed by incubation at 37° C. up to 48 hours in an incubator. As shown in FIG. 32, the conjugates were purified by KappaSelect affinity resin and performed high resolution mass spec on LCMS-QTOF and SDS-PAGE. In addition, conjugates exposed with various serum were collected/filtered and tested cytotoxicity using PMSA positive prostate cancer cell C4-2 and PSMA negative DU145 cell in mouse and human serum (FIG. 33A), as well as rat and monkey serum (FIG. 33B). Cytokine release from T-cells in the presence of prostate cancer cells was measured for mouse and human serum (FIG. 34A), as well as rat and monkey serum (FIG. 34B). No appreciable change in structure or loss of activity/function within 48 hr was observed for either huL5H2_DI-1×DUPA or huL5H2_DI-2×DUPA antibody conjugates.

In Vivo: C4-2 Xenograft Model

Six to eight weeks old male NOD.Cg-Prkdc$^{scid}$IL2rg$^{tm1Wjl/SzJ}$(NSG) mice were subcutaneously (SC) implanted with 1×10$^6$ C4-2 cells in Matrigel (Corning). Once tumors reached approximately 150-200 mm$^3$ in size, 20×10$^6$ human activated T-cells or 10×10$^6$ human PBMCs were infused via intraperitoneal (IP) and on the next day, daily intravenous (IV) treatment with indicated dose of huL5H2-DI antibody conjugates was initiated and carried out for 10 days. Tumor growth was monitored every 3 days using external calipers and calculated using the formula: (l×w×h)/2. Body weight was measured using an electronic scale every day during treatment and every 3 days post-treatment.

Figure 35A:
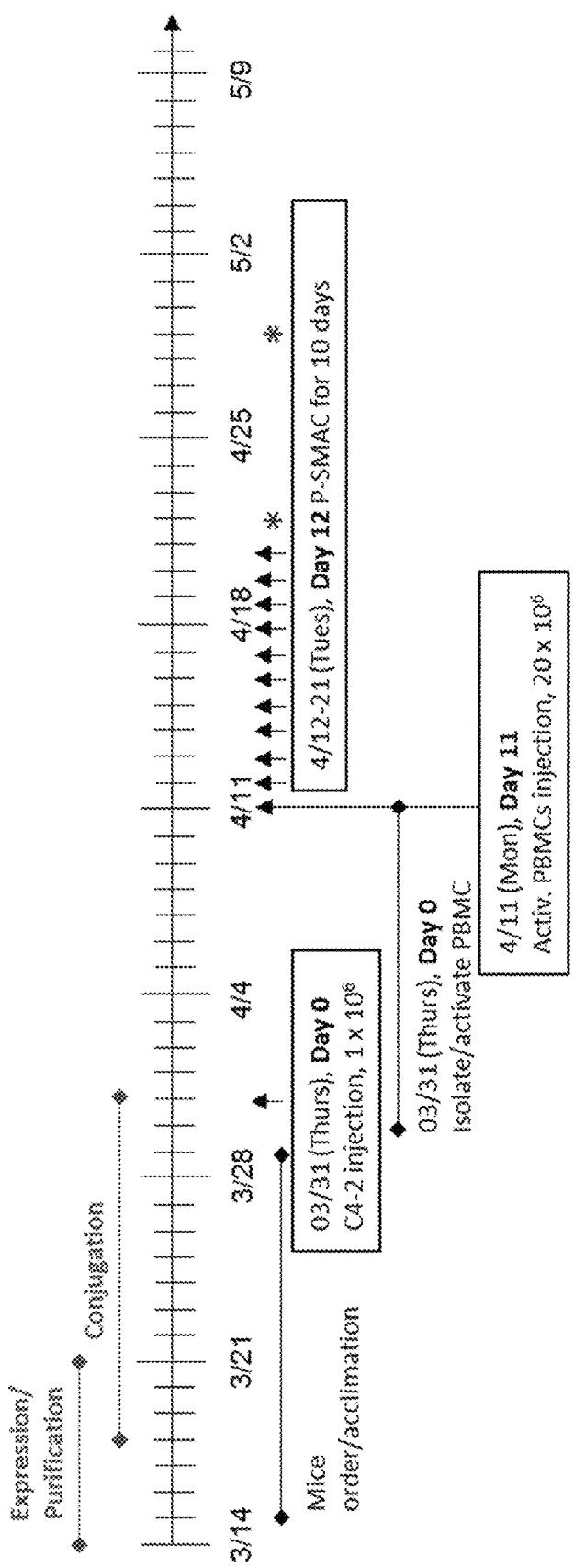
FIG. 35A shows an experimental setup for the treatment of C4-2 xenografts in a NSG mouse model reconstituted with human T cells using daily injections of huL5H2_DI-2×DUPA or huL5H2_DI-1×DUPA.
Figure 35B:
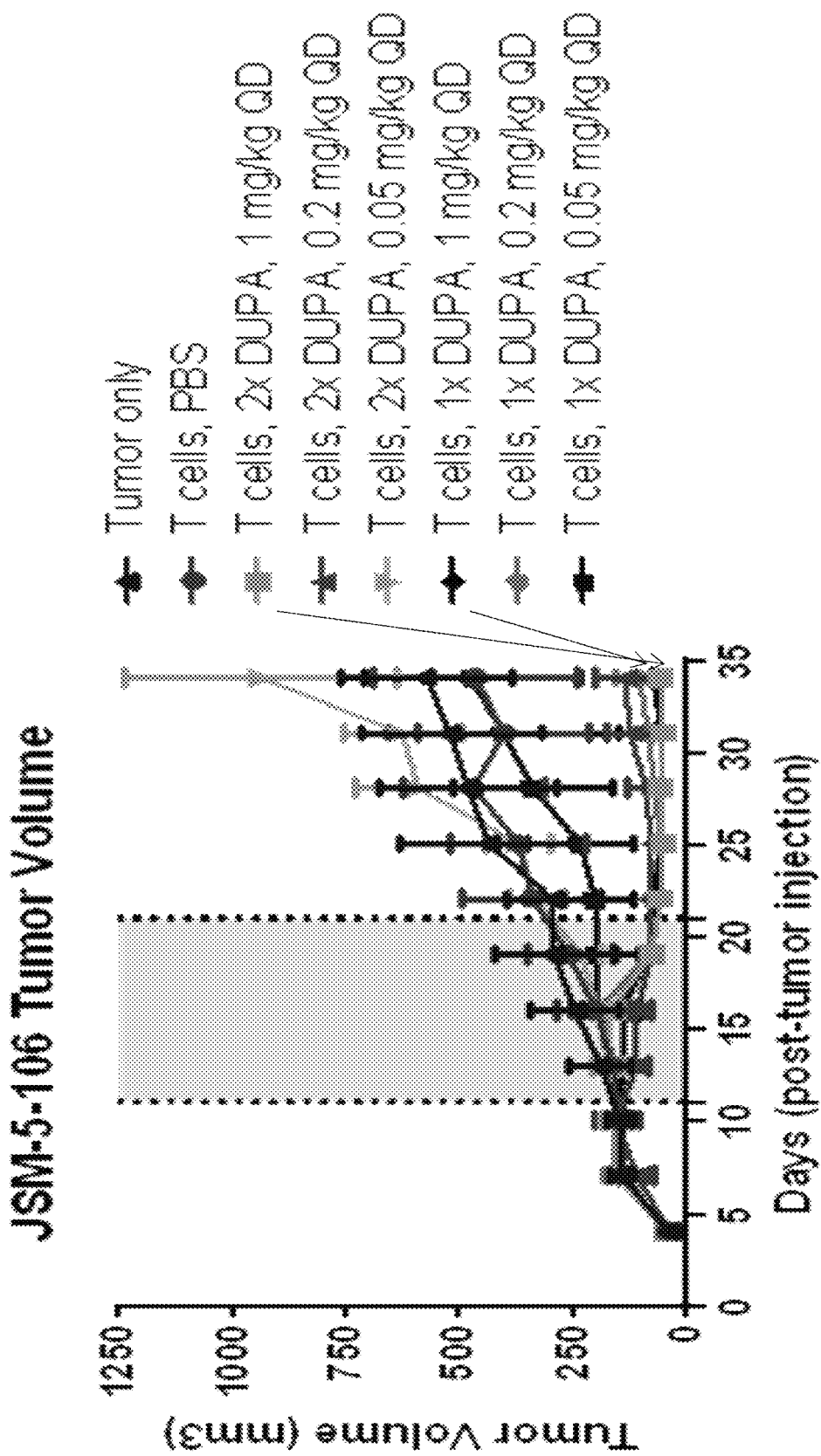
FIG. 35B shows a daily injection schedule of huL5H2_DI-2×DUPA or huL5H2_DI-1×DUPA demonstrated similar dose-dependent in vivo anti-tumor activity in the NSG mouse model reconstituted with human T cells
Figure 35C:
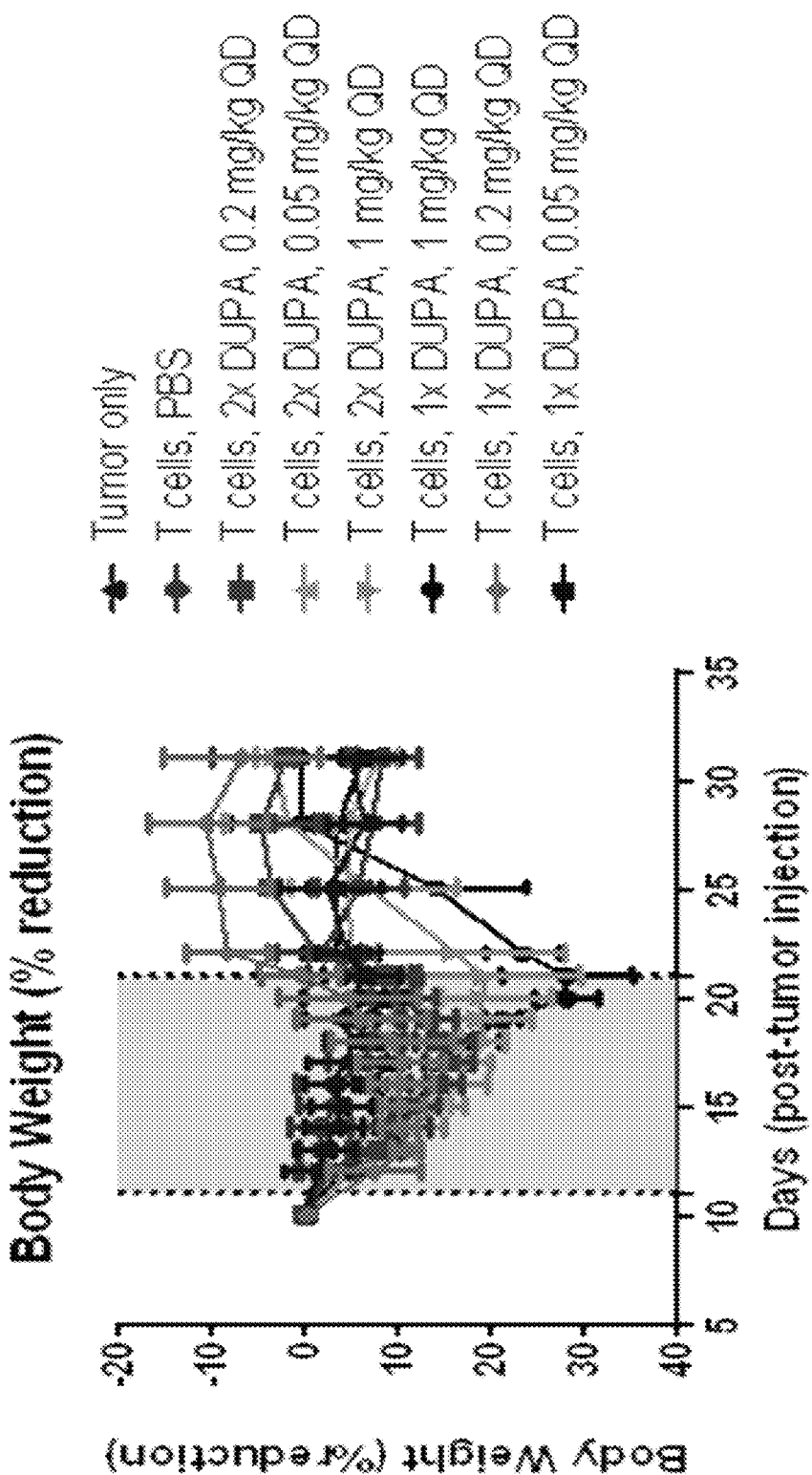
FIG. 35C shows a daily injection schedule of huL5H2_DI-2×DUPA and huL5H2_DI-1×DUPA demonstrated significant body weight reduction during treatment in the NSG mouse model reconstituted with human T cells.

To compare the efficacy of huL5H2_DI-1×DUPA and huL5H2_DI-2×DUPA in an in vivo setting, tumor bearing mice received 20×106 human activated T-cells via IP and daily IV injections of antibody conjugates at doses 0.05 mg/kg, 0.2 mg/kg, and 1.0 mg/kg for a total of 10 doses (FIG. 35A). Here, tumor regression was comparable in animals treated with either 0.2 mg/kg or 1 mg/kg of huL5H2_DI-1×DUPA or huL5H2_DI-2×DUPA (FIG. 35B, arrows denoting 1 mg/kg). However, significant body weight loss was observed in mice dosed with 1 mg/kg of both antibody conjugates (FIG. 35C).

Figure 36A:
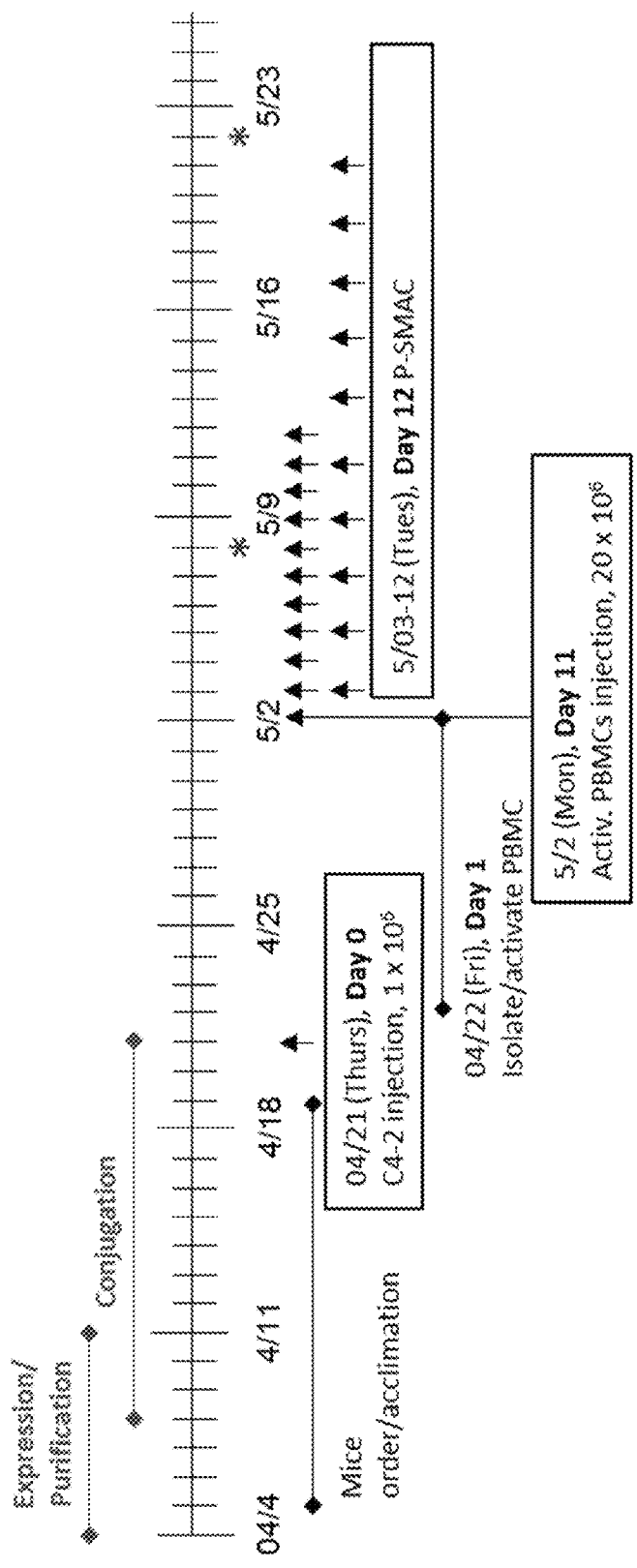
FIG. 36A shows an experimental setup for the treatment of C4-2 xenografts with huL5H2_DI-2×DUPA or huL5H2_DI-1×DUPA with a QOD (every other day) injection schedule.
Figure 36B:
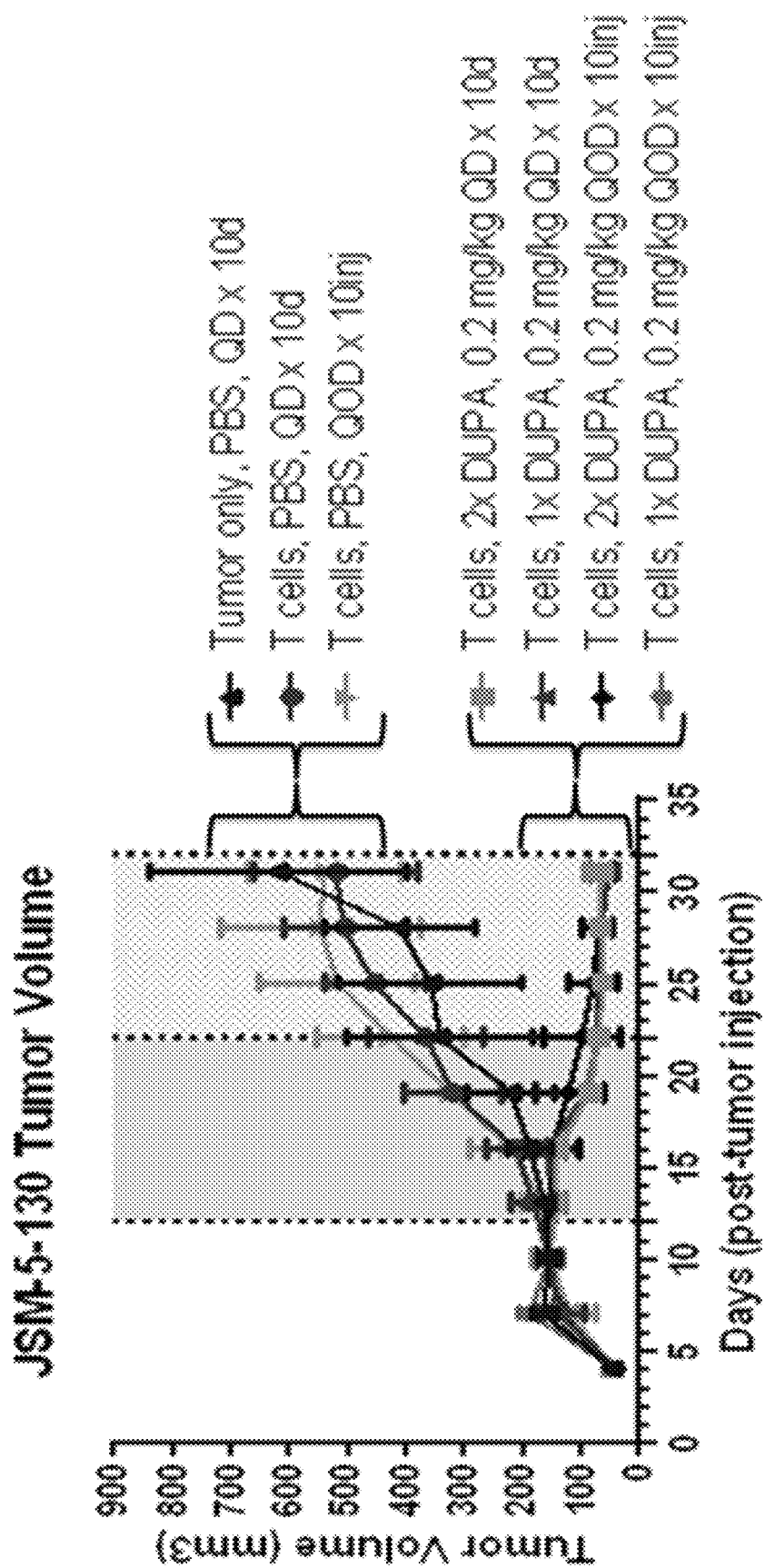
FIG. 36B shows a QOD injection schedule of huL5H2_DI-2×DUPA or huL5H2_DI-1×DUPA demonstrated similar dose-dependent in vivo anti-tumor activity in the NSG mouse model reconstituted with human T cells.
Figure 36C:
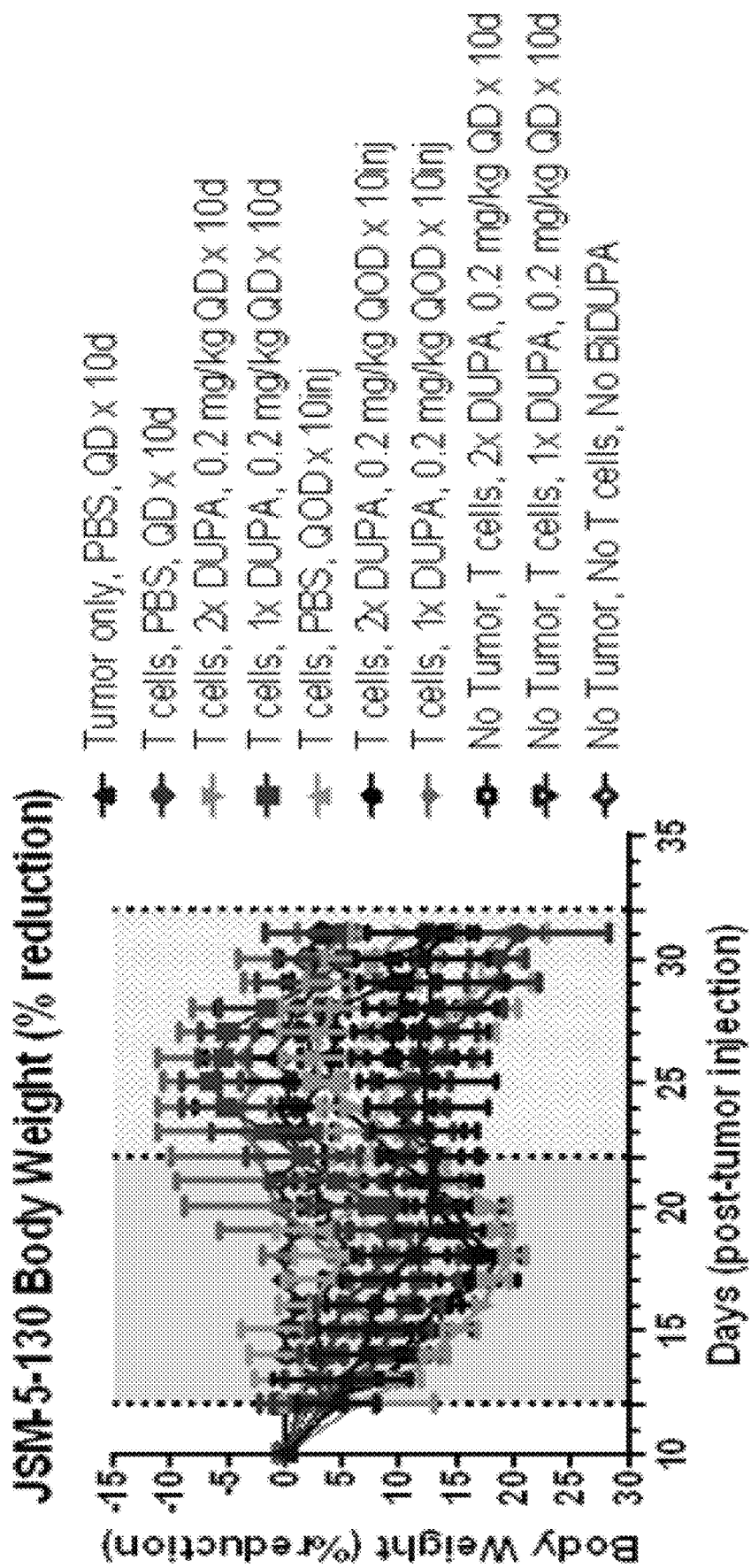
FIG. 36C shows a QOD injection schedule of huL5H2_DI-2×DUPA or huL5H2_DI-1×DUPA demonstrated significant body weight reduction during treatment in NSG mouse model reconstituted with human T cells.
Figure 37A:
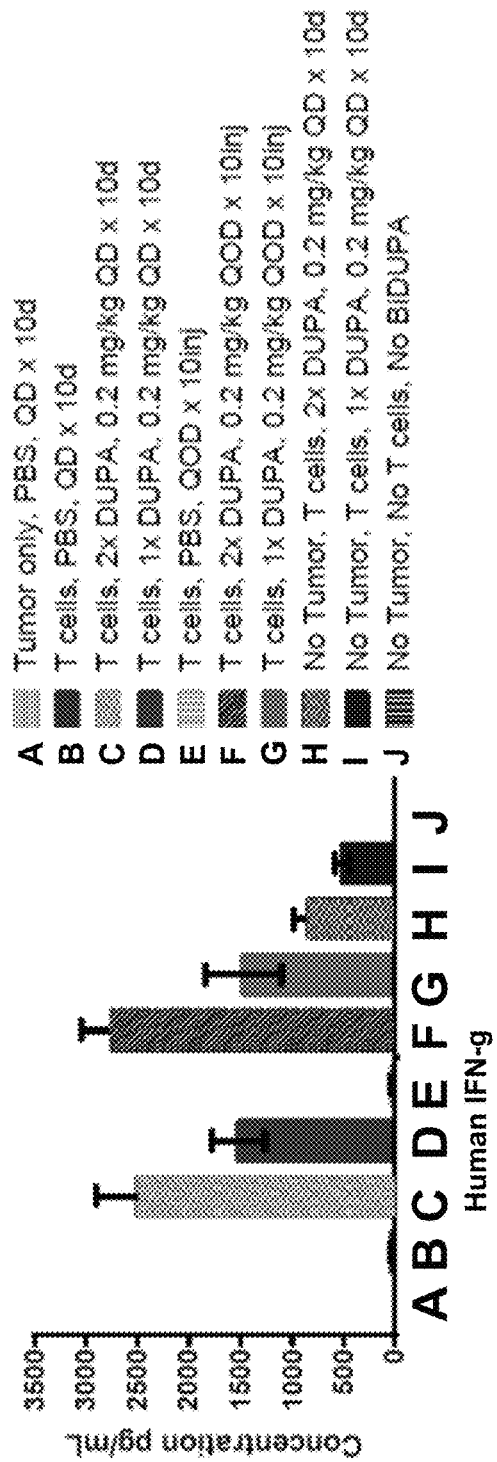
FIG. 37A shows huL5H2_DI-2×DUPA and huL5H2_DI-1×DUPA demonstrated significant cytokine release during treatment in the NSG mouse model reconstituted with human T cells for both QD (daily) and QOD (every other day) injection schedules.
Figure 37B:
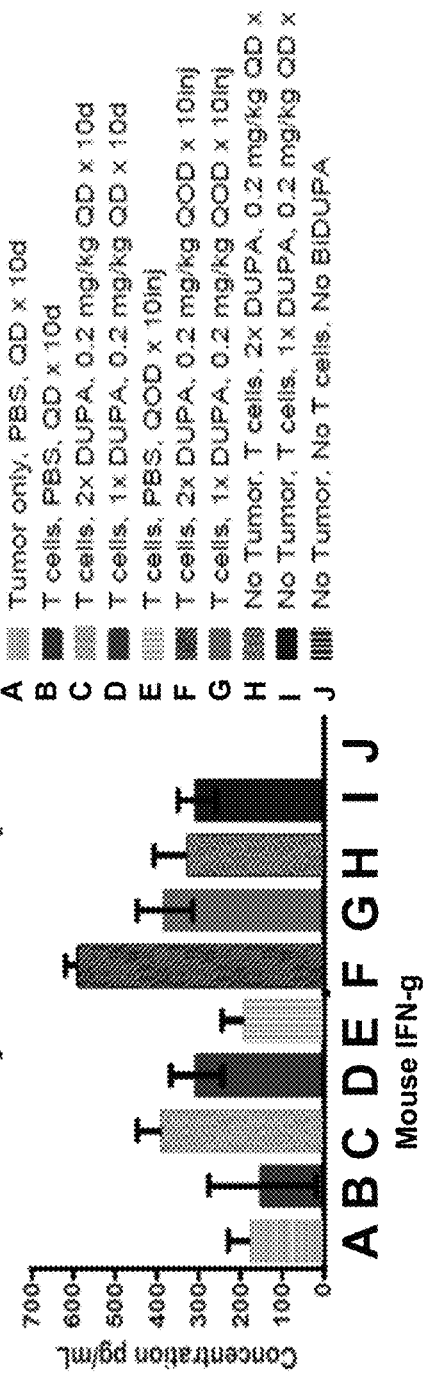
FIG. 37B shows huL5H2_DI-2×DUPA or huL5H2_DI-1×DUPA treatment demonstrated significant mouse cytokine release during treatment in the NSG mouse model reconstituted with human T cells for both QD (daily) and QOD (every other day) injection schedules.
Figure 38A:
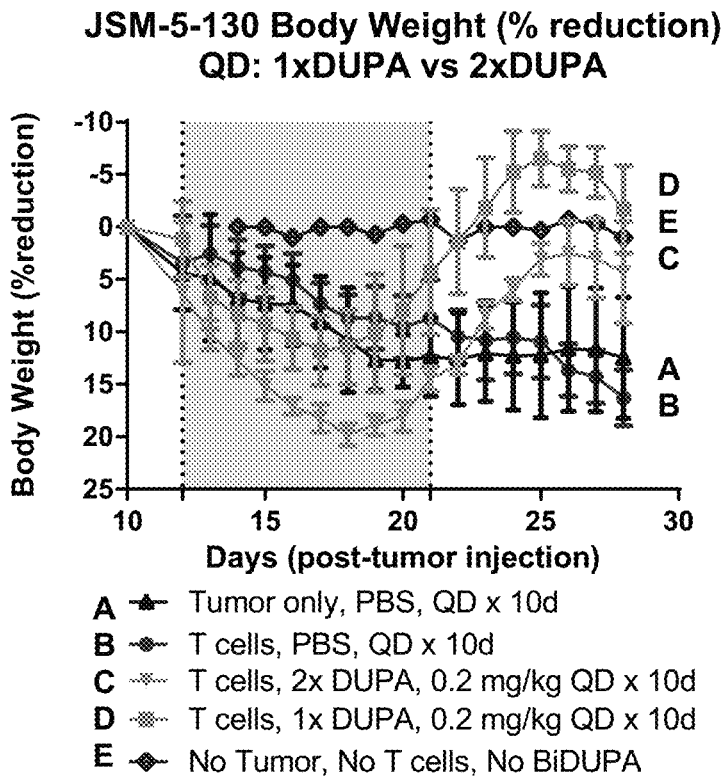
FIG. 38A shows huL5H2_DI-2×DUPA treatment led to a greater reduction in body weight than huL5H2_DI-1×DUPA with a QD (daily) injection schedule.
Figure 38B:
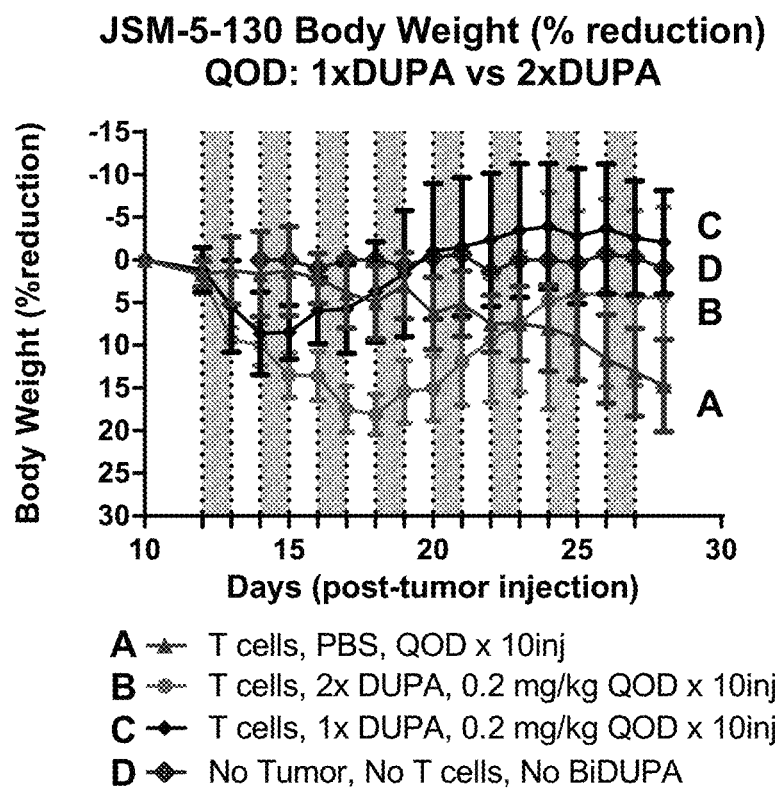
FIG. 38B shows huL5H2_DI-2×DUPA treatment led to a greater reduction in body weight than huL5H2_DI-1×DUPA with a QOD (every other day) injection schedule.
Figure 38C:
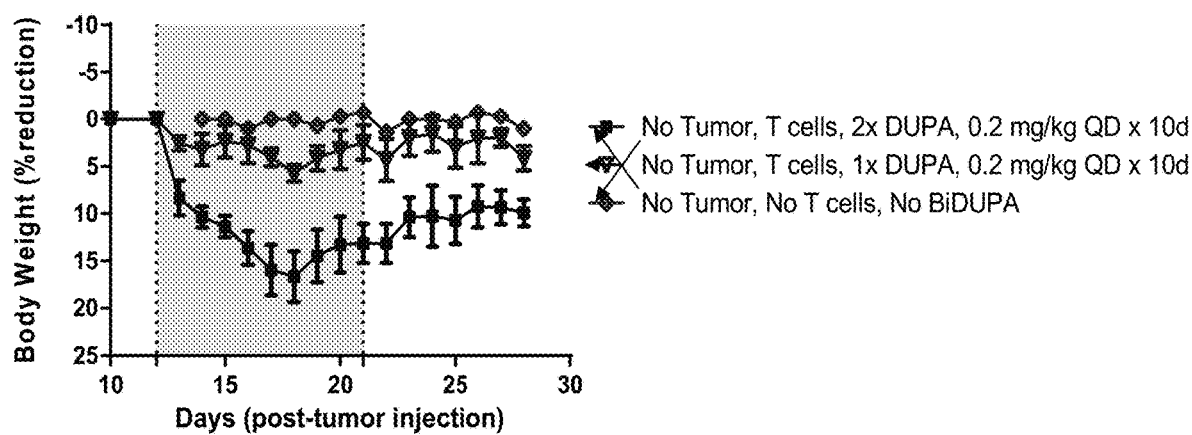
FIG. 38C shows huL5H2_DI-2×DUPA treatment led to a greater reduction in body weight than huL5H2_DI-1×DUPA in the absence of tumor cells.

In an attempt to circumvent the significant body weight loss observed above, the anti-tumor activity of huL5H2_DI-1×DUPA and huL5H2_DI-2×DUPA was assessed in an alternate treatment regimen that entails every other day dosing. As previously described in Example 4, C4-2 tumor bearing mice received 20×10$^6$ human activated T-cells via IP and daily (QD) or every-other-day (QOD) IV injections of antibody conjugates at 0.2 mg/kg for a total of 10 doses (FIG. 36A). In parallel, tumor-free mice also received the same treatment regimen. Plasma was collected after the 5$^{th}$ (QD) or 3$^{rd}$ (QOD) dose to measure in vivo cytokines using BD CBA Human Th1/Th2 Kit II (FIG. 37A) and BD CBA Mouse Inflammatory kit (BD Biosciences, FIG. 37B). Samples were acquired on a BD Accuri C6 and analyzed using the FCAP Array software. Regardless of treatment schedule, tumor regression was comparable with both huL5H2_DI antibody conjugates (FIG. 36B). FIG. 36C shows a QOD injection schedule of huL5H2_DI-2×DUPA or huL5H2_DI-1×DUPA demonstrated similar dose-dependent in vivo anti-tumor activity in the NSG mouse model reconstituted with human T cells. huL5H2_DI-2×DUPA was observed to afford greater weight loss in comparison to huL5H2_DI-1×DUPA (FIG. 38A and FIG. 38B). FIG. 38C shows a control experiment that measured weight loss in the absence of tumor.

Figure 39A:
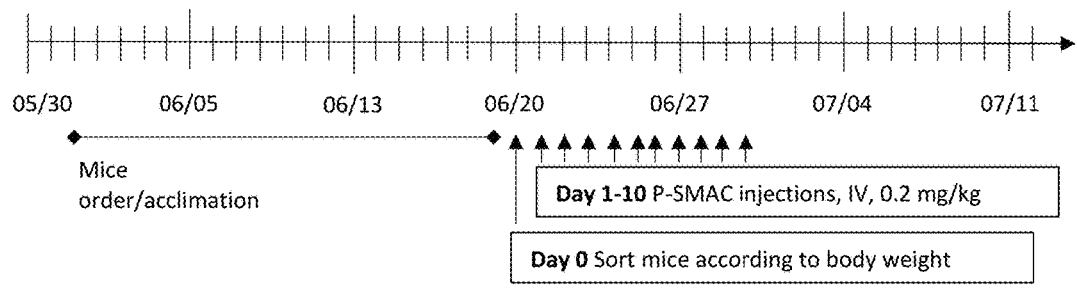
FIG. 39A shows an experimental setup for the treatment of C4-2 xenografts with daily injections of huL5H2_DI-2×DUPA or huL5H2_DI-1×DUPA, without the addition of human T-cells.
Figure 39B:
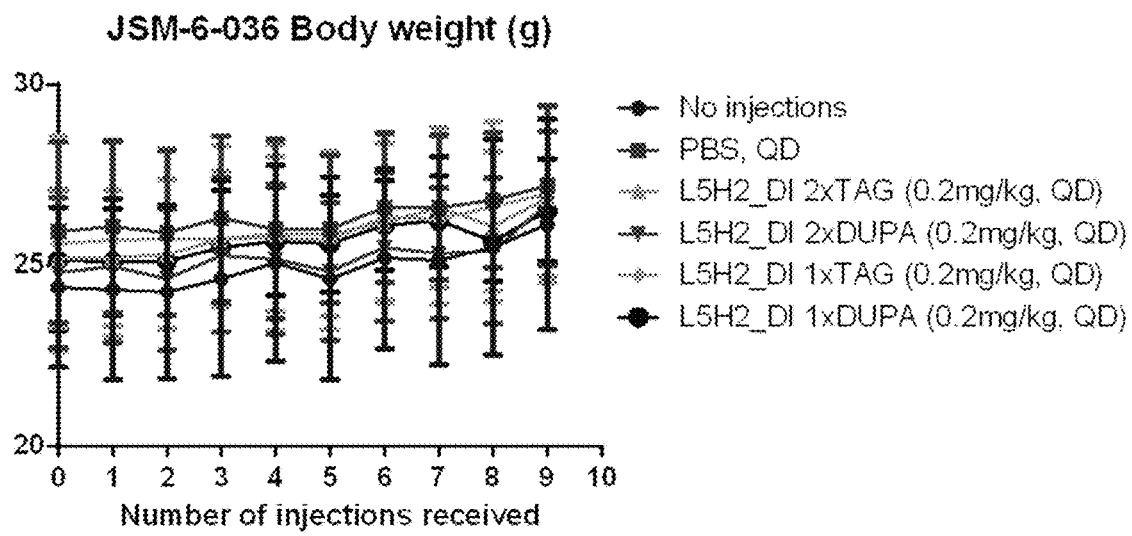
FIG. 39B and FIG. 39C show huL5H2_DI-2×DUPA and huL5H2_DI-1×DUPA demonstrated no significant loss in body weight in the absence of T cells, which suggests that toxicity is due to T cell activation.
Figure 39C:
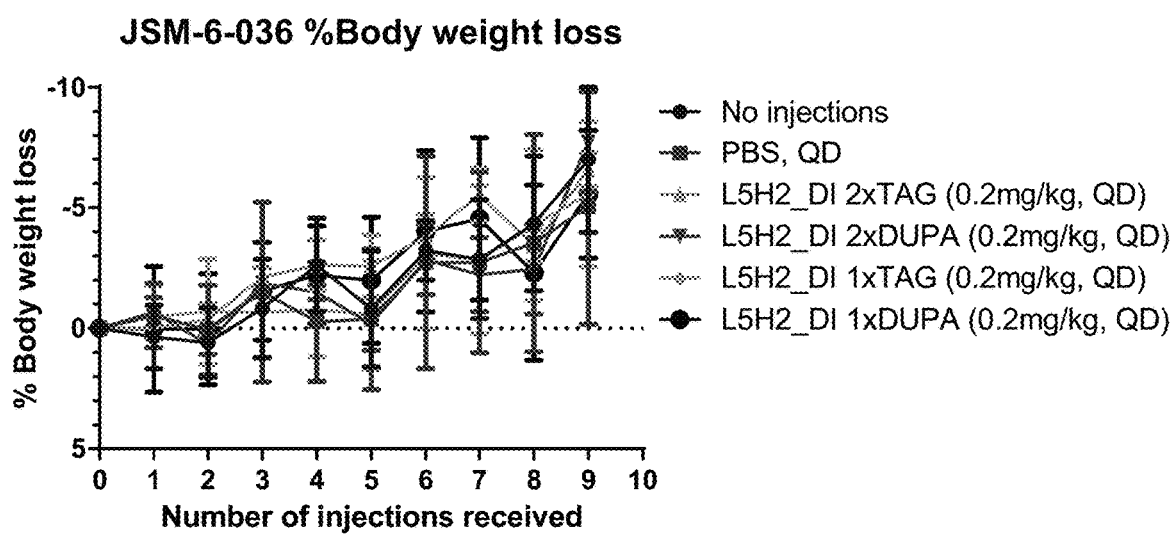
Figure 40A:
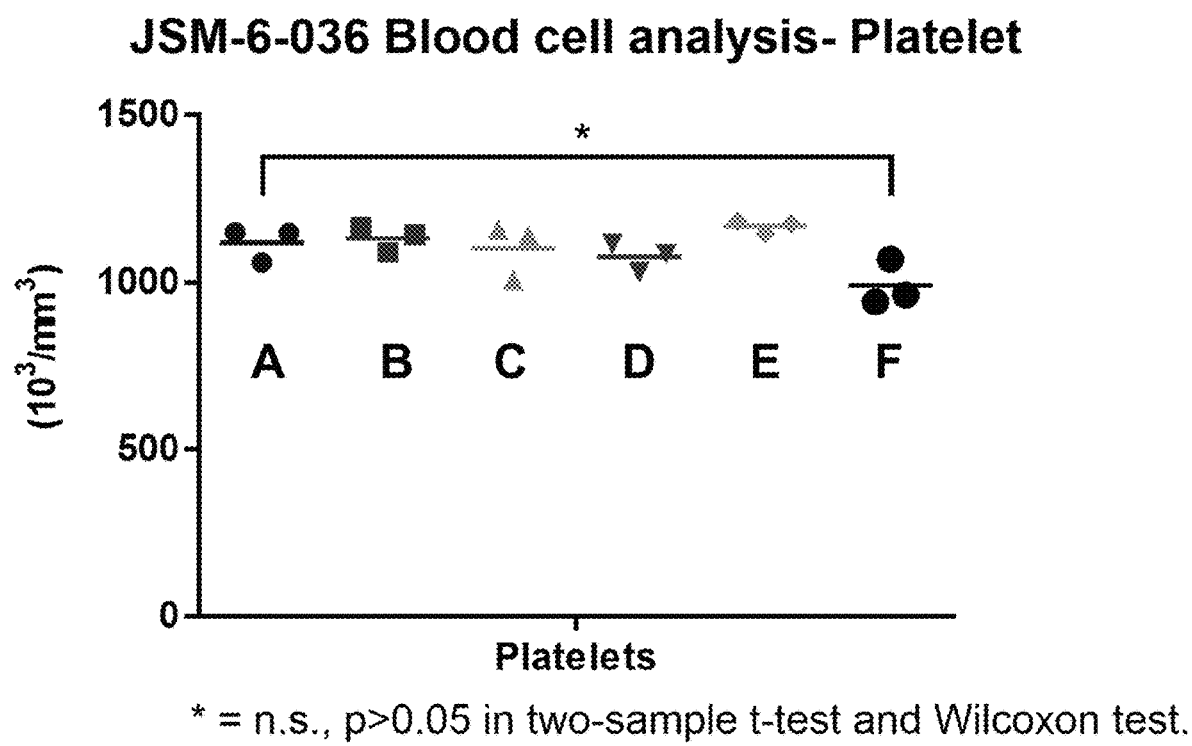
FIG. 40A, FIG. 40B, FIG. 40C, FIG. 40D, and FIG. 40E show huL5H2_DI-2×DUPA and huL5H2_DI-1×DUPA demonstrated no significant blood toxicity in the absence of T-cells.
Figure 40B:
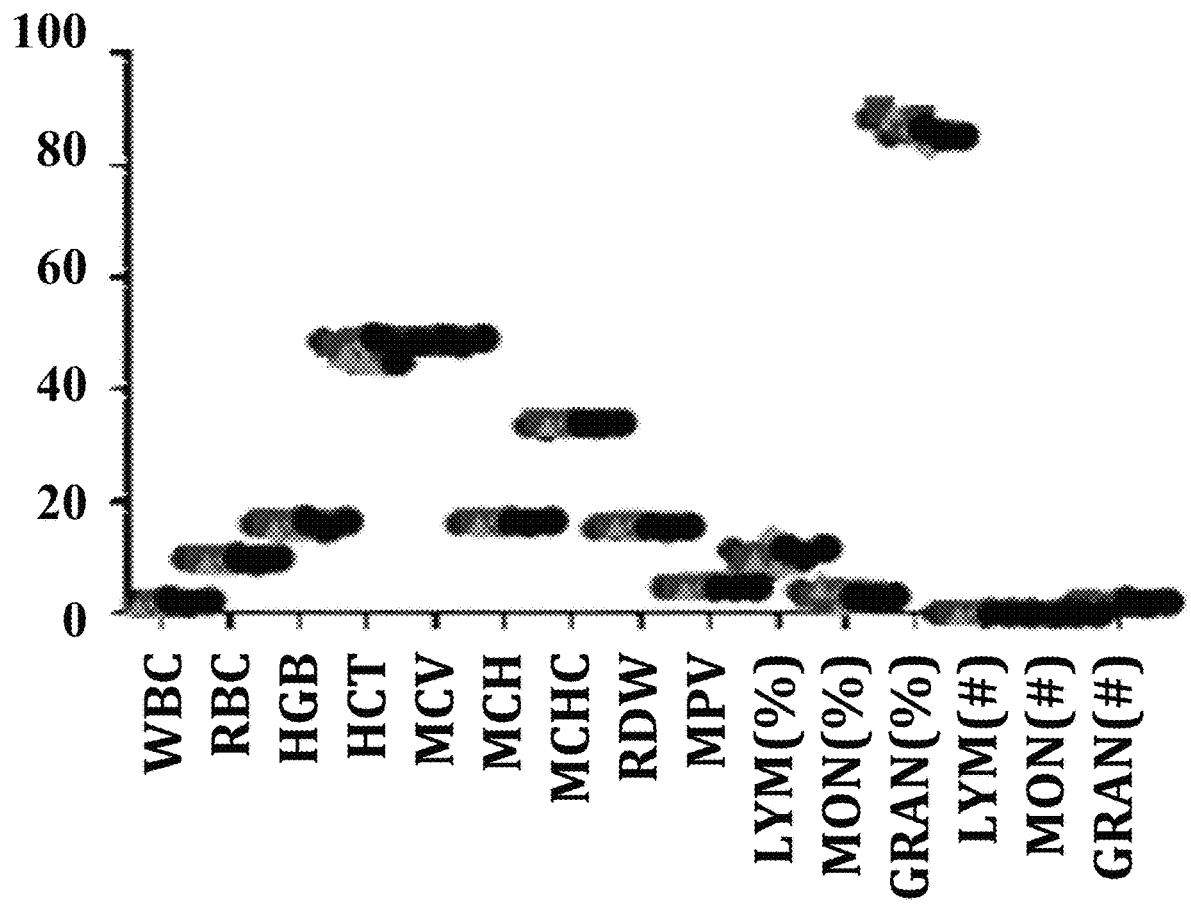
Figure 40C:
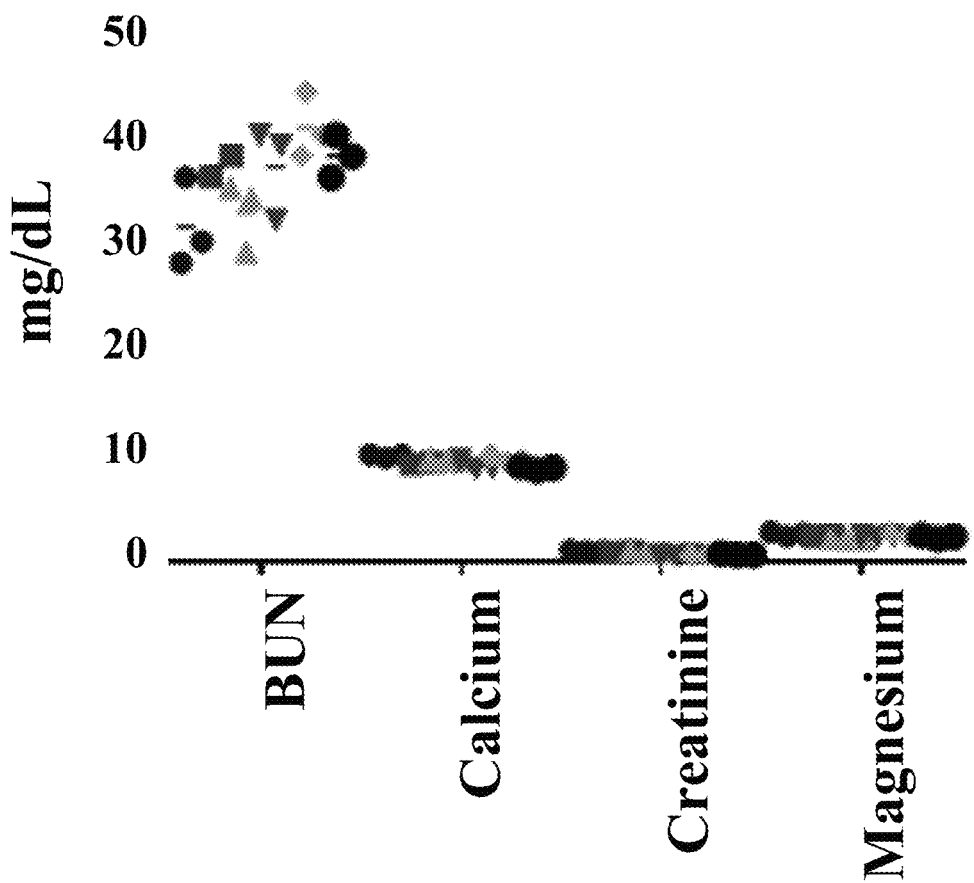
Figure 40D:
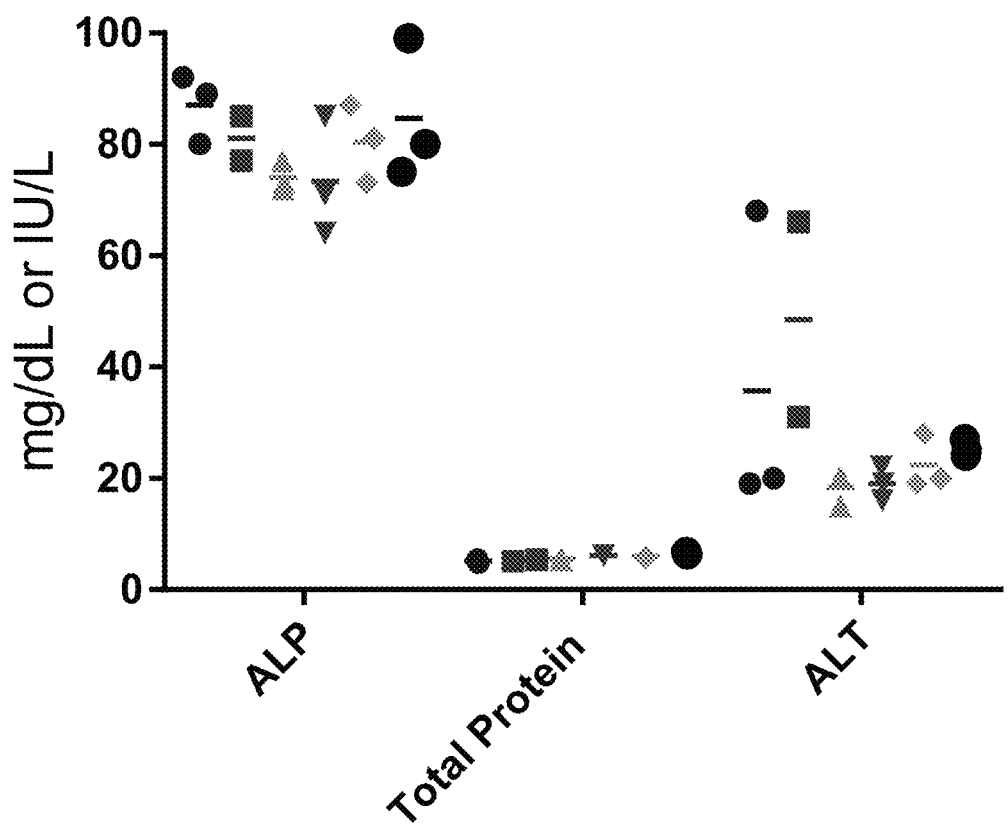
Figure 40E:
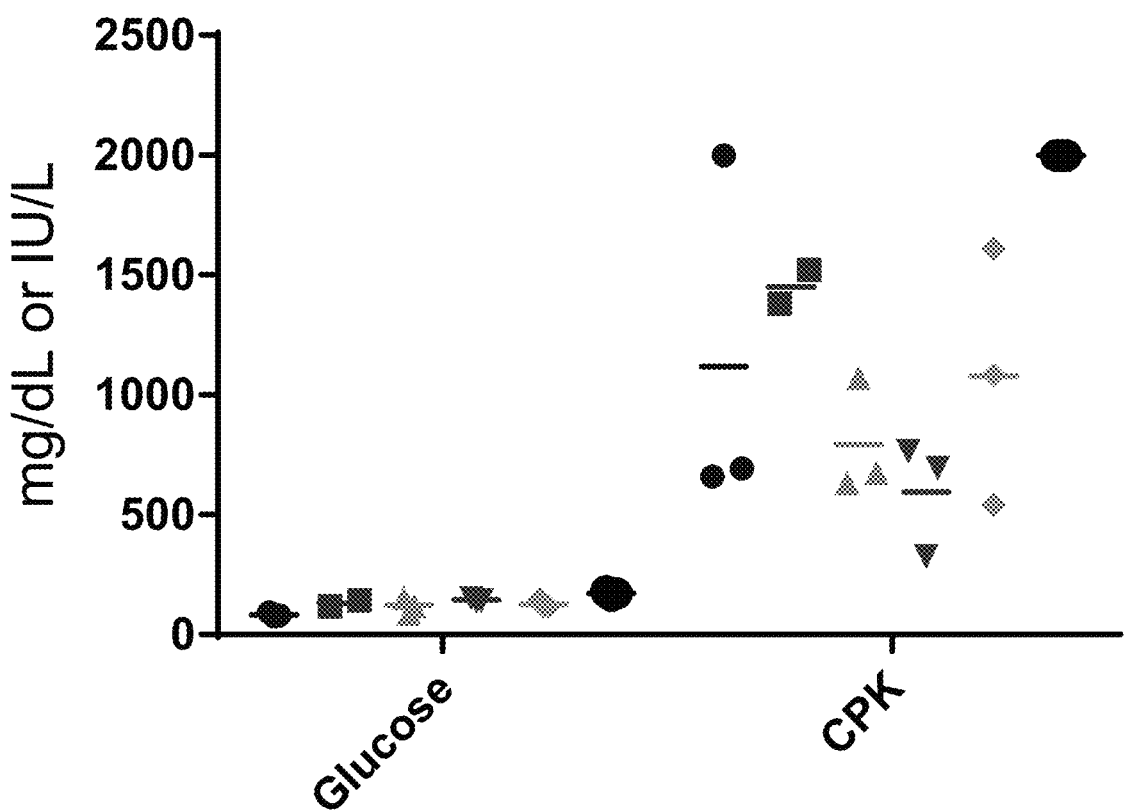

To determine whether huL5H2_DI antibody conjugates alone causes toxicity in NSG mice, tumor-free animals received daily injections of huL5H2_DI-1×DUPA and huL5H2_DI-2×DUPA at 0.2 mg/kg for a total of 10 doses (FIG. 39A). 24 hours after the last injection, animals were euthanized for sampling. Blood was collected for blood cell analysis using the scil Vet abc (scil) and to determine plasma chemistry profile using the Spotchem EZ (scil) (platelets; FIG. 40A; blood cells, FIG. 40B, renal function, FIG. 40C; liver function FIG. 401D; and miscellaneous analytes, FIG. 40E), and specified organs were harvested for H&E staining (tissue processing, staining and scoring provided by Histotox) (Table 29 and Table 30). Here, weight loss or aberrant number of blood cells and levels of serum proteins was not observed, which suggests that neither huL5H2_DI-1×DUPA nor huL5H2_DI-2×DUPA induce overt toxicity in the absence of T-cells (as a function of overall body weight, FIG. 39B, and percent body weight loss, FIG. 39C).

TABLE 29

| Group | Treatment (IV) | Protein ID | N = |
|---|---|---|---|
| A | | | 3 |
| B | PBS, QD × 10 d | | 3 |
| C | L5H2_DI-2xTAG (0.2 mg/kg), QD × 10 d | P00791 | 3 |
| D | L5H2_DI-2xDUPA (0.2 mg/kg), QD × 10 d | P00793 | 3 |
| E | L5H2_DI-1xTAG (0.2 mg/kg), QD × 10 d | P00790 | 3 |
| F | L5H2_DI-1xDUPA (0.2 mg/kg), QD × 10 d | P00792 | 3 |

TABLE 30

| Study Group | Group | Animal | Prostate Examined | Large intestine Examined | Small intestine Examined | Kidney Basophilic tubules | Kidney Inflammation, cortical | Kidney Dilatation, tubular, cortical | Brain Examined |
|---|---|---|---|---|---|---|---|---|---|
| No Therapeutic | A | 1 | 0 | 0 | 0 | 0 | 0 | 0 | 0 |
| | | 2 | 0 | 0 | 0 | 1 | 0 | 1 | 0 |

TABLE 30-continued

| Study Group | Group | Animal | Prostate Examined | Large intestine Examined | Small intestine Examined | Kidney Basophilic tubules | Kidney Inflammation, cortical | Kidney Dilatation, tubular, cortical | Brain Examined |
|---|---|---|---|---|---|---|---|---|---|
| | | 3 | 0 | 0 | 0 | 0 | 0 | 0 | 0 |
| | | AVERAGE | | | | 0.33 | 0.00 | 0.33 | |
| | | SD | | | | 0.58 | 0.00 | 0.58 | |
| Vehicle | B | 4 | 0 | 0 | 0 | 0 | 0 | 0 | 0 |
| | | 5 | 0 | 0 | 0 | 0 | 0 | 0 | 0 |
| | | 6 | 0 | 0 | 0 | 0 | 0 | 0 | 0 |
| | | AVERAGE | | | | 0.00 | 0.00 | 0.00 | |
| | | SD | | | | 0.00 | 0.00 | 0.00 | |
| L5H2_DI-2xTAG (0.2 mg/kg, QD × 10 d) | C | 7 | 0 | 0 | 0 | 0 | 0 | 0 | 0 |
| | | 8 | 0 | 0 | 0 | 1 | 0 | 0 | 0 |
| | | 9 | 0 | 0 | 0 | 1 | 0 | 0 | 0 |
| | | AVERAGE | | | | 0.67 | 0.00 | 0.00 | |
| | | SD | | | | 0.58 | 0.00 | 0.00 | |
| L5H2_DI-2xDUOA (0.2 mg/kg, QD × 10 d) | D | 10 | 0 | 0 | 0 | 0 | 0 | 0 | 0 |
| | | 11 | 0 | 0 | 0 | 1 | 1 | 0 | 0 |
| | | 12 | 0 | 0 | 0 | 0 | 0 | 0 | 0 |
| | | AVERAGE | | | | 0.33 | 0.33 | 0.00 | |
| | | SL | | | | 0.58 | 0.58 | 0.00 | |
| L5H2_DI-1xTAG (0.2 mg/kg, QD × 10 d) | E | 13 | 0 | 0 | 0 | 1 | 0 | 0 | 0 |
| | | 14 | 0 | 0 | 0 | 0 | 0 | 0 | 0 |
| | | 15 | | | 0 | 1 | 0 | 1 | 0 |
| | | AVERAGE | | | | 0.67 | 0.00 | 0.33 | |
| | | SD | | | | 0.58 | 0.00 | 0.58 | |
| L5H2_DI-1xDUOA (0.2 mg/kg, QD × 10 d) | F | 16 | 0 | 0 | 0 | 0 | 0 | 0 | 0 |
| | | 17 | | | | 0 | 0 | 0 | 0 |
| | | 18 | 0 | 0 | 0 | 0 | 0 | 0 | 0 |
| | | AVERAGE | | | | 0.00 | 0.00 | 0.00 | |
| | | SL | | | | 0.00 | 0.00 | 0.00 | |
| | | Toxicity: | 0 none | 1.00 minimal | 2.00 slight | 3.00 moderate | 4.00 marked | 5.00 severe | |

Figure 41:
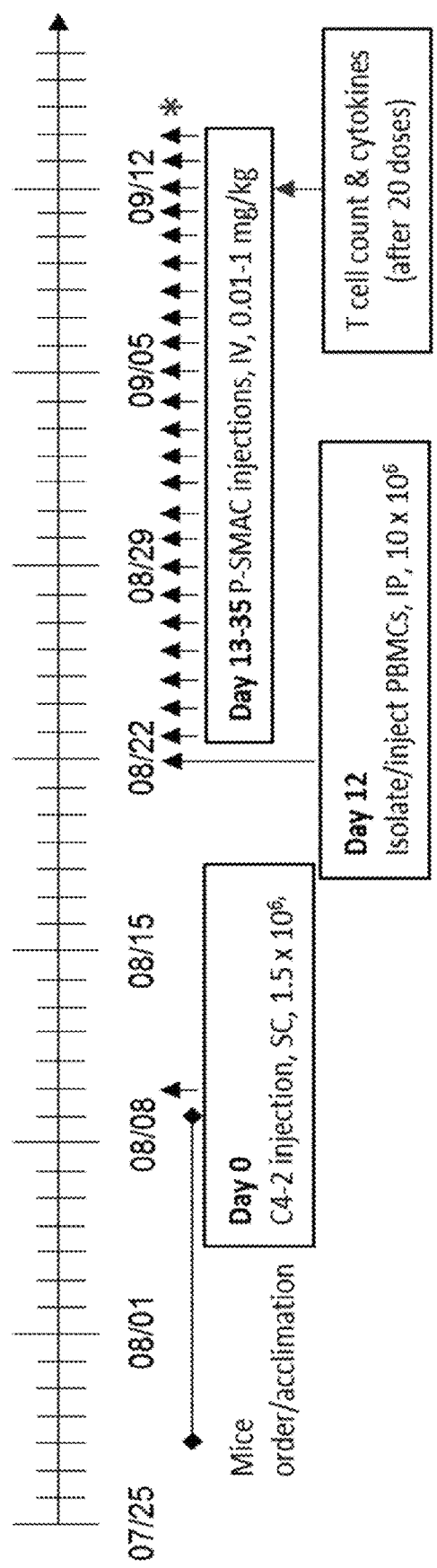
FIG. 41 shows an experimental set up for the treatment of C4-2 xenografts, with post-treatment analysis of T cell counts and cytokine levels.
Figure 44A:
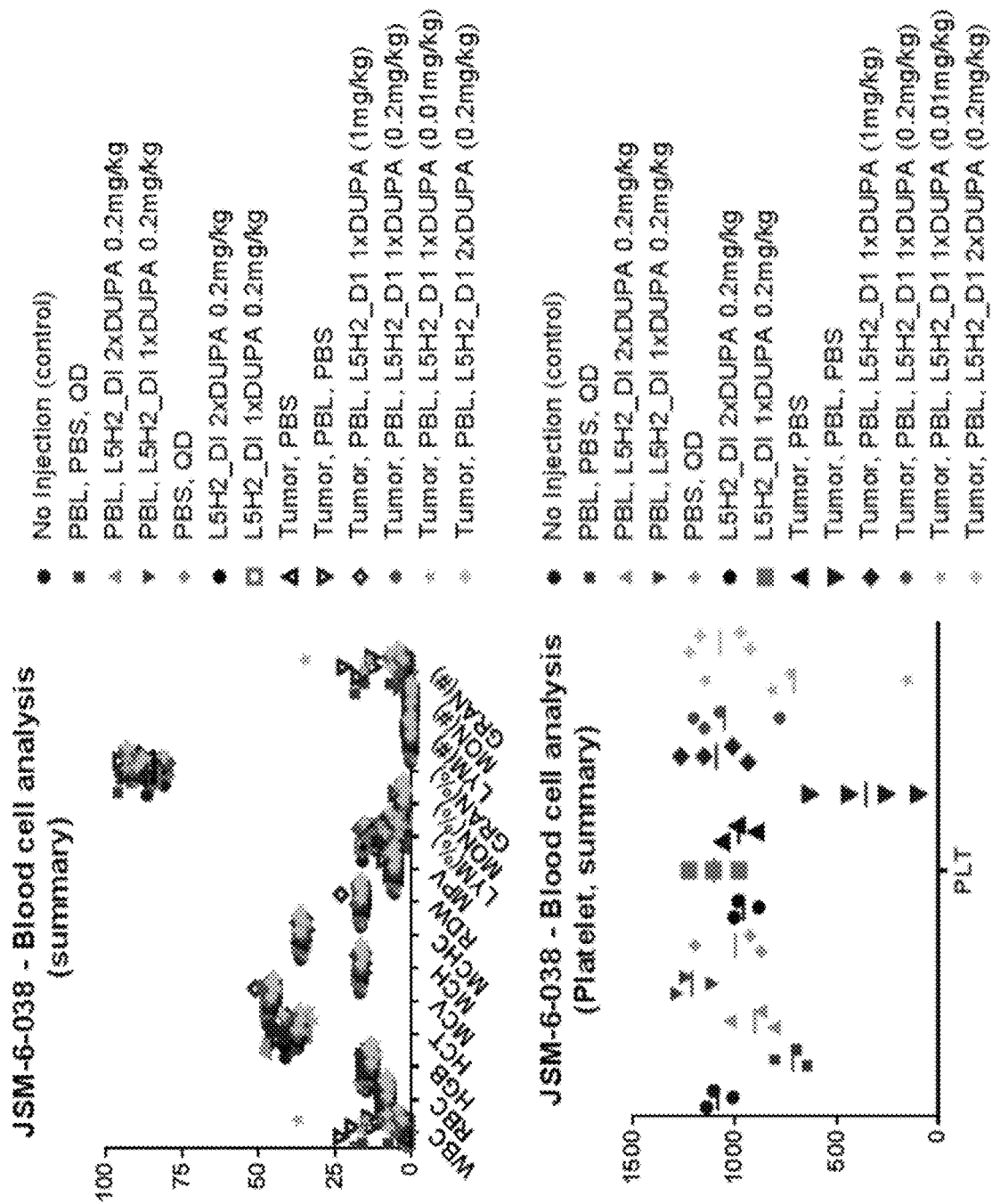
FIG. 44A, FIG. 44B, and FIG. 44C show huL5H2_DI-2×DUPA and huL5H2_DI-1×DUPA demonstrated no significant blood toxicity in the NSG mouse model reconstituted with human PBLs.
Figure 44B:
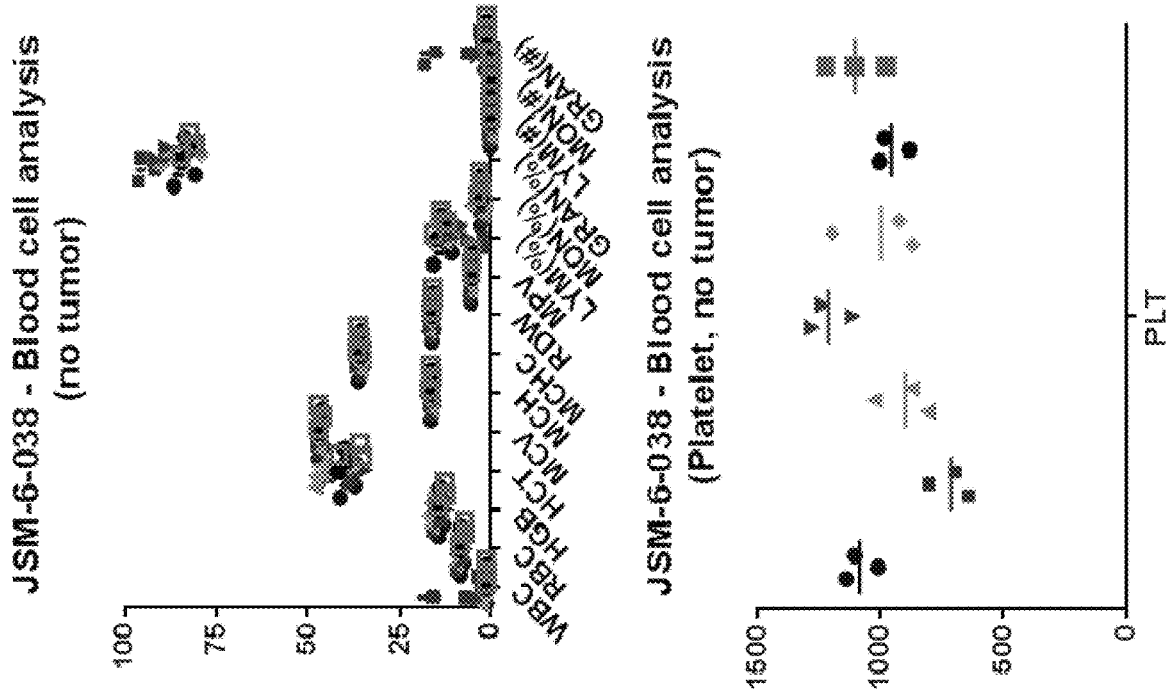
Figure 44C:
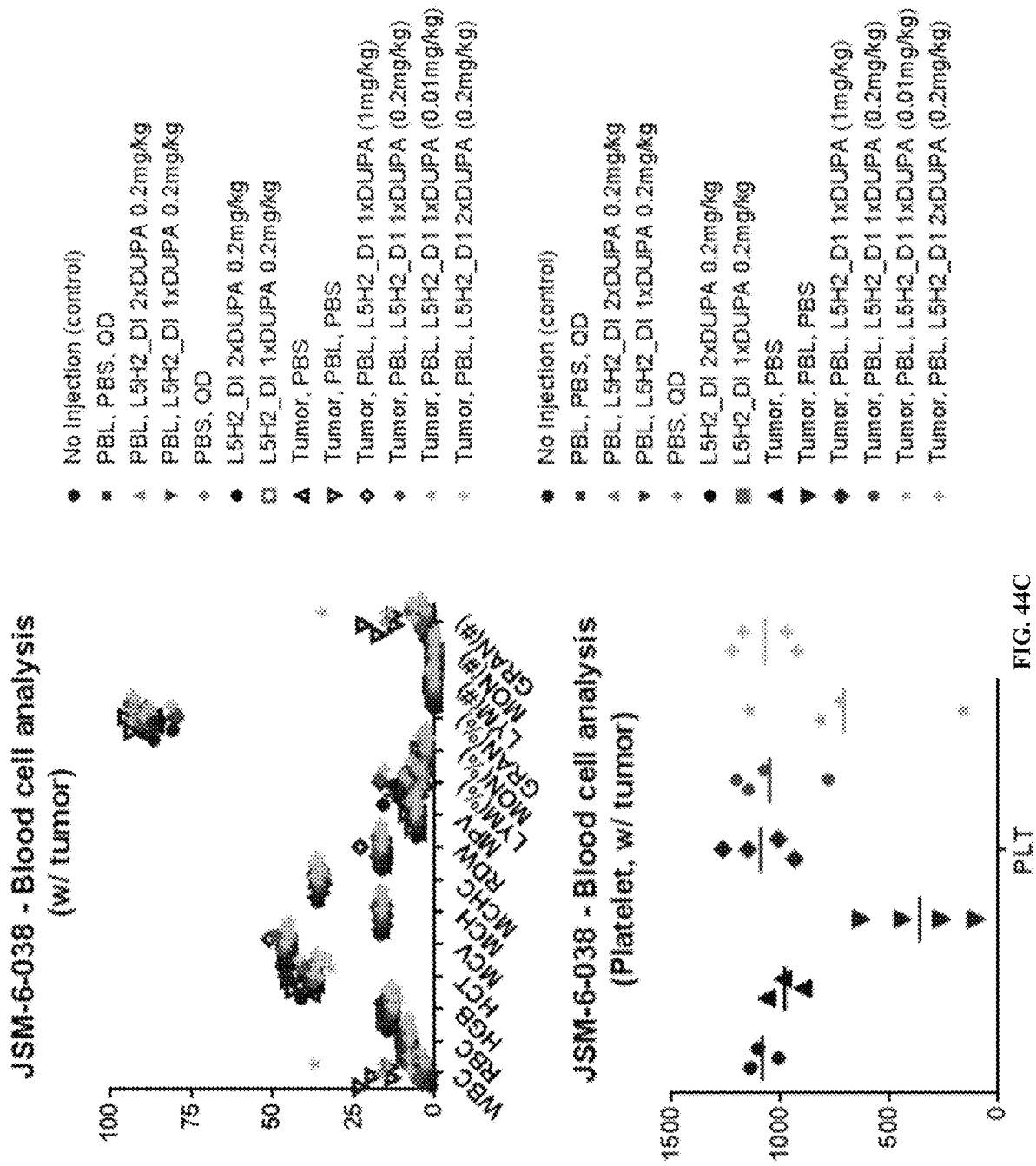
Figure 45A:
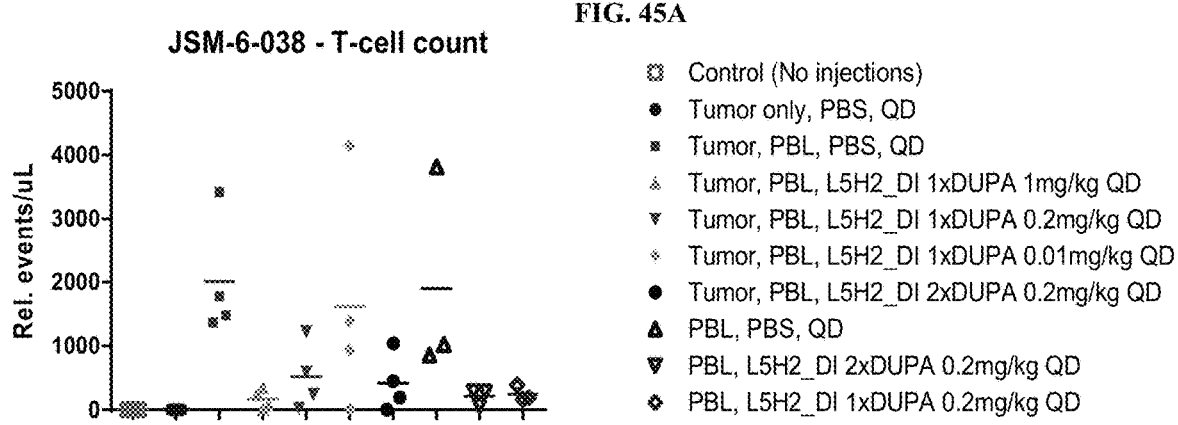
FIG. 45A and FIG. 45B show treatment with huL5H2_DI-2×DUPA or huL5H2_DI-1×DUPA demonstrated a decrease in peripheral human T cells, which indicated recruitment to the tumor.
Figure 45B:
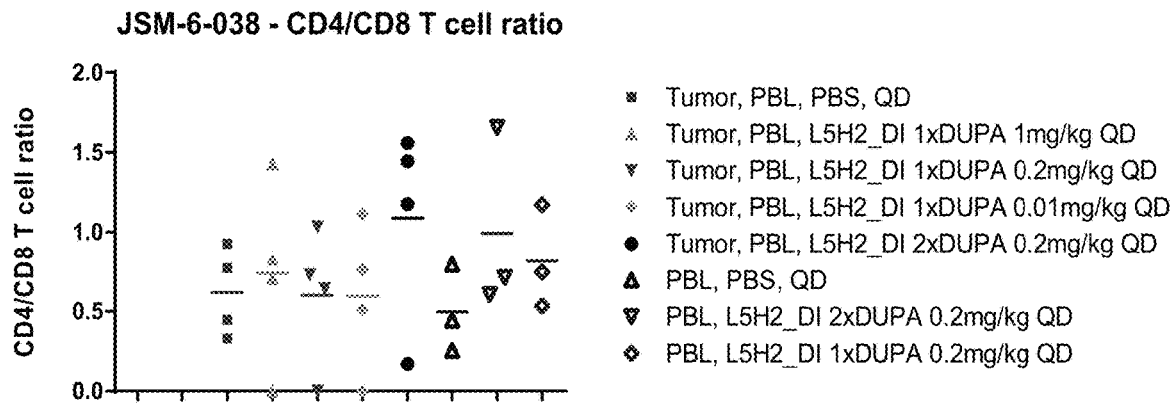
Figure 45C:
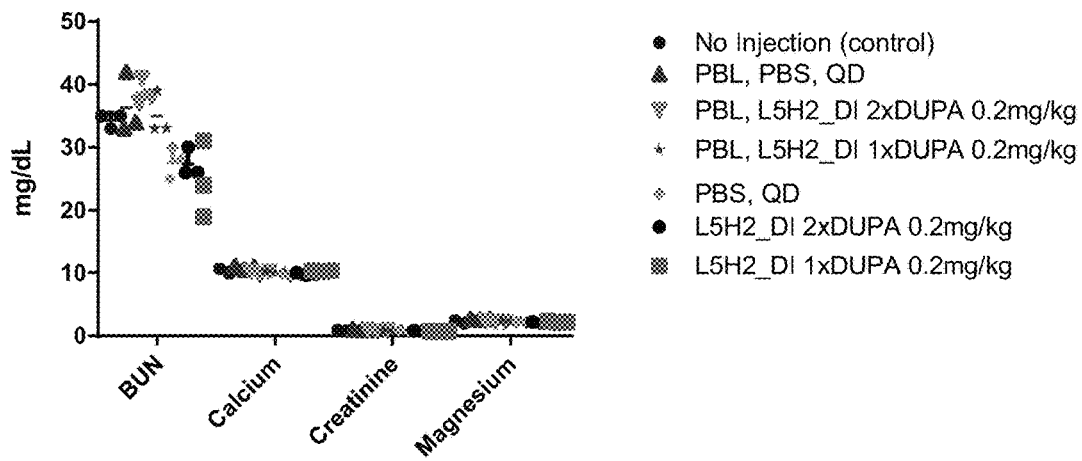
FIG. 45C, FIG. 45D, and FIG. 45E show treatment with huL5H2_DI-2×DUPA or huL5H2_DI-1×DUPA preserved renal and liver function as measured from blood plasma samples.
Figure 45D:
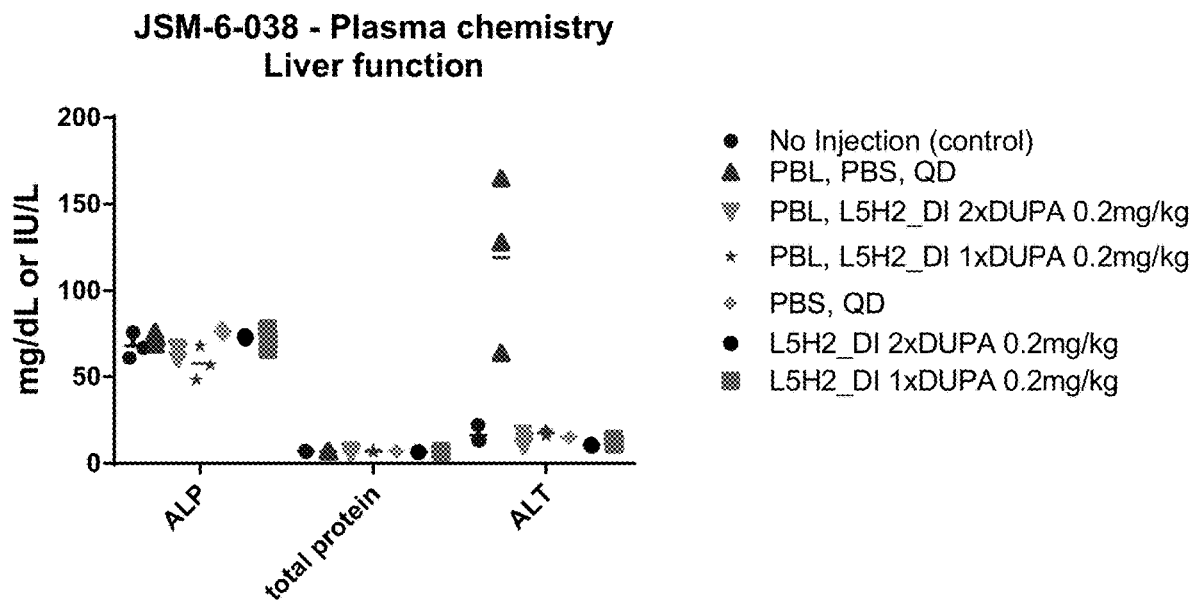
Figure 45E:
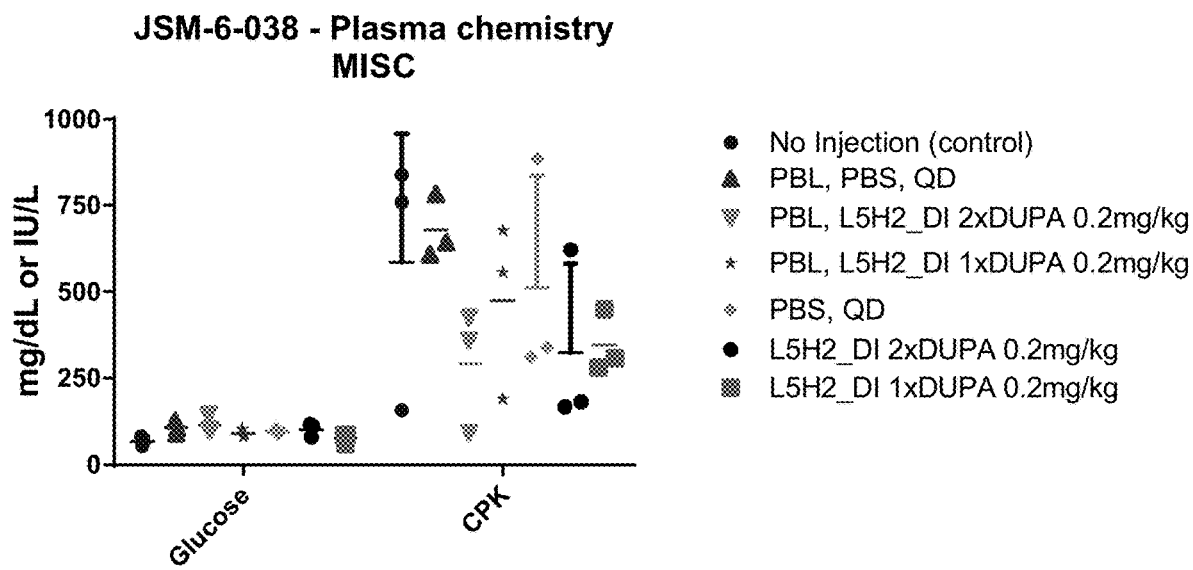

To compare the efficacy of huL5H2_DI-1×DUPA and huL5H2_DI-2×DUPA in an in vivo setting using human PBMC instead of activated T-cells, tumor bearing mice received 10×10$^6$ human PBMC via IP and daily IV injections of antibody conjugates at 0.2 mg/kg for a total of 23 doses (FIG. 41 and Table 31). After the 20$^{th}$ dose, blood was collected and stained for CD3, CD4 and CD8 T-cells. 24 hours after the last dose, blood was collected for blood cell analysis using the scil Vet abc (scil) and for plasma chemistry analysis using the Spotchem EZ (scil) (FIG. 44A-C, FIGS. 45A-E), and indicated organs were harvested for H&E staining (tissue processing, staining and scoring provided by Histotox) (Table 32 and Table 33, AVG=average). Here, the use of human PBMC instead of expanded T-cells in a C4-2 xenograft model resulted in delayed anti-tumor activity of huL5H2_DI-1×DUPA and huL5H2_DI-2×DUPA, where 1×DUPA provided a marginal advantage (FIG. 42). Weight loss was observed in mice receiving huL5H2_DI-2×DUPA only, which corresponded with beginning stages of tumor regression (each line=one mouse, FIG. 43). Indication of graft-versus-host disease (GvHD) was observed in mice that received PBMC alone, independent of huL5H2-DI treatment. However, no overt toxicity (i.e. body weight loss, aberrant blood cell analysis and chemistry, and tissue damage) was associated with huL5H2_DI-1×DUPA treatment.

TABLE 31

| Group | Target cells (SC) | Effector cells (IP) | Treatment (IV) | Protein ID | N = |
|---|---|---|---|---|---|
| A | | | | | 3 |
| B | C4-2 (1.5 × 10$^6$) | 1× DPBS | DPBS, QD | | 5 |
| C | C4-2 (1.5 × 10$^6$) | PBL (10 × 10$^6$) | DPBS, QD | | 5 |
| D | C4-2 (1.5 × 10$^6$) | PBL (10 × 10$^6$) | L5H2_DI-1×DUPA (1 mg/kg), QD | P00816, P00792 | 5 |
| E | C4-2 (1.5 × 10$^6$) | PBL (10×10$^6$) | L5H2_DI-1×DUPA (0.2 mg/kg), QD | P00816, P00792 | 5 |
| F | C4-2 (1.5 × 10$^6$) | PBL (10 × 10$^6$) | L5H2_DI-1×DUPA (0.01 g/kg), QD | P00816, P00792 | 5 |
| G | C4-2 (1.5 × 10$^6$) | PBL (10 × 10$^6$) | L5H2_DI-2×DUPA (0.2 mg/kg), QD | P00813, P00793 | 5 |
| H | | PBL (10 × 10$^6$) | DPBS, QD | | 3 |
| I | | PBL (10 × 10$^6$) | L5H2_DI-2×DUPA (0.2 mg/kg), QD | P00813, P00793 | 3 |
| J | | PBL (10 × 10$^6$) | L5H2_DI-1×DUPA (0.2 mg/kg), QD | P00816, P00792 | 3 |
| K | | PBS | DPBS, QD | | 3 |
| L | | PBS | L5H2_DI-2×DUPA (0.2 mg/kg), QD | P00813, P00793 | 3 |
| M | | PBS | L5H2_DI-1×DUPA (0.2 mg/kg), QD | P00816, P00792 | 3 |
| N | | | | | 3 |

TABLE 32

| Group | Tumor | Effector cells (IP) | Treatment (IV) | Protein ID | N = |
|---|---|---|---|---|---|
| H | None | PBL (10 × 10^6) | DPBS, QD | n/a | 3 |
| I | None | PBL (10 × 10^6) | L5H2_DI-2xDUPA (0.2 mg/kg), QD | P00813, P00793 | 3 |
| J | None | PBL (10 × 10^6) | L5H2_DI-1xDUPA (0.2 mg/kg), QD | P00816, P00792 | 3 |
| K | None | 1x DPBS | DPBS, QD | n/a | 3 |
| L | None | 1x DPBS | L5H2_DI-2xDUPA (0.2 mg/kg), QD | P00813, P00793 | 3 |
| M | None | 1x DPBS | L5H2_DI-1xDUPA (0.2 mg/kg), QD | P00816, P00792 | 3 |
| N | none | PBS | PBS | n/a | 3 |

TABLE 33

| Group | Animal | Brain Dilatation, ventricular | Basophilic tubules | Kidney Inflammation, subacute, cortex/pelvis | Kidney Dilatation, tubular, cortical | Small intestine Inflammation, subacute, pancreas | Large intestine Adhesion, serosa | Large intestine Inflammation, subacute, mucosa | Prostate Inflammation, subacute | Urinary Bladder Inflammation, subacute |
|---|---|---|---|---|---|---|---|---|---|---|
| H | 22 | 0 | 0 | 3 | 0 | 1 | 1 | 0 | 3 | 3 |
|   | 23 | 0 | 0 | 3 | 0 | 4 | 0 | 2 | 3 | 3 |
|   | 24 | 0 | 0 | 3 | 0 | 3 | 0 | 0 | 3 | 3 |
|   | AVG | 0.00 | 0.00 | 3.00 | 0.00 | 2.67 | 0.33 | 0.67 | 3.00 | 3.00 |
|   | SD | 0.00 | 0.00 | 0.00 | 0.00 | 1.53 | 0.58 | 1.15 | 0.00 | 0.00 |
| I | 25 | 0 | 0 | 2 | 0 | 0 | 0 | 0 | 2 | 2 |
|   | 26 | 0 | 0 | 3 | 0 | 2 | 0 | 0 | 1 | 1 |
|   | 27 | 2 | 0 | 2 | 0 | 0 | 0 | 0 | 3 | 3 |
|   | AVG | 0.67 | 0.00 | 2.33 | 0.00 | 0.67 | 0.00 | 0.00 | 2.00 | 2.00 |
|   | SD | 1.15 | 0.00 | 0.58 | 0.00 | 1.15 | 0.00 | 0.00 | 1.00 | 1.00 |
| J | 28 | 0 | 0 | 3 | 0 | 1 | 0 | 0 | 1 | 1 |
|   | 29 | 0 | 0 | 3 | 0 | 1 | 1 | 0 | 2 | 3 |
|   | 30 | 0 | 0 | 3 | 0 | 0 | 0 | 0 | 2 | 1 |
|   | AVG | 0.00 | 0.00 | 3.00 | 0.00 | 0.67 | 0.33 | 0.00 | 1.67 | 1.67 |
|   | SD | 0.00 | 0.00 | 0.00 | 0.00 | 0.58 | 0.58 | 0.00 | 0.58 | 1.15 |
| K | 31 | 0 | 0 | 0 | 0 | 0 | 0 | 0 | 0 | 0 |
|   | 32 | 0 | 0 | 0 | 0 | 0 | 0 | 0 | 0 | 0 |
|   | 33 | 0 | 0 | 0 | 0 | 0 | 0 | 0 | 0 | 0 |
|   | AVG | 0.00 | 0.00 | 0.00 | 0.00 | 0.00 | 0.00 | 0.00 | 0.00 | 0.00 |
|   | SD | 0.00 | 0.00 | 0.00 | 0.00 | 0.00 | 0.00 | 0.00 | 0.00 | 0.00 |
| L | 34 | 0 | 0 | 0 | 0 | 0 | 0 | 0 | 0 | 0 |
|   | 35 | 0 | 0 | 0 | 0 | 0 | 0 | 0 | 0 | 0 |
|   | 36 | 0 | 0 | 0 | 0 | 0 | 0 | 0 | 0 | 0 |
|   | AVG | 0.00 | 0.00 | 0.00 | 0.00 | 0.00 | 0.00 | 0.00 | 0.00 | 0.00 |
|   | SD | 0.00 | 0.00 | 0.00 | 0.00 | 0.00 | 0.00 | 0.00 | 0.00 | 0.00 |
| M | 37 | 0 | 0 | 0 | 0 | 0 | 0 | 0 | 0 | 0 |
|   | 38 | 0 | 0 | 0 | 0 | 0 | 0 | 0 | 0 | 0 |
|   | 39 | 0 | 0 | 0 | 0 | 0 | 0 | 0 | 0 | 0 |
|   | AVG | 0.00 | 0.00 | 0.00 | 0.00 | 0.00 | 0.00 | 0.00 | 0.00 | 0.00 |
|   | SD | 0.00 | 0.00 | 0.00 | 0.00 | 0.00 | 0.00 | 0.00 | 0.00 | 0.00 |
| N | 19 | 0 | 0 | 0 | 0 | 0 | 0 | 0 | 0 | 0 |
|   | 20 | 0 | 0 | 0 | 0 | 0 | 0 | 0 | 0 | 0 |
|   | 21 | 0 | 0 | 0 | 0 | 0 | 0 | 0 | 0 | 0 |
|   | AVG | 0.00 | 0.00 | 0.00 | 0.00 | 0.00 | 0.00 | 0.00 | 0.00 | 0.00 |
|   | SD | 0.00 | 0.00 | 0.00 | 0.00 | 0.00 | 0.00 | 0.00 | 0.00 | 0.00 |
|   |   | 0 | 1.00 | 2.00 | 3.00 | 4.00 | 5.00 |   |   |   |

Mouse PK Assay

Figure 46:
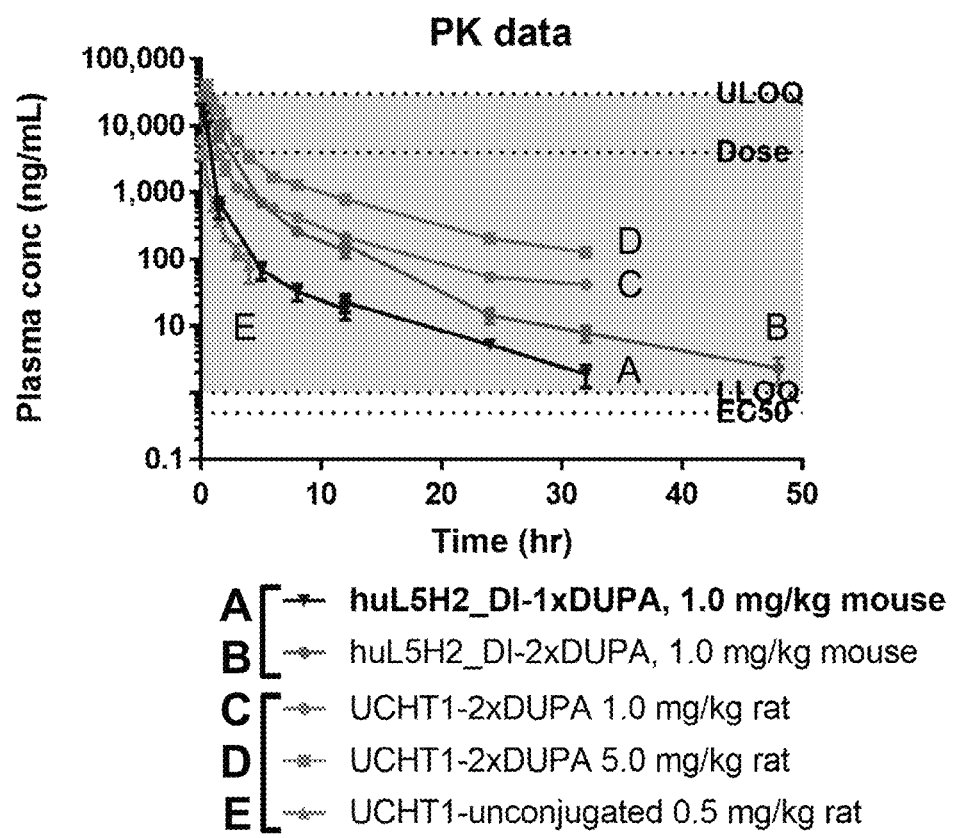
FIG. 46 shows that huL5H2_DI-2×DUPA demonstrated a prolonged exposure compared with huL5H2_DI-1×DUPA in a mouse model.

Male C57BL/6J mouse (Jackson laboratory) were injected i.v. at time 0 with 1 mg/kg conjugates (n=3 mouse per group). Blood was collected at regular intervals out to 48 h and was processed to plasma. Samples were quantified by electrochemiluminescence technology from Meso Scale Discovery. The capture was recombinant human PSMA (R&D System), and the detection antibody was CaptureSelect biotin anti-IgG-CH1 conjugate (Life Technologies). Pharmacokinetic parameters were determined by noncompartmental analysis using Phoenix WinNonlin 6.3 software (Certara USA, Inc). huL5H2-DI_2×DUPA demonstrated a prolonged exposure compared to huL5H2-DI_1×DUPA (Table 34 and FIG. 46).

TABLE 34

|  | $t_{1/2}$ (hrs) | $C_{max}$ (ng/ml) | $AUC_{last}$ (ng*hr/mL) | $AUC_{inf}$ (ng* hr/mL) |
|---|---|---|---|---|
| huL5H2-DI_1×DUPA | 5.87 | 18348 | 14228 | 14244 |
| huL5H2-DI_1×DUPA | 9.08 | 22789 | 43950 | 43980 |

TABLE 35

Antibody Domain Nucleotide Sequences

| SEQ ID NO. | Antibody Domain | Sequence |
|---|---|---|
| 1 | Murine anti-CD3 VL | CAAGCAGTTGTGACGCAAGAATCGGCCCTGACCACGAGTCCGGGTGA AACCGTTACGCTGACCTGTCGCTCAAGTACCGGCGCTGTTACCACGAG TAACTATGCGAATTGGGTGCAGGAAAAACCGGATCACCTGTTTACCG GCCTGATTGGCGGTACGAACAAACGTGCGCCGGGTGTTCCGGCACGTT TCTCGGGCAGCCTGATTGGTGATAAAGCAGCACTGACGATCACCGGC GCCCAAACCGAAGACGAAGCAATCTATTTTTGCGCTCTGTGGTACTCT AACCTGTGGGTGTTCGGCGGTGGCACGAAACTGACCGTTCTG |
| 2 | Murine anti-CD3 VH | GAAGTCCAGCTGGTTGAATCTGGTGGCGGTCTGGTGCAACCGAAAGG CTCTCTGAAACTGAGTTGCGCAGCTTCCGGTTTTACGTTCAACACCTAT GCGATGAATTGGGTTCGCCAGGCGCCGGGTAAAGGTCTGGAATGGGT CGCGCGTATCCGCAGCAAATATAACAATTACGCAACCTATTACGCTGA TTCAGTGAAAGACCGTTTTACGATTTCGCGCGATGACTCCCAGTCAAT CCTGTACCTGCAAATGAACAATCTGAAAACGGAAGATACCGCCATGT ATTACTGCGTCCGTCACGGCAACTTTGGTAATTCCTATGTGTCATGGTT CGCATACTGGGGCCAGGGTACGCTGGTTACCGTCAGCTCT |
| 3 | VH1 | GAAGTCCAGCTGGTTGAATCTGGTGGCGGTCTGGTTCAACCGGGCGGT TCGCTGAAACTGAGCTGCGCAGCTTCTGGCTTTACGTTCAACACCTAT GCGATGAATTGGGTTCGCCAGGCCTCAGGCAAAGGTCTGGAATGGGT CGGTCGTATTCGCTCGAAATATAACAATTACGCAACCTATTACGCTGA TAGCGTGAAAGACCGTTTCACCATCAGTCGCGATGACTCCAAAAACA CGCTGTATCTGCAAATGAATAGCCTGAAAACGGAAGATACCGCGGTC TATTACTGCGTGCGTCATGGCAACTTTGGTAATTCTTATGTGAGCTGGT TCGCCTACTGGGGCCAGGGTACGCTGGTTACCGTCAGCTCT |
| 4 | VH2 | GAAGTCCAGCTGGTTGAATCTGGTGGCGGTCTGGTTCAACCGGGCGGT TCGCTGAAACTGAGCTGCGCAGCTTCTGGCTTTACGTTCAACACCTAT GCGATGAATTGGGTTCGCCAGGCCTCAGGCAAAGGTCTGGAATGGGT CGCTCGTATTCGCTCGAAATATAACAATTACGCAACCTATTACGCTGA TAGCGTGAAAGACCGTTTCACCATCAGTCGCGATGACTCCAAAAACA CGCTGTATCTGCAAATGAATAGCCTGAAAACGGAAGATACCGCGGTC TATTACTGCGTGCGTCATGGCAACTTTGGTAATTCTTATGTGAGCTGGT TCGCCTACTGGGGCCAGGGTACGCTGGTTACCGTCAGCTCT |
| 5 | DI-VH2 | GAAGTCCAGCTGGTTGAATCTGGTGGCGGTCTGGTTCAACCGGGCGGT TCGCTGAGACTGAGCTGCGCAGCTTCTGGCTTTACGTTCAACACCTAT GCGATGAATTGGGTTCGCCAGGCCCCGGGCAAAGGTCTGGAATGGGT CGCTCGTATTCGCTCGAAATATAACAATTACGCAACCTATTACGCTGA TAGCGTGAAAGACCGTTTCACCATCAGTCGCGATGACTCCAAAAACA CGCTGTATCTGCAAATGAATAGCCTGAGAGCGGAAGATACCGCGGTC TATTACTGCGTGCGTCATGGCAACTTTGGTAATTCTTATGTGAGCTGGT TCGCCTACTGGGGCCAGGGTACGCTGGTTACCGTCAGCTCT |
| 6 | VL1 | CAAGCTGTTGTGACCCAAGAACCGAGTCTGACCGTGTCTCCGGGCGGC ACCGTTACGCTGACCTGTGGCTCCTCTACCGGCGCAGTCACCACGAGC AACTATGCAAATTGGTTCCAGCAAAAACCGGGTCAGGCTCCGCGTAC CCTGATTTACGGTACGAACAAACGTGCGCCGTGGACCCCGGCACGTTT TTCGGGCAGCCTGCTGGGCGGTAAAGCAGCACTGACCATCAGTGGTG CGCAGCCGGAAGATGAAGCAGAATATTACTGCGCTCTGTGGTATAGC AACCTGTGGGTCTTTGGCGGTGGCACGAAACTGACCGTGCTG |
| 7 | VL2 | CAAGCTGTTGTGACCCAAGAACCGAGTCTGACCGTGTCTCCGGGCGGC ACCGTTACGCTGACCTGTGGCTCCTCTACCGGCGCAGTCACCACGAGC AACTATGCAAATTGGGTGCAGCAAAAACCGGGTCAGGCTTTTCGTGG CCTGATTTACGGTACGAACAAACGTGCGCCGTGGACCCCGGCACGTTT |

TABLE 35-continued

Antibody Domain Nucleotide Sequences

| SEQ ID NO. | Antibody Domain | Sequence |
|---|---|---|
| | | TTCGGGCAGCCTGCTGGGCGGTAAAGCAGCACTGACCATCAGTGGTG<br>CGCAGCCGGAAGATGAAGCAGAATATTACTGCGCTCTGTGGTATAGC<br>AACCTGTGGGTCTTTGGCGGTGGCACGAAACTGACCGTGCTG |
| 8 | VL3 | CAAGCTGTTGTGACCCAAGAACCGAGTCTGACCGTGTCTCCGGGCGGC<br>ACCGTTACGCTGACCTGTGGCTCCTCTACCGGCGCAGTCACCACGAGC<br>AACTATGCAAATTGGGTGCAGCAAAAACCGGGTCAGGCTTTTCGTGG<br>CCTGATTGGCGGTACGAACAAACGTGCGCCGTGGACCCCGGCACGTTT<br>TTCGGGCAGCCTGCTGGGCGGTAAAGCAGCACTGACCATCAGTGGTG<br>CGCAGCCGGAAGATGAAGCAGAATATTACTGCGCTCTGTGGTATAGC<br>AACCTGTGGGTCTTTGGCGGTGGCACGAAACTGACCGTGCTG |
| 9 | VL4 | CAAGCTGTTGTGACCCAAGAACCGAGTCTGACCGTGTCTCCGGGCGGC<br>ACCGTTACGCTGACCTGTGGCTCCTCTACCGGCGCAGTCACCACGAGC<br>AACTATGCAAATTGGGTGCAGCAAAAACCGGGTCAGGCTTTTCGTGG<br>CCTGATTTACGGTACGAACAAACGTGCGCCGTGGACCCCGGCACGTTT<br>TTCGGGCAGCCTGCTGGGCGATAAAGCAGCACTGACCATCAGTGGTG<br>CGCAGCCGGAAGATGAAGCAGAATATTACTGCGCTCTGTGGTATAGC<br>AACCTGTGGGTCTTTGGCGGTGGCACGAAACTGACCGTGCTG |
| 10 | VL5 | CAAGCTGTTGTGACCCAAGAACCGAGTCTGACCGTGTCTCCGGGCGGC<br>ACCGTTACGCTGACCTGTCGCTCCTCTACCGGCGCAGTCACCACGAGC<br>AACTATGCAAATTGGGTGCAGCAAAAACCGGATCATCTGTTTCGTGG<br>CTGATTgGCGGTACGAACAAACGTGCGCCGGGGACCCCGGCACGTTTT<br>TCGGGCAGCCTGCTGGGCGATAAAGCAGCACTGACCATCAGTGGTGC<br>GCAGCCGGAAGATGAAGCAGAATATTACTGCGCTCTGTGGTATAGCA<br>ACCTGTGGGTCTTTGGCGGTGGCACGAAACTGACCGTGCTG |
| 11 | VL6 | CAAGCTGTTGTGACCCAAGAACCGAGTCTGACCGTGTCTCCGGGCGGC<br>ACCGTTACGCTGACCTGTCGCTCCTCTACCGGCGCAGTCACCACGAGC<br>AACTATGCAAATTGGTTCCAGCAAAAACCGGATCATCTGCCGCGTACC<br>CTGATTTACGGTACGAACAAACGTGCGCCGGGGACCCCGGCACGTTTT<br>TCGGGCAGCCTGCTGGGCGATAAAGCAGCACTGACCATCAGTGGTGC<br>GCAGCCGGAAGATGAAGCAGAATATTACTGCGCTCTGTGGTATAGCA<br>ACCTGTGGGTCTTTGGCGGTGGCACGAAACTGACCGTGCTG |
| 12 | VL7 | CAAGCTGTTGTGACCCAAGAACCGAGTCTGACCGTGTCTCCGGGCGGC<br>ACCGTTACGCTGACCTGTCGCTCCTCTACCGGCGCAGTCACCACGAGC<br>AACTATGCAAATTGGGTGCAGCAAAAACCGGGTCAGGCGTTTCGTGG<br>CCTGATTGGCGGTACGAACAAACGTGCGCCGGGGACCCCGGCACGTT<br>TTTCGGGCAGCCTGCTGGGCGATAAAGCAGCACTGACCATCAGTGGT<br>GCGCAGCCGGAAGATGAAGCAGAATATTACTGCGCTCTGTGGTATAG<br>CAACCTGTGGGTCTTTGGCGGTGGCACGAAACTGACCGTGCTG |
| 13 | VL8 | CAAGCTGTTGTGACCCAAGAACCGAGTCTGACCGTGTCTCCGGGCGGC<br>ACCGTTACGCTGACCTGTGGCTCCTCTACCGGCGCAGTCACCACGAGC<br>AACTATGCAAATTGGGTGCAGCAAAAACCGGATCATCTGTTTCGTGGC<br>CTGATTGGCGGTACGAACAAACGTGCGCCGGGGACCCCGGCACGTTT<br>TTCGGGCAGCCTGCTGGGCGGTAAAGCAGCACTGACCATCAGTGGTG<br>CGCAGCCGGAAGATGAAGCAGAATATTACTGCGCTCTGTGGTATAGC<br>AACCTGTGGGTCTTTGGCGGTGGCACGAAACTGACCGTGCTG |
| 14 | VL9 | CAAGCTGTTGTGACCCAAGAACCGAGTCTGACCGTGTCTCCGGGCGGC<br>ACCGTTACGCTGACCTGTGGCTCCTCTACCGGCGCAGTCACCACGAGC<br>AACTATGCAAATTGGGTGCAGCAAAAACCGGGTCAGGCGTTTCGTGG<br>CCTGATTGGCGGTACGAACAAACGTGCGCCGGGGGTCCCGGATCGTTT<br>TTCGGGCAGCCTGCTGGGCGGTAAAGCAGCACTGACCATCAGTGGTG<br>CGCAGCCGGAAGATGAAGCAGAATATTACTGCGCTCTGTGGTATAGC<br>AACCTGTGGGTCTTTGGCGGTGGCACGAAACTGACCGTGCTG |
| 15 | VL10 | CAAGCTGTTGTGACCCAAGAACCGAGTCTGACCACGTCTCCGGGCGG<br>CACCGTTACGCTGACCTGTCGCTCCTCTACCGGCGCAGTCACCACGAG<br>CAACTATGCAAATTGGGTGCAGCAAAAACCGGATCATCTGTTTACTGG<br>CCTGATTGGCGGTACGAACAAACGTGCGCCGGGGGTCCCGGCACGTT<br>TTTCGGGCAGCCTGATTGGCGATAAAGCAGCACTGACCATCAGTGGTG<br>CGCAGCCGGAAGATGAAGCAGAATATTACTGCGCTCTGTGGTATAGC<br>AACCTGTGGGTCTTTGGCGGTGGCACGAAACTGACCGTGCTG |
| 16 | VL5 lambda | CAAGCTGTTGTGACCCAAGAACCGAGTCTGACCGTGTCTCCGGGCGGC<br>ACCGTTACGCTGACCTGTCGCTCCTCTACCGGCGCAGTCACCACGAGC<br>AACTATGCAAATTGGGTGCAGCAAAAACCGGATCATCTGTTTCGTGGC<br>CTGATTgGCGGTACGAACAAACGTGCGCCGGGGACCCCGGCACGTTTT<br>TCGGGCAGCCTGCTGGGCGATAAAGCAGCACTGACCATCAGTGGTGC<br>GCAGCCGGAAGATGAAGCAGAATATTACTGCGCTCTGTGGTATAGCA |

TABLE 35-continued

Antibody Domain Nucleotide Sequences

| SEQ ID NO. | Antibody Domain | Sequence |
|---|---|---|
| | | ACCTGTGGGTCTTTGGCGGTGGCACGAAACTGACCGTGCTGGGTCAGC<br>CGAAAGCAGCTCCGAGCGTCACCCTGTTTCCGCCGAGCAGCGAAGAA<br>CTGCAAGCAAATAAAGCTACCCTGGTTTGTCTGATTAGCGATTTCTAT<br>CCGGGCGCAGTCACGGTGGCATGGAAAGCAGACAGTTCCCCGGTTAA<br>AGCTGGTGTCGAAACCACGACCCCGTCTAAACAGAGTAACAATAAAT<br>ATGCGGCCTCATCGTACCTGAGTCTGACCCCGGAACAGTGGAAATCCC<br>ATCGTTCTTACAGTTGCCAAGTGACCCACGAAGGCAGCACGGTGGAA<br>AAAACCGTTGCGCCGACGGAATGTAGC |
| 17 | VL5 kappa | CAAGCTGTTGTGACCCAAGAACCGAGTCTGACCGTGTCTCCGGGCGGC<br>ACCGTTACGCTGACCTGTCGCTCCTCTACCGGCGCAGTCACCACGAGC<br>AACTATGCAAATTGGGTGCAGCAAAAACCGGATCATCTGTTTCGTGGC<br>CTGATTGGCGGTACGAACAAACGTGCGCCGGGGACCCCGGCACGTTT<br>TTCGGGCAGCCTGCTGGGCGATAAAGCAGCACTGACCATCAGTGGTG<br>CGCAGCCGGAAGATGAAGCAGAATATTACTGCGCTCTGTGGTATAGC<br>AACCTGTGGGTCTTTGGCGGTGGCACGAAACTGACCGTTCTGAAACGA<br>ACTGTGGCTGCACCATCTGTCTTCATCTTCCCGCCATCTGATGAGCAGT<br>TGAAATCTGGAACTGCCTCTGTCGTGTGCCTGCTGAATAACTTCTATC<br>CCAGAGAGGCCAAAGTACAGTGGAAGGTGGATAACGCCCTCCAATCG<br>GGTAACTCCCAGGAGAGTGTCACAGAGCAGGACAGCAAGGACAGCAC<br>CTACAGCCTCAGCAGCACCCTGACGCTGAGCAAAGCAGACTACGAGA<br>AACACAAAGTCTACGCCTGCGAAGTCACCCATCAGGGCCTGTCTTCG<br>CCCGTCACAAAGAGCTTCAACAGGGGAGAGTGT |
| 18 | VL5 kappa-205TAG | CAAGCTGTTGTGACCCAAGAACCGAGTCTGACCGTGTCTCCGGGCGGC<br>ACCGTTACGCTGACCTGTCGCTCCTCTACCGGCGCAGTCACCACGAGC<br>AACTATGCAAATTGGGTGCAGCAAAAACCGGATCATCTGTTTCGTGGC<br>CTGATTGGCGGTACGAACAAACGTGCGCCGGGGACCCCGGCACGTTT<br>TTCGGGCAGCCTGCTGGGCGATAAAGCAGCACTGACCATCAGTGGTG<br>CGCAGCCGGAAGATGAAGCAGAATATTACTGCGCTCTGTGGTATAGC<br>AACCTGTGGGTCTTTGGCGGTGGCACGAAACTGACCGTTCTGAAACGA<br>ACTGTGGCTGCACCATCTGTCTTCATCTTCCCGCCATCTGATGAGCAGT<br>TGAAATCTGGAACTGCCTCTGTCGTGTGCCTGCTGAATAACTTCTATC<br>CCAGAGAGGCCAAAGTACAGTGGAAGGTGGATAACGCCCTCCAATCG<br>GGTAACTCCCAGGAGAGTGTCACAGAGCAGGACAGCAAGGACAGCAC<br>CTACAGCCTCAGCAGCACCCTGACGCTGAGCAAAGCAGACTACGAGA<br>AACACAAAGTCTACGCCTGCGAAGTCACCCATCAGGGCCTGTAGTCG<br>CCCGTCACAAAGAGCTTCAACAGGGGAGAGTGT |
| 19 | H2 | GAAGTCCAGCTGGTTGAATCTGGTGGCGGTCTGGTTCAACCGGGCGGT<br>TCGCTGAAACTGAGCTGCGCAGCTTCTGGCTTTACGTTCAACACCTAT<br>GCGATGAATTGGGTTCGCCAGGCCTCAGGCAAAGGTCTGGAATGGGT<br>CGCTCGTATTCGCTCGAAATATAACAATTACGCAACCTATTACGCTGA<br>TAGCGTGAAAGACCGTTTCACCATCAGTCGCGATGACTCCAAAAACA<br>CGCTGTATCTGCAAATGAATAGCCTGAAAACGGAAGATACCGCGGTC<br>TATTACTGCGTGCGTCATGGCAACTTTGGTAATTCTTATGTGAGCTGGT<br>TCGCCTACTGGGGCCAGGGTACGCTGGTTACCGTCAGCTCTGCCTCCA<br>CCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCG<br>AACCGGTGACGGTGTCGTGGAACTCAGGCGCCCTGACCAGCGGCGTG<br>CACACCTTCCCGGCTGTCCTACAGTCCTCAGGACTCTACTCCCTCAGC<br>AGCGTGGTGACTGTGCCCTCTAGCAGCTTGGGCACCCAGACCTACATC<br>TGCAACGTGAATCACAAGCCCAGCAACACCAAGGTGGACAAGAAAGT<br>TGAGCCCAAATCTTGTGACAAAACTCACACA |
| 20 | H2-141TAG | GAAGTCCAGCTGGTTGAATCTGGTGGCGGTCTGGTTCAACCGGGCGGT<br>TCGCTGAAACTGAGCTGCGCAGCTTCTGGCTTTACGTTCAACACCTAT<br>GCGATGAATTGGGTTCGCCAGGCCTCAGGCAAAGGTCTGGAATGGGT<br>CGCTCGTATTCGCTCGAAATATAACAATTACGCAACCTATTACGCTGA<br>TAGCGTGAAAGACCGTTTCACCATCAGTCGCGATGACTCCAAAAACA<br>CGCTGTATCTGCAAATGAATAGCCTGAAAACGGAAGATACCGCGGTC<br>TATTACTGCGTGCGTCATGGCAACTTTGGTAATTCTTATGTGAGCTGGT<br>TCGCCTACTGGGGCCAGGGTACGCTGGTTACCGTCAGCTCTGCCTCCA<br>CCAAGGGCCCATCGGTCTTCCCCCTGGCACCCTCCTCCTAGAGCACCT<br>CTGGGGGCACAGCGGCCCTGGGCTGCCTGGTCAAGGACTACTTCCCCG<br>AACCGGTGACGGTGTCGTGGAACTCAGGCGCCCTGACCAGCGGCGTG<br>CACACCTTCCCGGCTGTCCTACAGTCCTCAGGACTCTACTCCCTCAGC<br>AGCGTGGTGACTGTGCCCTCTTAGAGCTTGGGCACCCAGACCTACATC<br>TGCAACGTGAATCACAAGCCCAGCAACACCAAGGTGGACAAGAAAGT<br>TGAGCCCAAATCTTGTGACAAAACTCACACA |
| 21 | DI-H2 | GAAGTCCAGCTGGTTGAATCTGGTGGCGGTCTGGTTCAACCGGGCGGT<br>TCGCTGAGACTGAGCTGCGCAGCTTCTGGCTTTACGTTCAACACCTAT<br>GCGATGAATTGGGTTCGCCAGGCCCCGGGCAAAGGTCTGGAATGGGT |

TABLE 35-continued

Antibody Domain Nucleotide Sequences

| SEQ ID NO. | Antibody Domain | Sequence |
|---|---|---|
| | | CGCTCGTATTCGCTCGAAATATAACAATTACGCAACCTATTACGCTGA<br>TAGCGTGAAAGACCGTTTCACCATCAGTCGCGATGACTCCAAAAACA<br>CGCTGTATCTGCAAATGAATAGCCTGAGAGCGGAAGATACCGCGGTC<br>TATTACTGCGTGCGTCATGGCAACTTTGGTAATTCTTATGTGAGCTGGT<br>TCGCCTACTGGGGCCAGGGTACGCTGGTTACCGTCAGCTCTGCCTCCA<br>CCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCG<br>AACCGGTGACGGTGTCGTGGAACTCAGGCGCCCTGACCAGCGGCGTG<br>CACACCTTCCCGGCTGTCCTACAGTCCTCAGGACTCTACTCCCTCAGC<br>AGCGTGGTGACTGTGCCCTCCAGCAGCTTGGGCACCCAGACCTACATC<br>TGCAACGTGAATCACAAGCCCAGCAACACCAAGGTGGACAAGAAAGT<br>TGAGCCCAAATCTTGTGACAAAACTCACACA |
| 22 | DI-H2 141TAG | GAAGTCCAGCTGGTTGAATCTGGTGGCGGTCTGGTTCAACCGGGCGGT<br>TCGCTGAGACTGAGCTGCGCAGCTTCTGGCTTTACGTTCAACACCTAT<br>GCGATGAATTGGGTTCGCCAGGCCCCGGGCAAAGGTCTGGAATGGGT<br>CGCTCGTATTCGCTCGAAATATAACAATTACGCAACCTATTACGCTGA<br>TAGCGTGAAAGACCGTTTCACCATCAGTCGCGATGACTCCAAAAACA<br>CGCTGTATCTGCAAATGAATAGCCTGAGAGCGGAAGATACCGCGGTC<br>TATTACTGCGTGCGTCATGGCAACTTTGGTAATTCTTATGTGAGCTGGT<br>TCGCCTACTGGGGCCAGGGTACGCTGGTTACCGTCAGCTCTGCCTCCA<br>CCAAGGGCCCATCGGTCTTCCCCCTGGCACCCTCCTCCTAGAGCACCT<br>CTGGGGGCACAGCGGCCCTGGGCTGCCTGGTCAAGGACTACTTCCCCG<br>AACCGGTGACGGTGTCGTGGAACTCAGGCGCCCTGACCAGCGGCGTG<br>CACACCTTCCCGGCTGTCCTACAGTCCTCAGGACTCTACTCCCTCAGC<br>AGCGTGGTGACTGTGCCCTCTAGCAGCTTGGGCACCCAGACCTACATC<br>TGCAACGTGAATCACAAGCCCAGCAACACCAAGGTGGACAAGAAAGT<br>TGAGCCCAAATCTTGTGACAAAACTCACACA |

Abbreviations: VH = heavy chain variable domain; VL = light chain variable domain; DI = de-immunized; TAG = STOP codon, encodes an unnatural amino acid; H = heavy chain Fab (heavy chain variable + C$_H$1 domains); Bold/underlined codons are sites for (replacement with) unnatural amino acids.

TABLE 36

Antibody Domain Amino Acid Sequences

| SEQ ID NO. | Antibody Domain | Sequence |
|---|---|---|
| 23 | Murine Anti-CD3 VL | QAVVTQESALTTSPGETVTLTCRSSTGAVTTSNYANWVQEKPDHLFTGL<br>IGGTNKRAPGVPARFSGSLIGDKAALTITGAQTEDEAIYFCALWYSNLW<br>VFGGGTKLTVL |
| 24 | Murine Anti-CD3 VH | EVQLVESGGGLVQPKGSLKLSCAASGFTFNTYAMNWVRQAPGKGLEW<br>VARIRSKYNNYATYYADSVKDRFTISRDDSQSILYLQMNNLKTEDTAMY<br>YCVRHGNFGNSYVSWFAYWGQGTLVTVSS |
| 25 | VH1 | EVQLVESGGGLVQPGGSLKLSCAASGFTFNTYAMNWVRQASGKGLEW<br>VGRIRSKYNNYATYYADSVKDRFTISRDDSKNTLYLQMNSLKTEDTAV<br>YYCVRHGNFGNSYVSWFAYWGQGTLVTVSS |
| 26 | VH2 | EVQLVESGGGLVQPGGSLKLSCAASGFTFNTYAMNWVRQASGKGLEW<br>VARIRSKYNNYATYYADSVKDRFTISRDDSKNTLYLQMNSLKTEDTAV<br>YYCVRHGNFGNSYVSWFAYWGQGTLVTVSS |
| 27 | DI-VH2 | EVQLVESGGGLVQPGGSLRLSCAASGFTFNTYAMNWVRQAPGKGLEW<br>VARIRSKYNNYATYYADSVKDRFTISRDDSKNTLYLQMNSLRAEDTAV<br>YYCVRHGNFGNSYVSWFAYWGQGTLVTVSS |
| 28 | VL1 | QAVVTQEPSLTVSPGGTVTLTCGSSTGAVTTSNYANWFQQKPGQAPRIL<br>IYGTNKRAPWTPARFSGSLLGGKAALTISGAQPEDEAEYYCALWYSNL<br>WVFGGGTKLTVL |
| 29 | VL2 | QAVVTQEPSLTVSPGGTVTLTCGSSTGAVTTSNYANWVQQKPGQAFRG<br>LIYGTNKRAPWTPARFSGSLLGGKAALTISGAQPEDEAEYYCALWYSNL<br>WVFGGGTKLTVL |
| 30 | VL3 | QAVVTQEPSLTVSPGGTVTLTCGSSTGAVTTSNYANWVQQKPGQAFRG<br>LIGGTNKRAPWTPARFSGSLLGGKAALTISGAQPEDEAEYYCALWYSNL<br>WVFGGGTKLTVL |

TABLE 36-continued

Antibody Domain Amino Acid Sequences

| SEQ ID NO. | Antibody Domain | Sequence |
|---|---|---|
| 31 | VL4 | QAVVTQEPSLTVSPGGTVTLTCGSSTGAVTTSNYANWVQQKPGQAFRG<br>LIYGTNKRAPWTPARFSGSLLGDKAALTISGAQPEDEAEYYCALWYSNL<br>WVFGGGTKLTVL |
| 32 | VL5 | QAVVTQEPSLTVSPGGTVTLTCRSSTGAVTTSNYANWVQQKPDHLFRG<br>LIGGTNKRAPGTPARFSGSLLGDKAALTISGAQPEDEAEYYCALWYSNL<br>WVFGGGTKLTVL |
| 33 | VL6 | QAVVTQEPSLTVSPGGTVTLTCRSSTGAVTTSNYANWFQQKPDHLPRTL<br>IYGTNKRAPGTPARFSGSLLGDKAALTISGAQPEDEAEYYCALWYSNLW<br>VFGGGTKLTVL |
| 34 | VL7 | QAVVTQEPSLTVSPGGTVTLTCRSSTGAVTTSNYANWVQQKPGQAFRG<br>LIGGTNKRAPGTPARFSGSLLGDKAALTISGAQPEDEAEYYCALWYSNL<br>WVFGGGTKLTVL |
| 35 | VL8 | QAVVTQEPSLTVSPGGTVTLTCGSSTGAVTTSNYANWVQQKPDHLFRG<br>LIGGTNKRAPGTPARFSGSLLGGKAALTISGAQPEDEAEYYCALWYSNL<br>WVFGGGTKLTVL |
| 36 | VL9 | QAVVTQEPSLTVSPGGTVTLTCGSSTGAVTTSNYANWVQQKPGQAFRG<br>LIGGTNKRAPGVPDRFSGSLLGGKAALTISGAQPEDEAEYYCALWYSNL<br>WVFGGGTKLTVL |
| 37 | VL10 | QAVVTQEPSLTTSPGGTVTLTCRSSTGAVTTSNYANWVQQKPDHLFTGL<br>IGGTNKRAPGVPARFSGSLIGDKAALTISGAQPEDEAEYYCALWYSNLW<br>VFGGGTKLTVL |
| 38 | VL5 lambda | QAVVTQEPSLTVSPGGTVTLTCRSSTGAVTTSNYANWVQQKPDHLFRG<br>LIGGTNKRAPGTPARFSGSLLGDKAALTISGAQPEDEAEYYCALWYSNL<br>WVFGGGTKLTVLGQPKAAPSVTLFPPSSEELQANKATLVCLISDFYPGA<br>VTVAWKADSSPVKAGVETTTPSKQSNNKYAASSYLSLTPEQWKSHRSY<br>SCQVTHEGSTVEKTVAPTECS |
| 39 | VL5 kappa | QAVVTQEPSLTVSPGGTVTLTCRSSTGAVTTSNYANWVQQKPDHLFRG<br>LIGGTNKRAPGTPARFSGSLLGDKAALTISGAQPEDEAEYYCALWYSNL<br>WVFGGGTKLTVLKRTVAAPSVFIFPPSDEQLKSGTASVVCLLNNFYPRE<br>AKVQWKVDNALQSGNSQESVTEQDSKDSTYSLSSTLTLSKADYEKHKV<br>YACEVTHQGLSSPVTKSFNRGEC |
| 40 | VL5 kappa 205TAG | QAVVTQEPSLTVSPGGTVTLTCRSSTGAVTTSNYANWVQQKPDHLFRG<br>LIGGTNKRAPGTPARFSGSLLGDKAALTISGAQPEDEAEYYCALWYSNL<br>WVFGGGTKLTVLKRTVAAPSVFIFPPSDEQLKSGTASVVCLLNNFYPRE<br>AKVQWKVDNALQSGNSQESVTEQDSKDSTYSLSSTLTLSKADYEKHKV<br>YACEVTHQGLpAcFSPVTKSFNRGEC |
| 41 | H2 | EVQLVESGGGLVQPGGSLKLSCAASGFTFNTYAMNWVRQASGKGLEW<br>VARIRSKYNNYATYYADSVKDRFTISRDDSKNTLYLQMNSLKTEDTAV<br>YYCVRHGNFGNSYVSWFAYWGQGTLVTVSSASTKGPSVFPLAPSSKSTS<br>GGTAALGCLVKDYFPEPVTVSWNSGALTSGVHTFPAVLQSSGLYSLSSV<br>VTVPSSSLGTQTYICNVNHKPSNTKVDKKVEPKSCDKTHT |
| 42 | H2 141TAG | EVQLVESGGGLVQPGGSLKLSCAASGFTFNTYAMNWVRQASGKGLEW<br>VARIRSKYNNYATYYADSVKDRFTISRDDSKNTLYLQMNSLKTEDTAV<br>YYCVRHGNFGNSYVSWFAYWGQGTLVTVSSASTKGPSVFPLAPSSpAcF<br>STSGGTAALGCLVKDYFPEPVTVSWNSGALTSGVHTFPAVLQSSGLYSL<br>SSVVTVPSSSLGTQTYICNVNHKPSNTKVDKKVEPKSCDKTHT |
| 43 | DI-H2 | EVQLVESGGGLVQPGGSLRLSCAASGFTFNTYAMNWVRQAPGKGLEW<br>VARIRSKYNNYATYYADSVKDRFTISRDDSKNTLYLQMNSLRAEDTAV<br>YYCVRHGNFGNSYVSWFAYWGQGTLVTVSSASTKGPSVFPLAPSSKSTS<br>GGTAALGCLVKDYFPEPVTVSWNSGALTSGVHTFPAVLQSSGLYSLSSV<br>VTVPSSSLGTQTYICNVNHKPSNTKVDKKVEPKSCDKTHT |
| 44 | DI-H2 141TAG | EVQLVESGGGLVQPGGSLRLSCAASGFTFNTYAMNWVRQAPGKGLEW<br>VARIRSKYNNYATYYADSVKDRFTISRDDSKNTLYLQMNSLRAEDTAV<br>YYCVRHGNFGNSYVSWFAYWGQGTLVTVSSASTKGPSVFPLAPSSpAcF<br>STSGGTAALGCLVKDYFPEPVTVSWNSGALTSGVHTFPAVLQSSGLYSL<br>SSVVTVPSSSLGTQTYICNVNHKPSNTKVDKKVEPKSCDKTHT |
| 45 | DI-H2 (K19R) | EVQLVESGGGLVQPGGSLRLSCAASGFTFNTYAMNWVRQASGKGLEW<br>VARIRSKYNNYATYYADSVKDRFTISRDDSKNTLYLQMNSLKTEDTAV<br>YYCVRHGNFGNSYVSWFAYWGQGTLVTVSSASTKGPSVFPLAPSSKSTS |

TABLE 36-continued

Antibody Domain Amino Acid Sequences

| SEQ ID NO. | Antibody Domain | Sequence |
|---|---|---|
| | | GGTAALGCLVKDYFPEPVTVSWNSGALTSGVHTFPAVLQSSGLYSLSSV VTVPSSSLGTQTYICNVNHKPSNTKVDKKVEPKSCDKTHT |
| 46 | DI-H2 (S41P) | EVQLVESGGGLVQPGGSLKLSCAASGFTFNTYAMNWVRQAPGKGLEW VARIRSKYNNYATYYADSVKDRFTISRDDSKNTLYLQMNSLKTEDTAV YYCVRHGNFGNSYVSWFAYWGQGTLVTVSSASTKGPSVFPLAPSSKSTS GGTAALGCLVKDYFPEPVTVSWNSGALTSGVHTFPAVLQSSGLYSLSSV VTVPSSSLGTQTYICNVNHKPSNTKVDKKVEPKSCDKTHT |
| 47 | DI-H2 (K89R) | EVQLVESGGGLVQPGGSLKLSCAASGFTFNTYAMNWVRQASGKGLEW VARIRSKYNNYATYYADSVKDRFTISRDDSKNTLYLQMNSLRTEDTAV YYCVRHGNFGNSYVSWFAYWGQGTLVTVSSASTKGPSVFPLAPSSKSTS GGTAALGCLVKDYFPEPVTVSWNSGALTSGVHTFPAVLQSSGLYSLSSV VTVPSSSLGTQTYICNVNHKPSNTKVDKKVEPKSCDKTHT |
| 48 | DI-H2 (T90A) | EVQLVESGGGLVQPGGSLKLSCAASGFTFNTYAMNWVRQASGKGLEW VARIRSKYNNYATYYADSVKDRFTISRDDSKNTLYLQMNSLRAEDTAV YYCVRHGNFGNSYVSWFAYWGQGTLVTVSSASTKGPSVFPLAPSSKSTS GGTAALGCLVKDYFPEPVTVSWNSGALTSGVHTFPAVLQSSGLYSLSSV VTVPSSSLGTQTYICNVNHKPSNTKVDKKVEPKSCDKTHT |
| 49 | DI-VH2 Minimal | RLSCAASGFTFNTYAMNWVRQAPGKGLEWVARIRSKYNNYATYYADS VKDRFTISRDDSKNTLYLQMNSLRA |
| 50 | DI-VH2 Super Minimal | PGKGLEWVARIRSKYNNYATYYADSVKDRFTISRDDSKNTLYLQMNSL RA |

Abbreviations: VH = heavy chain variable domain; VL = light chain variable domain; DI = de-immunized; Bold/underlined amino acids are sites for (replacement with) unnatural amino acids; H = heavy chain Fab (heavy chain variable + $C_H1$ domains); pAcF = p-acetylphenylalanine.

TABLE 37

Inter-CDR Antibody Domain Amino Acid Sequences

| SEQ ID NO. | Antibody Domain | Sequence |
|---|---|---|
| 51 | LCDR1 | RSSTGAVTTSNYAN |
| 52 | LCDR2 | GTNKRAP |
| 53 | LCDR3 | ALWYSNLWV |
| 54 | HCDR1 | GFTFNTYAMN |
| 55 | HCDR2 | RIRSKYNNYATYYADSVKD |
| 56 | HCDR3 | HGNFGNSYVSWFAY |
| 57 | LC Inter-CDR1/2 Region Option 1 | WVQQKPGQAFRGLIY |
| 58 | LC Inter-CDR1/2 Region Option 2 | WVQQKPGQAFRGLIG |
| 59 | LC Inter-CDR1/2 Region Option 3 | WVQQKPDHLFRGLIG |
| 60 | LC Inter-CDR1/2 Region Option 4 | WFQQKPDHLFRTLIY |
| 61 | LC Inter-CDR1/2 Region Option 5 | WVQQKPGQAFRGLIG |
| 62 | Super Minimal LC Inter-CDR1/2 Region Option 1 | DHLFR |
| 63 | Super Minimal LC Inter-CDR1/2 Region Option 2 | KPDHLFR |

TABLE 37-continued

Inter-CDR Antibody Domain Amino Acid Sequences

| SEQ ID NO. | Antibody Domain | Sequence |
|---|---|---|
| 64 | Minimal LC Inter-CDR1/2 Region | QKPDHLFR |
| 65 | Variable Minimal LC Inter-CDR 1/2 Region | Q $X_1X_2$DHLFR, wherein $X_1$ and $X_2$ are selected from any amino acid |
| 66 | Variable LC Inter-CDR1/2 Region Arginine | $X_1VX_2X_3X_4X_5$DHLFRG$X_6X_7$G, wherein $X_1$ $X_2$ $X_3$ $X_4$ $X_5$ $X_6$, and $X_7$ are selected from any amino acid. |
| 67 | Variable LC Inter-CDR1/2 Region Glutamine | $X_1VX_2Q$ $X_3X_4$DHLF$X_5$G$X_6X_7$G, wherein $X_1$ $X_2$ $X_3$ $X_4$ $X_5$ $X_6$, and $X_7$ are selected from any amino acid. |
| 68 | Variable LC Inter-CDR1/2 Region | $X_1VX_2X_3X_4X_3$DHLF$X_6$G$X_7X_8$G, wherein $X_1$ $X_2$ $X_3$ $X_4$ $X_5$ $X_6$, and $X_7$ are selected from any amino acid. |
| 69 | HC Pre-CDR1 Region Option 1 | EVQLVESGGGLVQPGGSLXLSCAAS, wherein X is selected from Lysine (K) and Arginine (R) |
| 70 | HC Inter-CDR1/2 Region Option 1 | WVRQASGKGLEWVX, wherein X is selected from Glycine (G) and Alanine (A) |
| 71 | HC Inter-CDR1/2 Region Option 2 | WVRQAPGKGLEWVX, wherein X is selected from Glycine (G) and Alanine (A) |
| 72 | LC Inter-CDR2/3 Region Option 1 | WTPARFSGSLLGGKAALTISGAQPEDEAEYYC |
| 73 | LC Inter-CDR2/3 Region Option 2 | WTPARFSGSLLGDKAALTISGAQPEDEAEYYC |
| 74 | LC Inter-CDR2/3 Region Option 3 | GTPARFSGSLLGDKAALTISGAQPEDEAEYYC |
| 75 | LC Inter-CDR2/3 Region Option 4 | GTPARFSGSLLGGKAALTISGAQPEDEAEYYC |
| 76 | LC Inter-CDR2/3 Region Option 5 | GVPDRFSGSLLGGKAALTISGAQPEDEAEYYC |
| 77 | LC Inter-CDR2/3 Region Option 6 | GVPARFSGSLLGGKAALTISGAQPEDEAEYYC |
| 78 | HC Inter-CDR2/3 Region Option 1 | RFTISRDDSKNTLYLQMNSLKTEDTAVYYCVR |
| 79 | HC Inter-CDR2/3 Region Option 2 | RFTISRDDSKNTLYLQMNSL $X_1$ $X_2$EDTAVYYCVR, wherein $X_1$ is selected from Lysine (K) and Arginine (R), and $X_2$ is selected from Threonine (T) and Alanine (A) |

Abbreviations: LC = light chain; HC = heavy chain

TABLE 38

Targeting Agent Antibody Conjugate Amino Acid Sequences

| SEQ ID NO. | | Sequence |
|---|---|---|
| 80 | DI-H2 N terminus | EVQLVESGGGLVQPGGSLRLSCAASGFTFNTYAMNWV RQAPGKGLEWVARIRSKYNNYATYYADSVKDRFTISR DDSKNTLYLQMNSLRAEDTAVYYCVRHGNFGNSYVS WFAYWGQGTL VTVSSASTK GPSVFPLAPSS |
| 81 | DI-H2 C terminus | STSGGTAALGCLVKDYFPEPVTVSWNSGALTSGVHTFP AVLQSSGLYSLSSVVTVPSSSLGTQTYICNVNHKPSNT KVDKKVEPKSCDKTHT |
| 82 | LC kappa N terminus | QAVVTQEPSLTVSPGGTVTLTCRSSTGAVTTSNYANW VQQKPDHLFRGLIGGTNKRAPGTPARFSGSLLGDKAAL TISGAQPEDEAEYYCALWYSNLWVFGGGTKLTVLKRT |

TABLE 38-continued

Targeting Agent Antibody Conjugate Amino Acid Sequences

| SEQ ID NO. | | Sequence |
|---|---|---|
| | | VAAPSVFIFPPSDEQLKSGTASVVCLLNNFYPREAKVQ WKVDNALQSGNSQESVTEQDSKDSTYSLSSTLTLSKA DYEKHKVYACEVTHQGL |
| 83 | LC kappa C terminus | SPVTKSFNRGEC |

Abbreviations: LC = light chain; DI = de-immunized; H = heavy chain Fab (heavy chain variable + $C_H1$ domains)

TABLE 39

Additional Amino Acid Sequences

| SEQ ID NO. | | Sequence |
|---|---|---|
| 84 | UCHT-1 HC | DIQMTQSPSSLSASVGDRVTITCRASQDIRNYLNWYQQ KPGKAPKLLIYYTSRLESGVPSRFSGSGSGTDYTLTISSL QPEDFATYYCQQGNTLPWTFGQGTKVEIKRTVAAPSV FIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC |
| 85 | UCHT-1 LC | EVQLVESGGGLVQPGGSLRLSCAASGYSFTGYTMNWV RQAPGKGLEWVALINPYKGVSTYNQKFKDRFTISVDK SKNTAYLQMNSLRAEDTAVYYCARSGYYGDSDWYFD VWGQGTLVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKKVEPKS CDKTHT |
| 86 | HC CH1 | ASTKGPSVFPLAPSSKSTSGGTAALGCLVKDYFPEPVT VSWNSGALTSGVHTF̄PAVLQSSGLYSLSSVVTVPSSSL GTQTYICNVNHKPSNTKVDKKVEPKSCDKTHT |
| 87 | HC Pre-CDR1 Region Option 2 | EVQLVESGGGLVQPGGSLRLSCAAS |
| 88 | HC Pre-CDR1 Region Option 3 | EVQLVESGGGLVQPGGSLKLSCAAS |
| 89 | HC Inter-CDR1/2 Region Option 3 | WVRQASGKGLEWVG |
| 90 | HC Inter-CDR1/2 Region Option 3 | WVRQASGKGLEWVA |
| 91 | HC Inter-CDR1/2 Region Option 4 | WVRQAPGKGLEWVG |
| 92 | HC Inter-CDR1/2 Region Option 5 | WVRQAPGKGLEWVA |
| 93 | HC Inter-CDR2/3 Region Option 3 | RFTISRDDSKNTLYLQMNSLKTEDTAVYYCVR |
| 94 | HC Inter-CDR2/3 Region Option 4 | RFTISRDDSKNTLYLQMNSLKAEDTAVYYCVR |
| 95 | HC Inter-CDR2/3 Region Option 5 | RFTISRDDSKNTLYLQMNSLRTEDTAVYYCVR |
| 96 | HC Inter-CDR2/3 Region Option 6 | RFTISRDDSKNTLYLQMNSLRAEDTAVYYCVR |
| 97 | LC Pre-CDR1 Region Option 1 | QAVVTQEPSLTVSPGGTVTLTC |
| 98 | HC CH1 | ASTKGPSVFPLAPSSpAcFSTSGGTAALGCLVKDYFPEP VTVSWNSGALTSGVHTFPAVLQSSGLYSLSSVVTVPSS SLGTQTYICNVNHKPSNTKVDKKVEPKSCDKTHT |
| 99 | HC CH1 A | ASTKGPSVFPLAPSS |

TABLE 39-continued

Additional Amino Acid Sequences

| SEQ ID NO. | | Sequence |
|---|---|---|
| 100 | HC CH1 B | STSGGTAALG |
| 101 | HC CH1 C | CLVKDYFPEP |
| 102 | HC CH1 D | VTVSWNSGAL |
| 103 | HC CH1 E | TSGVHTFPAV |
| 104 | HC CH1 F | LQSSGLYSLS |
| 105 | HC CH1 G | SVVTVPSSSL |
| 106 | HC CH1 H | GTQTYICNVN |
| 107 | HC CH1 I | HKPSNTKVDK |
| 108 | HC CH1 J | KVEPKSCDKTHT |
| 109 | HC CH1 K | STSGGTAALGCLVKDYFPEPVTVSWNSGALTSGVHTFP<br>AVLQSSGLYSLSSVVTVPSSSLGTQTYICNVNHKPSNT<br>KVDKKVEPKSCDKTHT |
| 110 | LC End Region | FGGGTKLTVL |
| 111 | VL5 CL1 | KRTVAAPSVFIFPPSDEQLKSGTASVVCLLNNFYPREA<br>KVQWKVDNALQSGNSQESVTEQDSKDSTYSLSSTLTL<br>SKADYEKHKVYACEVTHQGLSSPVTKSFNRGEC |
| 112 | VL5 CL2 | KRTVAAPSVFIFPPSDEQLKSGTASVVCLLNNFYPREA<br>KVQWKVDNALQSGNSQESVTEQDSKDSTYSLSSTLTL<br>SKADYEKHKVYACEVTHQGLpAcFSPVTKSFNRGEC |
| 113 | VL CLA | KRTVAAPSVFIFPPSDEQLKSGTASVVCLLNNFYPREA<br>KVQWKVDNALQSGNSQESVTEQDSKDSTYSLSSTLTL<br>SKADYEKHKVYACEVTHQGL |
| 114 | VL CLB | SPVTKSFNRGEC |
| 115 | VL CLA1 | KRTVAAPSVF |
| 116 | VL CLA2 | IFPPSDEQLK |
| 117 | VL CLA3 | SGTASVVCLL |
| 118 | VL CLA4 | NNFYPREAKV |
| 119 | VL CLA5 | QWKVDNALQS |
| 120 | VL CLA6 | GNSQESVTEQ |
| 121 | VL CLA7 | DSKDSTYSLS |
| 122 | VL CLA8 | STLTLSKADY |
| 123 | VL CLA9 | EKHKVYACEVTHQGL |
| 124 | VH2 end | WGQGTLVTVSS |

Abbreviations: LC = light chain; DI= de-immunized; H = heavy chain Fab (heavy chain variable + C$_H$1 domains

---

What is claimed is:

1. An antibody or antigen-binding fragment thereof that binds to cluster of differentiation 3 (CD3), comprising (a) a heavy chain variable region comprising an amino acid sequence at least 96% identical to SEQ ID NO: 27, and (b) a light chain variable region comprising an amino acid sequence at least 96% identical to SEQ ID NO: 32; wherein (i) the light chain variable region comprises the light chain complementarity determining region 1 (CDR1), the light chain CDR2, and the light chain CDR3 of SEQ ID NO: 32, and the heavy chain variable region comprises the heavy chain CDR1, the heavy chain CDR2, and the heavy chain CDR3 of SEQ ID NO: 27.

2. The antibody or antigen-binding fragment of claim 1, wherein (i) the light chain CDR1 comprises SEQ ID NO: 51, the light chain CDR2 comprises SEQ ID NO: 52, and the light chain CDR3 comprises SEQ ID NO: 53, and (ii) the heavy chain CDR1 comprises SEQ ID NO: 54, the heavy chain CDR2 comprises SEQ ID NO: 55, and the heavy chain CDR3 comprises SEQ ID NO: 56.

3. The antibody or antigen-binding fragment of claim 1, wherein the light chain variable region comprises SEQ ID NO: 32, and the heavy chain variable region comprises SEQ ID NO: 27.

4. The antibody or antigen-binding fragment of claim 1, comprising an unnatural amino acid, wherein the unnatural amino acid optionally comprises para-acetylphenylalanine (pAcF).

5. The antibody or antigen-binding fragment of claim 4, comprising a first heavy chain constant region (CH1), wherein the unnatural amino acid is positioned in the CH1 at position 129 per Kabat numbering.

6. The antibody or antigen-binding fragment of claim 1, comprising a first heavy chain constant region (CH1) comprising a sequence at least 95% identical to SEQ ID NO: 98, wherein the CH1 comprises the para-acetylphenylalanine of SEQ ID NO: 98.

7. The antibody or antigen-binding fragment of claim 1, wherein the antibody or antigen-binding fragment thereof comprises a heavy chain at least 95% identical to SEQ ID NO: 44, and a light chain at least 95% identical to SEQ ID NO-39.

8. The antibody or antigen-binding fragment of claim 7, wherein the heavy chain comprises SEQ ID NO: 44 and the light chain comprises SEQ ID NO: 39.

9. An antibody or antigen-binding fragment thereof that binds to cluster of differentiation 3 (CD3), comprising:
(a) a heavy chain variable domain comprising
a first heavy chain framework region comprising EVQLVESGGGLVQPGGSL(X1)LSCAAS (SEQ ID NO: 69), wherein X1 is selected from lysine (K) and arginine (R),
a heavy chain CDR1 comprising GFTFNTYAMN (SEQ ID NO: 54),
a second heavy chain framework region comprising WVRQAPGKGLEWV(X2) (SEQ ID NO: 71), wherein X2 is selected from glycine (G) and alanine (A),
a heavy chain CDR2 comprising RIRSKYNNYATYY-ADSVKD (SEQ ID NO: 55),
a third heavy chain framework region comprising RFTISRDDSKNTLYLQMNSL(X3)(X4)ED-TAVYYCVR (SEQ ID NO: 79), wherein X3 is selected from lysine (K) and arginine (R), and X4 is selected from threonine (T) and alanine (A),
a heavy chain CDR3 comprising HGNFGNSYVSW-FAY (SEQ ID NO: 56), and
a fourth heavy chain framework region comprising WGQGTLVTVSS (SEQ ID NO: 124); and
(b) a light chain variable domain comprising
a first light chain framework region comprising QAVVTQEPSLTVSPGGTVTLTC (SEQ ID NO: 97),
a light chain CDR1 comprising RSSTGAVTTSNYAN (SEQ ID NO: 51),
a second light chain framework region comprising DHLFR (SEQ ID NO: 62),
a light chain CDR2 comprising GTNKRAP (SEQ ID NO: 52),
a third light chain framework region comprising GTPARFSGSLLGDKAALTISGAQPEDEAEYYC (SEQ ID NO: 74),
a light chain CDR3 comprising ALWYSNLWV (SEQ ID NO: 53), and
a fourth light chain framework region comprising FGGGTKLTVL (SEQ ID NO: 110).

10. The antibody or antigen-binding fragment of claim 9, wherein (i) X1 is arginine, (ii) X2 is alanine, (iii) X3 is arginine, (iv) X4 is alanine, or (v) any combination of one or more of (i) to (iv).

11. The antibody or antigen-binding fragment of claim 9, wherein the second light chain framework region comprises (i) (X5)V(X6)(X7)(X8)(X9)DHLFRG(X10)(X11)G (SEQ ID NO: 66), wherein X5, X6, X7, X8, X9, X10, and X11 are selected from any amino acid, or
(ii) (X12)V(X13)Q (X14)(X15)DHLF(X16)G(X17)(X18)G (SEQ ID NO: 67), wherein X12, X13, X14, X15, X16, X17, and X18 are selected from any amino acid.

12. The antibody or antigen-binding fragment of claim 9, wherein the second light chain framework region comprises WVQQKPDIILFRGLIG (SEQ ID NO: 59).

13. The antibody or antigen-binding fragment of claim 9, comprising an unnatural amino acid, where the unnatural amino acid comprises para-acetylphenylalanine (pAcF).

14. The antibody or antigen-binding fragment of claim 13, comprising a first heavy chain constant region (CH1), wherein the unnatural amino acid is positioned in the CH1 at position 129 using Kabat numbering.

15. The antibody or antigen-binding fragment of claim 9, comprising a first heavy chain constant region (CH1) comprising a sequence at least 95% identical to SEQ ID NO: 98, wherein the CH1 comprises the para-acetylphenylalanine of SEQ ID NO: 98.

16. A composition comprising a sequence at least 95% identical to SEQ ID NO: 98, wherein the sequence comprises the para-acetylphenylalanine of SEQ ID NO: 98.

17. The composition of claim 16, comprising a human or humanized antibody or antigen-binding fragment thereof.

18. The composition of claim 17, wherein the antibody or antigen-binding fragment binds to cluster of differentiating 3 (CD3).

19. The composition of claim 17, wherein the antibody or antigen-binding fragment comprises a light chain complementarity determining region 1 (CDR1) comprising SEQ ID NO: 51, a light chain CDR2 comprising SEQ ID NO: 52, and a light chain CDR3 comprising SEQ ID NO: 53, and (ii) a heavy chain CDR1 comprising SEQ ID NO: 54, a heavy chain CDR2 comprising SEQ ID NO: 55, and a heavy chain CDR3 comprising SEQ ID NO: 56.

20. The composition of claim 19, comprising SEQ ID NO: 98.

* * * * *